United States Patent
Tan et al.

(10) Patent No.: US 10,087,447 B2
(45) Date of Patent: *Oct. 2, 2018

(54) ANTIPROLIFERATIVE AGENT

(71) Applicant: NANYANG TECHNOLOGICAL UNIVERSITY, Singapore (SG)

(72) Inventors: Nguan Soon Tan, Singapore (SG); Han Chung Chong, Singapore (SG); Ming Jie Tan, Singapore (SG); Royston Huang, Singapore (SG)

(73) Assignee: Nanyang Technologies University, Singapore (SG)

( * ) Notice: Subject to any disclaimer, the term of this patent is extended or adjusted under 35 U.S.C. 154(b) by 17 days.

This patent is subject to a terminal disclaimer.

(21) Appl. No.: 14/590,397

(22) Filed: Jan. 6, 2015

(65) Prior Publication Data

US 2016/0053268 A1    Feb. 25, 2016

Related U.S. Application Data

(62) Division of application No. 13/501,768, filed as application No. PCT/SG2010/000392 on Oct. 14, 2010, now abandoned.

(51) Int. Cl.
*C12N 15/113* (2010.01)
*C07K 16/22* (2006.01)
*A61K 39/00* (2006.01)

(52) U.S. Cl.
CPC .......... *C12N 15/1136* (2013.01); *C07K 16/22* (2013.01); *C12N 15/1138* (2013.01); *A61K 2039/505* (2013.01); *C12N 2310/14* (2013.01); *C12N 2310/531* (2013.01); *C12N 2330/50* (2013.01)

(58) Field of Classification Search
None
See application file for complete search history.

(56) References Cited

U.S. PATENT DOCUMENTS

| 7,371,384 B2 | 5/2008 | Gerber et al. |
| 7,740,846 B2 | 6/2010 | Gerber et al. |
| 2006/0019284 A1 | 1/2006 | Huang et al. |
| 2006/0031949 A1* | 2/2006 | Shen ............... A01K 67/0271 800/8 |
| 2006/0093607 A1 | 5/2006 | Gerber et al. |
| 2007/0054856 A1 | 3/2007 | Gerber et al. |
| 2014/0242084 A1* | 8/2014 | Tan ............... C07K 16/2842 424/139.1 |

FOREIGN PATENT DOCUMENTS

| WO | 2006014678 A2 | 2/2006 |
| WO | 2006014729 A2 | 2/2006 |
| WO | 2006074228 A1 | 7/2006 |

OTHER PUBLICATIONS

Goh et al. (J. Biol. Chem. Aug. 21, 2010, 285 (43): 32999-33009).*
System Biosciences (Double-Promoter pFIV-H1/u6 siRNA Cloning and Expressing Vectors, User Manual, 2004).*
Murata et al. (J. Orthopaedic Res. Jan. 2009).*
OriGene-Rnai-HuSH Collection (https://web.archive.org/web/20090412152852/http://www.origene.com/shRNA/vector_information.aspx Apr. 12, 2009).*
*Homo sapiens* angiopoietin-like 4 (ANGPTL4), transcript variant 1, mRNA (NM_139314.1 Apr. 5, 2009).*
Sun et al., "Adiponectin Deficiency Promotes Tumor Growth in Mice by Reducing Macrophage Infiltration", PLoS ONE, Aug. 2010, vol. 5 Issue 8, pp. 1-9.
Ushio-Fukai et al., "Reactive oxygen species and angiogenesis: NADPH oxidase as target for cancer therapy", Elsevier, Cancer Letters, 266 (2008), pp. 37-52.
Verine et al., "Determination of Angptl4 mRNA as Diagnostic Marker of Primary and Metastatic Clear Cell Renal-Cell Carcinoma", PLoS ONE, Apr. 2010, vol. 5 Issue 4, pp. 1-11.
Wagner et al., "Doxorubicin increases intracellular hydrogen peroxide in PC3 prostate cancer cells", Elsevier, Archives of Biochemistry and Biophysics, 440 (2005), pp. 181-190.
Wagner et al., "Peroxisome proliferator-activated receptor beta/delta (PPARβ/δ) acts as regulator of metabolism linked to multiple cellular functions", Elsevier, Pharmacology & Therapeutics, 125 (2010), pp. 423-435.
Wang et al., "Overexpression of Angiopoietin-Like Protein 4 Alters Mitochondria Activities and Modulates Methionine Metabolic Cycle in the Liver Tissues of db/db Diabetic Mice", Molecular Endocrinology, Apr. 2007, 21(4); pp. 972-986.
Wang et al., "Expression of angiopoietin-like 4 and tenascine C but not cathepsin C mRNA predicts prognosis of oral tongue squamous cell carcinoma", Biomakers, 2010; 15(1); pp. 39-46.
Werner et al., Integrins engage mitochondrial function for signal transduction by a mechanism dependent on Tho GTPases, Journal of Cell Biology, Jul. 22, 2002, vol. 158 No. 2, pp. 357-368.
Westhoff et al., "Adhesion-mediated apoptosis resistance in cancer", Elsevier, Drug Resistance Updates 12 (2009) pp. 127-136.
Wu, "The signaling mechanism of ROS in tumor progression", Cancer Metastasis Rev (2006) 25, pp. 695-705.
Zhan et al., "Signalling mechanisms of anoikis", Histol Histopathol (2004) 19, pp. 973-983.
Extended European Search Report for Application No. 108237058-1401/2488640, PCT/SG2010/000392, dated Dec. 4, 2013.
International Search Report for International Application No. PCT/SG/2010/000392, dated Dec. 7, 2010.

(Continued)

*Primary Examiner* — Peter J Reddig
(74) *Attorney, Agent, or Firm* — Intellectual Property Law Group LLP

(57) ABSTRACT

The invention provides an antibody specific to the ANGPTL4 protein capable of neutralizing proliferation and methods of making and using the same. The antibody of the invention is further directed to the C terminal region of the protein and may be capable of neutralizing cell proliferation and treating cancer. The antibody may be monoclonal and/or humanized antibody.

13 Claims, 91 Drawing Sheets

Specification includes a Sequence Listing.

(56) References Cited

OTHER PUBLICATIONS

Ma et al., "Viral G protein-coupled receptor up-regulates Angiopoietin-like 4 promoting angiogenesis and vascular permeability in Kaposi's sarcoma", Proceedings of the National Academy of Sciences, Early Edition, 2010, published Jul. 26, 2010 (Online Journal), pp. 1-6.
Chong et al., "Regulation of epithelial-mesenchymal IL-1 signaling by PPARβ/δ is essential for skin homeostasis and wound healing", The Journal of Cell Biology, J. Cell Biol., vol. 184 No. 6, 2009, pp. 817-831.
Desai et al., "Lipid-lowering effects of anti-angiopoietin-like 4 antibody recapitulate the lipid phenotype found in angiopoietin-like 4 knockout mice", PNAS, vol. 104 No. 28, Jul. 10, 2007, pp. 11766-11771.
Di-Poi et al., "Antiapoptotic Role of PPARβ in Keratinocytes via Transcriptional Control of the Akt1 Signaling Pathway", Molecular Cell, vol. 10, Oct. 2002, pp. 721-733.
Tang, "Proteomic and bioinformatic analysis of epithelial tight junction reveals an unexpected cluster of synaptic molecules", Biology Direct 2006, pp. 1-30.
Aggarwal et al., "Inflammation and cancer: how friendly is the relationship for cancer patients?" Elsevier, ScienceDirect, Current Opinion in Pharamacology, 2009, 9, pp. 351-369.
Tan et al., "Regulation of Cell Proliferation and Migration by TAK1 via Transcriptional Control of von Hippel-Lindau Tumor Suppressor", Journal of Biological Chemistry, vol. 284, No. 27, Jul. 3, 2009, pp. 18047-18058.
Akram et al., "Reactive oxygen species-mediated regulation of the Na+—H+ exchanger 1 gene expression connects intracellular redox status with cells' sensitivity to death triggers", Cell Death and Differentiation (2006) 13, pp. 628-641.
Belanger et al., "Hypoxio Up-regulates Expression of Peroxisome Proliferator-activated Receptor γ Angiopoietin-related Gene (PGAR) in Cardiomyocytes: Role of Hypoxia Inducible Factor 1α", J. Mol Cell Cardiol 34, 2002 Elsevier Science Ltd, pp. 765-774.
Bouillet et al., "BH3-only proteins—evolutionarily conserved pro-apoptotic Bcl-2 family members essential for initiating programmed call death", Journal of Cell Science 115 (8); pp. 1567-1574, 2002.
Bridge et al., "Induction of an interferon response by RNAi vectors in mammalian cells", Nature Genetics, vol. 34 No. 3, Jul. 2003, pp. 263-264.
Chiarugi, "From Anchorage Dependent Proliferation to Survival: Lessons from Redox Signalling", IUBMB Life, 60 (5) May 2008, pp. 301-307.
Chiarugi et al., "Redox signalling in anchorage-dependent cell growth", Elsevier, Cellular Signalling, 19 (2007) pp. 672-682.
Desgrosellier et al., "Integrins in cancer: biological implications and therapeutic opportunities", Nature Reviews Cancer, vol. 10, Jan. 2010.
Eble et al., "Integrins in Cancer Treatment", Current Cancer Drug Targets, 2006, 6, pp. 89-105.
Ferraro et al., "Pro-metastic signaling by c-Met through RAC-1 and reactive oxygen species (ROS)", Oncogene (2006) 25, pp. 3689-3698.
Fidler, "Critical determinants of cancer metastasis: rationale for therapy", Cancer Chemother Pharmacol (1999) 43 (Suppl), pp. S3-S10.
Galaup et al., "Angiopoietin-like 4 prevents metastasis through inhabition of vascular permeability and tumor cell motility and invasiveness", PNAS, Dec. 5, 2006, vol. 103 No. 49, pp. 18721-18726.
Ge et al., "Oligomerization and Regulated Proteolytic Processing of Angiopoietin-like Protein 4", The Journal of Biological Chemistry, vol. 279 No. 3, Issue of Jan. 16, 2004, pp. 2038-2045.
Giannoni et al., "Redox regulation of anoikis: reactive oxygen species as essential mediators of cell survival", Cell Death and Differentiation (2008) 15, pp. 867-878.
Hanahan et al., "The Hallmarks of Cancer", Cell, Jan. 7, 2000, vol. 100, pp. 57-70.

Irani et al., "Mitogenic Signaling Mediated by Oxidants in Ras-Transformed Fibroblasts", Science, Mar. 14, 1997, vol. 275, pp. 1649-1652.
Ito et al., "Inhibition of Angiogenesis and Vascular Leakiness by Angiopoietin-Related Protein 41", Cancer Research, 63, Oct. 15, 2003, pp. 6651-6657.
Joneson et al., "A Rac1 Effector Site Controlling Mitogenesis through Superoxide Production", The Journal of Biological Chemistry, vol. 273 No. 29, Issue of Jul. 17, 1998, pp. 17991-17994.
Kersten et al., "Characterization of the Fasting-induced Adipose Factor FIAF, a Novel Peroxisome Proliferator-activated Receptor Target Gene", The Journal of Biological Chemistry, vol. 275 No. 37, Issue of Sep. 15, 2000, pp. 28488-28493.
Komatsu et al., "NADPH oxidase 1 plays a critical mediating role in oncogenic Ras-induced vascular endothelial growth factor expression", Oncogene (2008) 27, pp. 4724-4732.
Köster et al., "Transgenic Angiopoietin-Like (Angptl)4 Overexpression and Targeted Disruption of Angptl4 and Angptl3: Regulation of Triglyceride Metabolism", Endocrinology, Nov. 2005, 146 (11), pp. 4943-4950.
Le Jan et al., "Angiopoietin-Like 4 Is a Proangiogenic Factor Produced during Ischemia and in Conventional Renal Cell Carcinoma", American Journal of Pathology, May 2003, vol. 162 No. 5, pp. 1521-1528.
Liou et al., "Reactive oxygen species in cancer", Free Radical Research, May 2010, 44 (5), paged 479-496.
MacFarlane et al., "NADPH oxidase activity is necessary for acute intermittent hypoxia-induced phrenic long-term facilitation", J Physical 587.9 (2009) pp. 1931-1942.
Minn et al., "Genes that mediate breast cancer metastasis to lung", Nature, Jul. 2005, vol. 436, pp. 518-524.
Mueller et al., "Tumor Progression of Skin Carcinoma Cells in Vivo Promoted by Clonal Selection, Mutagenesis, and Autocrine Growth Regulation by Granulocyte Colony-Stimulating Factor and Granulocyte-Macrophage Colony-Stimulating Factor", American Journal of Pathology, Oct. 2011, vol. 159 No. 4, pp. 1567-1579.
Murphy et al., "PPAR-γ agonists: therapeutic role in diabetes, inflammation and cancer", TiPS, Dec. 2000, vol. 21, pp. 469-474.
Münzel et al., "Detection of Superoxide in Vascular Tissue", Arteriosclerosis, Thrombosis, and Vascular Biology, Journal of The American Heart Association, Aug. 15, 2002, 22, pp. 1761-7168.
Oike et al., "Angiopoietin-like proteins: potential new targets for metabolic syndrome therapy", Elsevier, Trends in Molecular Medicine, vol. 11 No. 10, Oct. 2005, pp. 473-479.
Padua et al., "TGFβ Primes Breast Tumors for Lung Metastasis Seeding through Angiopoietin-like 4", Cell 133, Apr. 4, 2008, pp. 66-77.
Paffenholz et al., "Vestibular defects in head-tilt mice result from mutations in Nox3, encoding an NADPH oxidase", Genes & Development, 2004, 18, pp. 486-491.
Panigrahy et al., "PPAR-γ as a Therapeutic Target for Tumor Angiogenesis and Metastasis", Cancer Biology & Therapy, Landes Bioscience, Jul. 2005, 4:7, pp. 687-693.
Pervaiz et al., "Superoxide anion: Oncogenic reactive oxygen species?", Elsevier, The International Journal of Biochemistry & Cell Biology 39 (2007), pp. 1297-1304.
Pervaiz et al., "A Permissive Apoptotic Environment: Function of a Decrease in Intracellular Superoxide Anion and Cytosolic Acidification", Biochemical and Biophysical Research Communications, 2002, vol. 290 No. 4, pp. 1145-1150.
Pervaiz et al., "Superoxide anion inhibits drug-induced tumor cell death", FEBS Letters (1999) pp. 343-348.
Peters et al., "Sorting out the functional role(s) of peroxisome proliferator-activated receptor-β/δ (PPARβ/δ) in cell proliferation and cancer", Elsevier, Biochimica et Biophysica Acta 1796 (2009) pp. 230-241.
Salmon, "Human Tumor Colony Assay and Chemosensitivity Testing <1>", U.S. Department of Health and Human Services Cancer Treatment Reports, Cancer Treat Rep, Jan. 1984; 68, pp. 1-11.
She et al., "The BAD protein integrates survival signaling by EGFR/MAPK and PI3K/Akt kinase pathways in PTEN-deficient tumor cells", Cancer Cell, Oct. 2005, vol. 8, pp. 287-297.

(56) References Cited

OTHER PUBLICATIONS

Shibanuma et al., "Superoxide as a Signal for Increase in Intracellular pH", Journal of Cellular Physiology; 136 (1988), pp. 379-383.
Singh et al., "Chemokines in tumor angiogenesis and metastasis", Cancer Metastasis Rev (2007) 26, pp. 453-467.
Suh et al., "Cell transformation by the superoxide-generating oxidase Mox1", Nature, Sep. 2, 1999, vol. 401, pp. 79-82.
Sukonina et al., "Angiopoietin-like protein 4 converts lipoprotein lipase to inactive monomers and modulates lipase activity in adipose tissue", PNAS, Nov. 14, 2006, vol. 103 No. 46, pp. 17450-17455.
Clontech Laboratories Inc., Knockout™ Single Vector Inducible RNAi System User Manual, Dec. 14, 2007.

* cited by examiner

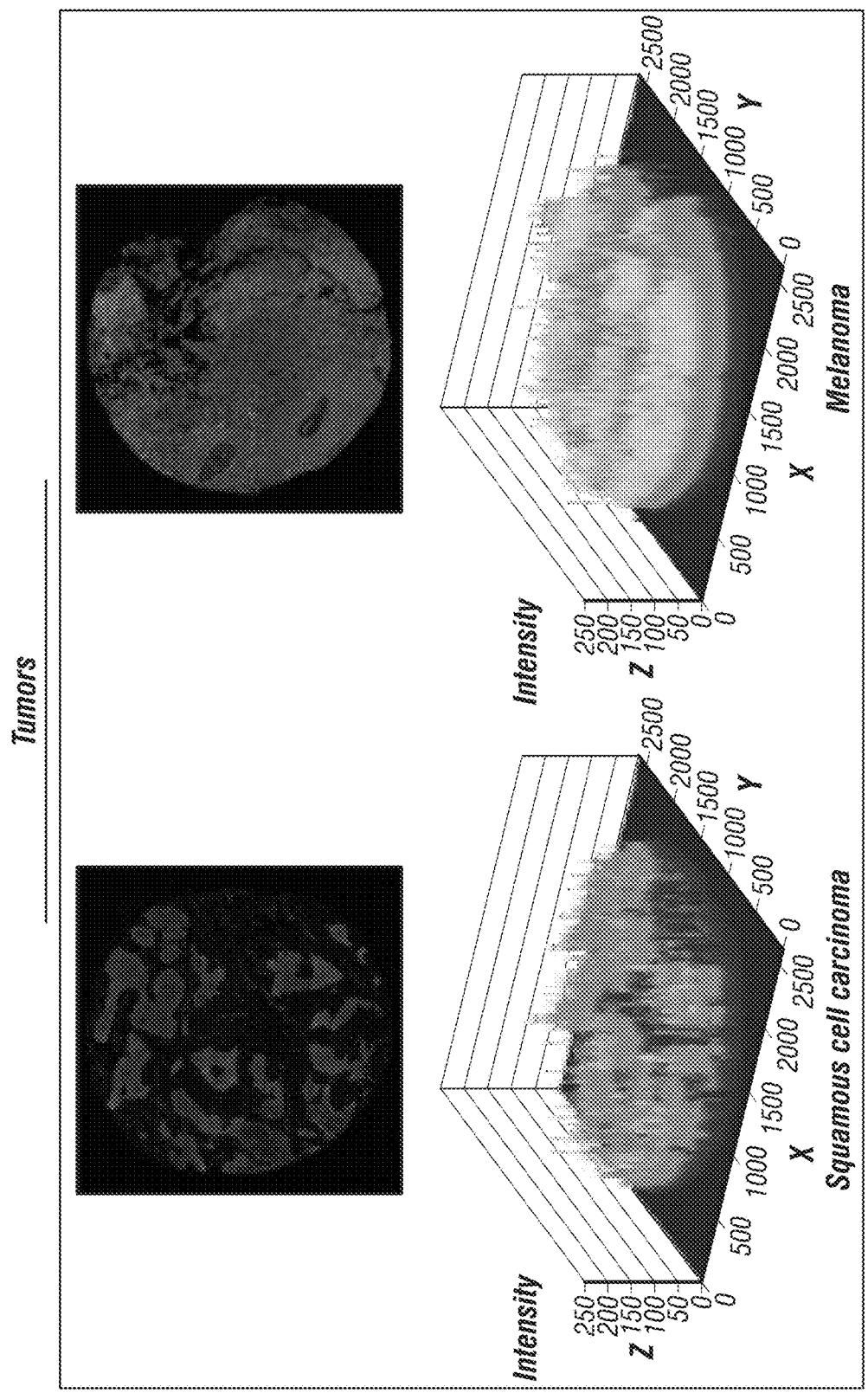
FIG. 3C1

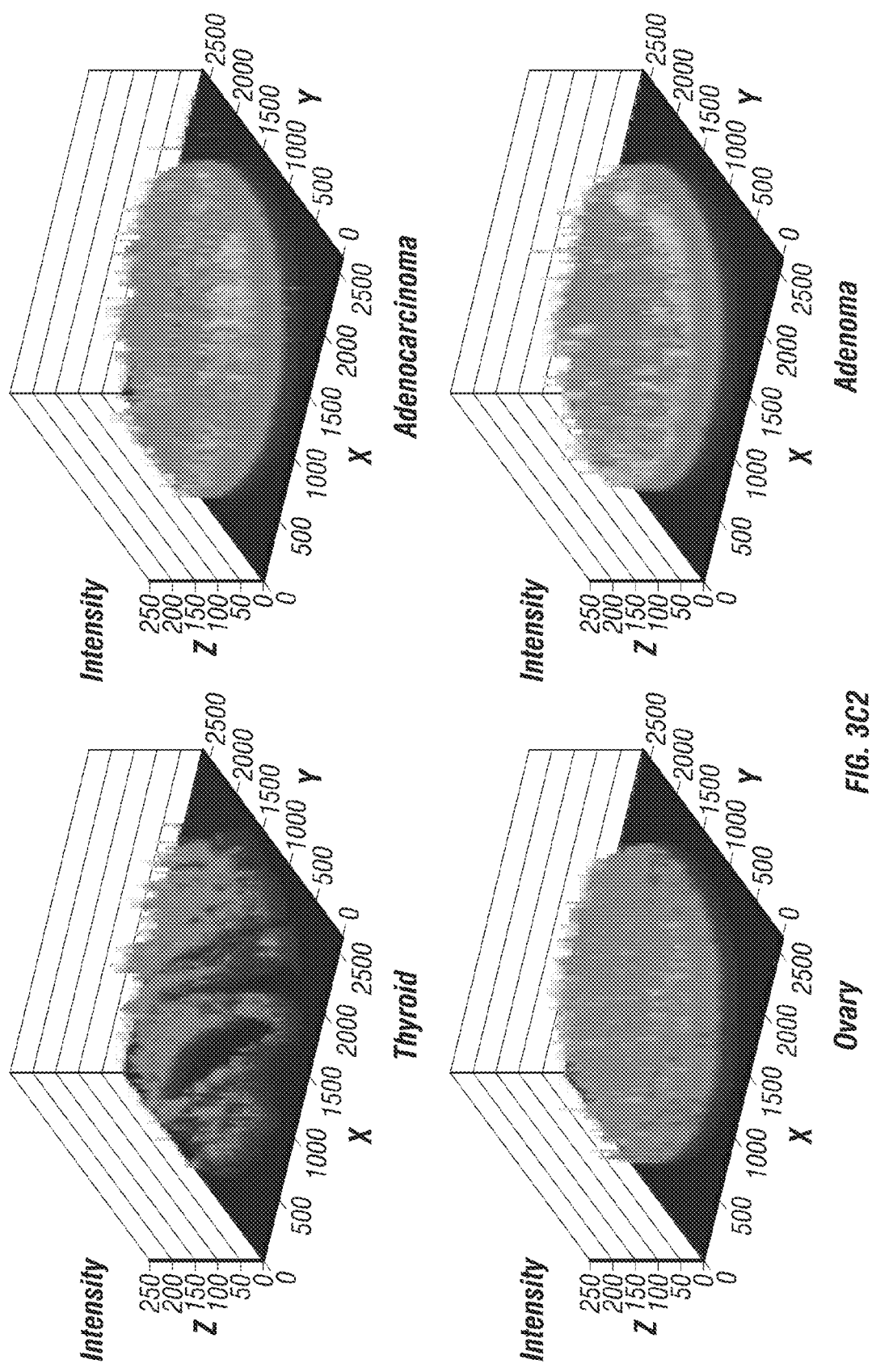
FIG. 3C2

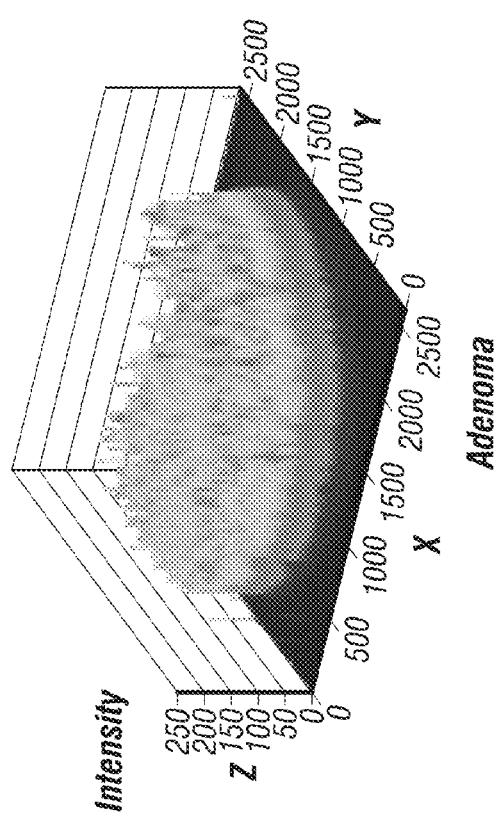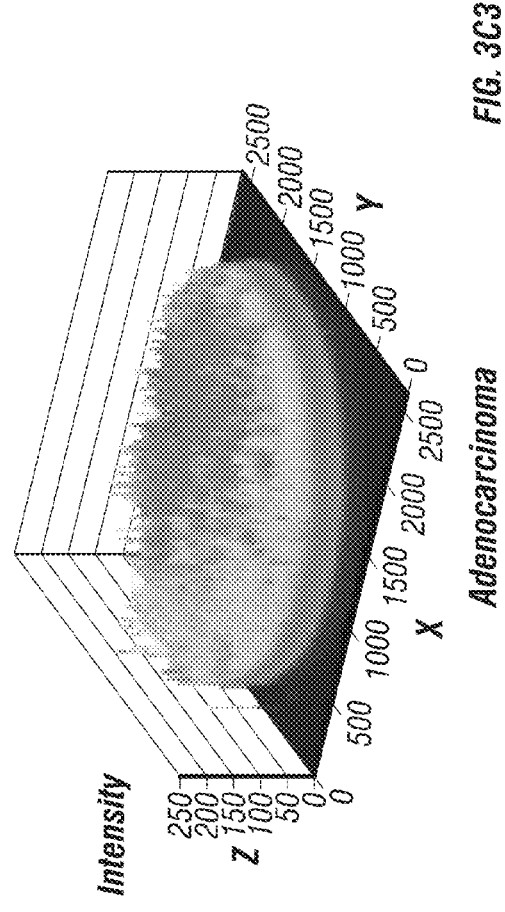
FIG. 3C3

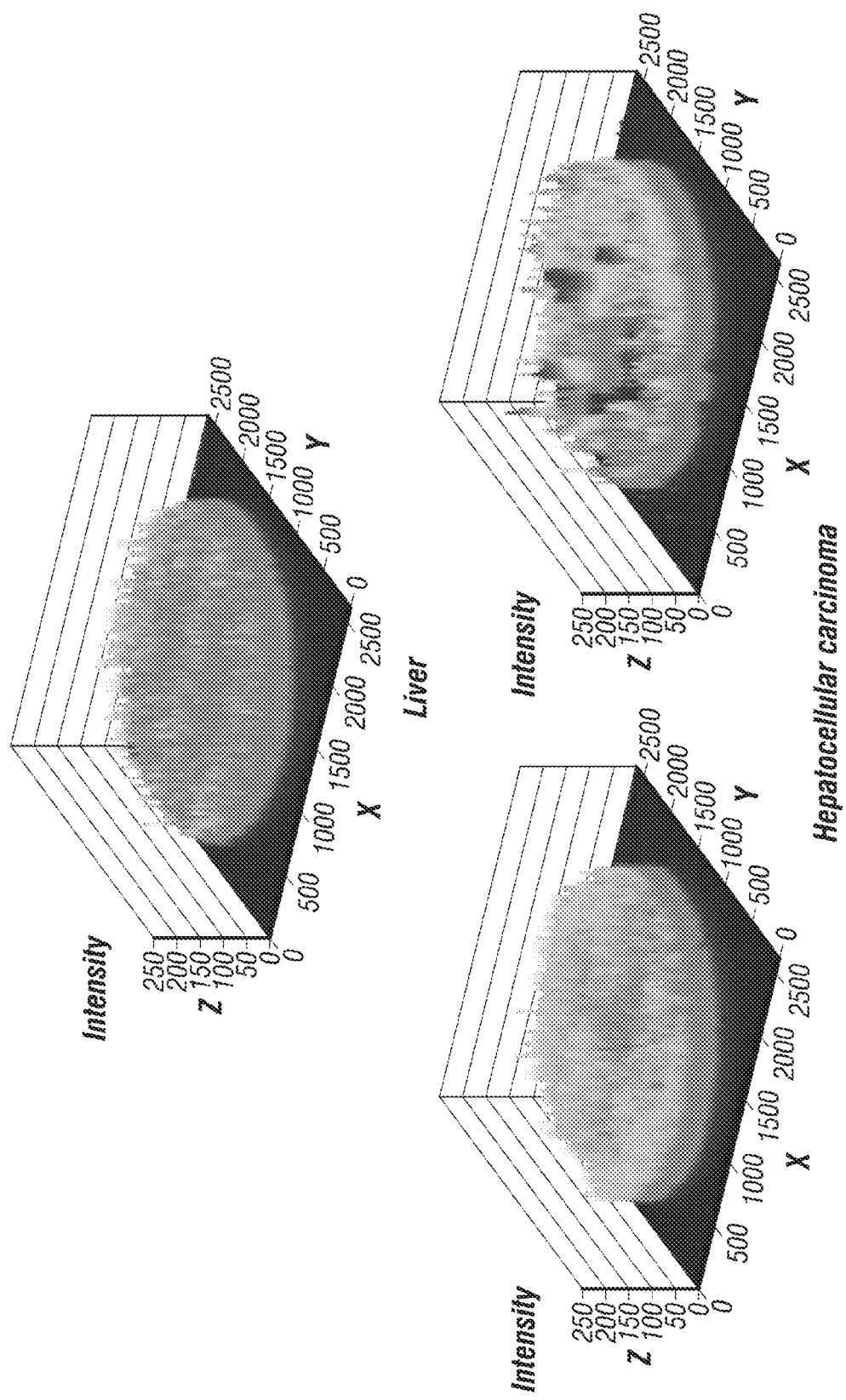
FIG. 3C4

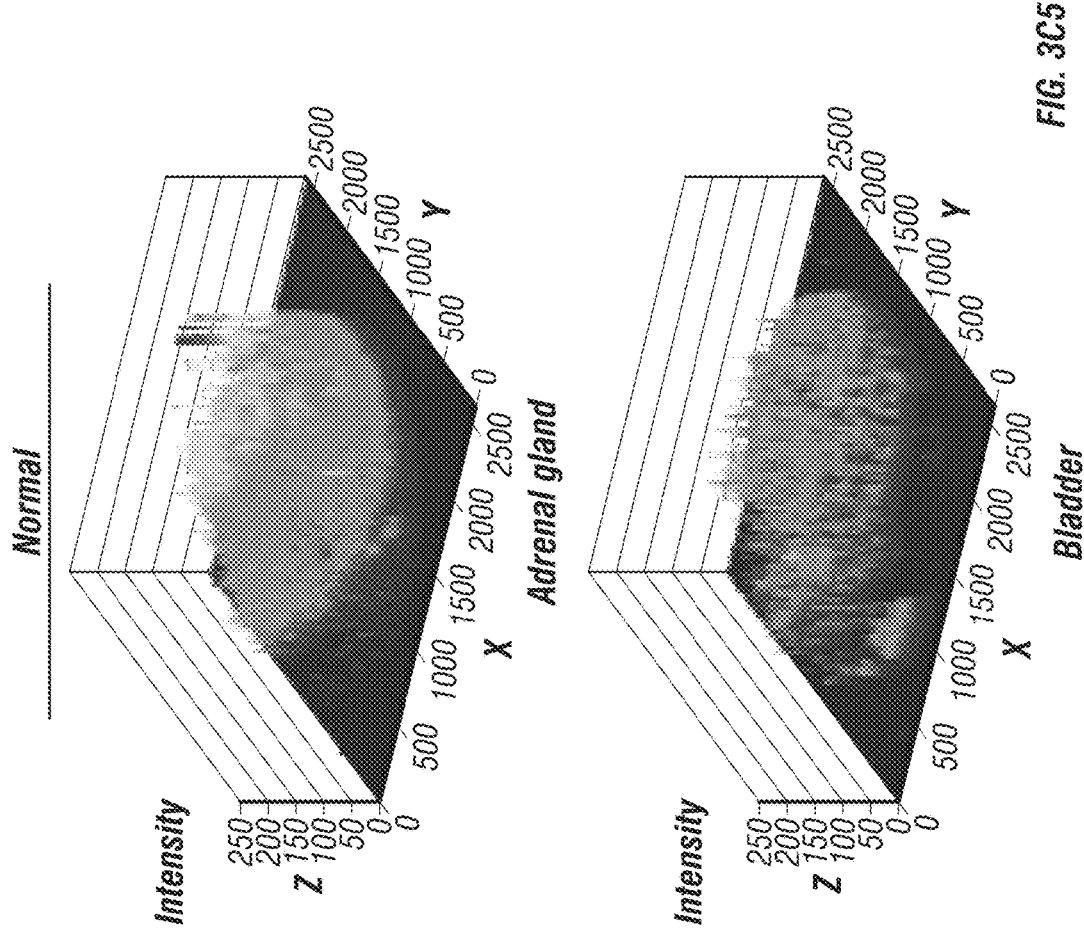
FIG. 3C5

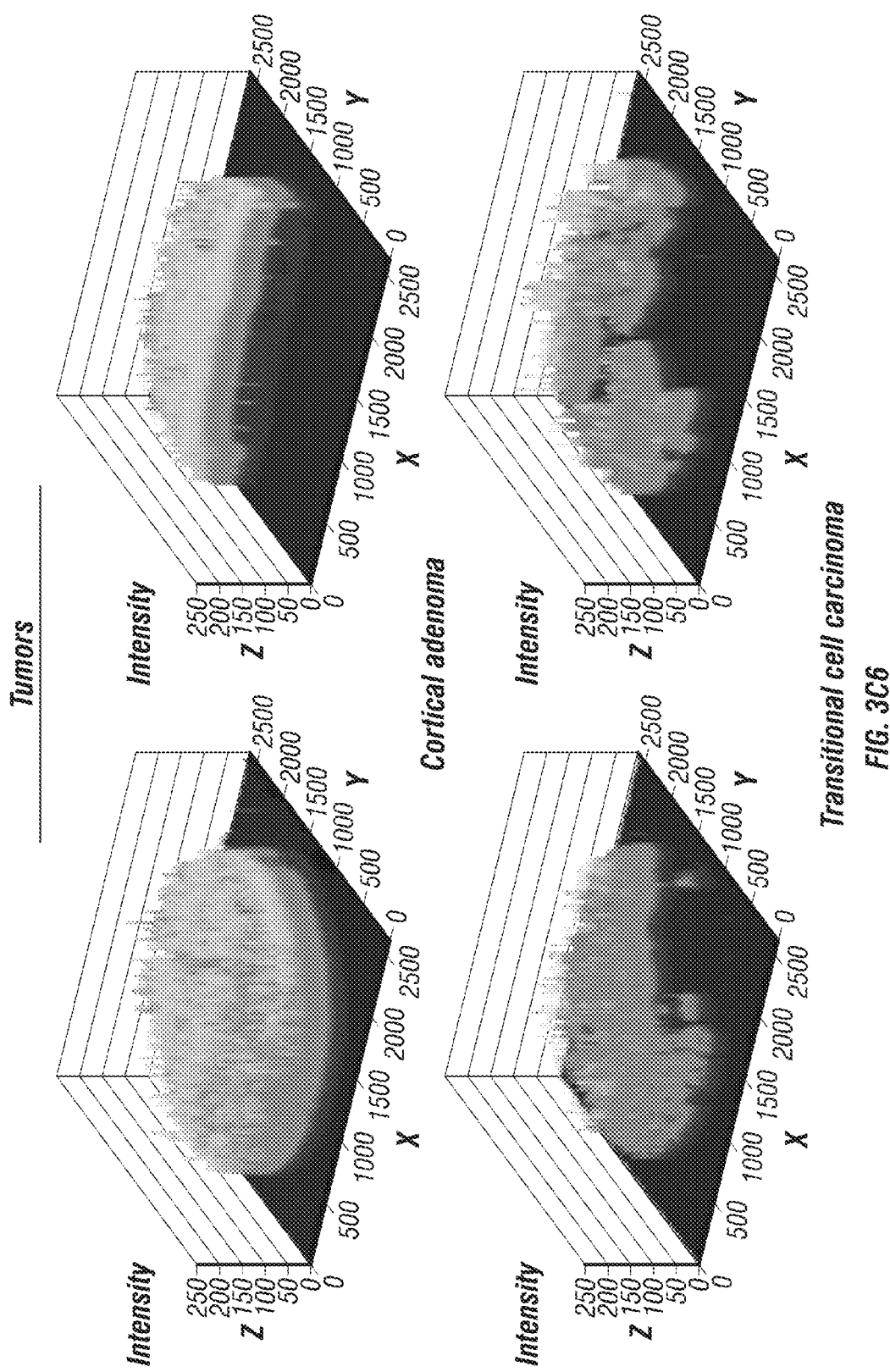

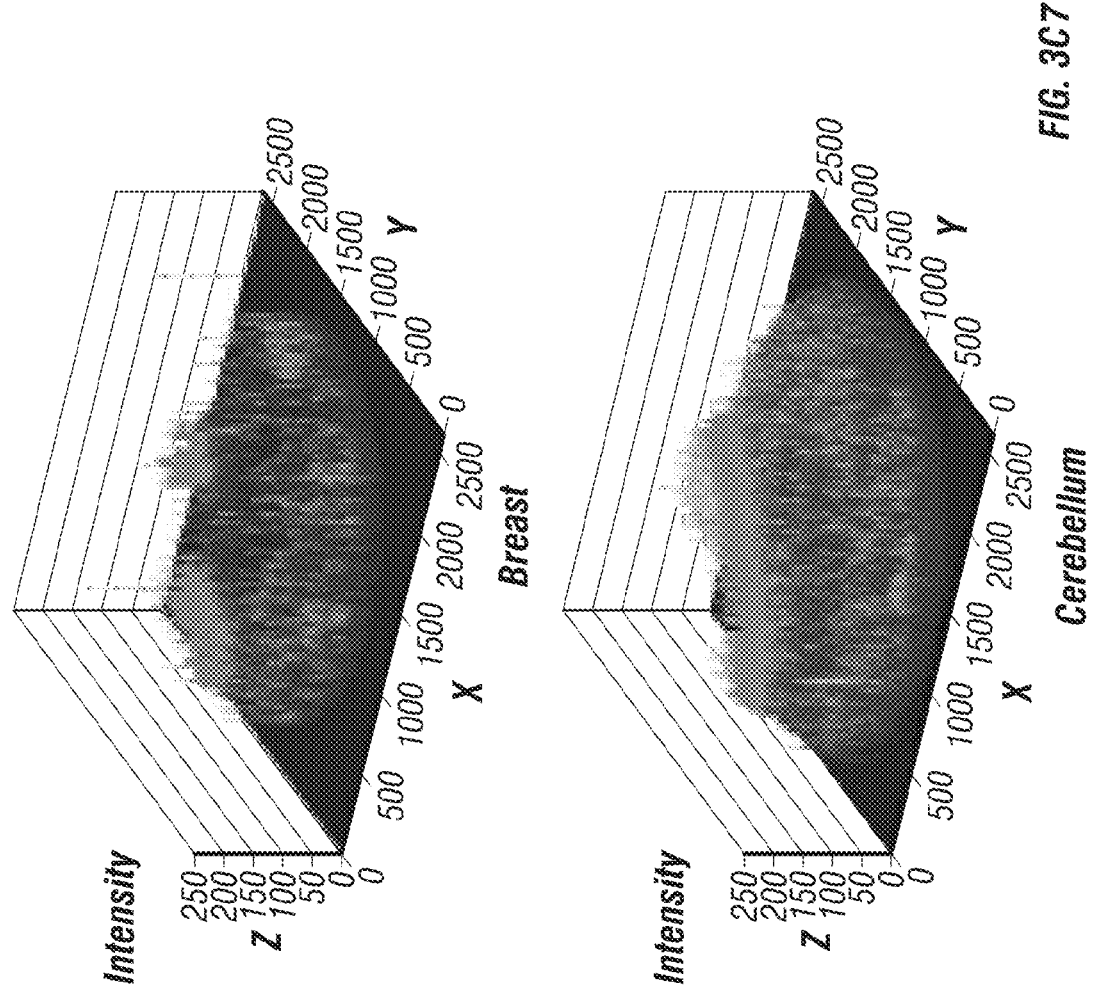
FIG. 3C7

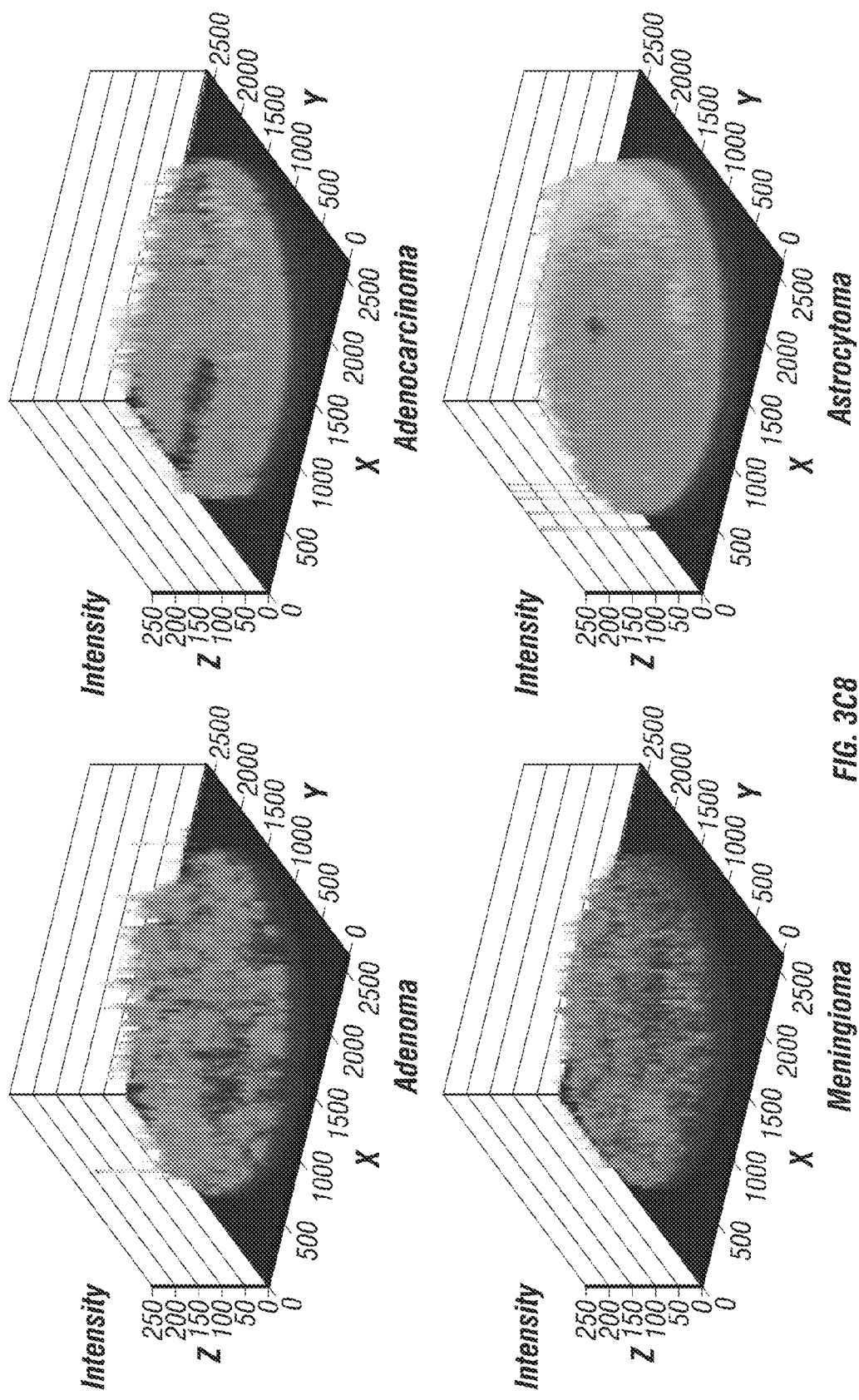
FIG. 3C8

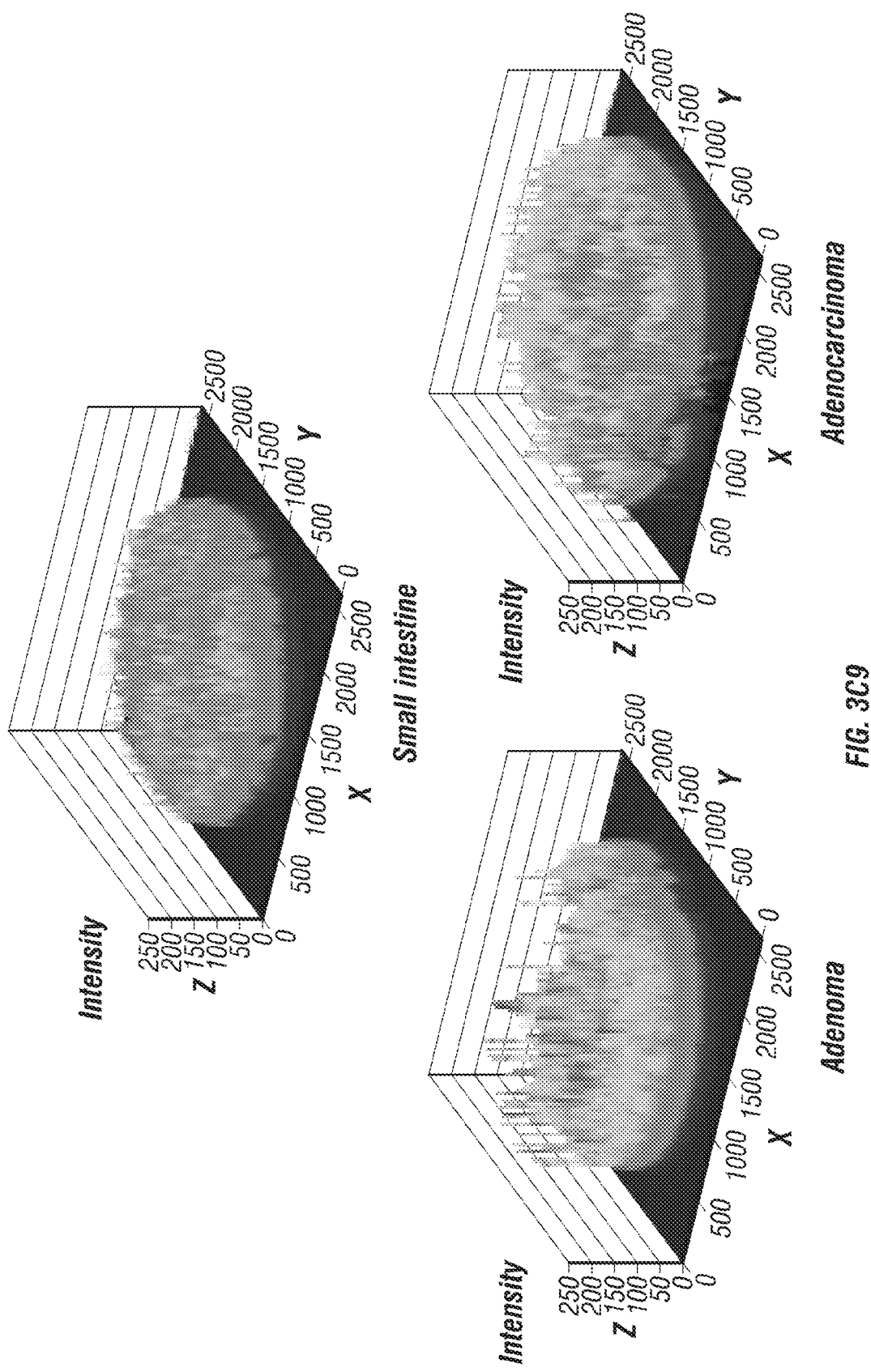
FIG. 3C9

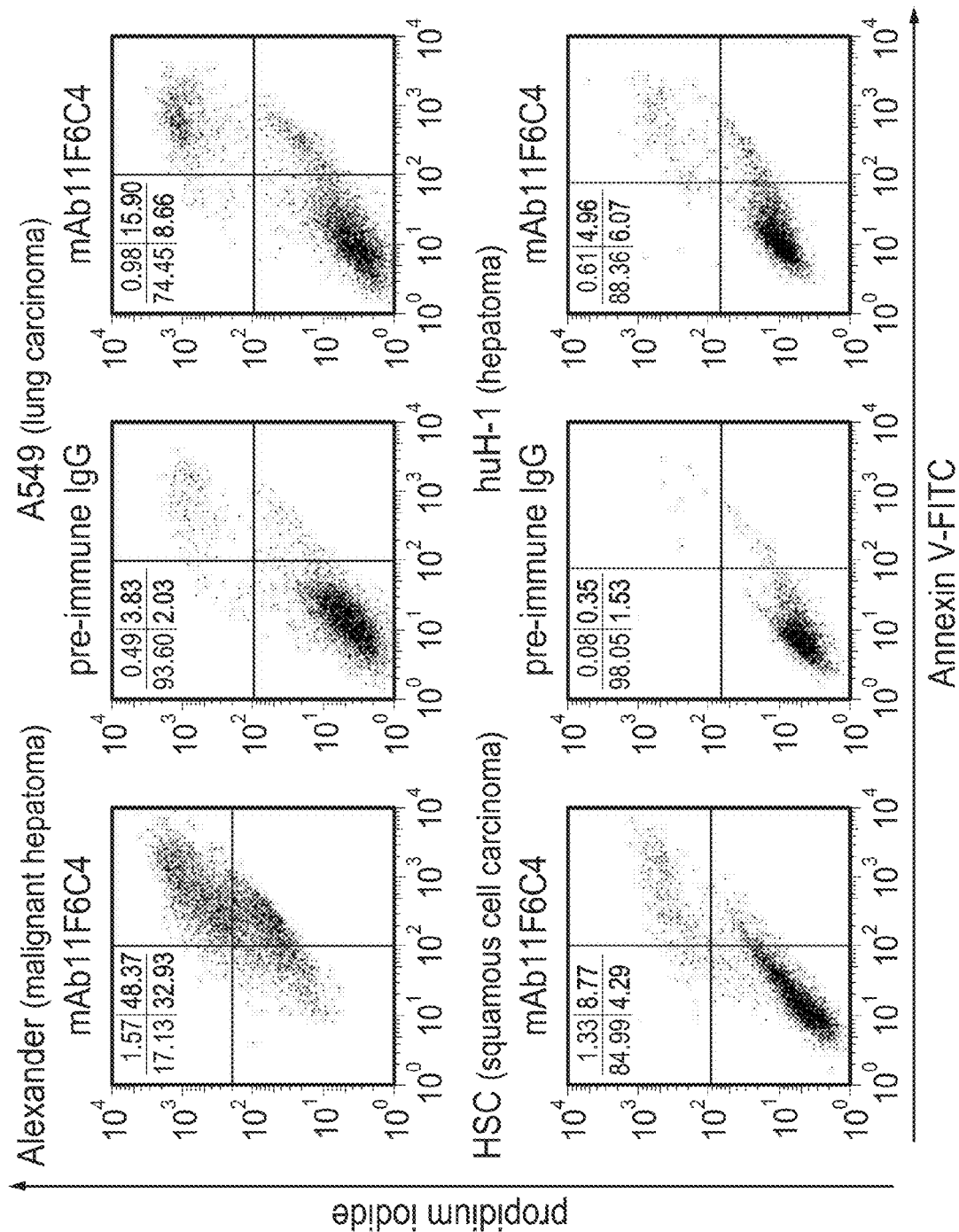
FIG. 6B1

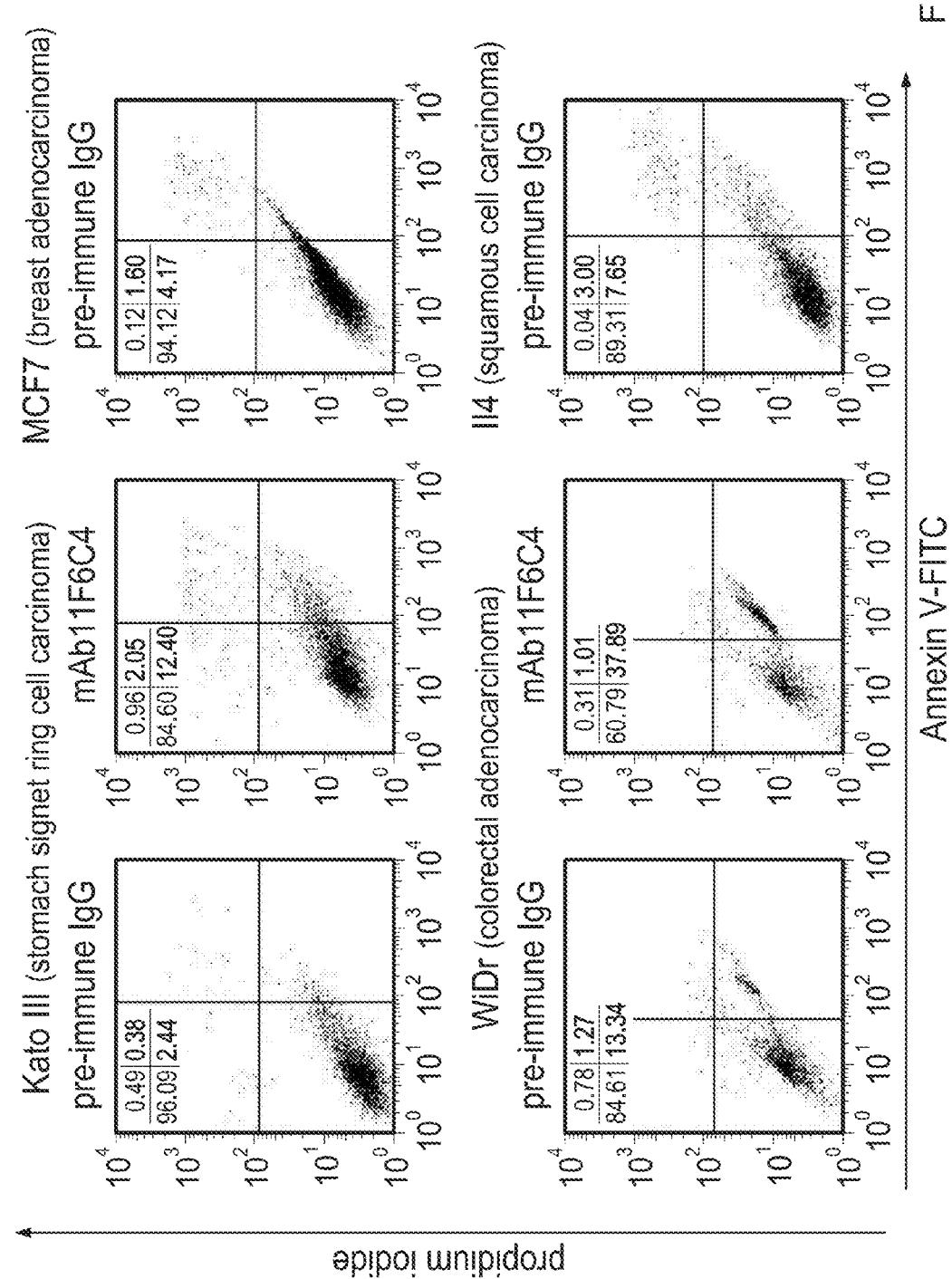
FIG. 6B2

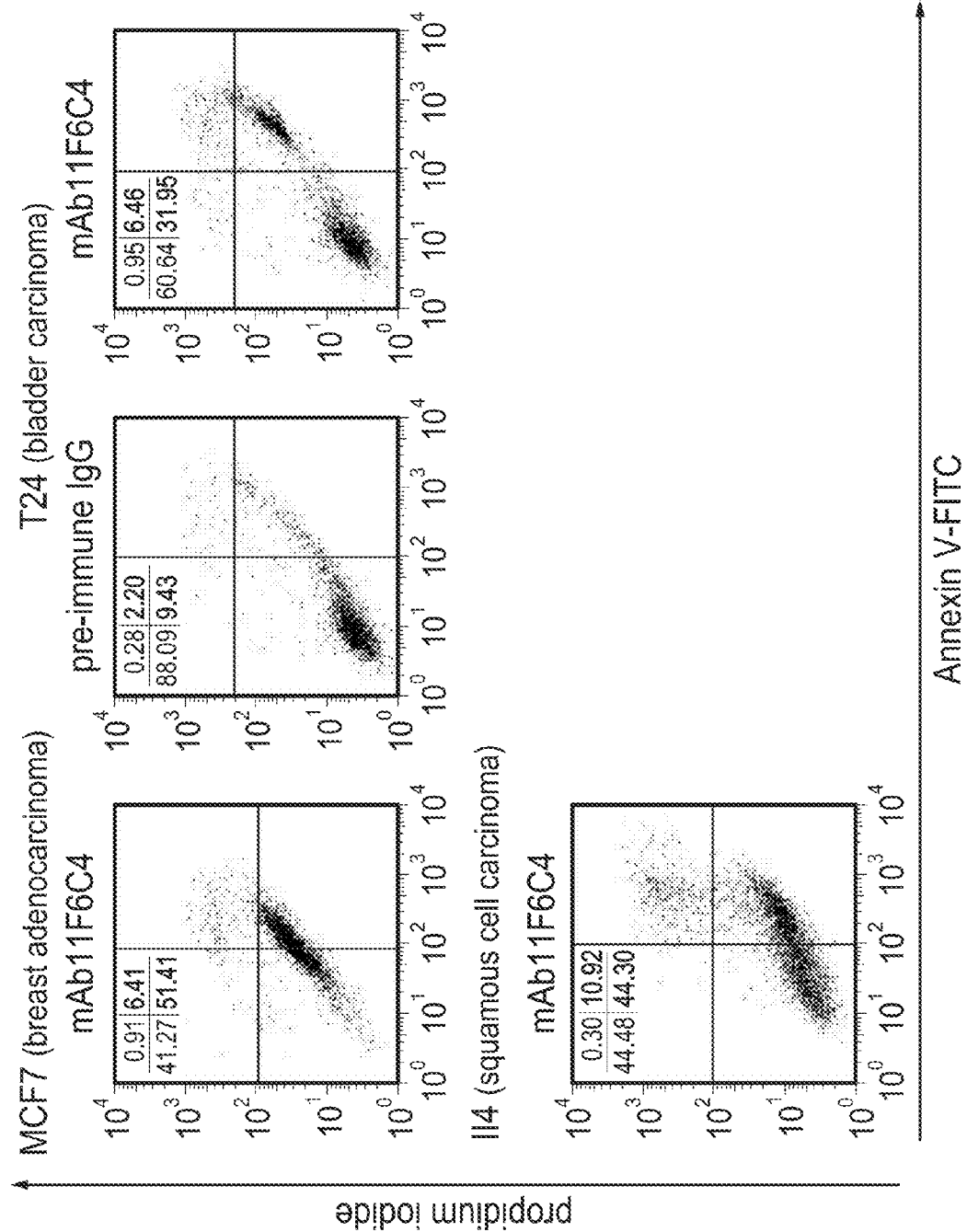
FIG. 6B3

C

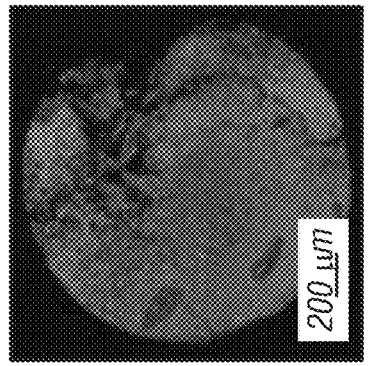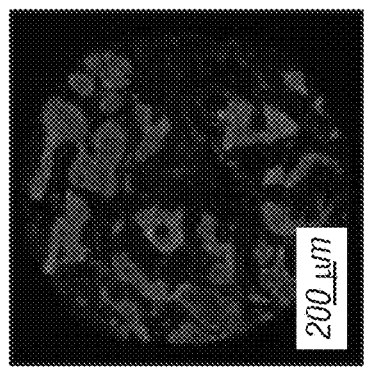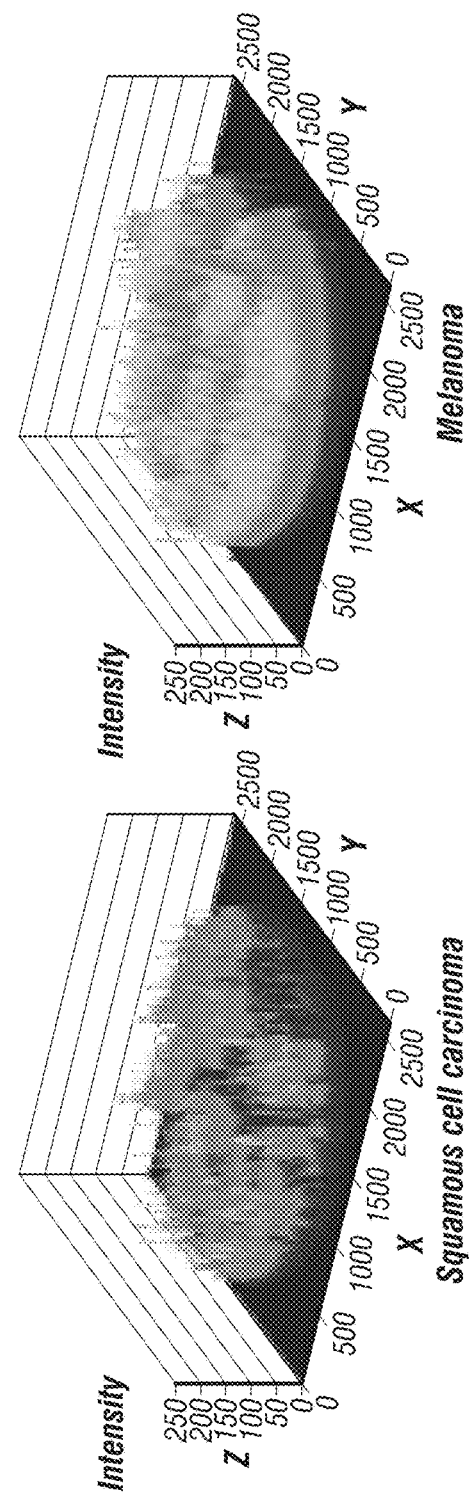
FIG. 10A1

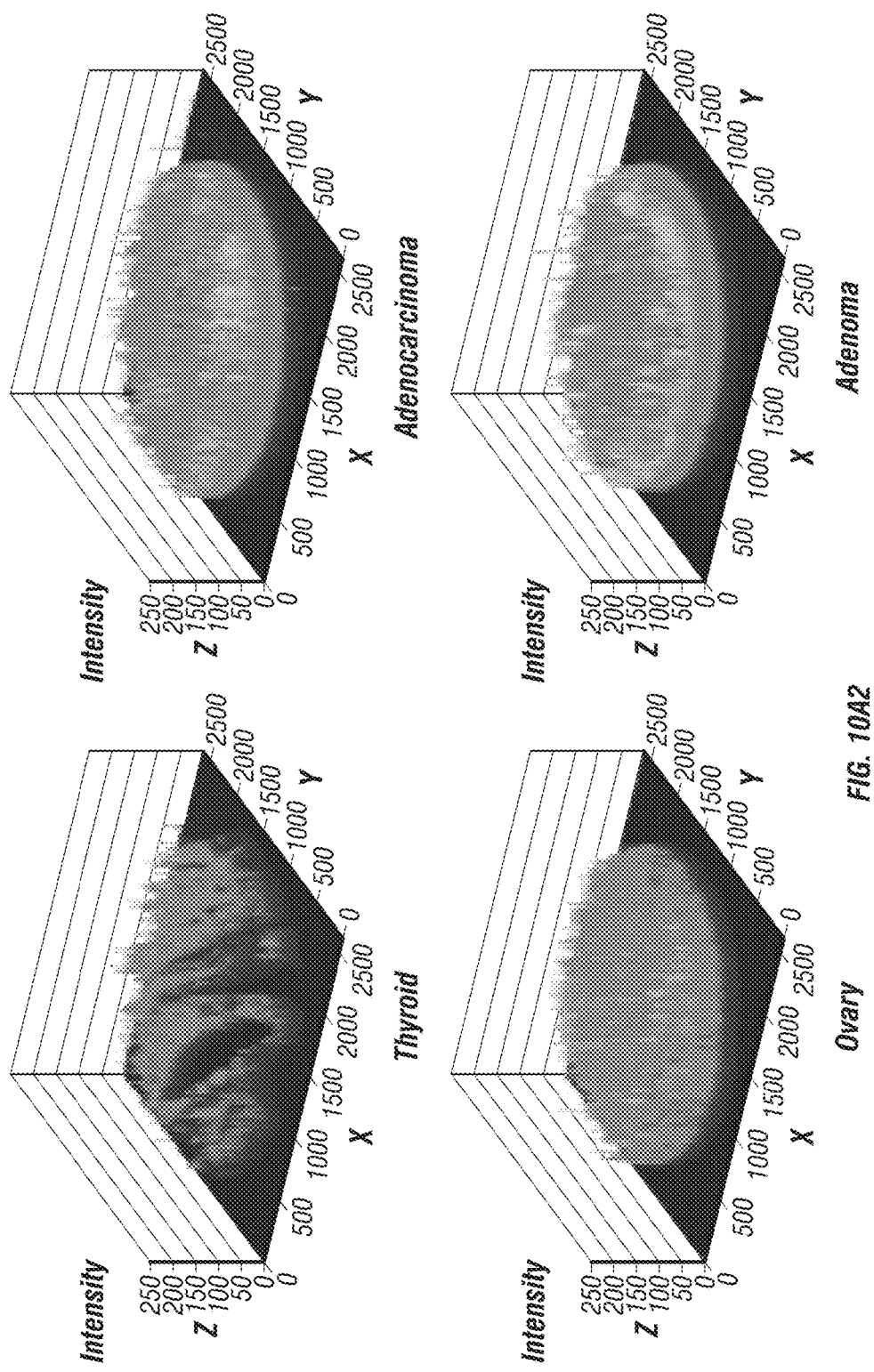
FIG. 10A2

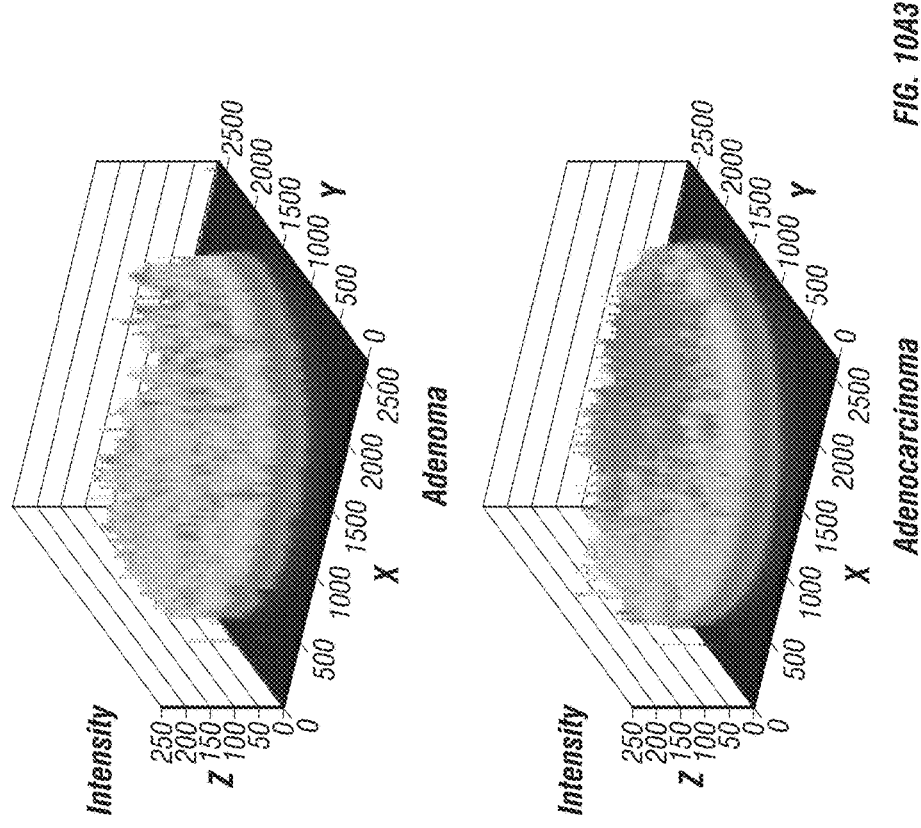

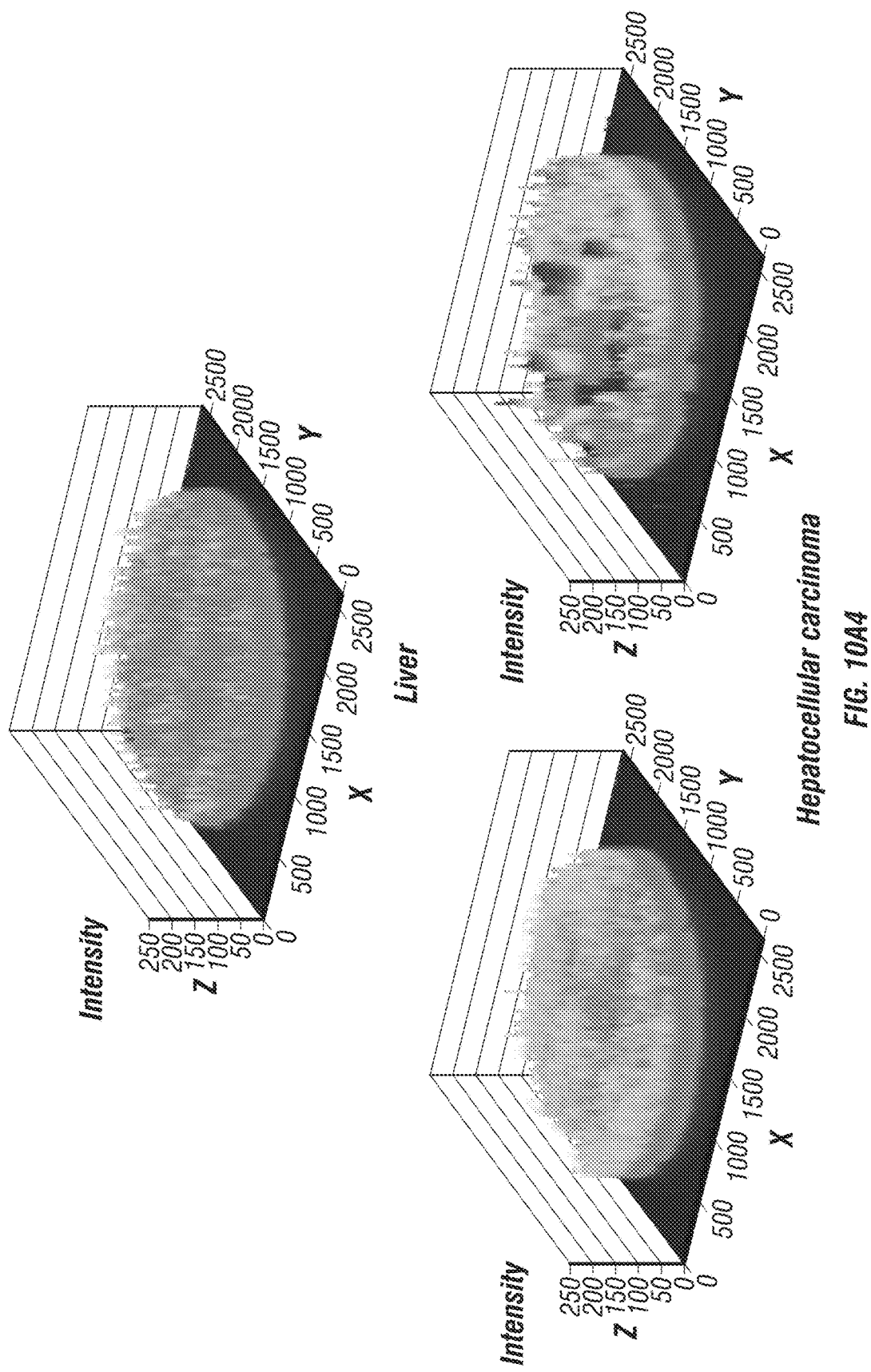

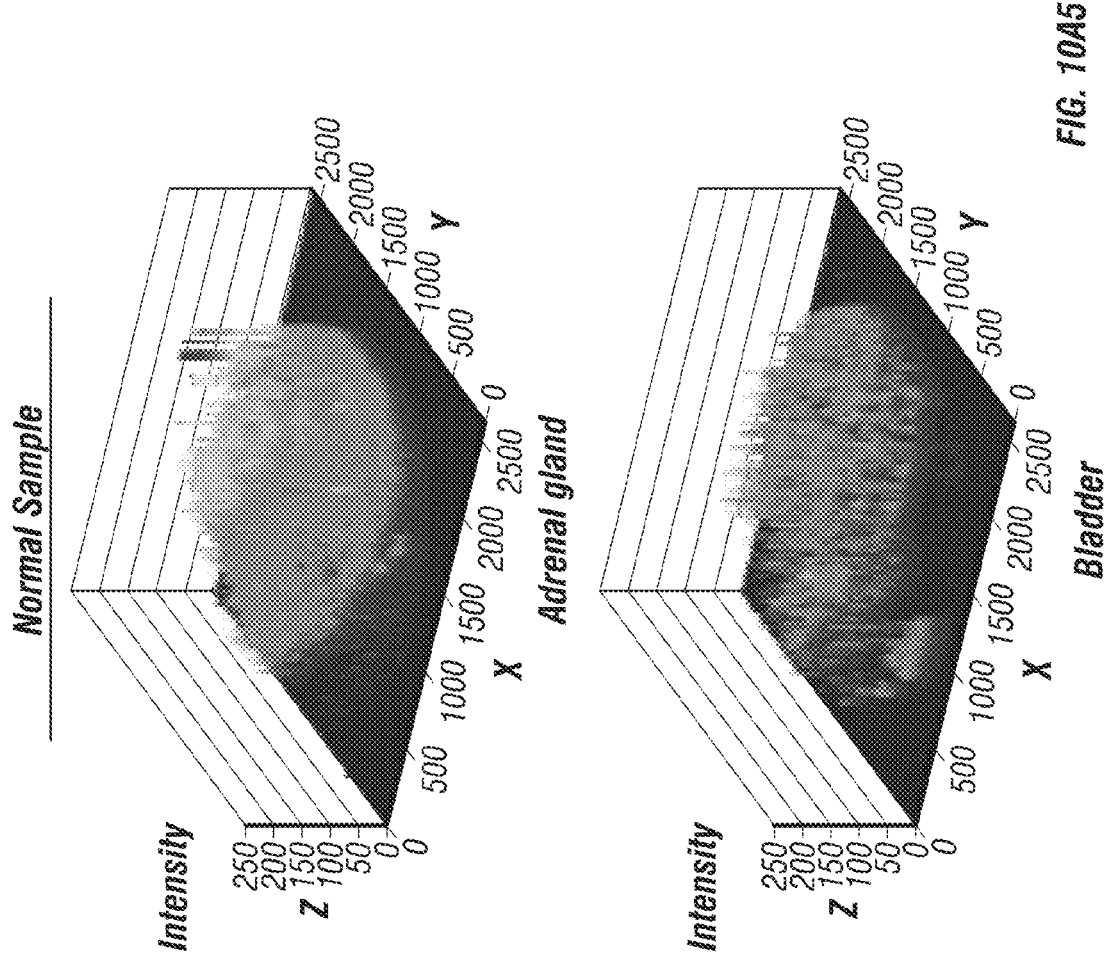
FIG. 10A5

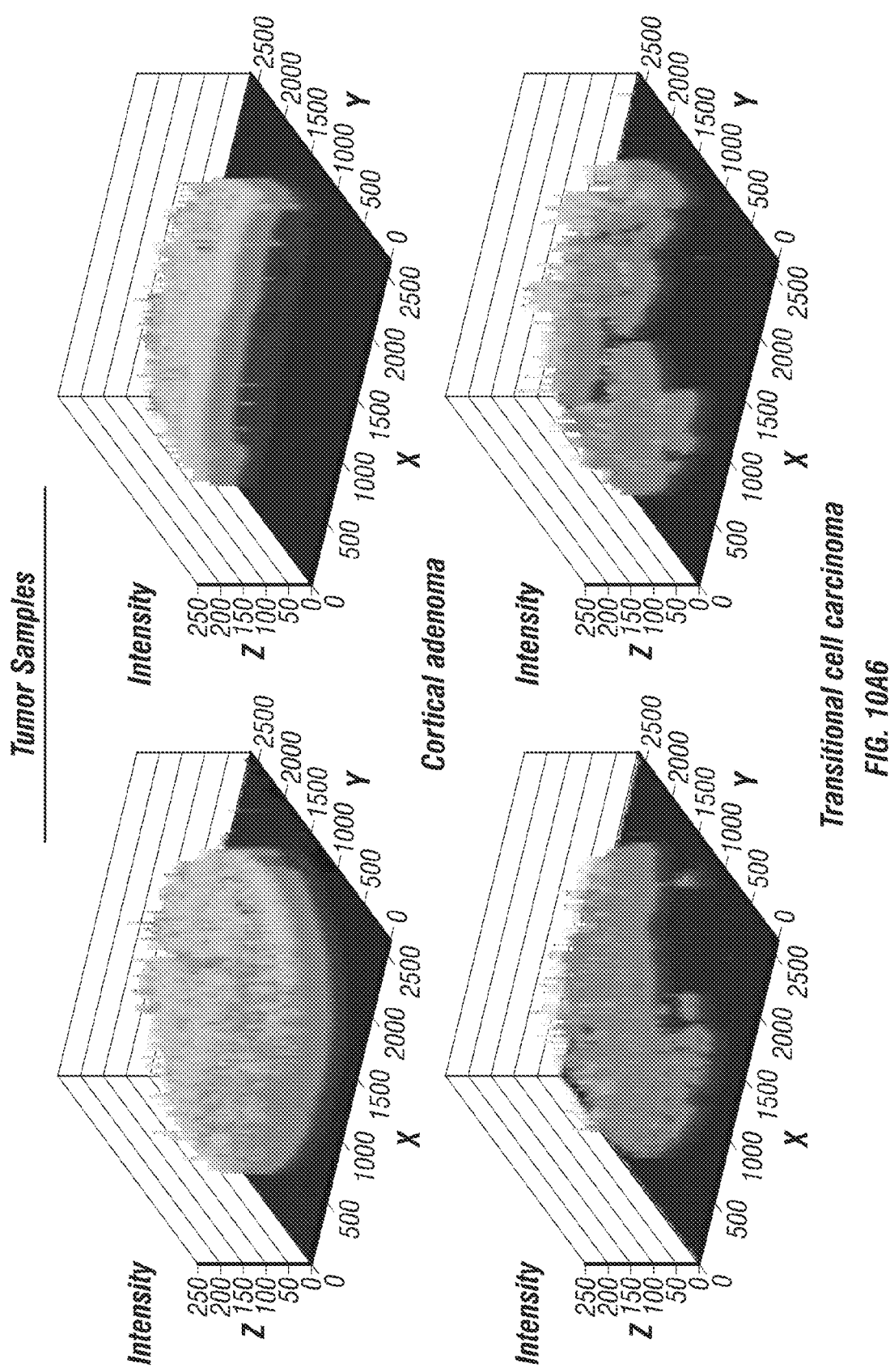

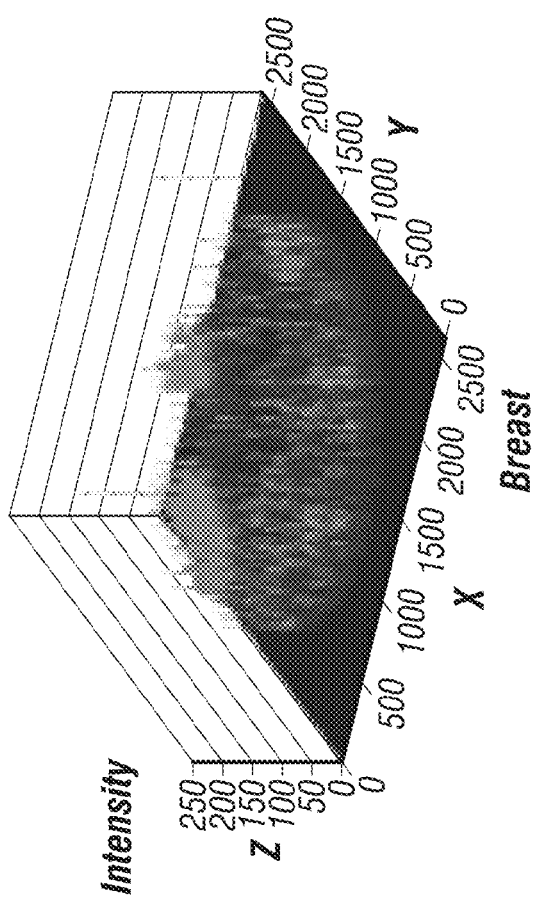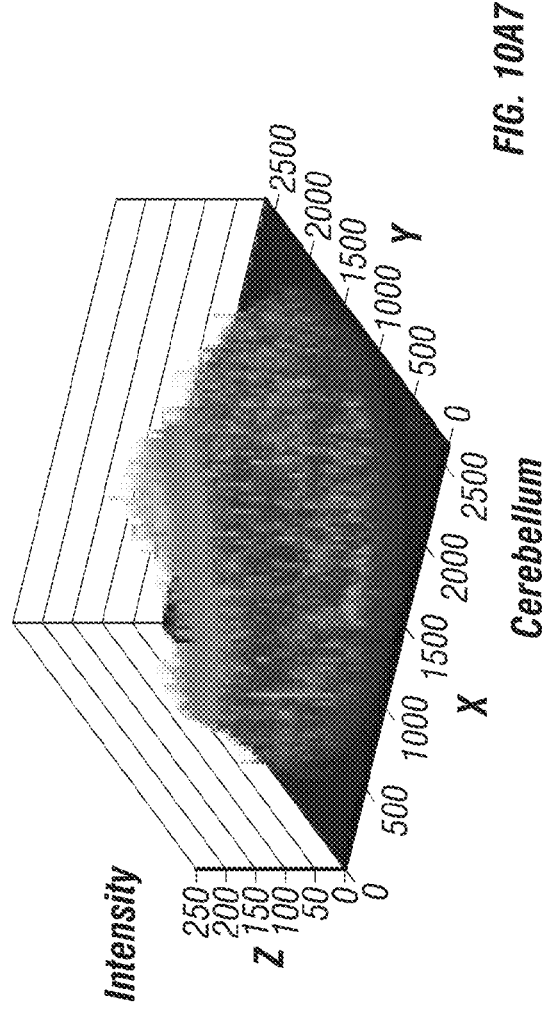
FIG. 10A7

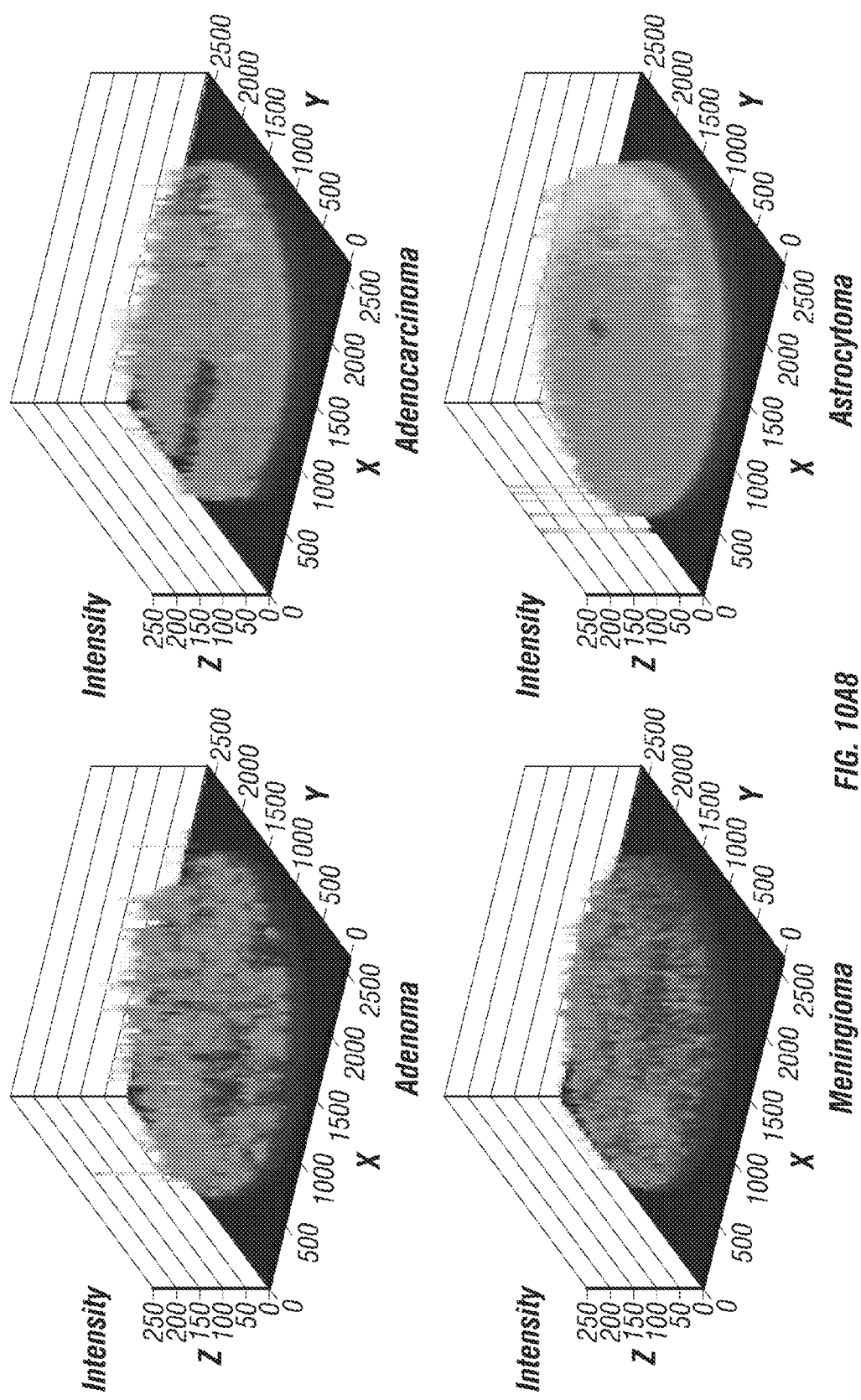
FIG. 10A8

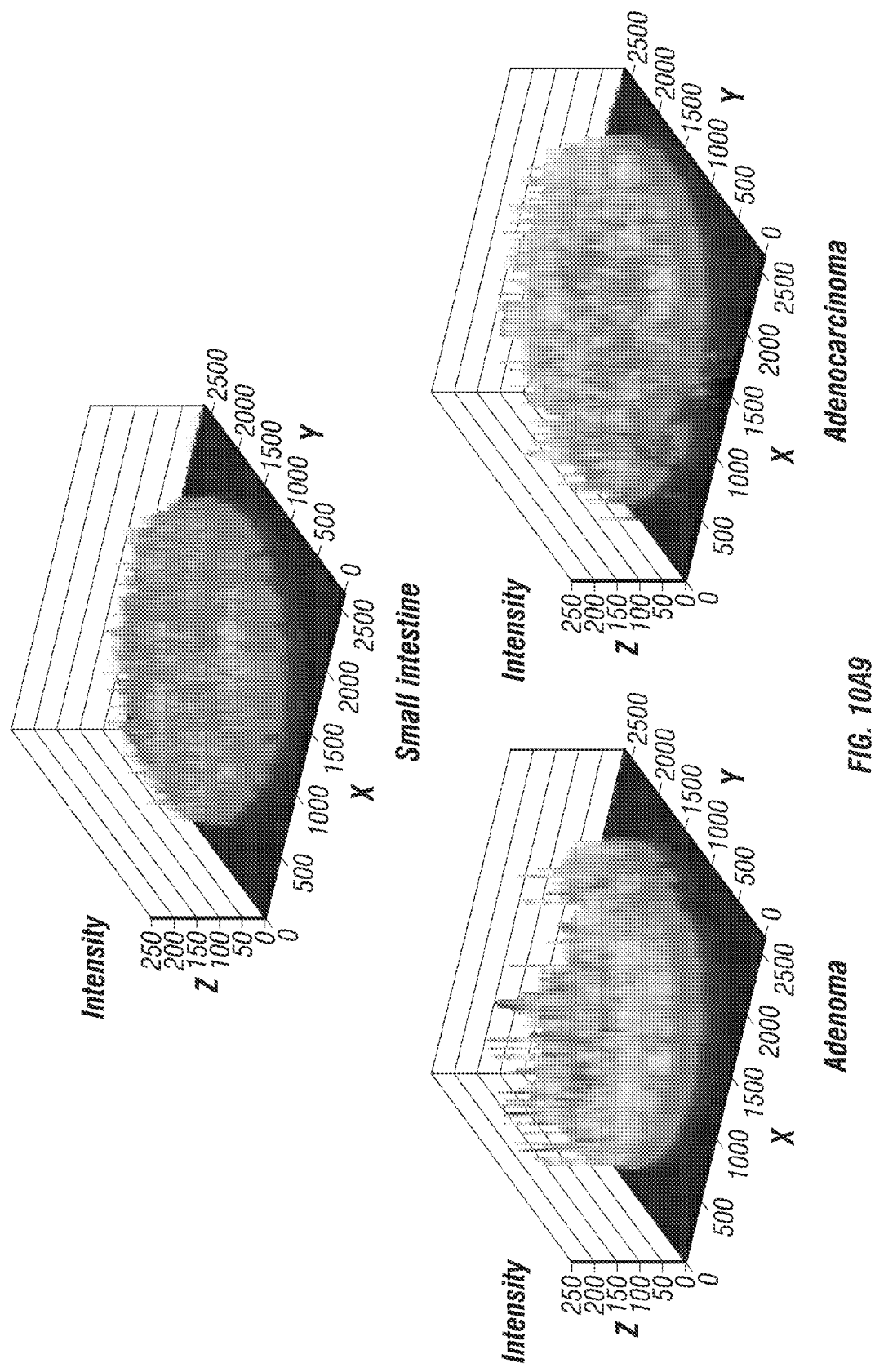
FIG. 10A9

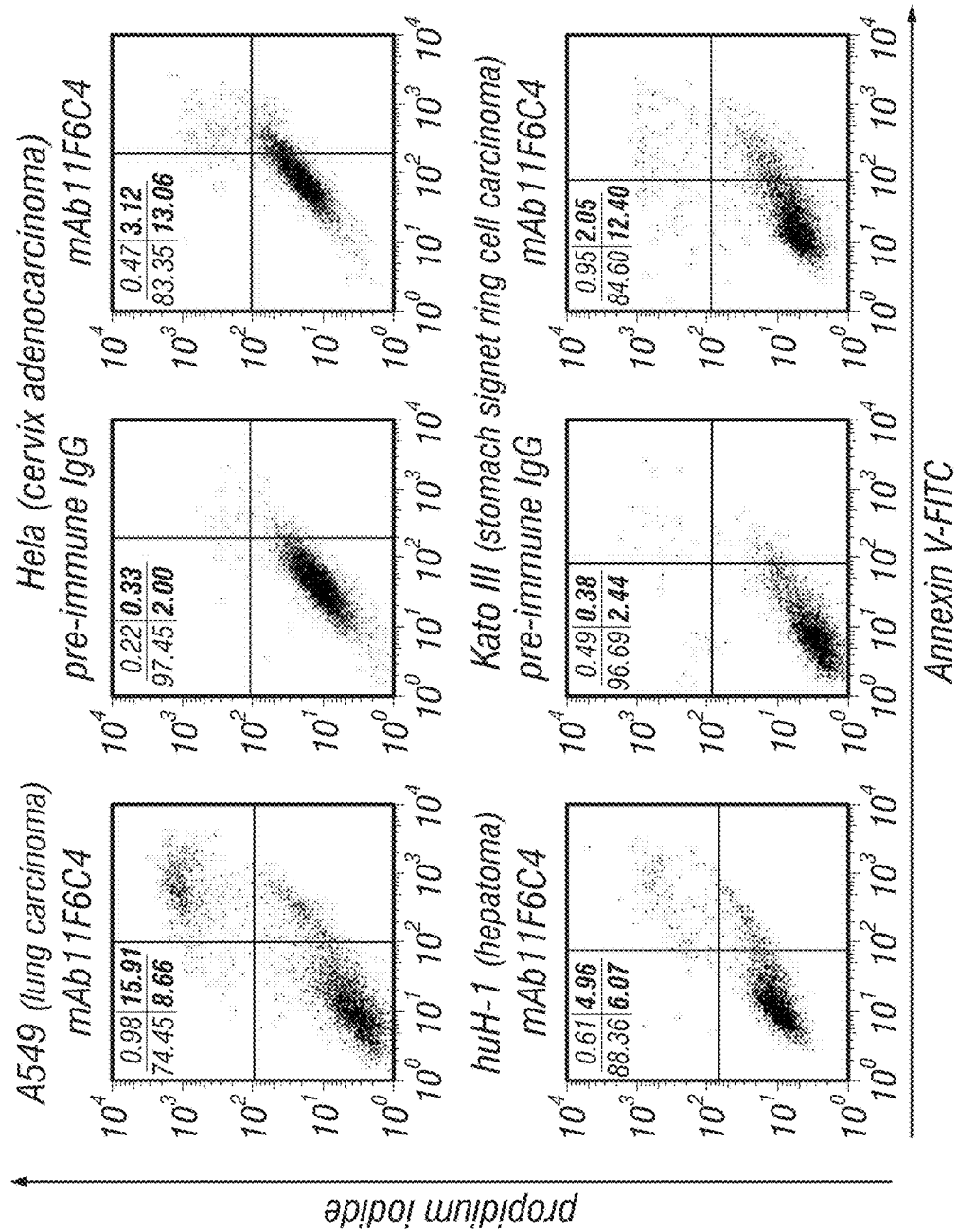
FIG. 16B1

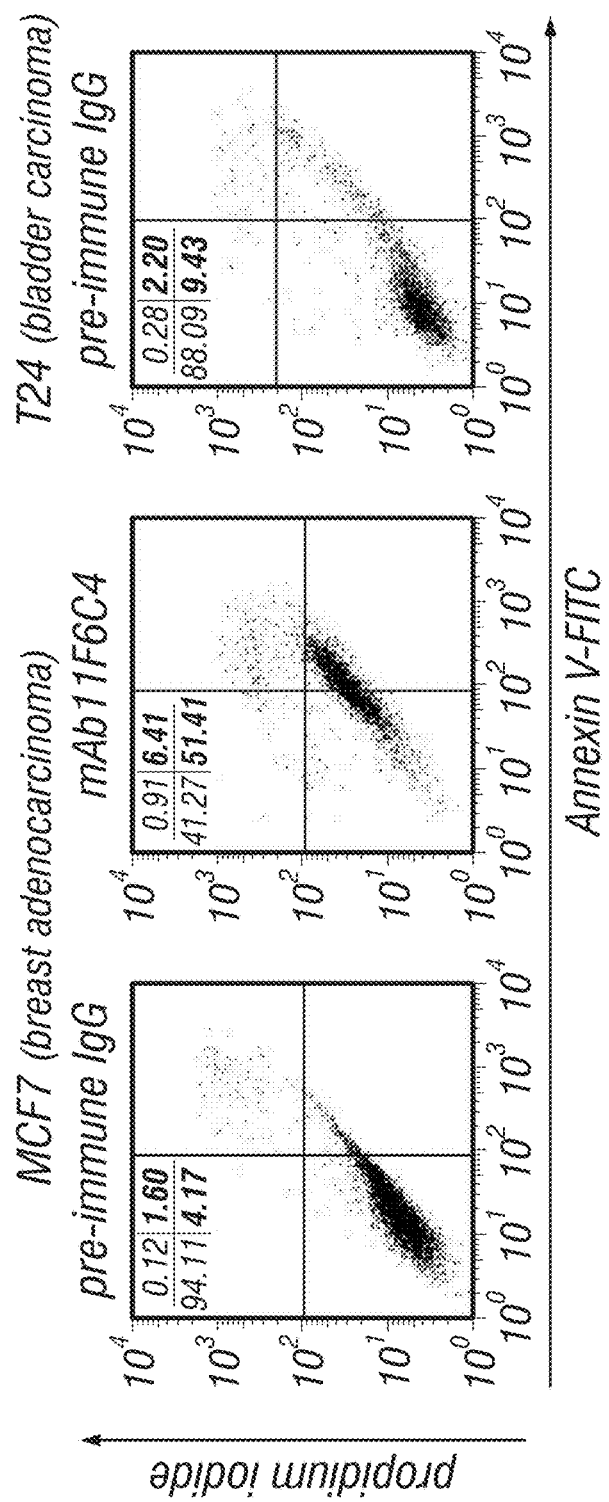
FIG. 16B2

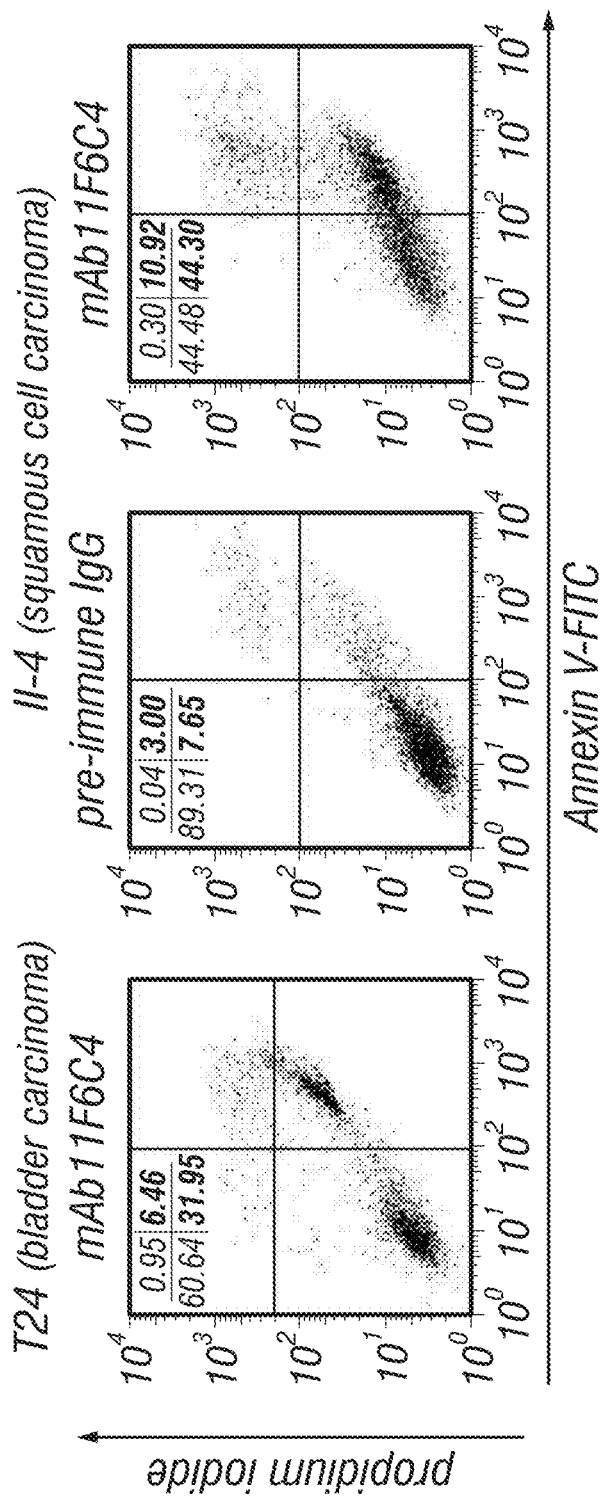
FIG. 16B3

SEQUENCE LISTING

```
<160> NUMBER OF SEQ ID NOS: 87

<210> SEQ ID NO 1
<211> LENGTH: 406
<212> TYPE: PRT
<213> ORGANISM: Homo sapiens

<400> SEQUENCE: 1

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Asp Gly Gly Trp
    210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
        275                 280                 285

Phe Ser Val His Leu Gly Gly Glu Asp Thr Ala Tyr Ser Leu Gln Leu
    290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335
```

```
Arg Asp Lys Asn Cys Ala Lys Ser Leu Ser Gly Gly Trp Trp Phe Gly
            340                 345                 350
Thr Cys Ser His Ser Asn Leu Asn Gly Gln Tyr Phe Arg Ser Ile Pro
        355                 360                 365
Gln Gln Arg Gln Lys Leu Lys Lys Gly Ile Phe Trp Lys Thr Trp Arg
    370                 375                 380
Gly Arg Tyr Tyr Pro Leu Gln Ala Thr Thr Met Leu Ile Gln Pro Met
385                 390                 395                 400
Ala Ala Glu Ala Ala Ser
            405
```

```
<210> SEQ ID NO 2
<211> LENGTH: 221
<212> TYPE: PRT
<213> ORGANISM: Homo sapiens

<400> SEQUENCE: 2

Arg Asp Cys Gln Glu Leu Phe Gln Val Gly Glu Arg Gln Ser Gly Leu
1               5                   10                  15
Phe Glu Ile Gln Pro Gln Gly Ser Pro Pro Phe Leu Val Asn Cys Lys
            20                  25                  30
Met Thr Ser Asp Gly Gly Trp Thr Val Ile Gln Arg Arg His Asp Gly
        35                  40                  45
Ser Val Asp Phe Asn Arg Pro Trp Glu Ala Tyr Lys Ala Gly Phe Gly
50                  55                  60
Asp Pro His Gly Glu Phe Trp Leu Gly Leu Glu Lys Val His Ser Ile
65                  70                  75                  80
Thr Gly Asp Arg Asn Ser Arg Leu Ala Val Gln Leu Arg Asp Trp Asp
                85                  90                  95
Gly Asn Ala Glu Leu Leu Gln Phe Ser Val His Leu Gly Gly Glu Asp
            100                 105                 110
Thr Ala Tyr Ser Leu Gln Leu Thr Ala Pro Val Ala Gly Gln Leu Gly
        115                 120                 125
Ala Thr Thr Val Pro Pro Ser Gly Leu Ser Val Pro Phe Ser Thr Trp
130                 135                 140
Asp Gln Asp His Asp Leu Arg Arg Asp Lys Asn Cys Ala Lys Ser Leu
145                 150                 155                 160
Ser Gly Gly Trp Trp Phe Gly Thr Cys Ser His Ser Asn Leu Asn Gly
                165                 170                 175
Gln Tyr Phe Arg Ser Ile Pro Gln Gln Arg Gln Lys Leu Lys Lys Gly
            180                 185                 190
Ile Phe Trp Lys Thr Trp Arg Gly Arg Tyr Tyr Pro Leu Gln Ala Thr
        195                 200                 205
Thr Met Leu Ile Gln Pro Met Ala Ala Glu Ala Ala Ser
    210                 215                 220
```

```
<210> SEQ ID NO 3
<211> LENGTH: 221
<212> TYPE: PRT
<213> ORGANISM: Mus musculus

<400> SEQUENCE: 3

Arg Asp Cys Gln Glu Leu Phe Gln Glu Gly Glu Arg His Ser Gly Leu
1               5                   10                  15
Phe Gln Ile Gln Pro Leu Gly Ser Pro Pro Phe Leu Val Asn Cys Glu
            20                  25                  30
```

Met Thr Ser Asp Gly Gly Trp Thr Val Ile Gln Arg Arg Leu Asn Gly
         35                  40                  45

Ser Val Asp Phe Asn Gln Ser Trp Glu Ala Tyr Lys Asp Gly Phe Gly
 50                  55                  60

Asp Pro Gln Gly Glu Phe Trp Leu Gly Leu Glu Lys Met His Ser Ile
 65                  70                  75                  80

Thr Gly Asn Arg Gly Ser Gln Leu Ala Val Gln Leu Gln Asp Trp Asp
                 85                  90                  95

Gly Asn Ala Lys Leu Leu Gln Phe Pro Ile His Leu Gly Gly Glu Asp
                100                 105                 110

Thr Ala Tyr Ser Leu Gln Leu Thr Glu Pro Thr Ala Asn Glu Leu Gly
            115                 120                 125

Ala Thr Asn Val Ser Pro Asn Gly Leu Ser Leu Pro Phe Ser Thr Trp
130                 135                 140

Asp Gln Asp His Asp Leu Arg Gly Asp Leu Asn Cys Ala Lys Ser Leu
145                 150                 155                 160

Ser Gly Gly Trp Trp Phe Gly Thr Cys Ser His Ser Asn Leu Asn Gly
                165                 170                 175

Gln Tyr Phe His Ser Ile Pro Arg Gln Arg Gln Glu Arg Lys Lys Gly
            180                 185                 190

Ile Phe Trp Lys Thr Trp Lys Gly Arg Tyr Tyr Pro Leu Gln Ala Thr
        195                 200                 205

Thr Leu Leu Ile Gln Pro Met Glu Ala Thr Ala Ala Ser
    210                 215                 220

<210> SEQ ID NO 4
<211> LENGTH: 31
<212> TYPE: DNA
<213> ORGANISM: Artificial Sequence
<220> FEATURE:
<223> OTHER INFORMATION: siRNA against human ANGPTL4 sense strand

<400> SEQUENCE: 4
aaagctgcaa gatgacctca gatggaggct g                                    31

<210> SEQ ID NO 5
<211> LENGTH: 31
<212> TYPE: DNA
<213> ORGANISM: Artificial Sequence
<220> FEATURE:
<223> OTHER INFORMATION: siRNA against human ANGPTL4 antisense strand

<400> SEQUENCE: 5
aaaacagcct ccatctgagg tcatcttgca g                                    31

<210> SEQ ID NO 6
<211> LENGTH: 81
<212> TYPE: DNA
<213> ORGANISM: Artificial Sequence
<220> FEATURE:
<223> OTHER INFORMATION: shRNA against human ANGPTL4 sense strand

<400> SEQUENCE: 6
tcgaggcagc acctgcgaat tcagcatctg cattcaagag atgcagatgc tgaattcgca    60
ggtgctgctt ttttacgcgt a                                               81

<210> SEQ ID NO 7
<211> LENGTH: 79
<212> TYPE: DNA
<213> ORGANISM: Artificial Sequence

```
<220> FEATURE:
<223> OTHER INFORMATION: shRNA against human ANGPTL4 antisense strand

<400> SEQUENCE: 7
agcttacgcg taaaaagcag cacctgcgaa ttcagcatct gcatctcttg aatgcagatg       60
ctgaattgca ggtgctgcc                                                    79

<210> SEQ ID NO 8
<211> LENGTH: 31
<212> TYPE: DNA
<213> ORGANISM: Artificial Sequence
<220> FEATURE:
<223> OTHER INFORMATION: Nox1 sense strand

<400> SEQUENCE: 8
aaagggccac agatggctcc cttgcctcca t                                      31

<210> SEQ ID NO 9
<211> LENGTH: 31
<212> TYPE: DNA
<213> ORGANISM: Artificial Sequence
<220> FEATURE:
<223> OTHER INFORMATION: Nox1 antisense strand

<400> SEQUENCE: 9
aaaaatggag gcaagggagc catctgtggc c                                      31

<210> SEQ ID NO 10
<211> LENGTH: 31
<212> TYPE: DNA
<213> ORGANISM: Artificial Sequence
<220> FEATURE:
<223> OTHER INFORMATION: Nox2 sense strand

<400> SEQUENCE: 10
aaagggccag atgttctttc tacagaagaa t                                      31

<210> SEQ ID NO 11
<211> LENGTH: 31
<212> TYPE: DNA
<213> ORGANISM: Artificial Sequence
<220> FEATURE:
<223> OTHER INFORMATION: Nox2 antisense strand

<400> SEQUENCE: 11
aaaaattctt ctgtagaaag aacatctggc c                                      31

<210> SEQ ID NO 12
<211> LENGTH: 31
<212> TYPE: DNA
<213> ORGANISM: Artificial Sequence
<220> FEATURE:
<223> OTHER INFORMATION: Mouse ANGPTL4 sense strand

<400> SEQUENCE: 12
aaagctgtga gatgacttca gatggaggct g                                      31

<210> SEQ ID NO 13
<211> LENGTH: 31
<212> TYPE: DNA
<213> ORGANISM: Artificial Sequence
<220> FEATURE:
<223> OTHER INFORMATION: Mouse ANGPTL4 antisense strand

<400> SEQUENCE: 13
```

```
aaaacagcct ccatctgaag tcatctcaca g                                    31
```

<210> SEQ ID NO 14
<211> LENGTH: 32
<212> TYPE: DNA
<213> ORGANISM: Artificial Sequence
<220> FEATURE:
<223> OTHER INFORMATION: Control siRNA sense strand

<400> SEQUENCE: 14

```
aaagctgtct tcaagcttga tatcgaagac ta                                   32
```

<210> SEQ ID NO 15
<211> LENGTH: 32
<212> TYPE: DNA
<213> ORGANISM: Artificial Sequence
<220> FEATURE:
<223> OTHER INFORMATION: Control siRNA antisense strand

<400> SEQUENCE: 15

```
aaaatagtct tcgatatcaa gcttgaagac ag                                   32
```

<210> SEQ ID NO 16
<211> LENGTH: 19
<212> TYPE: DNA
<213> ORGANISM: Artificial Sequence
<220> FEATURE:
<223> OTHER INFORMATION: Bax sense primer

<400> SEQUENCE: 16

```
gggtggttgg gtgagactc                                                  19
```

<210> SEQ ID NO 17
<211> LENGTH: 23
<212> TYPE: DNA
<213> ORGANISM: Artificial Sequence
<220> FEATURE:
<223> OTHER INFORMATION: Bax antisense primer

<400> SEQUENCE: 17

```
agacacgtaa ggaaaacgca tta                                             23
```

<210> SEQ ID NO 18
<211> LENGTH: 21
<212> TYPE: DNA
<213> ORGANISM: Artificial Sequence
<220> FEATURE:
<223> OTHER INFORMATION: Bbc3 sense primer

<400> SEQUENCE: 18

```
gacctcaacg cacagtacga g                                               21
```

<210> SEQ ID NO 19
<211> LENGTH: 22
<212> TYPE: DNA
<213> ORGANISM: Artificial Sequence
<220> FEATURE:
<223> OTHER INFORMATION: Bbc3 antisense primer

<400> SEQUENCE: 19

```
aggagtccca tgatgagatt gt                                              22
```

<210> SEQ ID NO 20
<211> LENGTH: 21
<212> TYPE: DNA
<213> ORGANISM: Artificial Sequence

```
<220> FEATURE:
<223> OTHER INFORMATION: Bcl2l1 sense primer

<400> SEQUENCE: 20
tgcgtggaaa gcgtagacaa g                                              21

<210> SEQ ID NO 21
<211> LENGTH: 20
<212> TYPE: DNA
<213> ORGANISM: Artificial Sequence
<220> FEATURE:
<223> OTHER INFORMATION: Bcl2l1 antisense primer

<400> SEQUENCE: 21
gctgctgcat tgttcccata                                                20

<210> SEQ ID NO 22
<211> LENGTH: 21
<212> TYPE: DNA
<213> ORGANISM: Artificial Sequence
<220> FEATURE:
<223> OTHER INFORMATION: Bcl2l2 sense primer

<400> SEQUENCE: 22
gcggagttca cagctctata c                                              21

<210> SEQ ID NO 23
<211> LENGTH: 21
<212> TYPE: DNA
<213> ORGANISM: Artificial Sequence
<220> FEATURE:
<223> OTHER INFORMATION: Bcl2l2 antisense primer

<400> SEQUENCE: 23
aaaaggcccc tacagttacc a                                              21

<210> SEQ ID NO 24
<211> LENGTH: 21
<212> TYPE: DNA
<213> ORGANISM: Artificial Sequence
<220> FEATURE:
<223> OTHER INFORMATION: Bid sense primer

<400> SEQUENCE: 24
gacagcatgg accgtagcat c                                              21

<210> SEQ ID NO 25
<211> LENGTH: 23
<212> TYPE: DNA
<213> ORGANISM: Artificial Sequence
<220> FEATURE:
<223> OTHER INFORMATION: Bid antisense primer

<400> SEQUENCE: 25
aggtgcgtag gttctggtta ata                                            23

<210> SEQ ID NO 26
<211> LENGTH: 22
<212> TYPE: DNA
<213> ORGANISM: Artificial Sequence
<220> FEATURE:
<223> OTHER INFORMATION: Birc2 sense primer

<400> SEQUENCE: 26
gtttcaggtc tgtcactgga ag                                             22
```

<210> SEQ ID NO 27
<211> LENGTH: 21
<212> TYPE: DNA
<213> ORGANISM: Artificial Sequence
<220> FEATURE:
<223> OTHER INFORMATION: Birc2 antisense primer

<400> SEQUENCE: 27
tggcatacta ccagatgacc a                                              21

<210> SEQ ID NO 28
<211> LENGTH: 23
<212> TYPE: DNA
<213> ORGANISM: Artificial Sequence
<220> FEATURE:
<223> OTHER INFORMATION: Birc3 sense primer

<400> SEQUENCE: 28
tcctggatag tctactaact gcc                                            23

<210> SEQ ID NO 29
<211> LENGTH: 23
<212> TYPE: DNA
<213> ORGANISM: Artificial Sequence
<220> FEATURE:
<223> OTHER INFORMATION: Birc3 antisense primer

<400> SEQUENCE: 29
gcttcttgca gagagtttct gaa                                            23

<210> SEQ ID NO 30
<211> LENGTH: 23
<212> TYPE: DNA
<213> ORGANISM: Artificial Sequence
<220> FEATURE:
<223> OTHER INFORMATION: Casp1 sense primer

<400> SEQUENCE: 30
tccaataatg gacaagtcaa gcc                                            23

<210> SEQ ID NO 31
<211> LENGTH: 23
<212> TYPE: DNA
<213> ORGANISM: Artificial Sequence
<220> FEATURE:
<223> OTHER INFORMATION: Casp1 antisense primer

<400> SEQUENCE: 31
gctgtacccc agattttgta gca                                            23

<210> SEQ ID NO 32
<211> LENGTH: 22
<212> TYPE: DNA
<213> ORGANISM: Artificial Sequence
<220> FEATURE:
<223> OTHER INFORMATION: Casp10 sense primer

<400> SEQUENCE: 32
attggtccca agacatgaag ac                                             22

<210> SEQ ID NO 33
<211> LENGTH: 21
<212> TYPE: DNA
<213> ORGANISM: Artificial Sequence
<220> FEATURE:
<223> OTHER INFORMATION: Casp10 antisense primer

```
<400> SEQUENCE: 33
tgttccctgt ttgtccactc t                                              21

<210> SEQ ID NO 34
<211> LENGTH: 22
<212> TYPE: DNA
<213> ORGANISM: Artificial Sequence
<220> FEATURE:
<223> OTHER INFORMATION: Casp2 sense primer

<400> SEQUENCE: 34
aaacgaggtt cctggtacat cg                                             22

<210> SEQ ID NO 35
<211> LENGTH: 21
<212> TYPE: DNA
<213> ORGANISM: Artificial Sequence
<220> FEATURE:
<223> OTHER INFORMATION: Casp2 antisense primer

<400> SEQUENCE: 35
tccttgataa gtgcgttcac c                                              21

<210> SEQ ID NO 36
<211> LENGTH: 20
<212> TYPE: DNA
<213> ORGANISM: Artificial Sequence
<220> FEATURE:
<223> OTHER INFORMATION: Casp7 sense primer

<400> SEQUENCE: 36
agtgacaggt atgggcgttc                                                20

<210> SEQ ID NO 37
<211> LENGTH: 21
<212> TYPE: DNA
<213> ORGANISM: Artificial Sequence
<220> FEATURE:
<223> OTHER INFORMATION: Casp7 antisense primer

<400> SEQUENCE: 37
gaggttgcag tcttccgaga t                                              21

<210> SEQ ID NO 38
<211> LENGTH: 23
<212> TYPE: DNA
<213> ORGANISM: Artificial Sequence
<220> FEATURE:
<223> OTHER INFORMATION: Ccna2 sense primer

<400> SEQUENCE: 38
gatggtagtt ttgagtcacc aca                                            23

<210> SEQ ID NO 39
<211> LENGTH: 23
<212> TYPE: DNA
<213> ORGANISM: Artificial Sequence
<220> FEATURE:
<223> OTHER INFORMATION: Ccna2 antisense primer

<400> SEQUENCE: 39
cacgaggata gctctcatac tgt                                            23

<210> SEQ ID NO 40
```

```
<211> LENGTH: 20
<212> TYPE: DNA
<213> ORGANISM: Artificial Sequence
<220> FEATURE:
<223> OTHER INFORMATION: Ccnd1 sense primer

<400> SEQUENCE: 40
gctggagccc gtgaaaaaga                                                 20

<210> SEQ ID NO 41
<211> LENGTH: 19
<212> TYPE: DNA
<213> ORGANISM: Artificial Sequence
<220> FEATURE:
<223> OTHER INFORMATION: Ccnd1 antisense primer

<400> SEQUENCE: 41
ctccgcctct ggcattttg                                                  19

<210> SEQ ID NO 42
<211> LENGTH: 21
<212> TYPE: DNA
<213> ORGANISM: Artificial Sequence
<220> FEATURE:
<223> OTHER INFORMATION: Cdk4 sense primer

<400> SEQUENCE: 42
cagatggcac ttacacccgt g                                               21

<210> SEQ ID NO 43
<211> LENGTH: 21
<212> TYPE: DNA
<213> ORGANISM: Artificial Sequence
<220> FEATURE:
<223> OTHER INFORMATION: Cdk4 antisense primer

<400> SEQUENCE: 43
gcagcccaat caggtcaaag a                                               21

<210> SEQ ID NO 44
<211> LENGTH: 19
<212> TYPE: DNA
<213> ORGANISM: Artificial Sequence
<220> FEATURE:
<223> OTHER INFORMATION: Cdk5 sense primer

<400> SEQUENCE: 44
gccgcaatgt gctacacag                                                  19

<210> SEQ ID NO 45
<211> LENGTH: 21
<212> TYPE: DNA
<213> ORGANISM: Artificial Sequence
<220> FEATURE:
<223> OTHER INFORMATION: Cdk5 antisense primer

<400> SEQUENCE: 45
gagtaacagc ggacgggaat c                                               21

<210> SEQ ID NO 46
<211> LENGTH: 22
<212> TYPE: DNA
<213> ORGANISM: Artificial Sequence
<220> FEATURE:
<223> OTHER INFORMATION: Cdkn1a sense primer

<400> SEQUENCE: 46
```
gtcactgtct tgtacccttg tg                                              22

<210> SEQ ID NO 47
<211> LENGTH: 21
<212> TYPE: DNA
<213> ORGANISM: Artificial Sequence
<220> FEATURE:
<223> OTHER INFORMATION: Cdkn1a antisense primer

<400> SEQUENCE: 47
cggcgtttgg agtggtagaa a                                               21

<210> SEQ ID NO 48
<211> LENGTH: 19
<212> TYPE: DNA
<213> ORGANISM: Artificial Sequence
<220> FEATURE:
<223> OTHER INFORMATION: Cdkn1c sense primer

<400> SEQUENCE: 48
acatccacga tggagcgtc                                                  19

<210> SEQ ID NO 49
<211> LENGTH: 20
<212> TYPE: DNA
<213> ORGANISM: Artificial Sequence
<220> FEATURE:
<223> OTHER INFORMATION: Cdkn1c antisense primer

<400> SEQUENCE: 49
ggaagtcgta atcccagcgg                                                 20

<210> SEQ ID NO 50
<211> LENGTH: 21
<212> TYPE: DNA
<213> ORGANISM: Artificial Sequence
<220> FEATURE:
<223> OTHER INFORMATION: Chuk sense primer

<400> SEQUENCE: 50
cagccattta cctggcatga g                                               21

<210> SEQ ID NO 51
<211> LENGTH: 22
<212> TYPE: DNA
<213> ORGANISM: Artificial Sequence
<220> FEATURE:
<223> OTHER INFORMATION: Chuk antisense primer

<400> SEQUENCE: 51
gagggtccca attcaacatc aa                                              22

<210> SEQ ID NO 52
<211> LENGTH: 21
<212> TYPE: DNA
<213> ORGANISM: Artificial Sequence
<220> FEATURE:
<223> OTHER INFORMATION: Cox10 sense primer

<400> SEQUENCE: 52
ccagcaagta agacccaagc c                                               21

<210> SEQ ID NO 53
<211> LENGTH: 22
<212> TYPE: DNA

```
<213> ORGANISM: Artificial Sequence
<220> FEATURE:
<223> OTHER INFORMATION: Cox10 antisense primer

<400> SEQUENCE: 53
tcatctcttt ccaccgcttt tc                                              22

<210> SEQ ID NO 54
<211> LENGTH: 22
<212> TYPE: DNA
<213> ORGANISM: Artificial Sequence
<220> FEATURE:
<223> OTHER INFORMATION: Diablo sense primer

<400> SEQUENCE: 54
ggtacagaca gtgtttgtgt gt                                              22

<210> SEQ ID NO 55
<211> LENGTH: 23
<212> TYPE: DNA
<213> ORGANISM: Artificial Sequence
<220> FEATURE:
<223> OTHER INFORMATION: Diablo antisense primer

<400> SEQUENCE: 55
ctactaaggg aatgaggctc tga                                             23

<210> SEQ ID NO 56
<211> LENGTH: 23
<212> TYPE: DNA
<213> ORGANISM: Artificial Sequence
<220> FEATURE:
<223> OTHER INFORMATION: Fas sense primer

<400> SEQUENCE: 56
tatcaccact attgctggag tca                                             23

<210> SEQ ID NO 57
<211> LENGTH: 23
<212> TYPE: DNA
<213> ORGANISM: Artificial Sequence
<220> FEATURE:
<223> OTHER INFORMATION: Fas antisense primer

<400> SEQUENCE: 57
acgaagcagt tgaactttct gtt                                             23

<210> SEQ ID NO 58
<211> LENGTH: 23
<212> TYPE: DNA
<213> ORGANISM: Artificial Sequence
<220> FEATURE:
<223> OTHER INFORMATION: Ki67 sense primer

<400> SEQUENCE: 58
tgttcccact acacaatgtc ttg                                             23

<210> SEQ ID NO 59
<211> LENGTH: 21
<212> TYPE: DNA
<213> ORGANISM: Artificial Sequence
<220> FEATURE:
<223> OTHER INFORMATION: Ki67 antisense primer

<400> SEQUENCE: 59
acttacgcga gaccaacagt t                                               21
```

```
<210> SEQ ID NO 60
<211> LENGTH: 21
<212> TYPE: DNA
<213> ORGANISM: Artificial Sequence
<220> FEATURE:
<223> OTHER INFORMATION: Mcl1 sense primer

<400> SEQUENCE: 60
gtgcctttgt ggctaaacac t                                              21

<210> SEQ ID NO 61
<211> LENGTH: 21
<212> TYPE: DNA
<213> ORGANISM: Artificial Sequence
<220> FEATURE:
<223> OTHER INFORMATION: Mcl1 antisense primer

<400> SEQUENCE: 61
agtcccgttt tgtccttacg a                                              21

<210> SEQ ID NO 62
<211> LENGTH: 21
<212> TYPE: DNA
<213> ORGANISM: Artificial Sequence
<220> FEATURE:
<223> OTHER INFORMATION: Parp1 sense primer

<400> SEQUENCE: 62
gatgcctatt actgcactgg g                                              21

<210> SEQ ID NO 63
<211> LENGTH: 23
<212> TYPE: DNA
<213> ORGANISM: Artificial Sequence
<220> FEATURE:
<223> OTHER INFORMATION: Parp1 antisense primer

<400> SEQUENCE: 63
cggtcctgct ttttaacctt caa                                            23

<210> SEQ ID NO 64
<211> LENGTH: 21
<212> TYPE: DNA
<213> ORGANISM: Artificial Sequence
<220> FEATURE:
<223> OTHER INFORMATION: Perp sense primer

<400> SEQUENCE: 64
caaccctgct gtcacttaca t                                              21

<210> SEQ ID NO 65
<211> LENGTH: 21
<212> TYPE: DNA
<213> ORGANISM: Artificial Sequence
<220> FEATURE:
<223> OTHER INFORMATION: Perp antisense primer

<400> SEQUENCE: 65
aggtcatctt cgtagttggg g                                              21

<210> SEQ ID NO 66
<211> LENGTH: 22
<212> TYPE: DNA
<213> ORGANISM: Artificial Sequence
<220> FEATURE:
```

<223> OTHER INFORMATION: Pcna sense primer

<400> SEQUENCE: 66
acactaaggg ccgaagataa cg                                               22

<210> SEQ ID NO 67
<211> LENGTH: 22
<212> TYPE: DNA
<213> ORGANISM: Artificial Sequence
<220> FEATURE:
<223> OTHER INFORMATION: Pcna antisense primer

<400> SEQUENCE: 67
cggcatatac gtgcaaattc ac                                               22

<210> SEQ ID NO 68
<211> LENGTH: 20
<212> TYPE: DNA
<213> ORGANISM: Artificial Sequence
<220> FEATURE:
<223> OTHER INFORMATION: Pxn sense primer

<400> SEQUENCE: 68
gcggacttgg agtctaccac                                                  20

<210> SEQ ID NO 69
<211> LENGTH: 21
<212> TYPE: DNA
<213> ORGANISM: Artificial Sequence
<220> FEATURE:
<223> OTHER INFORMATION: Pxn antisense primer

<400> SEQUENCE: 69
tccagttggg tatgagtagg g                                                21

<210> SEQ ID NO 70
<211> LENGTH: 21
<212> TYPE: DNA
<213> ORGANISM: Artificial Sequence
<220> FEATURE:
<223> OTHER INFORMATION: Xiap sense primer

<400> SEQUENCE: 70
gacaggccat ctgagacaca t                                                21

<210> SEQ ID NO 71
<211> LENGTH: 22
<212> TYPE: DNA
<213> ORGANISM: Artificial Sequence
<220> FEATURE:
<223> OTHER INFORMATION: Xiap antisense primer

<400> SEQUENCE: 71
ggggttaggt gagcatagtc tg                                               22

<210> SEQ ID NO 72
<211> LENGTH: 20
<212> TYPE: DNA
<213> ORGANISM: Artificial Sequence
<220> FEATURE:
<223> OTHER INFORMATION: Ahcy sense primer

<400> SEQUENCE: 72
gcatccgagg catctctgag                                                  20

<210> SEQ ID NO 73
<211> LENGTH: 23
<212> TYPE: DNA
<213> ORGANISM: Artificial Sequence
<220> FEATURE:
<223> OTHER INFORMATION: Ahcy antisense primer

<400> SEQUENCE: 73
gccatagagg ttgtcaaact tgc                                    23

<210> SEQ ID NO 74
<211> LENGTH: 22
<212> TYPE: DNA
<213> ORGANISM: Artificial Sequence
<220> FEATURE:
<223> OTHER INFORMATION: Bhmt sense primer

<400> SEQUENCE: 74
gacaccttca taccttagct gc                                     22

<210> SEQ ID NO 75
<211> LENGTH: 23
<212> TYPE: DNA
<213> ORGANISM: Artificial Sequence
<220> FEATURE:
<223> OTHER INFORMATION: Bhmt antisense primer

<400> SEQUENCE: 75
acaggtttac cggatgctat caa                                    23

<210> SEQ ID NO 76
<211> LENGTH: 23
<212> TYPE: DNA
<213> ORGANISM: Artificial Sequence
<220> FEATURE:
<223> OTHER INFORMATION: Hacl1 sense primer

<400> SEQUENCE: 76
ccttcttatc atcgggaaag gtg                                    23

<210> SEQ ID NO 77
<211> LENGTH: 21
<212> TYPE: DNA
<213> ORGANISM: Artificial Sequence
<220> FEATURE:
<223> OTHER INFORMATION: Hacl1 antisense primer

<400> SEQUENCE: 77
cccatagggg tgggcaaaaa t                                      21

<210> SEQ ID NO 78
<211> LENGTH: 21
<212> TYPE: DNA
<213> ORGANISM: Artificial Sequence
<220> FEATURE:
<223> OTHER INFORMATION: Khk sense primer

<400> SEQUENCE: 78
gctattctgt ggacctacgc t                                      21

<210> SEQ ID NO 79
<211> LENGTH: 21
<212> TYPE: DNA
<213> ORGANISM: Artificial Sequence
<220> FEATURE:
<223> OTHER INFORMATION: Khk antisense primer

<400> SEQUENCE: 79
agtataggat ggtgcggcta c                                           21

<210> SEQ ID NO 80
<211> LENGTH: 21
<212> TYPE: DNA
<213> ORGANISM: Artificial Sequence
<220> FEATURE:
<223> OTHER INFORMATION: Mat1a sense primer

<400> SEQUENCE: 80
catcaagcac atcggctacg a                                           21

<210> SEQ ID NO 81
<211> LENGTH: 22
<212> TYPE: DNA
<213> ORGANISM: Artificial Sequence
<220> FEATURE:
<223> OTHER INFORMATION: Mat1a antisense primer

<400> SEQUENCE: 81
ccgaacatca aaccctgatc tc                                          22

<210> SEQ ID NO 82
<211> LENGTH: 20
<212> TYPE: DNA
<213> ORGANISM: Artificial Sequence
<220> FEATURE:
<223> OTHER INFORMATION: Oat sense primer

<400> SEQUENCE: 82
tgctgtcaac caagggcatt                                             20

<210> SEQ ID NO 83
<211> LENGTH: 23
<212> TYPE: DNA
<213> ORGANISM: Artificial Sequence
<220> FEATURE:
<223> OTHER INFORMATION: Oat antisense primer

<400> SEQUENCE: 83
gcctccactc ctgtattcat agg                                         23

<210> SEQ ID NO 84
<211> LENGTH: 19
<212> TYPE: DNA
<213> ORGANISM: Artificial Sequence
<220> FEATURE:
<223> OTHER INFORMATION: L27 sense primer

<400> SEQUENCE: 84
tgatggcacc tcagatcgc                                              19

<210> SEQ ID NO 85
<211> LENGTH: 22
<212> TYPE: DNA
<213> ORGANISM: Artificial Sequence
<220> FEATURE:
<223> OTHER INFORMATION: L27 antisense primer

<400> SEQUENCE: 85
agagtacctt gtgggcatta gg                                          22

<210> SEQ ID NO 86
<211> LENGTH: 27

```
<212> TYPE: DNA
<213> ORGANISM: Artificial Sequence
<220> FEATURE:
<223> OTHER INFORMATION: shRNA against human ANGPTL4 sense strand

<400> SEQUENCE: 86
gcagcacctg cgaattcagc atctgca                                        27

<210> SEQ ID NO 87
<211> LENGTH: 27
<212> TYPE: DNA
<213> ORGANISM: Artificial Sequence
<220> FEATURE:
<223> OTHER INFORMATION: shRNA against human ANGPTL antisense strand

<400> SEQUENCE: 87
tgcagatgct gaattcgcag gtgctgc                                        27
```

ANTIPROLIFERATIVE AGENT

CROSS REFERENCE TO RELATED APPLICATIONS

This application is a divisional application and claims priority to co-pending U.S. patent application Ser. No. 13/501,768, entitled ANTIPROLIFERATIVE AGENT, having a filing date of Apr. 13, 2012, now abandoned which is a national stage application and claims priority to PCT/SG2010/000392, having a filing date of Oct. 14, 2010, which claims priority to U.S. Provisional Patent Application No. 61/251,485, filed on Oct. 14, 2009. The aforementioned patent applications are incorporated by reference in their entireties herein.

INCORPORATION OF ELECTRONICALLY SUBMITTED SEQUENCE LISTING

The entirety of the sequence listing submitted electronically at the same time of the filing of the instant application is incorporated by reference herein.

The entirely of the electronically filed sequence listing text file named Sequence_Listing_ST25.txt, created Dec. 21, 2017, 24 kB, is incorporated by reference herein.

FIELD OF THE INVENTION

The invention relates to antagonist of ANGPTL4 and methods of using the same including methods for the treatment of cancer and proliferative disorders.

BACKGROUND

Cancer is one of the main diseases of the 21$^{st}$ century causing 13% of all deaths. While there are several chemicals that can affect rapidly dividing cancer cells, most of these chemicals are toxic with adverse side effects.

Cancer is expected to be the leading cause of death worldwide in the near future. Tumor cells exploit various signaling molecules to promote their growth, invasion and metastasis. A clear understanding of the mechanisms of actions of these molecules in malignancy will provide new insights into therapeutic interventions.

In response to stresses in the tumor microenvironment, such as hypoxia and inflammation, tumor cells exploit various signaling molecules to sustain and promote their growth, invasiveness and metastasis. Aggressive tumor metastasis and invasiveness is the main cause of mortality in cancer patients. The constitutive activation of intracellular signaling by these molecules in tumor cells causes changes in cellular functions, including increased proliferation and the ability of cells to grow outside their original confined milieu, leading to metastasis. Among these changes, the loss of dependence on integrin-mediated extracellular matrix contact for growth, or anoikis resistance, is an essential feature of tumor cells, yet how it is acquired remains an unsolved problem in cancer biology.

Although low levels of reactive oxygen species (ROS) regulate cellular signaling and play an important role in normal cell proliferation, recent studies show that tumors exhibit an excessive amount or persistent elevation of ROS (specifically the superoxide anion $O_2^-$) and utilize a redox-based mechanism to evade death by anoikis Previous studies have indicated that ROS are involved in tumor initiation, progression and maintenance. Furthermore, deregulated ROS production is also associated with an invasive tumor phenotype. Oncogenic and mitogenic Ras activity is superoxide-dependent, and a sustained increase in ROS following the overexpression of Mox1 (the catalytic subunit of NADPH oxidase) leads to cell transformation and aggressive tumor metastasis. Elevated production of ROS following activation of the c-Met proto-oncogene leads to cell transformation and malignant growth, and Rac-dependent redox signals increase the secretion of metalloproteases and induce the epithelial-mesenchymal transition, which are two key features of invasive cancers. Thus, a clear understanding of the underlying redox-based anoikis escape mechanism and its connection to malignancy will provide new insights into therapeutic interventions.

Anoikis resistance, a hallmark of tumor malignancies, is an integrin-dependent process. Reactive oxygen species (ROS) generated due to intergrin engagement oxidizes and activates Src, which stimulates the ERK and Akt pro-survival pathways. Both pathways regulate the subcellular location or stability of BH3-only apoptotic proteins (eg Bad and Bim), essential for executing anoikis Resistance to anoikis has been suggested to be a prerequisite for cancer cells to metastasize. The mechanism by which invading tumor cells survive the anoikis process remains largely unknown.

Angiopoietin-like protein 4 (ANGPTL4) are secreted proteins mainly expressed in liver that have been demonstrated to regulate triglyceride metabolism by inhibiting the lipolysis of triglyceride-rich lipoproteins. Experimental results show that ANGPTL4 function to regulate circulating triglyceride levels during different nutritional states and therefore play a role in lipid metabolism during feeding/fasting through differential inhibition of Lipoprotein lipase (LPL). The N-terminal domain of Angiopoietin-like proteins has been shown to play an active role in lipid metabolism. Using deletion mutants, it was demonstrated that the N-terminal domain containing fragment—(17-207) and not the C-terminal fibrinogen-like domain containing fragment—(207-460) increased the plasma triglyceride levels in mice. ANGPTL4 has been identified as a novel paracrine and, possibly, endocrine regulator of lipid metabolism and a target of peroxisome proliferators-activated receptors (PPARs). It is expressed in numerous cell types, such as adipocytes and hepatocytes, and is upregulated after fasting and hypoxia. Importantly, ANGPTL4 undergoes proteolytic processing to release its C-terminal fibrinogen-like domain (cANGPTL4), which circulates as a monomer yet whose function remains unclear. The N-terminal coiled-coil domain of ANGPTL4 (nANGPTL4) mediates the oligomerization of ANGPTL4 and binds to lipoprotein lipase to modulate lipoprotein metabolism. It is now established that the nANGPTL4 mediates its oligomerization and binds to lipoprotein lipase to modulate lipoprotein metabolism. In contrast, cANGPTL4 exists as a monomer, and its function still remains unknown.

ANGPTL4 was recently linked to tumor progression. The angiopoietin-like 4 protein (ANGPTL4) has well-studied roles in metabolism, yet its role in cancer biology remains undefined as a predictive gene for breast cancer metastasis, where it disrupts endothelial integrity. However, whether ANGPTL4 promotes or inhibits vascular permeability, and thus cancer metastasis remains controversial. There is apparently conflicting results as to the underlying mechanism of ANGPTL4 activity in tumor cells that have not been clarified, hampering our understanding of its precise role in cancer metastasis. The role of ANGPTL4 in cancer biology remains unesertianed.

SUMMARY

The present invention seeks to ameliorate the above mentioned problems by providing composition such as an antibody or an SiRNA specific to angiopoietin like 4 protein (ANGPTL4) capable of neutralizing or knocking down the protein to halt or reduce cell proliferation and methods of making and using the same.

The invention provides an antagonist to angiopoietin like 4 protein (ANGPTL4) such as an antibody specific to angiopoietin like 4 protein (ANGPTL4) or an SiRNA capable of neutralizing or knocking down the protein to halt or reduce cell proliferation and methods of making and using the same.

The antagonist of the invention is further directed to the C terminal region of the protein and may be capable of neutralizing cell proliferation. The antagonist may be a monoclonal antibody and or a humanized antibody.

The present invention also provides a method of treating a patient to at least affect cell proliferation, which comprises the step of: contacting proliferating cell with an antagonist to angiopoietin like 4 protein (ANGPTL4). Preferably, the antagonist comprises (a) an antibody specific to angiopoietin like 4 protein (ANGPTL4) or (b) an antibody specific to the C terminal region of angiopoietin like 4 protein (ANGPTL4).

An alternative form of the present invention resides in the use of an antaognost to angiopoietin like 4 protein (ANGPTL4) for the treatment of a tumor. Preferably, the antagonist comprises an antibody specific to angiopoietin like 4 protein (ANGPTL4) or an antibody specific to the C terminal region of angiopoietin like 4 protein (ANGPTL4) preferably the use at least affects growth of the tumor by either stopping the growth or reducing the size of the tumor.

The present invention also relates to compositions including pharmaceutical compositions comprising a therapeutically effective amount of an antagonist to angiopoietin like 4 protein (ANGPTL4). Preferably, the antagonist comprises (a) an antibody specific to or (b) an antibody specific to the C terminal region of. As used herein a compound will be therapeutically effective if it is able to affect cell proliferation.

The invention also provides a method of diagnosing proliferative disorders, comprising the steps of the determining an amount of the angiopoietin like 4 protein (ANGPTL4) protein in body fluids or tissue sampled from a person suspected of having a proliferative disorder.

Accordingly, the methods and compounds described herein may be used in diagnostic and therapeutic methods. Other aspects and advantages of the invention will become apparent to those skilled in the art from a review of the ensuing description, which proceeds with reference to the following illustrative drawings of preferred embodiments.

Figure 1:
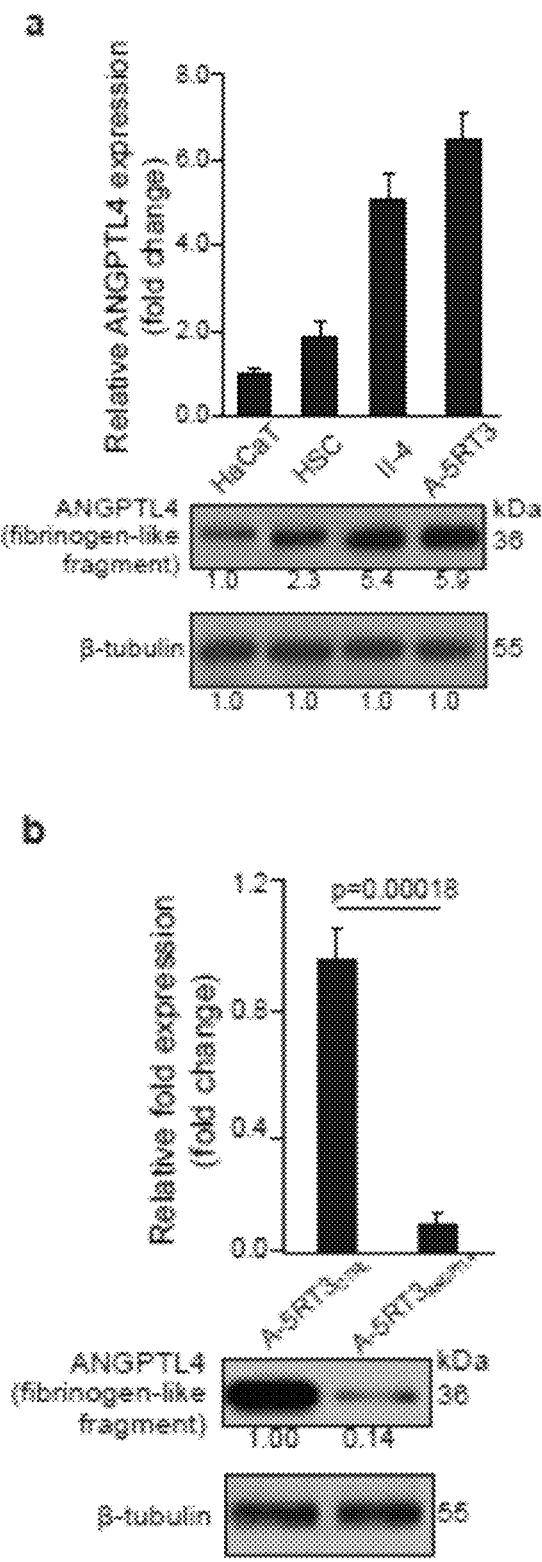
FIG. 1. Suppression of ANGPTL4 impairs tumorigencity. Relative ANGPTL4 mRNA and protein levels in (a) HaCaT, HSC, II-4 and A-5RT3, (b) A-5RT3$_{ANGPTL4}$ and A-5RT3$_{CTRL}$ as evaluated by qPCR and immunoblotting. Only the C-terminal fibrinogen-like fragment of ANGPTL4 was detected. Values (mean±S.D.) from 5 independent analyses. (c) Tumour size induced by A-5RT3$_{ANGPTL4}$ compared to A-5RT3$_{CTRL}$ at 8 weeks post injection. Each circle (mean±S.D.) represents 3 measurements from each mouse. (d) Immunodetection of proliferation (cyclin D1, PCNA), and apoptosis (cleaved capsase 3, PARP, Bax) markers in A-5RT3$_{ANGPTL4}$ and A-5RT3$_{CTRL}$ induced tumors. (e) Tumour size in mice injected s.c. with A-5RT3$_{CTRL}$ and treated i.v. with either mAb11F6C4 or control IgG. Values (mean±S.D.) from 5 mice. *:p<0.05, **:p<0.01. (f) Quantification of A-5 RT3$_{CTRL}$ and A-5RT3$_{ANGPTL4}$ tumour colonies on soft agar. Values (mean±S.D.) from four assays. (g) Apoptotic cells (%) after 2 h anoikis was analyzed by FACS (events=5000) of three independent experiments.
Figure 1:
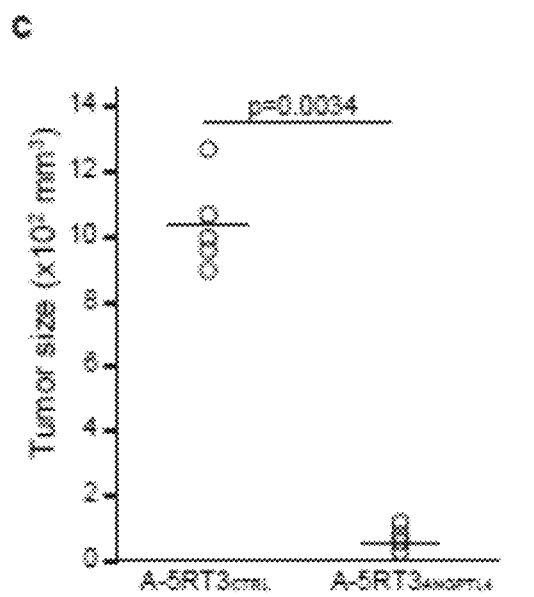
Figure 1:
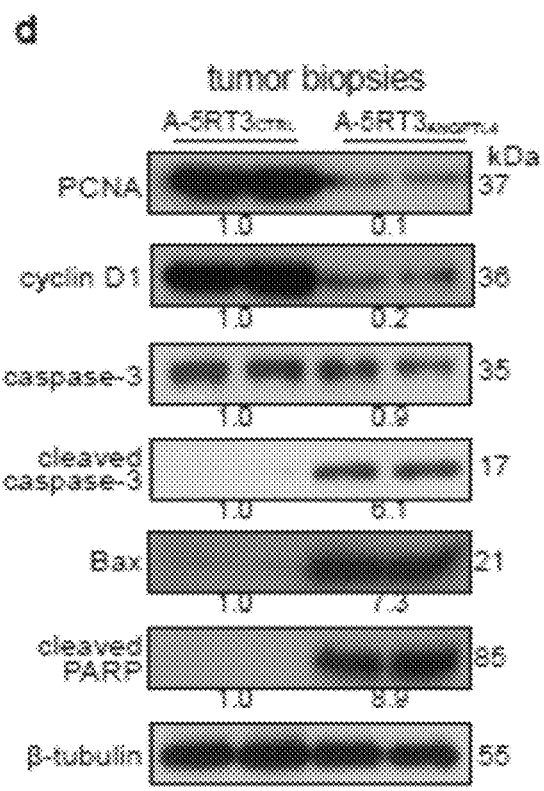
Figure 1:
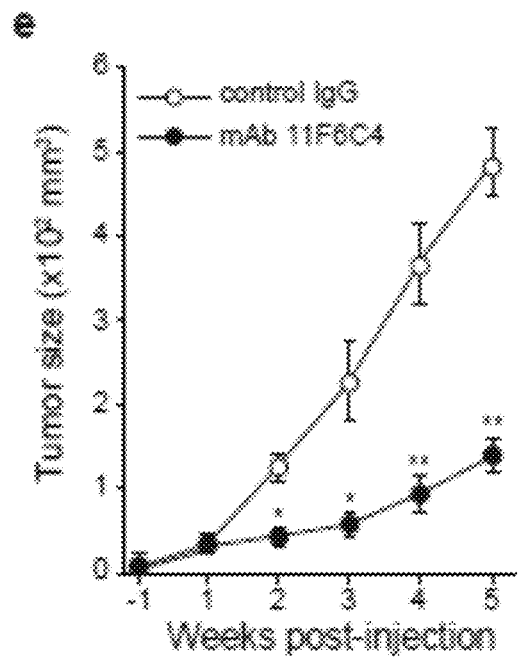
Figure 1:
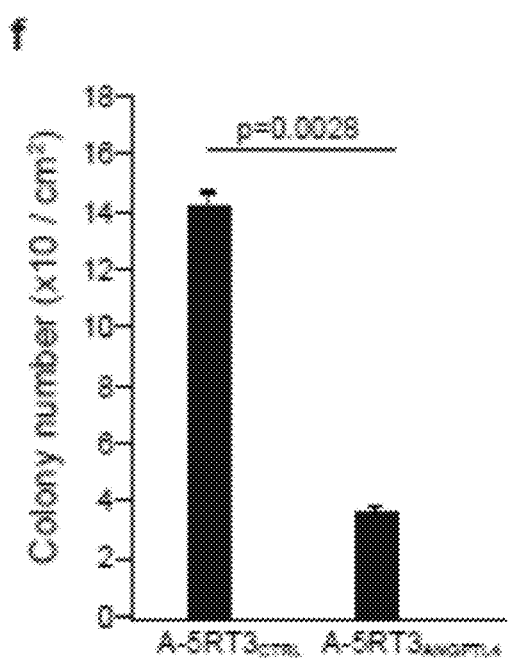
Figure 1:
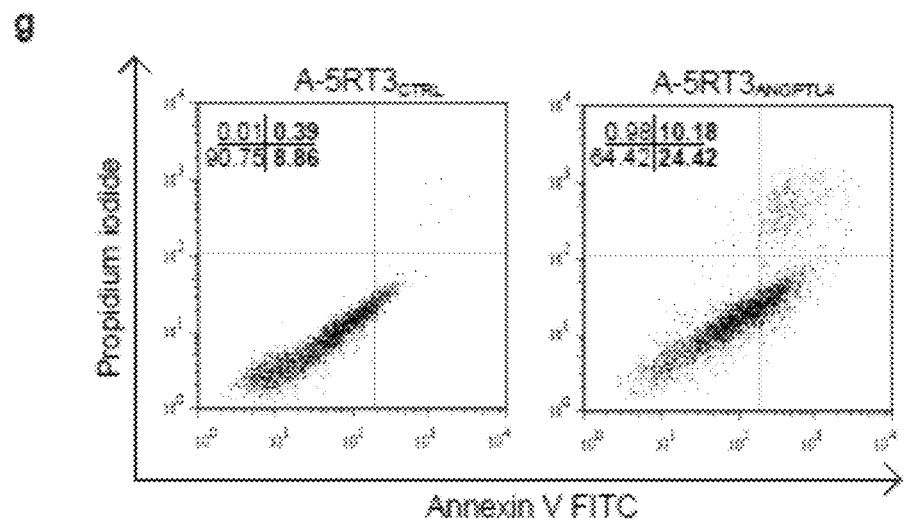

(a) Surface Plasmon resonance sensogram showing dose-dependent binding profiles of integrin 01 with immobilized-ANGPTL4 GLC chip. Sensorgram was corrected against a reference flow cell with no immobilized protein. $K_D \sim 10^{-7}$M was determined after global fitting (Langmuir 1:1 model) using Scrubber2. In situ PLA detection of (b) ANGPTL4-integrin 131 complexes in indicated tumors; phosphorylated FAK and 14-3-3/Bad complexes in (c) A-5RT3$_{CTRL}$ and A-5RT3$_{ANGPTL4}$ (d) tumors. PLA signals (red) and Hoechst-stained nuclei (blue); negative control without primary antibodies. Values (mean±S.D.) from 200 cells using Blob-Finder (Uppsula University). Scale bars 40 μm. *:p<0.05. (e) Representative immunoblot of total or phosphorylated FAK. ERK and 14-3-3 from indicated tumors. Immunoprecipitation of reduced and activated c-Src in (f) A-5RT3$_{ANGPTL4}$ cells and (g) tumors. Cells were suspended for 1-2 h (S1 h, S2 h). Cell lysates were labeled with 100 μM N-(biotinoyl)-N'-(iodoacetyl)ethylenediamine to evaluate Src redox state. hHRP-Streptavidin immunoblot performed on anti-Src immunoprecipitates showed reduced Src. Immunoprecipitates were probed with anti-Src for normalization. Activated Src, Na$^+$/H$^-$ exchanger 1 and catalase were assessed using cognate antibodies. Representative pictures from three experiments. (h) Intracellular ROS of A-5RT3$_{CTRL}$ and A-5RT3$_{ANGPTL4}$ evaluated by 5-(and 6-)-chloromethyl-2',7'-dichlorodihydro-fluorescein diacetate acetyl ester. Data are normalized to total protein content. (i) Activities of caspases in A-5RT3$_{ANGPTL4}$ after 2 h suspension. Values (mean±S.D.) represent a fold change above A-5RT3$_{CTRL}$ (n=3). *:p<0.05, **:p<0.01.

Figure 3:
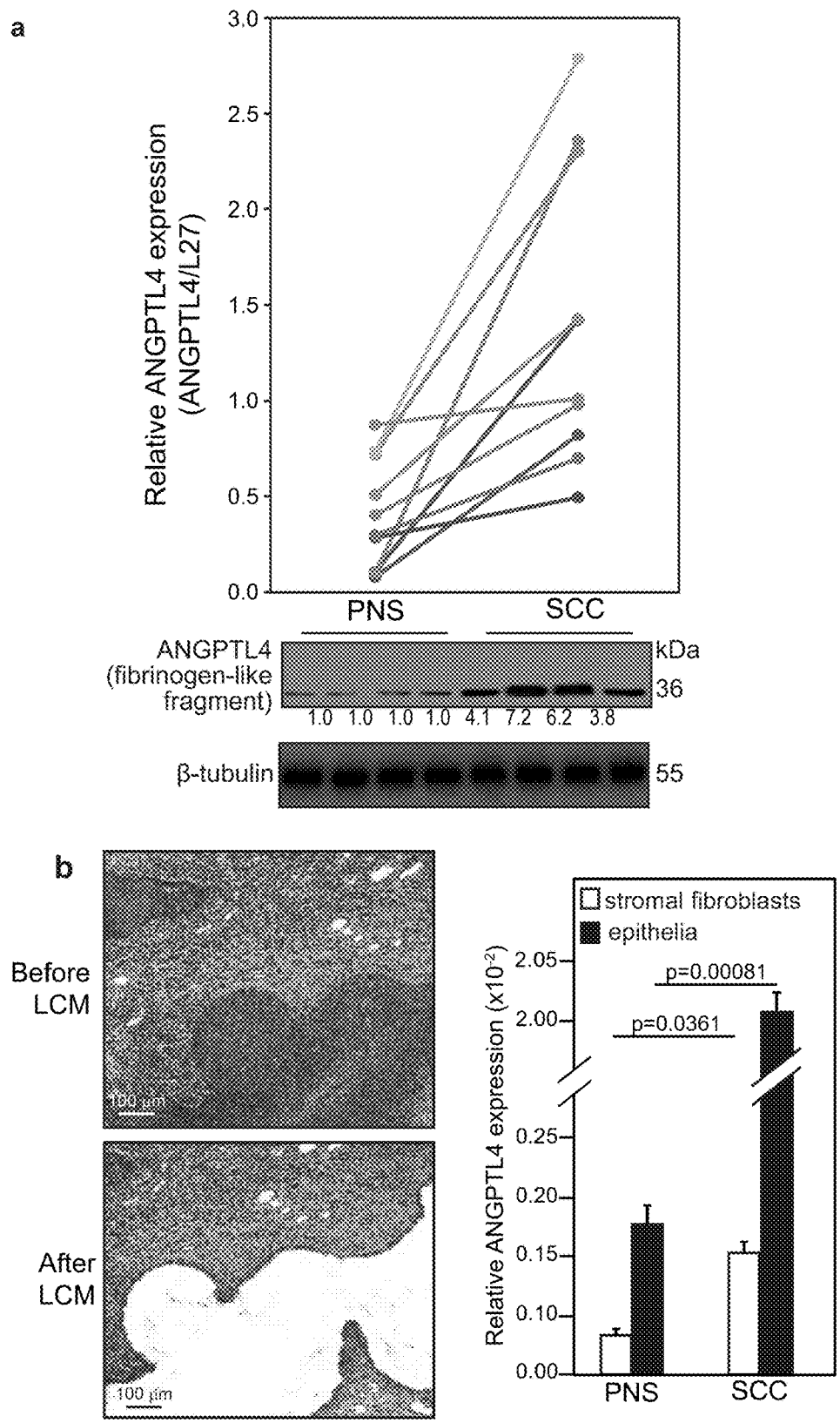

FIG. 3—Elevated expression of ANGPTL4 in tumors.

Figure 3C:
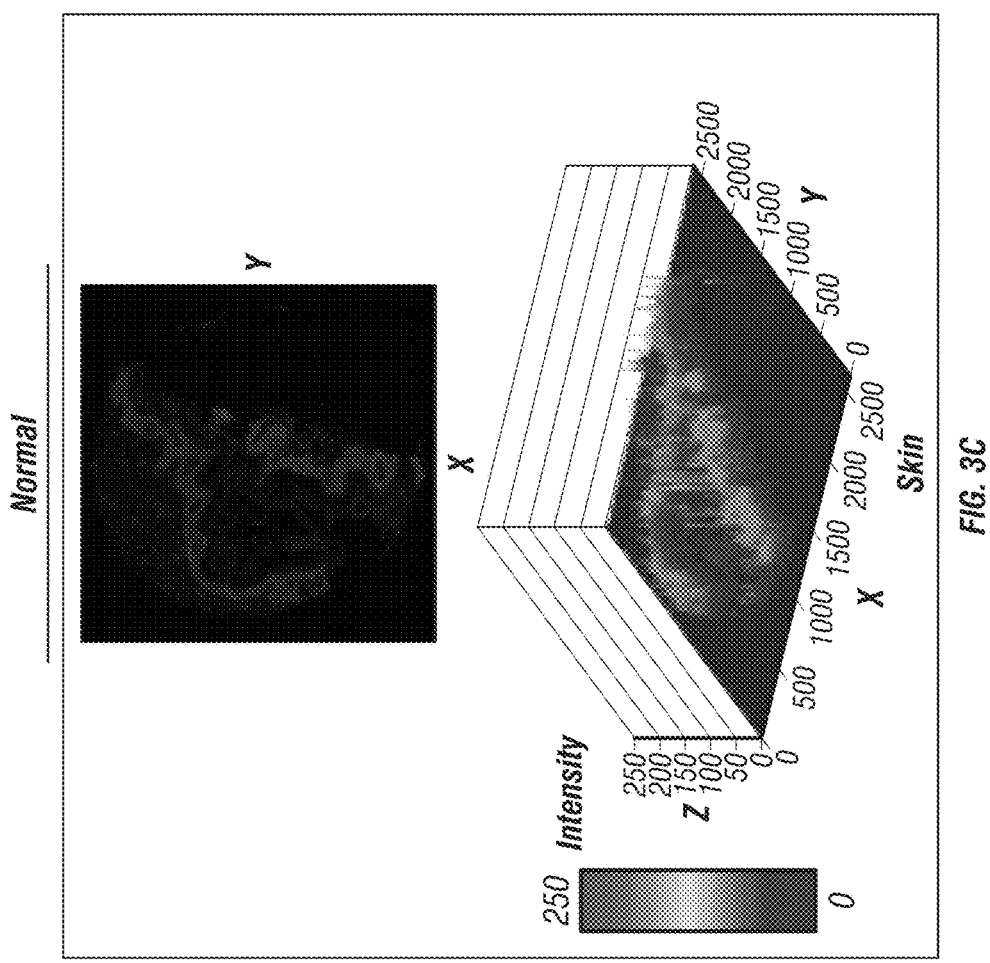
Figure 9:
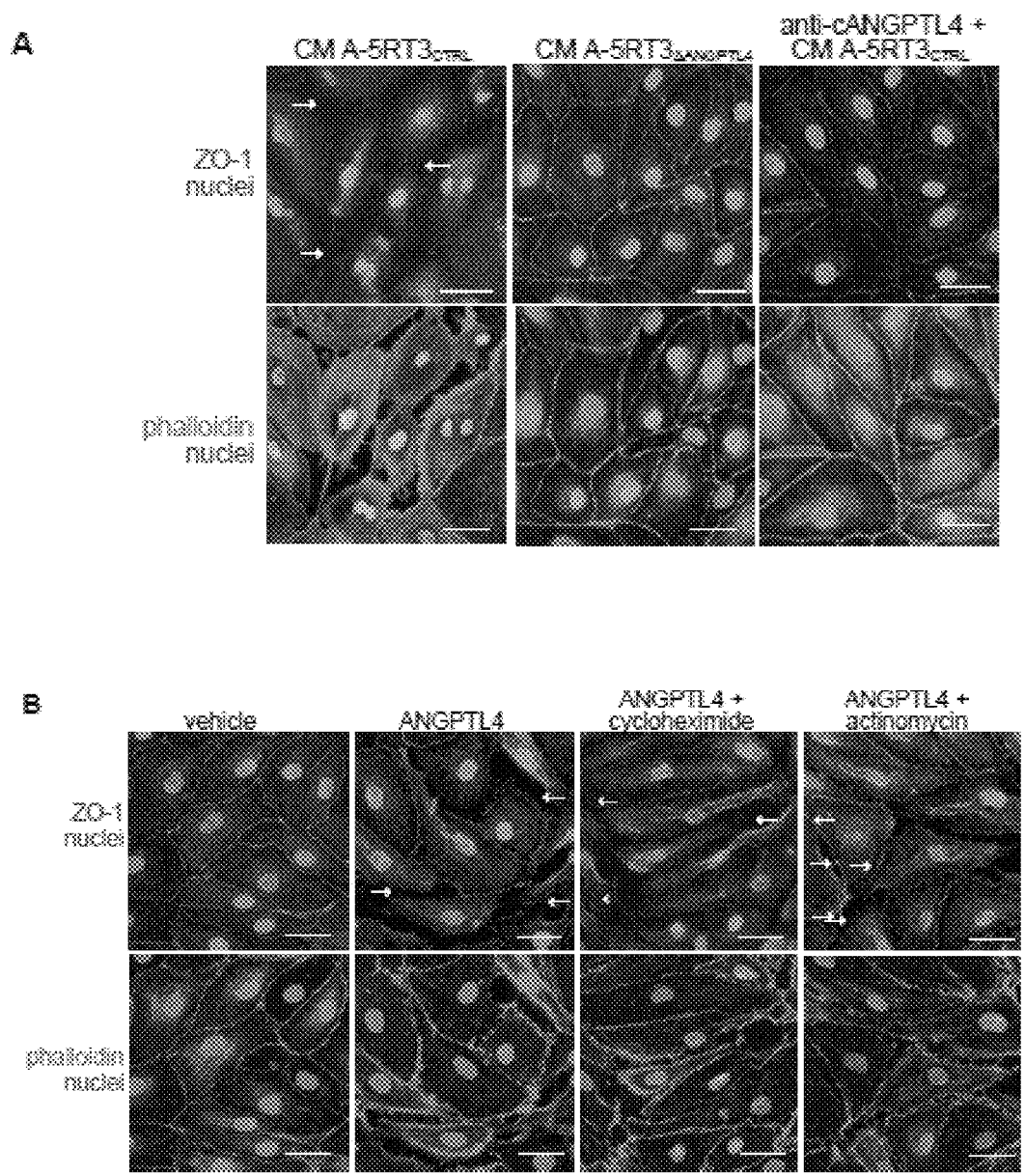
Figure 9:
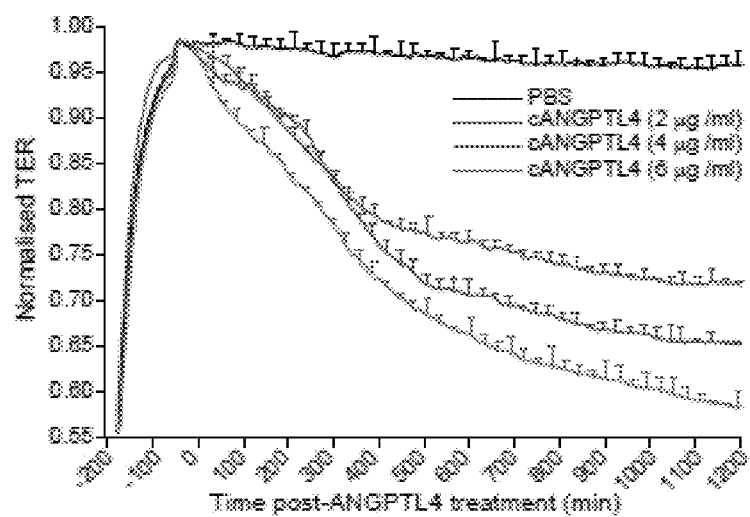

Relative ANGPTL4 protein and mRNA levels in (a) paired human squamous cell carcinomas (SCC) and peri-tumor normal samples (PNSs) determined using immunoblotting and qPCR. Values (mean±S.D.) represent a fold change compared to HaCaT or cognate PNS samples. For paired human samples, each spot was the mean value of 3 different paraffin sections from an individual sample. Tissues from same individual are linked by coloured lines. Three SCCs with the highest ANGPTL4 corresponded to an invasive prognosis, (b) Expression of ANGPTL4 from laser capture microdissected (LCM) epithelial tumor and stromal fibroblasts from SSC and PNS. Hematoxylin and eosin images of SCC section, before and after LCM of epithelial tumor tissue. Microdissected tissues were processed for qPCR. Values (mean±S.D.) represent expression level from 5LCM pairs of PNS and SSC. FIGS. 3C-3C9 illustrate ANGPTL4 expression varies among solid tumors procured from different anatomic sites. Heatmap profiles generated from immunofluorescence images using IMARIS (Bitplane Scientific Software). The X-Y axis represents the length and width, while the Z axis represents the immunofluorescence intensity. Representative image of normal skin and skin tumor with its corresponding heatmap was shown. The heatmaps were grouped horizontally by respective anatomic sites.

Figure 4:
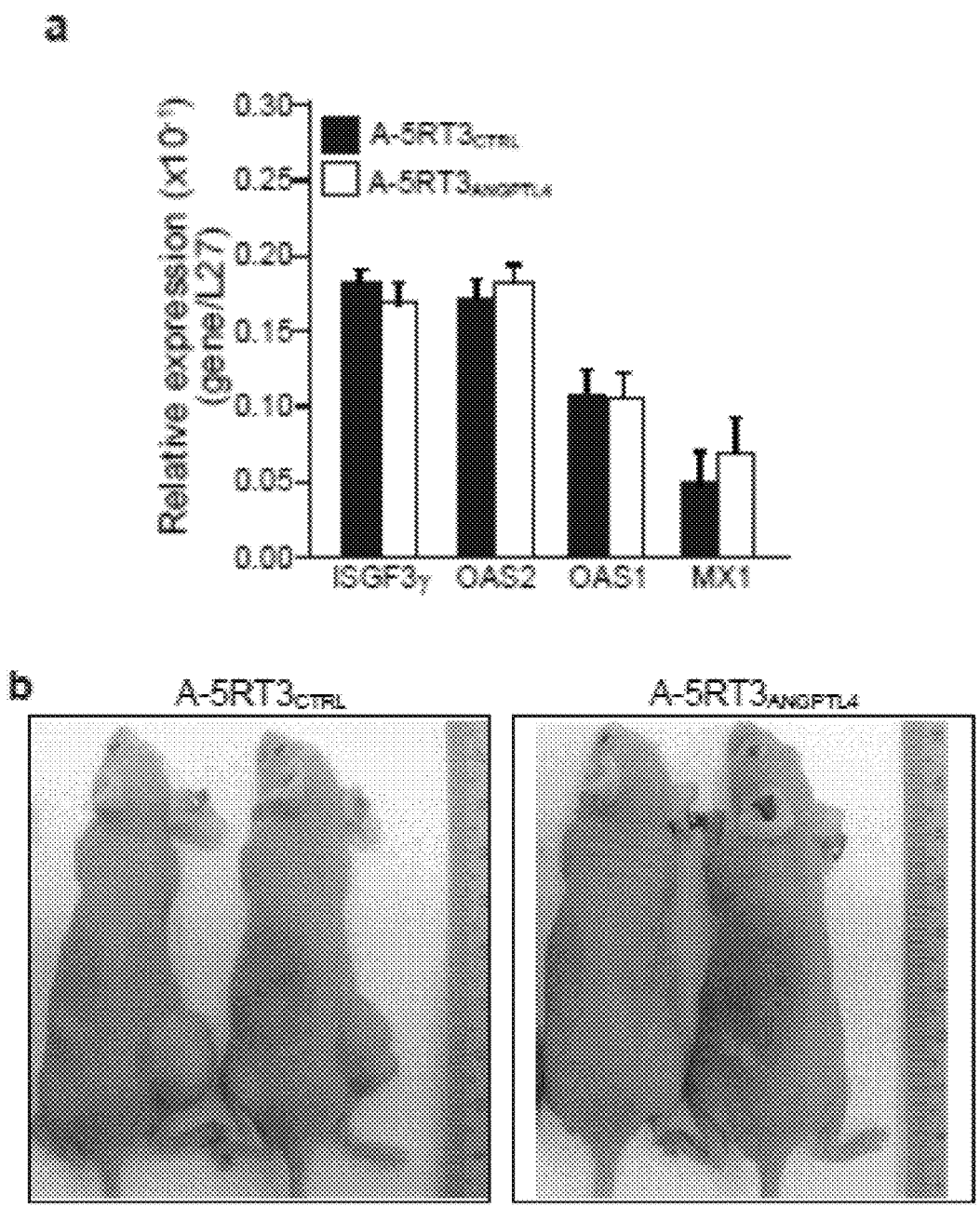
Figure 4:
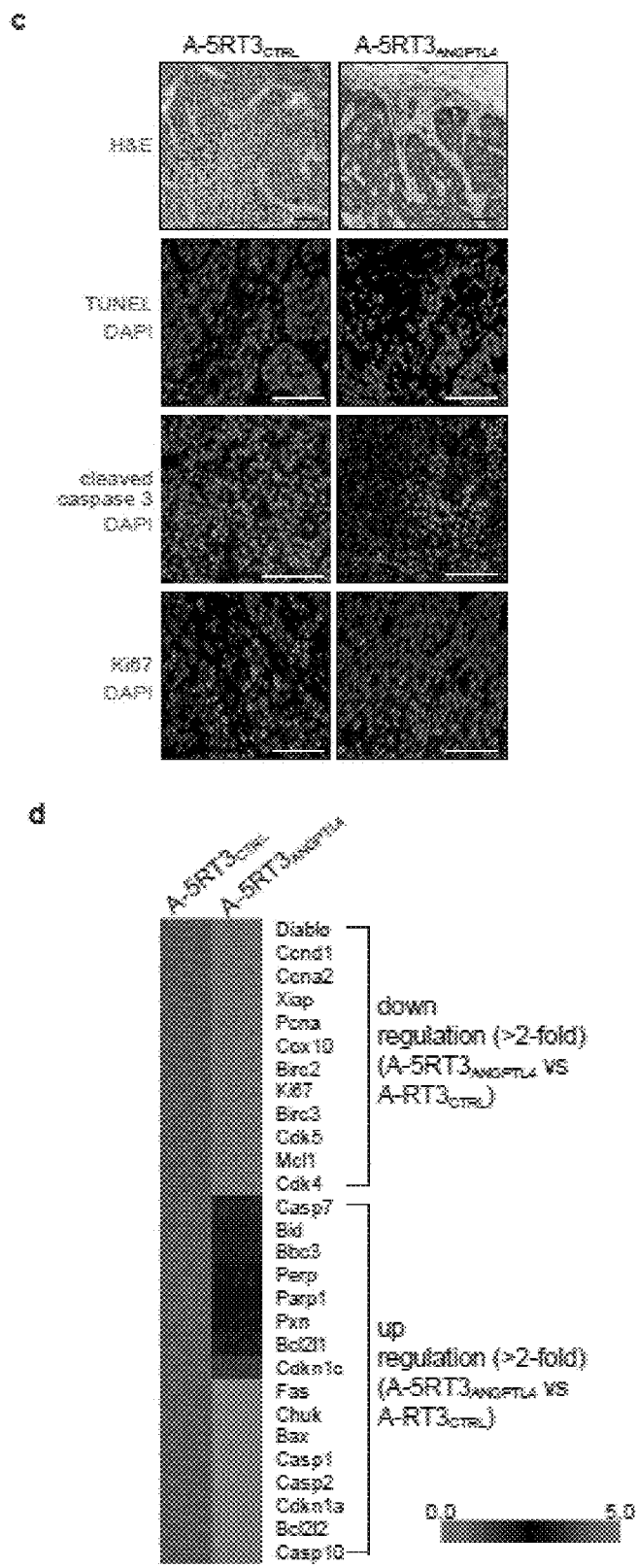
Figure 4:
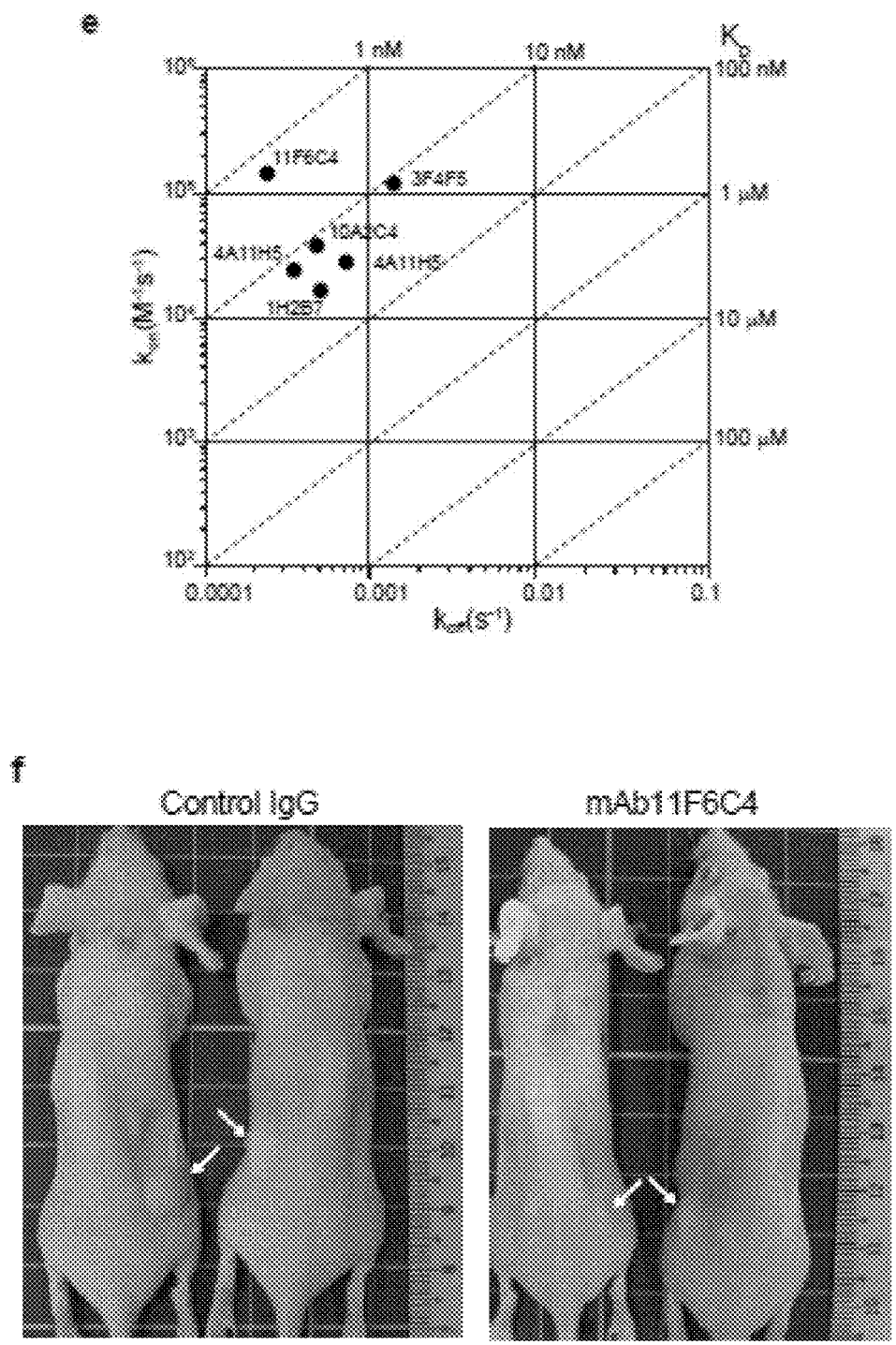

FIG. 4—Suppression of ANGPTL4 in A-5RT3 cells impair tumorigenicity in vivo.

(a) Lentivirus mediated suppression of ANGPTL4 has no off target effect. mRNA level of 2'5'-oligoadenylate synthetase isoforms 1 and 2 (OAS1, OAS2), interferon-induced myxovirus resistance 1 (MX1 and interferon-stimulated transcription factor 3γ (ISGF3γ) in A-5RT3$_{ANGPTL4}$ and A-5RT3$_{CTRL}$ determined by qPCR. Ribosomal protein L27 was used as a normalizing housekeeping gene. (b) Representative pictures of A-5RT3$_{CTRL}$ and A-5RT3$_{ANGPTL4}$ induced tumors in two mice. Total of 5 mice per group. (c) Immunofluorescence staining of A-5RT3$_{CTRL}$ and A-5RT3$_{ANGPTL4}$ induced tumors. Hematoxylin and eosin (H&E) stain of tumor sections. Proliferating (Ki67) and apoptotic (TUNEL- or cleved caspase 3) cells were identified using indicated antibodies or assay. Sections were counterstanined with DAPI (blue). Scale bars 40 μm. (d) Heatmap showing the genes up- and down regulated in A-5RT3$_{CTRL}$ and A-5RT3$_{ANGPTL4}$ induced tumors as determined by qPCR. Results were generated from three pairs of indicated tumors. Detailed description of the genes and expression in fold changes is in Table 1. (e) ANGPTL4 interaction kinetic maps for mAbs, shown as association and dissociation rate constant ($K_{on}$ and $K_{off}$) and a combination of $K_{on}$ and $K_{off}$ that results in the same affinity constant ($K_D$) values (diagonal lines) as determined by ProteOn XPR36 (Bio-Rad). Lables in maps identify the 6 mAb clones. mAb11F6C4 was chosen for subsequent immunotherapy experiment based on its superior $K_{on}$, $K_{off}$ and $K_D$ value. (f) Representative pictures of control IgG- or mAb 11F6C4-treated nude mice injected A-5RT3. Total of 6 mice per group. White arrows indicate injection site.

Figure 5:
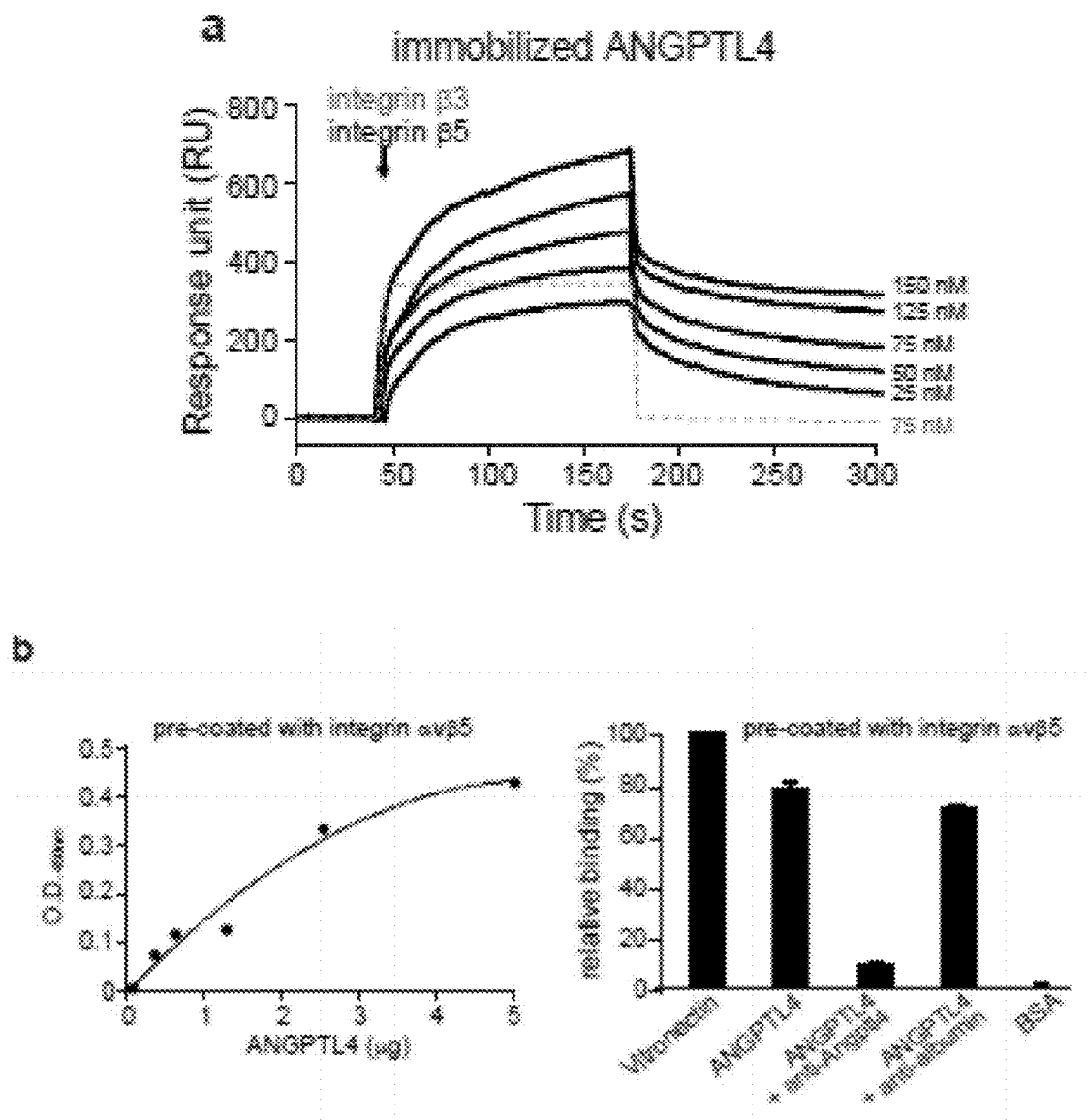
Figure 5:
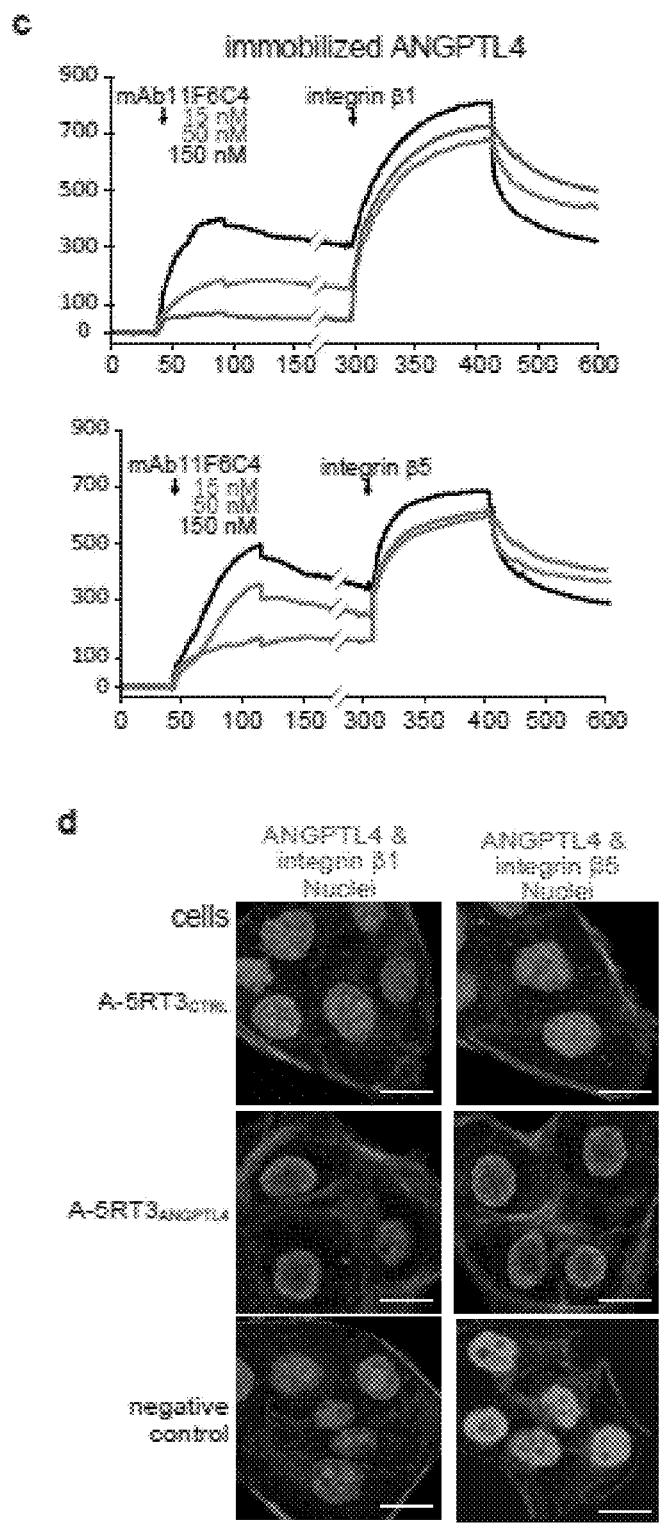
Figure 5:
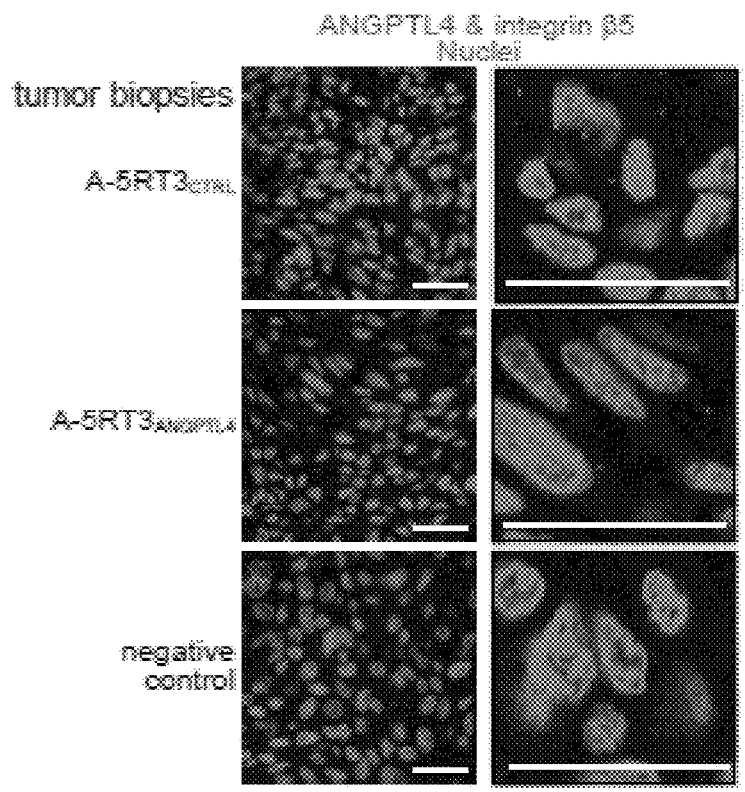
Figure 5:
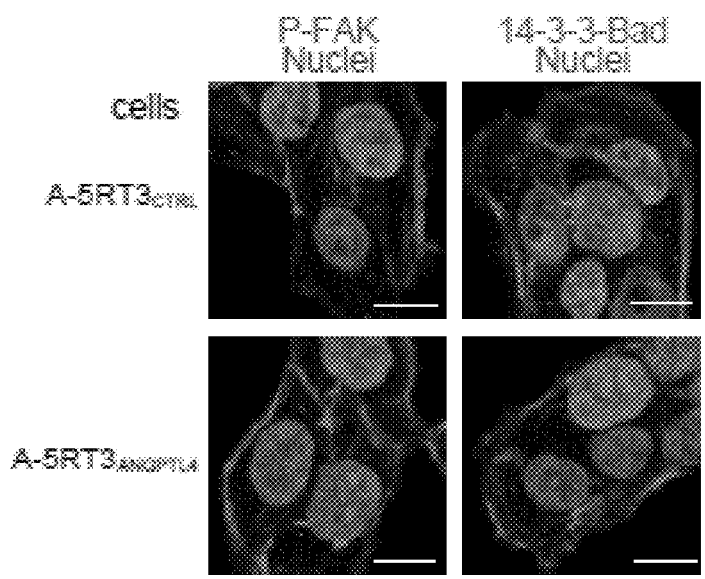

FIG. 5—ANGPTL4 interacts with integrins β5, but not β3, in vitro and in vivo (a) Sensorgram showed binding profiles between different concentrations of integrin β5 and immobilized ANGPTL4 chip. Each sensorgram was corrected as described in FIG. 2a. Integrin β at 75 nM did not show any detectable interaction (dotted red). (b) Dose dependent ANGPTL4 binding to immobilized integrin αvβ5 (left panel) which was specifically blocked by anti-cANGPTL4 (right panel) as determined by ELISA. (c) Sensorgrams showed dose depen- dant blocking of integrin 131 (upper panel) and 135 (lower panel) to immobilized ANGPATL4 by pre-injection with different concentrations of mAb11F6C4. In situ PLA detection of ANGPTL4-integrin 131 and ANGPTL4-integrin 135 complexes in (d) A-5RT3$_{CTRL}$ and A-5RT3$_{ANGPTL4}$ (e) A-5RT3$_{CTRL}$ and A-5RT3$_{ANGPTL4}$ induced tumors, and of phosphorylated FAK and 14-3-3/Bad complexes in (f) A-5RT3$_{CTRL}$ and A-5RT3$_{ANGPTL4}$. Higher magnification images of 5e in left panel. PLA signals (red) and Hoechst-stained nuclei (blue). Negative control was without primary antibodies.

Figure 6:
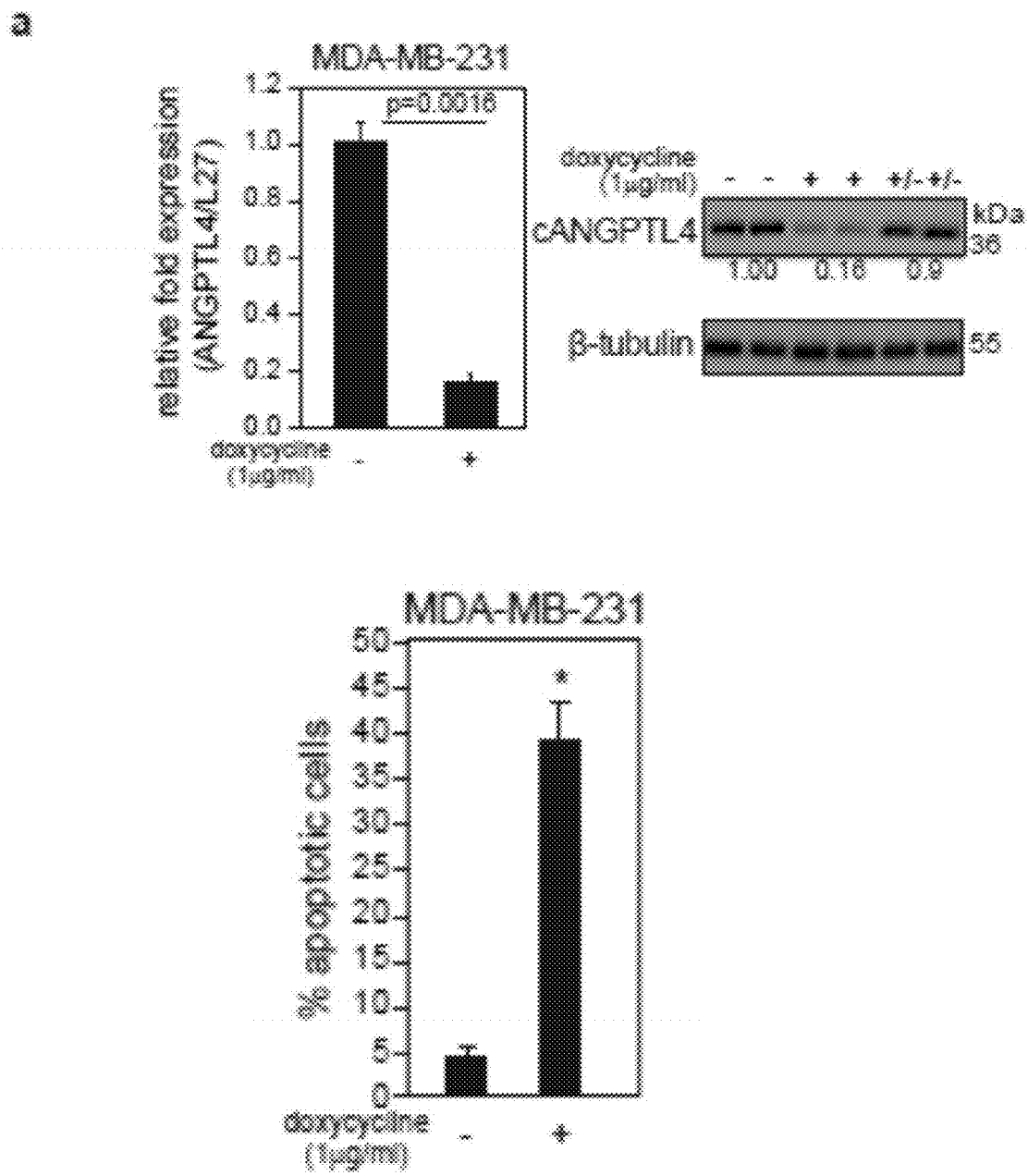

FIG. 6—Deficiency in ANGPTL4 induces apoptosis by anoikis.

Figure 6B:
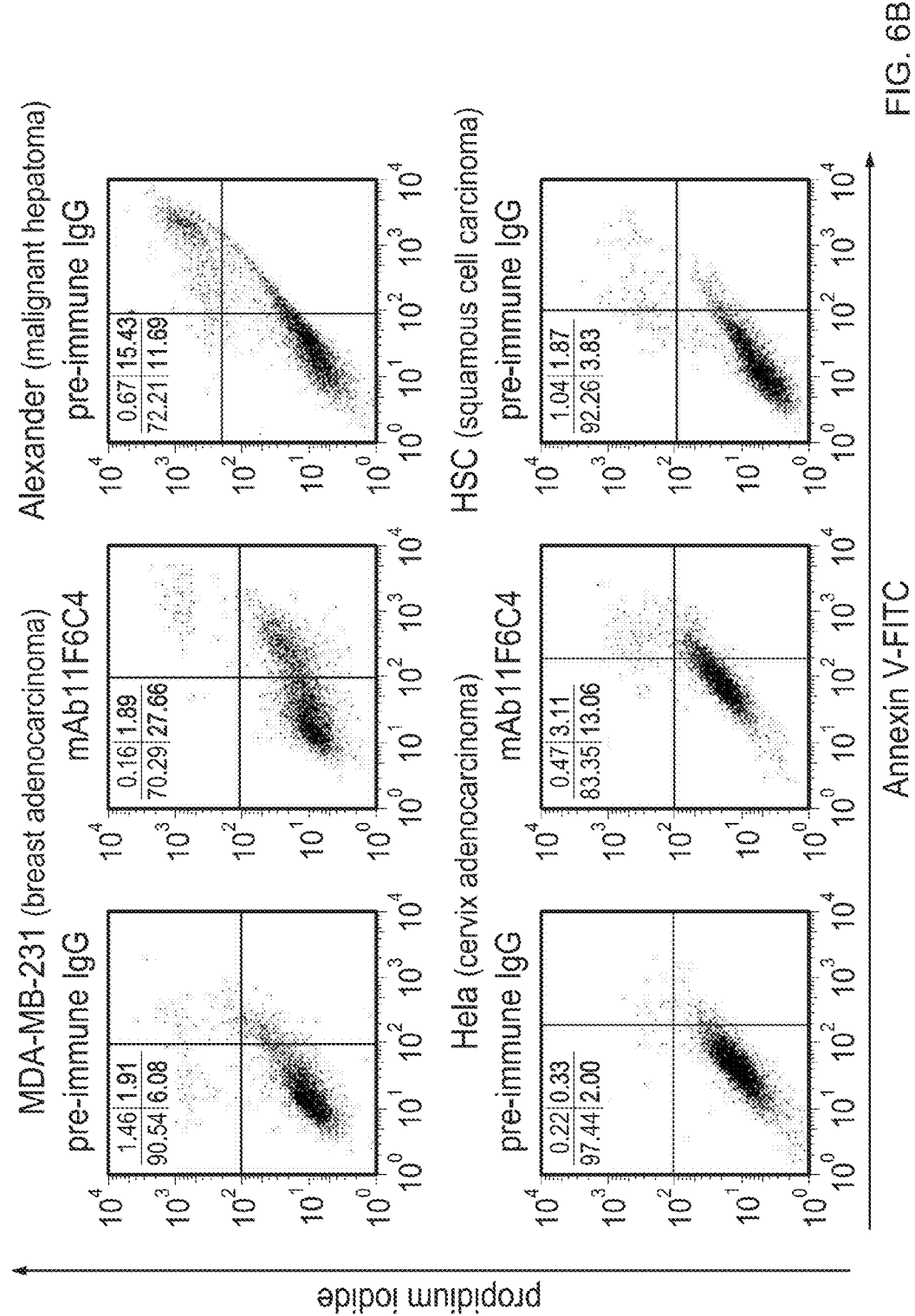

(a) Relative ANGPTL4 mRNA and protein levels in doxycycline-inducible suppression of ANGPTL4 in MDA-MB-231. A stable MDA-MB-231 cell line, that expresses an anti-ANGPTL4 shRNA (Table 2) was produced using the Knockout Singe Vector System (Clontech). Cells were grown in the absence (−) or presence (+) of doxycycline (1 μg/ml) for 24 h. +/− denotes the removal of doxycycline after 24 h doxycycline treatment. Percentage of apoptotic cells of FIGS. 6B 6B3 MDA-MB-231 and (c) 11 different tumor cell lines after 2 h of forced suspension was evaluated by Annexin V-FITC/propidium iodide labeling followed by FACS analysis (5000 events). MDA-MB-231 cells were treated with doxycycline for 24 h prior anoikis assay (right panel of (b)). Tumor cell lines were also exposed to mAb11F6C4 (10 kg/ml). Values (mean±S.D.) from three independent experiments. All examined tumor cell lines, the suppression of ANGPTL4 resulted in statistically more apoptotic cells, *:p<0.05 (student t-test).

Figure 7:
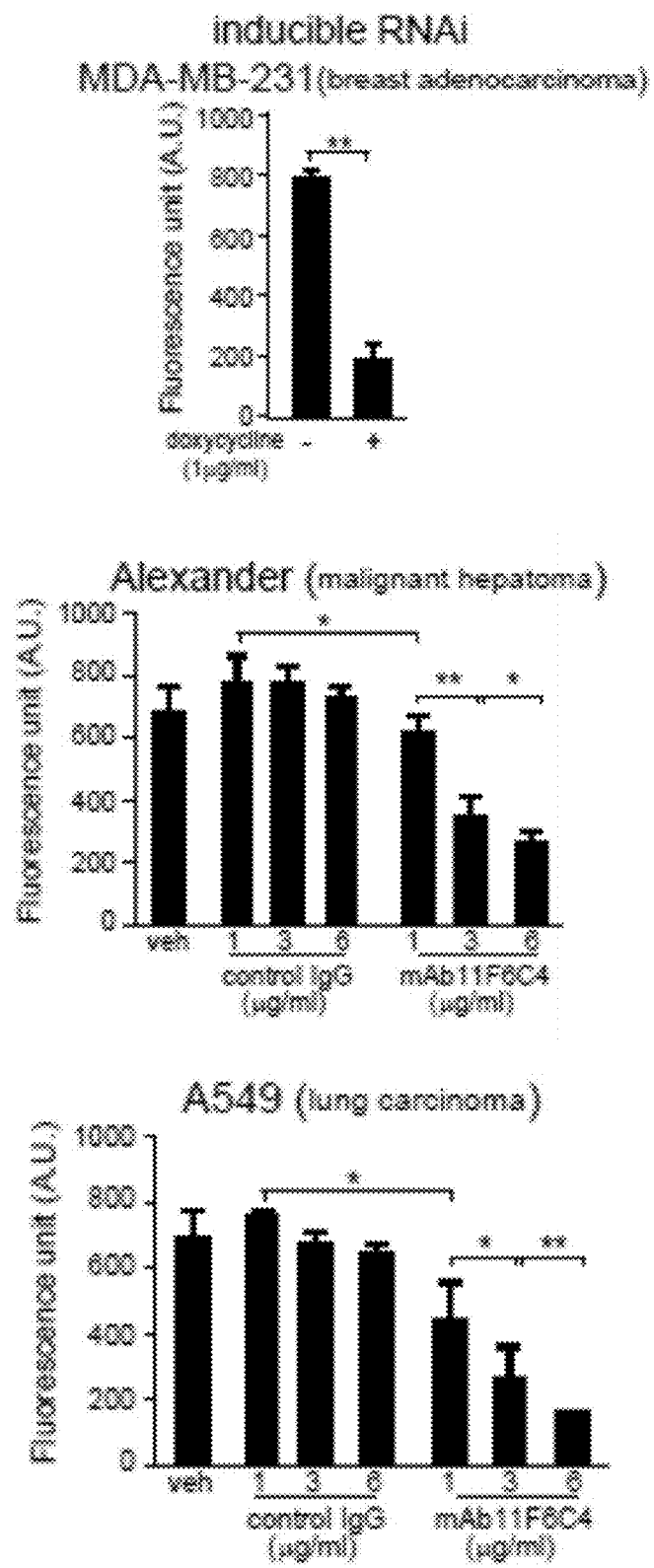
Figure 7:
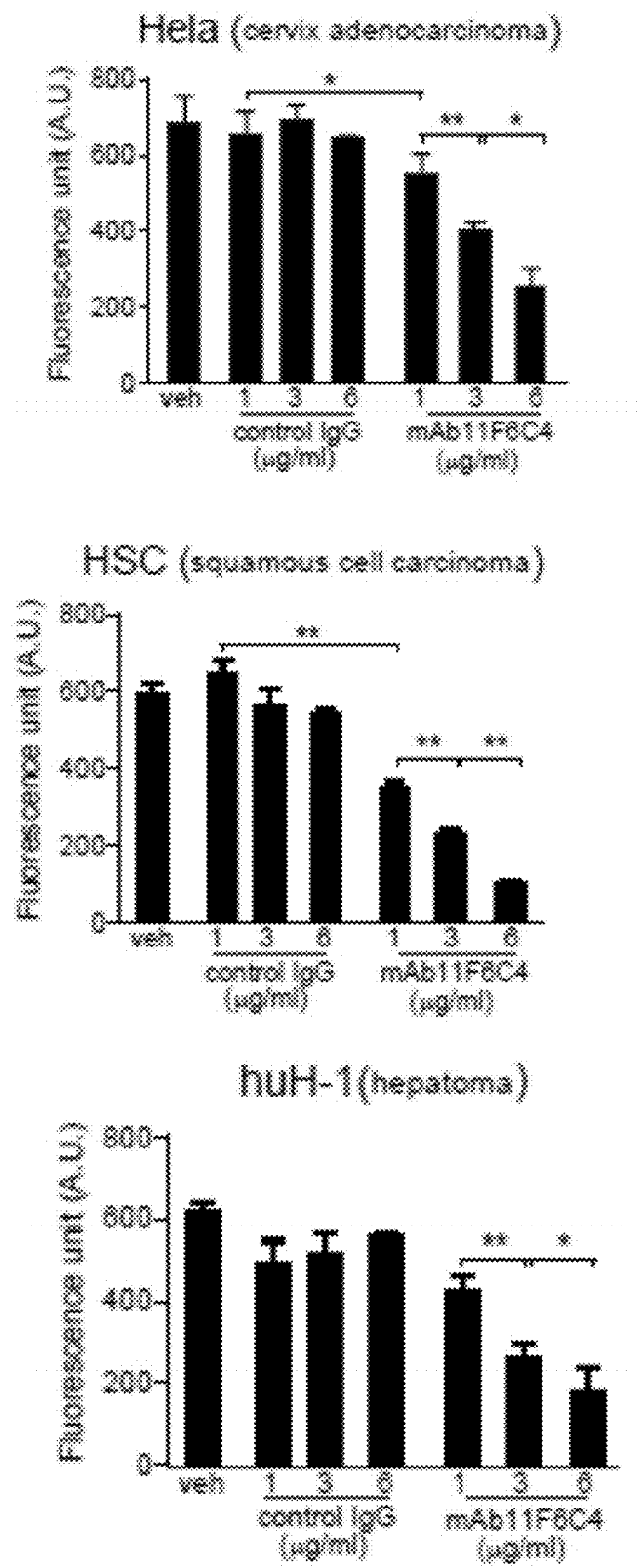
Figure 7:
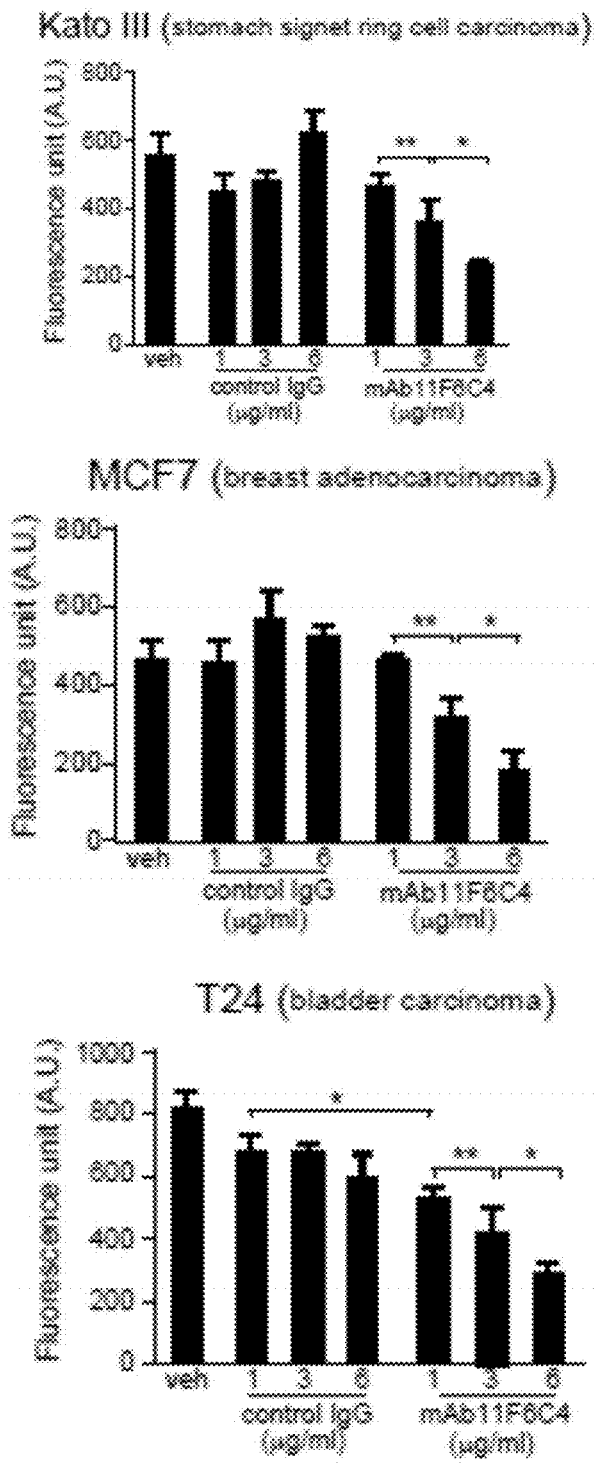
Figure 7:
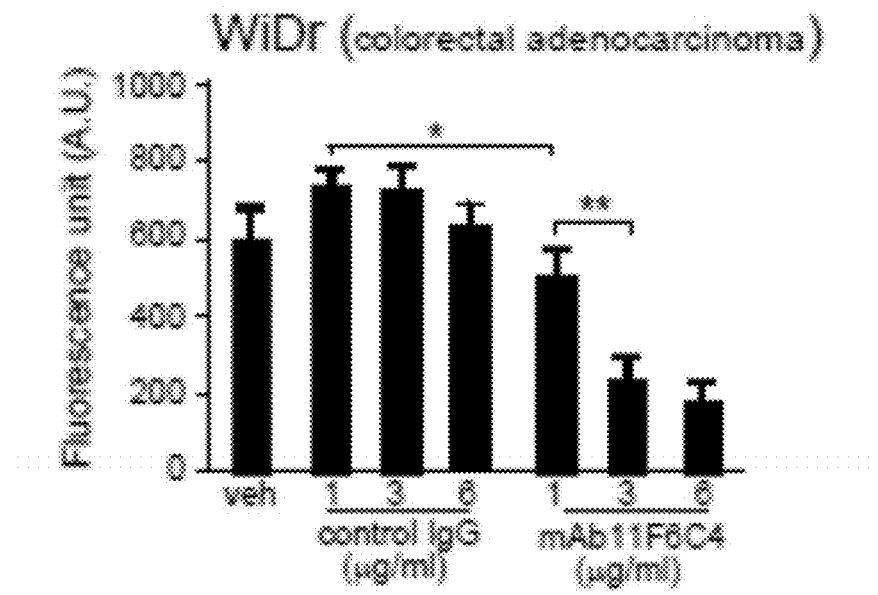
Figure 7:
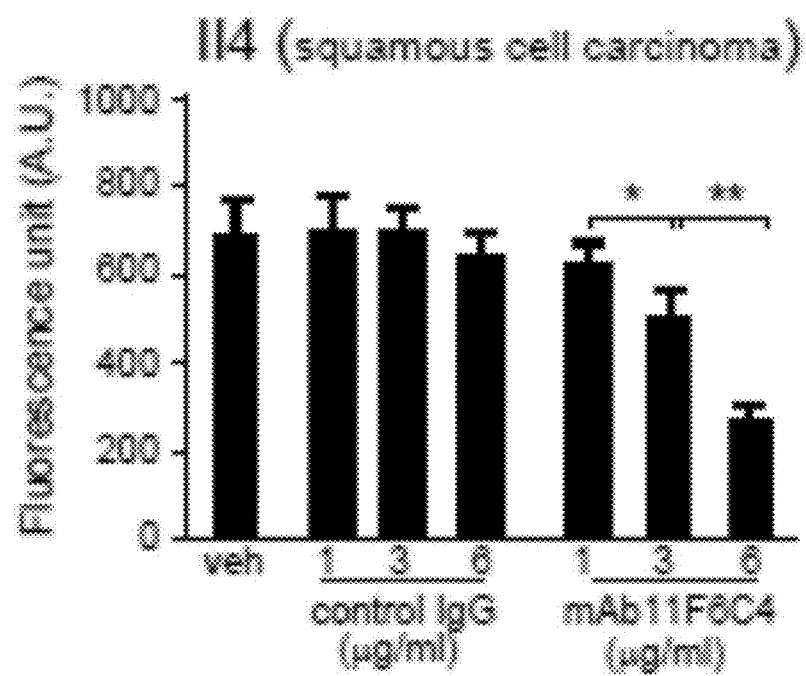

FIG. 7—Deficiency in ANGPTL4 down regulates ROS production in tumor cells.

ANGPTL4 level was suppressed either by inducible RNAi or by immunosuppression with mAb11F6C4 (10 μg/ml). Intracellular ROS production (in fluorescence units) was evaluated by means of CM-H$_2$DCFDA fluorescence dye. For MDA-MB-231, ROS was measured after 24 h treatment with 1 μg/ml doxycycline which suppressed endogenous ANGPTL4 by 85% (see FIG. 4). Other cells were placed in suspension for 2 h in the presence of increasing concentrations of either pre-immune IgG or Ab11F6C4, Values (mean±S.D.) from three independent experiments. *:p<0.05, **:p<0.01.

Figure 8:
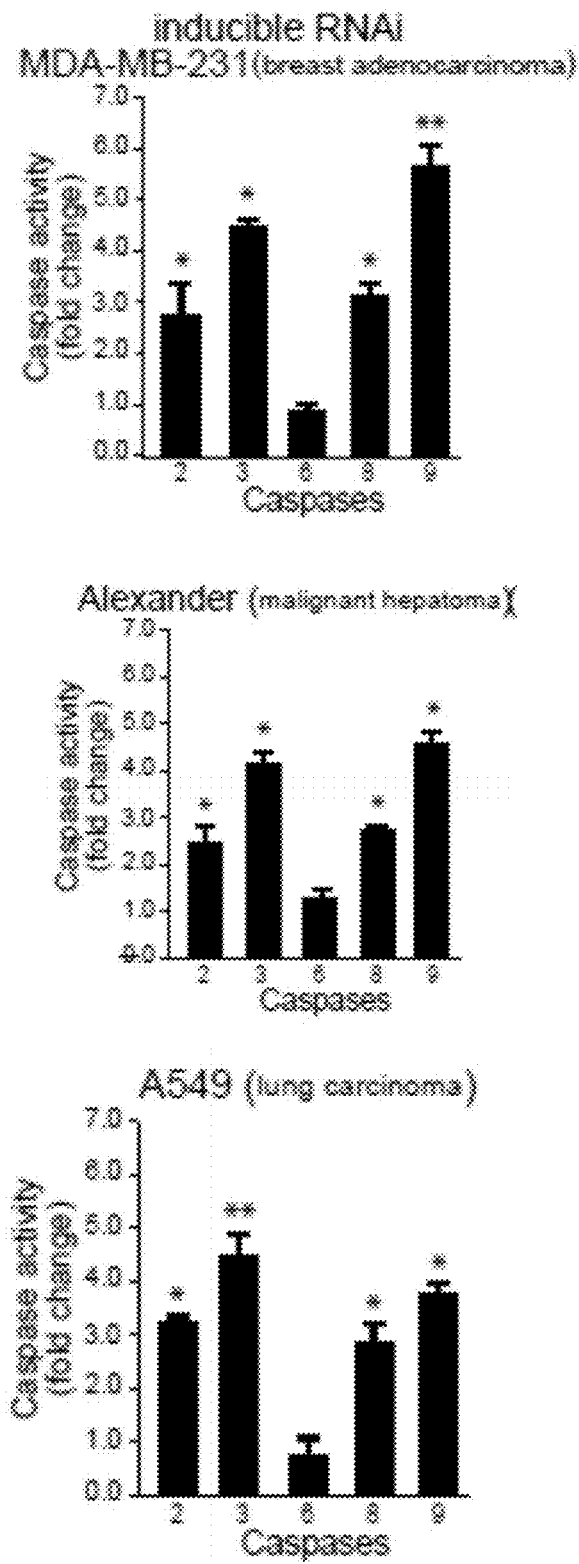
Figure 8:
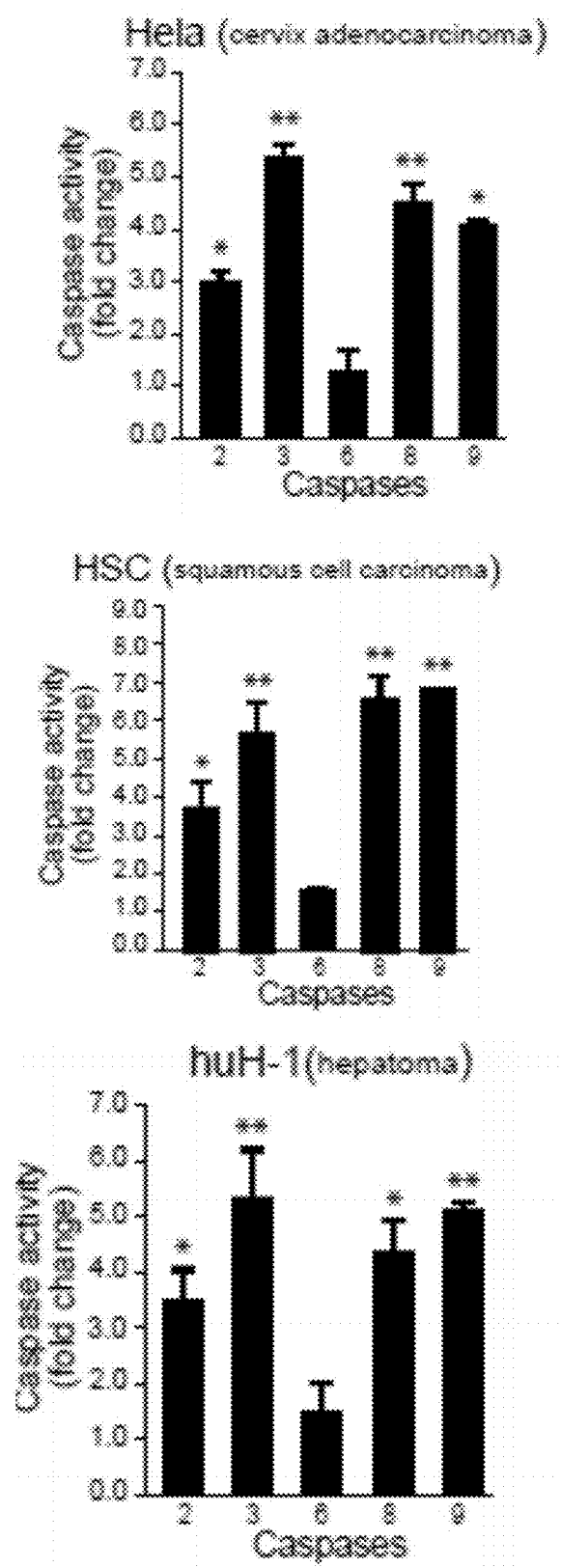
Figure 8:
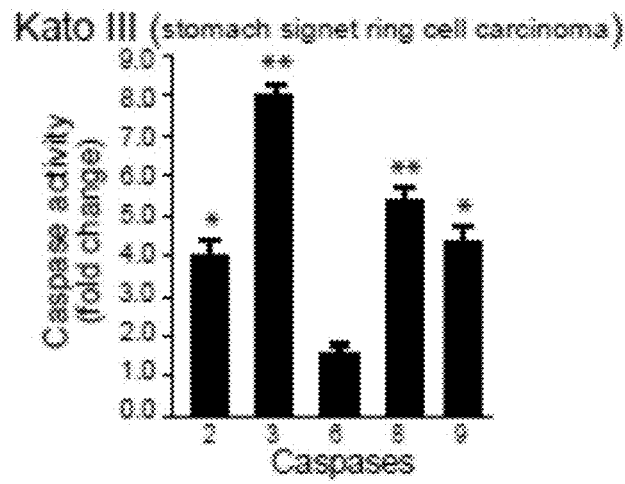
Figure 8:
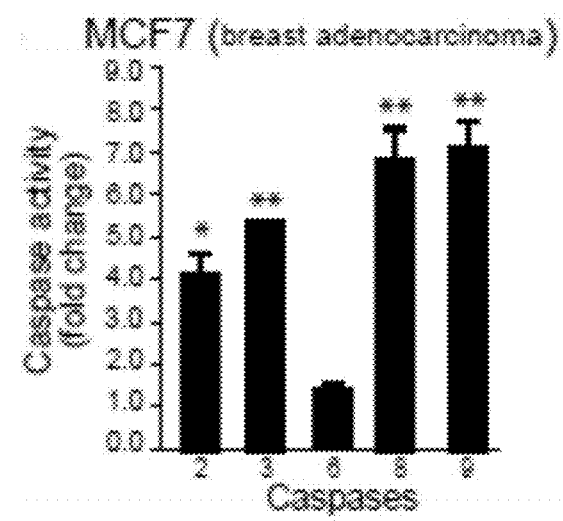
Figure 8:
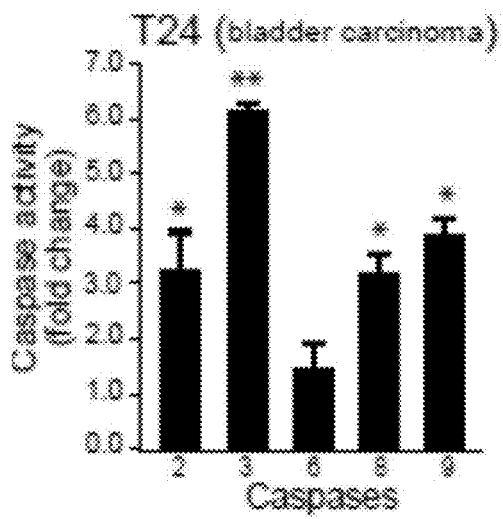
Figure 8:
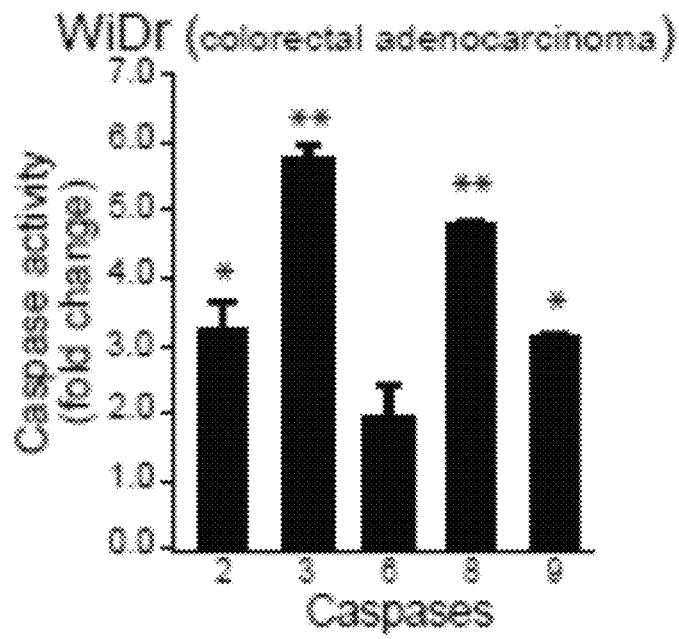
Figure 8:
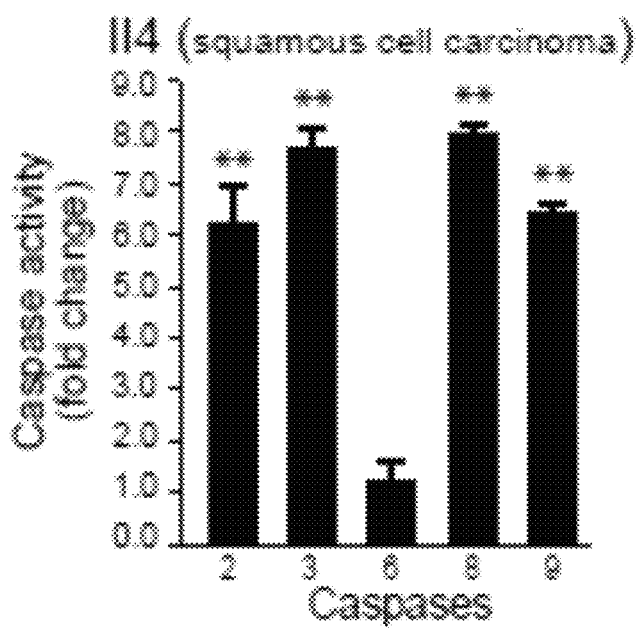

FIG. 8—Deficiency in ANGPTL4 stimulates caspases 2, 3, 8 and 9 activities in tumor cell lines.

Activities of caspases 2, 3, 6, 8, 9 were measured after 2 h of anoikis Fold-increase in caspase activities was calculated by comparing with the caspase activities with pre-immune IgG or, for MDA-MB-231 in the absence of doxycycline. Values (mean±S.D.) from three independent experiments. *:p<0.05, **:p<0.01.

FIG. 9—The effect of the antibody on vascularisation A-C.

Figure 10A:
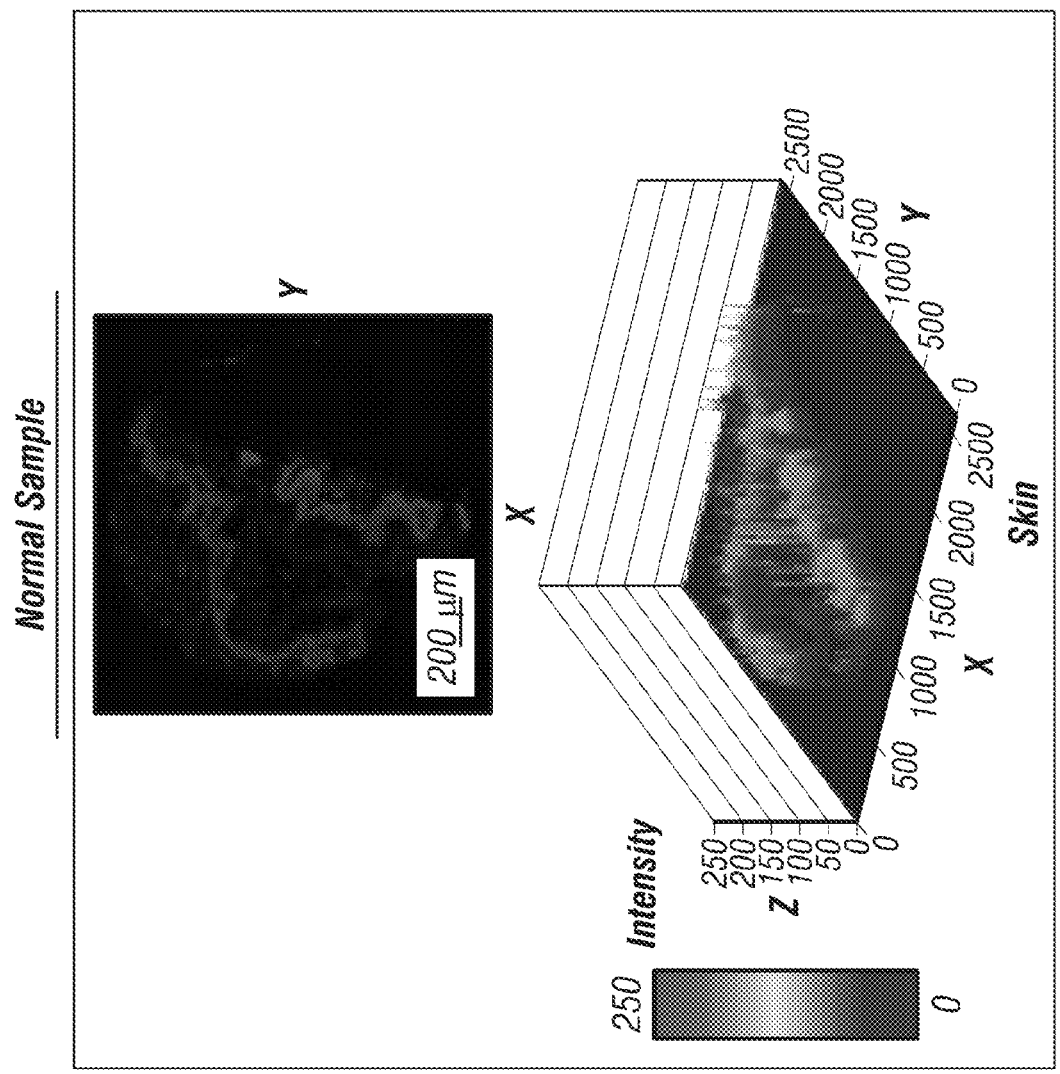
Figure 10:
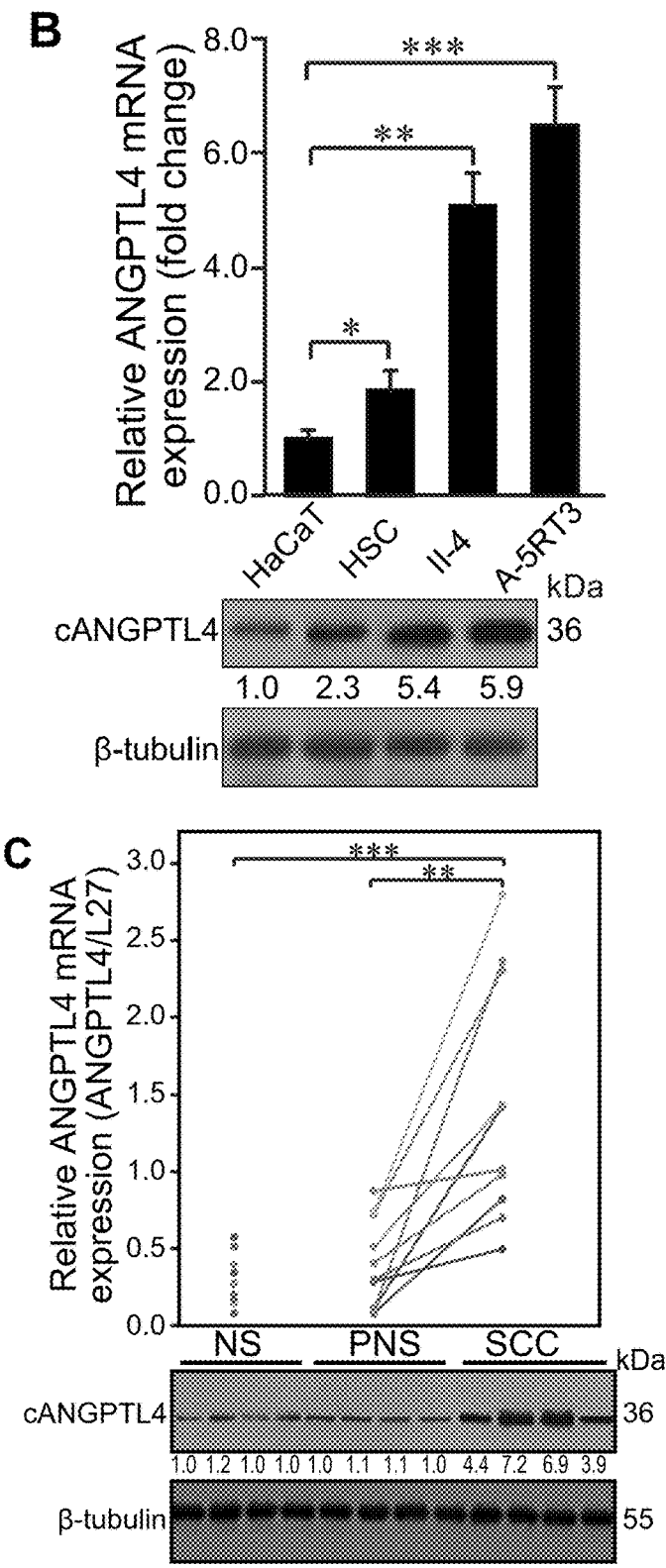
Figure 10:
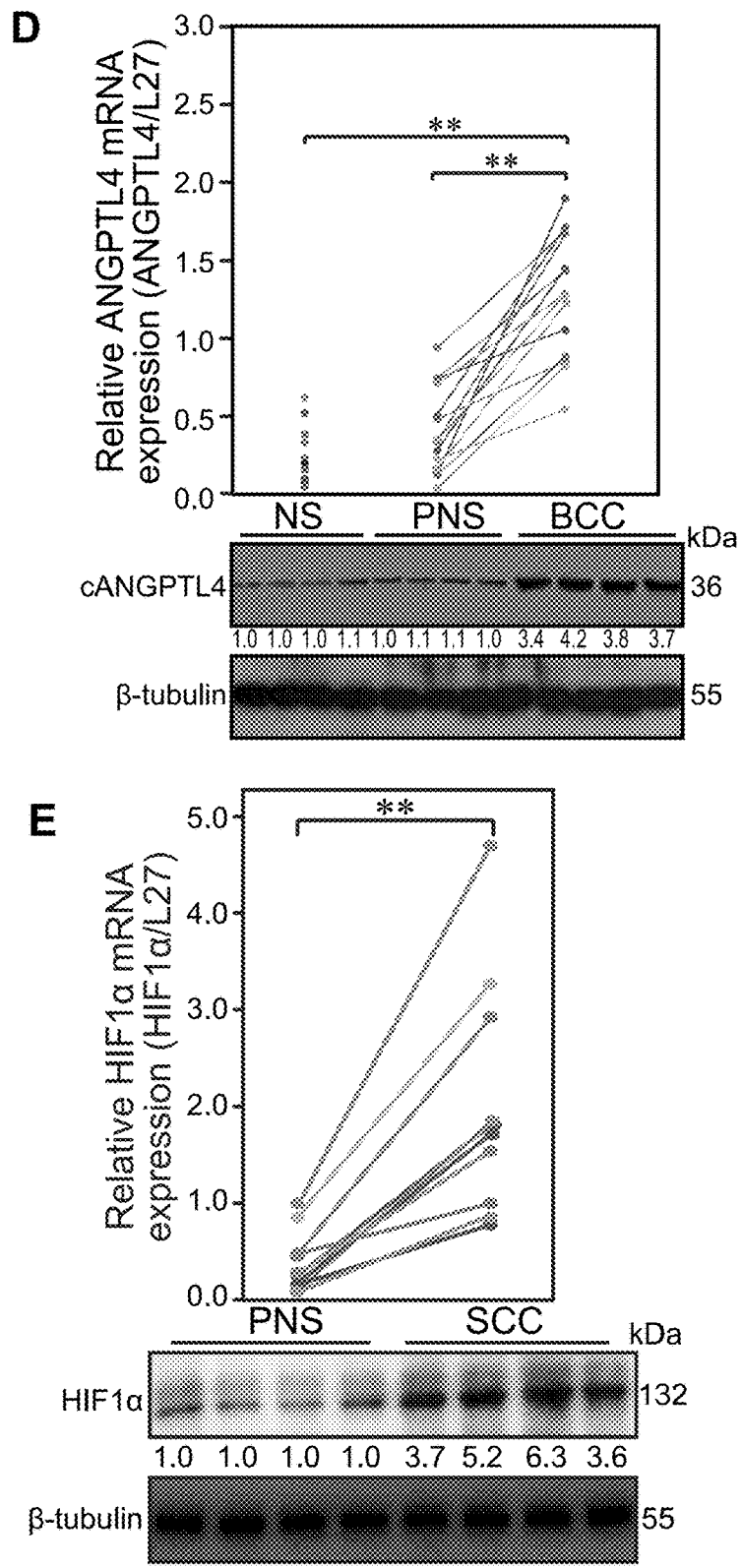
Figure 10:
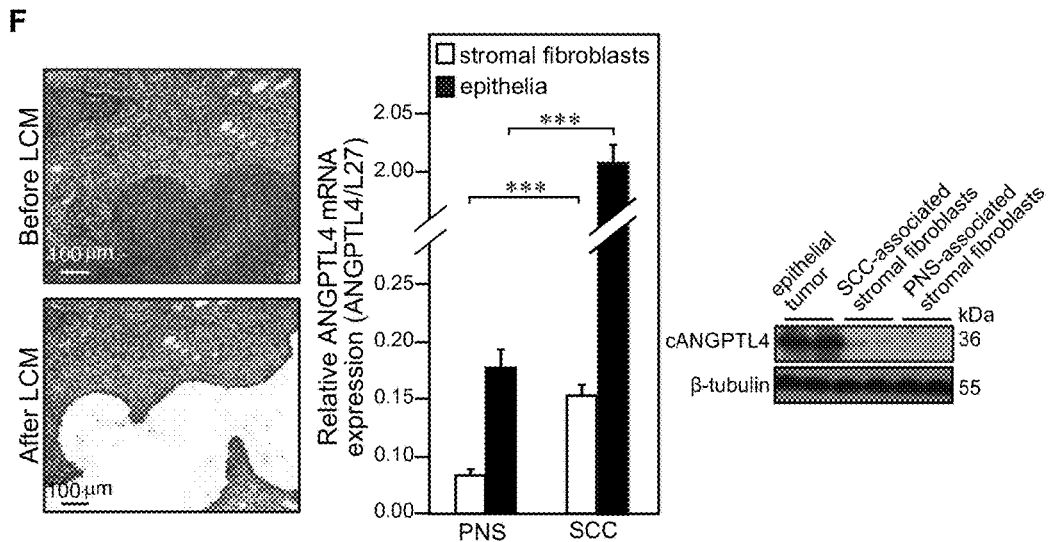

FIG. 10. Elevated Expression of ANGPTL4 in Various Tumor Types.

FIGS. 10A-10A9 illustrate ANGPTL4 expression varied among tumors procured from different anatomic sites. Heatmap profiles generated from immunofluorescence images using IMAMS (Bitplane Scientific Software). X and Y axes represent the length and width; Z axis represents in intensity. Representative images of normal skin and skin tumor samples with their corresponding heatmaps were shown. The heatmaps from same anatomic sites were grouped horizontally. Results are representative of two independent experiments with duplicates, Scale bars represent 200 lam, See Figure S1A-C.

(B) Relative ANGPTL4 mRNA and protein levels in non-tumorigenic skin line HaCaT and tumorigenic skin lines HSC, II-4, and A-5RT3. See FIG. 18D.

(C-D) Relative ANGPTL4 mRNA and protein levels in paired human squamous cell carcinoma (SCC) (C) or basal cell carcinoma (BCC) (D) and cognate peri-tumor normal sample (PNS). Skin biopsies from normal human skin (NS) served as additional controls. Three SSCs with the highest mRNA ANGPTL4 levels corresponded with an invasive prognosis. See FIG. 18E.

(E) Relative mRNA and protein levels of HIF1α in paired human SCC and PNS. For qPCR results, data spots from same individual were linked by coloured lines. See FIG. 18F.

(B-E) mRNA data shown are mean±SD from two independent qPCR experiments with triplicates. Ribosomal protein L27 (L27) was used as reference housekeeping gene. *p<0.05; p<0.01; *p<0.001. Immunoblot data was from three independent experiments with duplicates. For immunoblot, -tubulin served as loading and transfer control, and only cANGPTL4 was detected for immunoblot.

(F) Relative ANGPTL4 mRNA and protein levels in laser capture microdissected (LCM) epithelial cells and stromal fibroblasts from paired SCC and PNS. Hematoxylin and eosin images of SCC section, before and after LCM of epithelial tissue were shown in the left panel. Scale bars represent 100 μm. Microdissected tissues were processed for qPCR (middle panel) and immunoblot (right panel) analyses.

Figure 11:
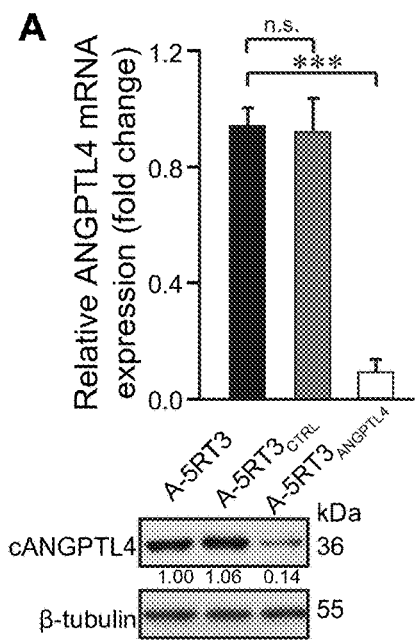
Figure 11:
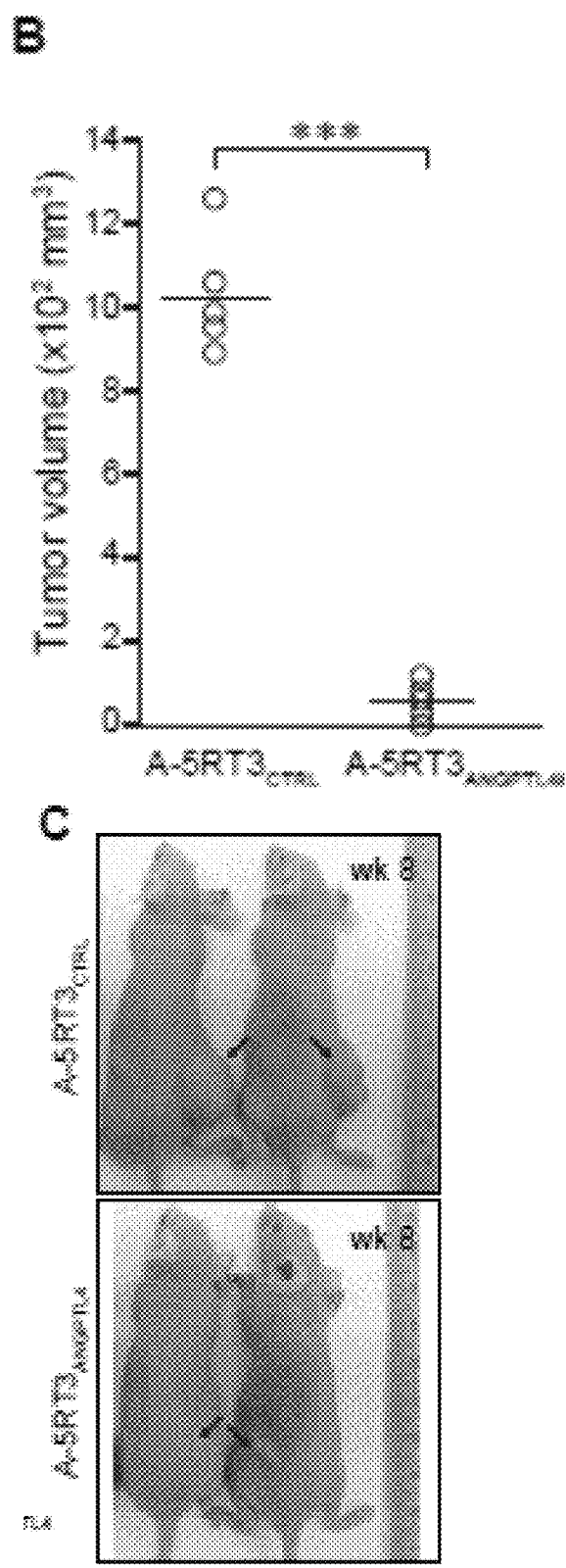
Figure 11:
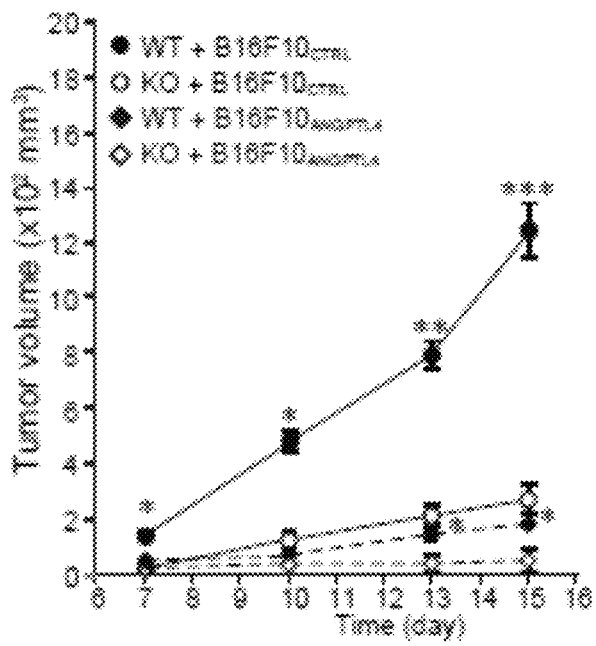
Figure 11:
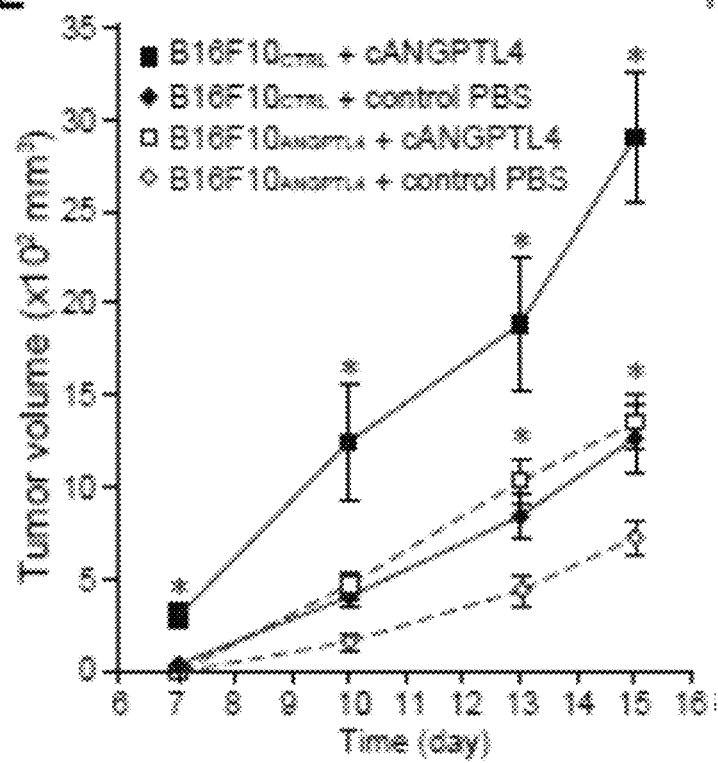
Figure 11:
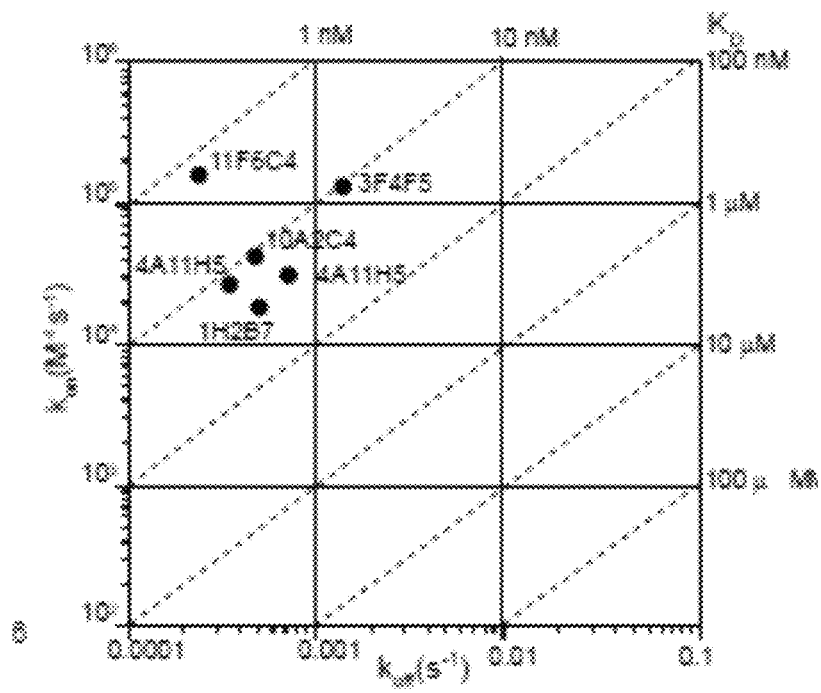
Figure 11:
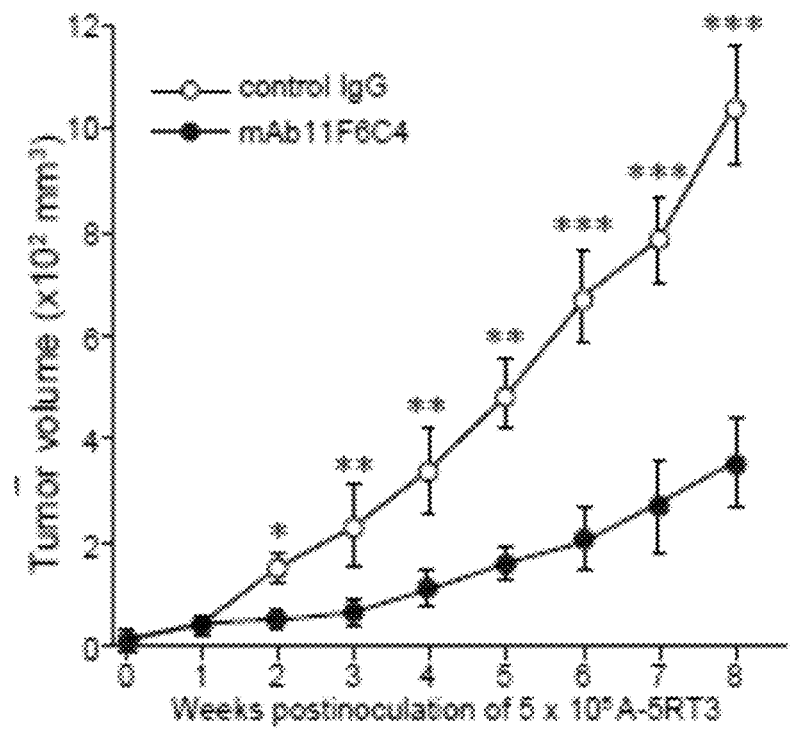
Figure 11:
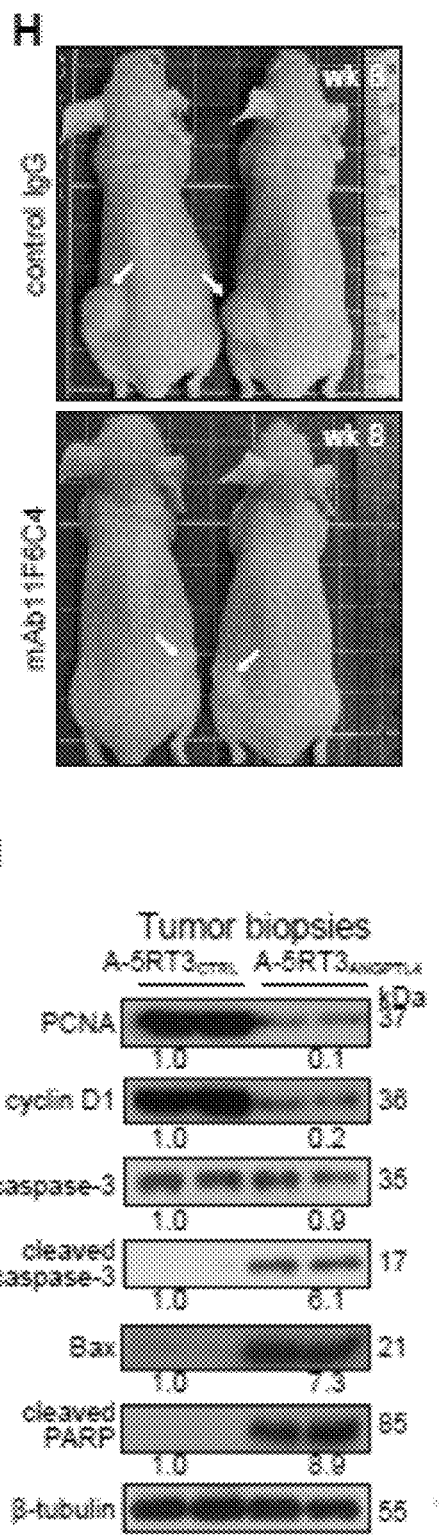
Figure 11:
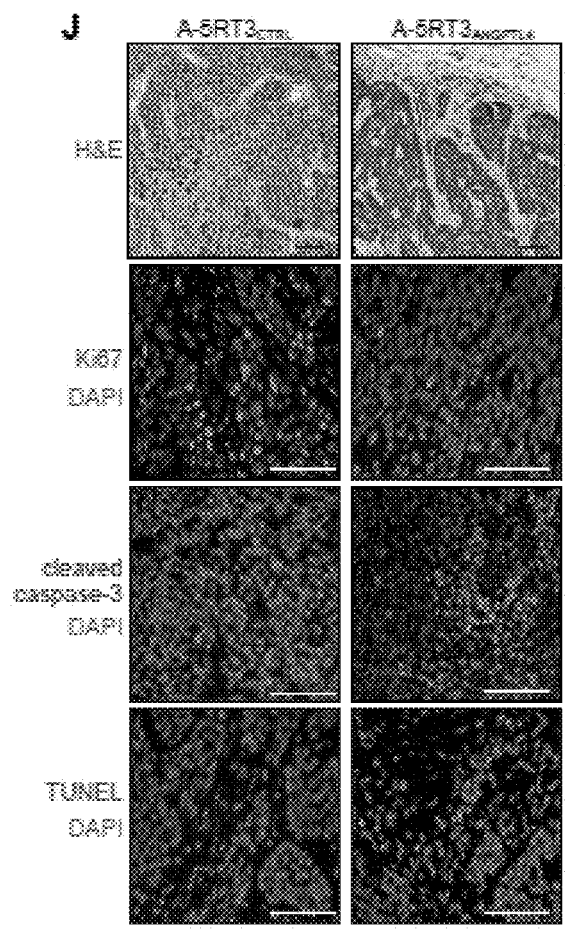
Figure 11:
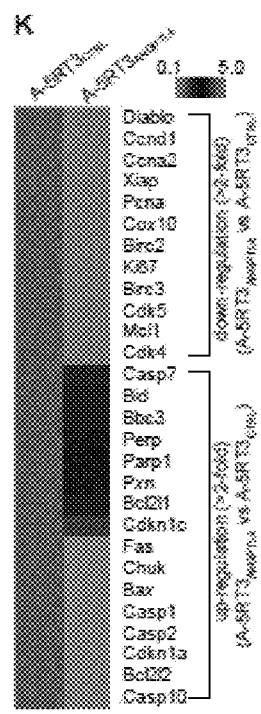

FIG. 11. Suppression of ANGPTL4 Impairs Tumorigenicity.

(A) Relative ANGPTL4 mRNA and protein levels in A-5RT3 (parental), A-5RT3$_{CTRL}$ (scrambled control) and A-5RT3$_{ANGPTL4}$ (knockdown) cells. Data are mean±SD from three independent qPCR experiments with triplicates. Ribosomal protein L27 (L27) was used as reference housekeeping gene. Immunoblot data was from three independent experiments with duplicates. -tubulin served as loading and transfer control. ***p<0.001; n.s. denotes not significant.

(B) Size of xenograft tumors induced in nude mice by 5×10$^5$ of A-5RT3$_{ANGPTL4}$ or A-5RT3$_{CTRL}$ after 8 weeks post-inoculation (n=5 each group). Each circle represents mean size from three measurements on each mouse at wk 8. ***p<0.001. See FIG. 19B.

(C) Representative pictures of A-5RT3$_{CTRL}$ and A-5RT3$_{ANGPTL4}$-induced tumors (wk 8) in (B). Black arrows indicate inoculation sites.

(D-E) Size of tumor volume induced in ANGPTL-knockout (KO) and wildtype (WT) mice (D), and PBS- or recombinant cANGPTL4-treated C57BL/6J WT mice (E) by B16F10 melanoma (B16F10$_{CTRL}$, control) and ANGPTL4-knockdown (B16F10$_{ANGPTL4}$). 1×10$^6$ indicated cells were s.c. inoculated for each mice. Mice were treated i.v. with either 3 mg/kg of cANGPTL4 or vehicle PBS thrice weekly (n=6 each group) Values are mean±SEM from three measurements on each mouse. *p<0.05; p<0.01; *p<0.001). See FIG. 19C-D.

(F) ANGPTL4 interaction kinetic maps for human monoclonal antibodies (mAbs), shown as association and dissociation rate constant ($k_{on}$ and $k_{off}$), and a combination of $k_{on}$ and $k_{off}$ that results in the same affinity constant ($K_D$) values (diagonal lines) as determined by surface plasmon resonance (SPR). Labels in maps identify the 6 mAb clones. mAb11F6C4 was chosen for subsequent immunotherapy experiment based on its superior $k_{on}$, $k_{off}$ and $K_D$ value.

(G) Tumor volume in nude mice injected s.c. with 5×10$^5$ of A-5RT3 and treated i.v. with 30 mg/kg/week of either mAb11F6C4 or control IgG as a function of time (n=6 for each group). Each circle represents mean±SEM from three measurements on each mouse. *p<0.05; p<0.01; *p<0.001.

(H) Representative pictures of control IgG- or mAb11F6C4-treated nude mice (wk 8) as described in (G). White arrows indicate A-5RT3 inoculation sites (I) Immunoblot of proliferation (PCNA and cyclin D1), and apoptosis (cleaved caspase-3, Bax and cleaved PARP) markers in A-5RT3$_{ANGPTL4}$- and A-5RT3$_{CTRL}$-induced tumor biopsies. Immunoblot data was from three independent experiments with duplicates. β-tubulin served as loading and transfer control (J) Hematoxylin and eosin (H&E) and immunofluorescence staining of A-5RT3$_{CTRL}$- and A-5RT3$_{ANGPTL4}$-induced tumor sections. Proliferating (Ki67) and apoptotic (cleaved caspase-3 or TUNEL) cells were identified using indicated antibodies or assay. Sections were counterstained with DAPI (blue). Scale bars represent 40 μm.

(K) Heatmap showing genes up- and down-regulated in A-5RT3$_{ANGPTL4}$-induced tumors relative to A-5RT3$_{CTRL}$-induced tumors as determined by qPCR. Results were generated from three pairs of indicated tumors. Three independent qPCR experiments with triplicates were performed. Ribosomal protein L27 (L27) was used as reference housekeeping gene. Detailed description of the genes and expression see Table 1.

(I-K) All experiments were performed using tumor biopsies harvested from mice described in (B-C) at wk 8.

Figure 12:
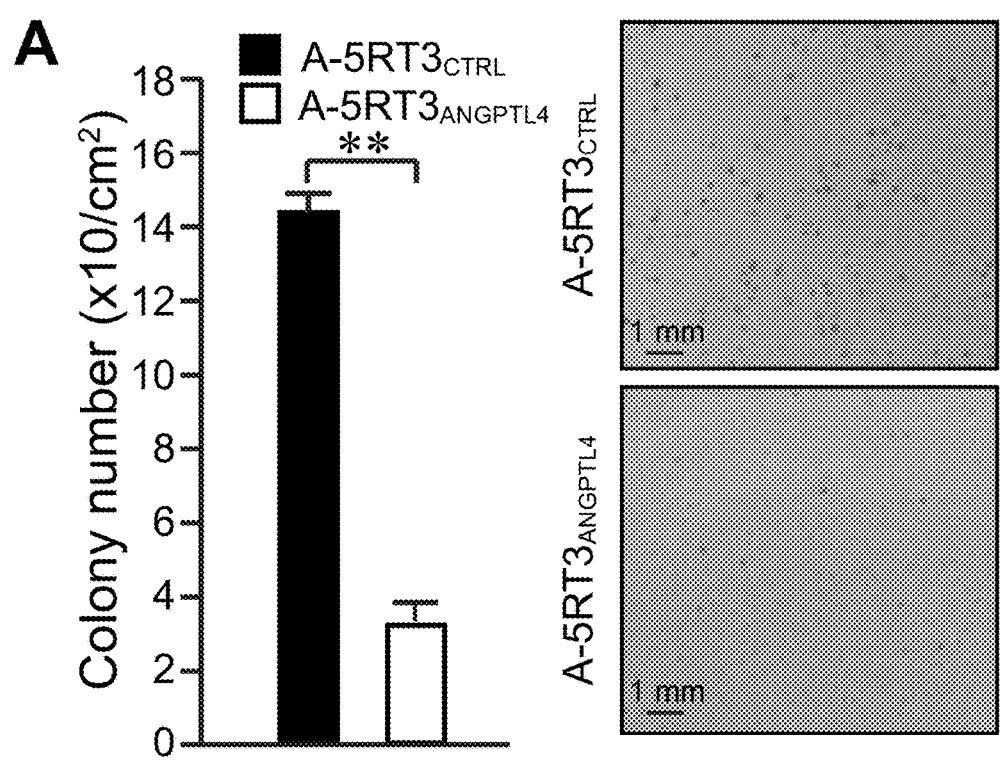

FIG. 12. ANGPTL4 Interacts with Integrins β1 and β5 to Confer Tumor Cells Anoikis Resistance.

(A) Quantification of A-5RT3$_{CTRL}$ and A-5RT3$_{ANGPTL4}$ tumor colonies on soft agar (left panel). Values (means±SD) were obtained from four independent assays with triplicates. **p<0.01. Representative pictures were shown in the right panel. Scale bars represent 1 mm.

(B) Percentage of apoptotic A-5RT3$_{CTRL}$ and A-5RT3$_{ANGPTL4}$ after 2 h of anoikis as analyzed by FACS (5000 events). The sum of Annexin V$^+$/PI$^-$ (early apoptosis) and Annexin V$^+$/PI$^+$ (late apoptosis) cells were considered apoptotic. Values (bold) denote apoptotic cells (%). Results are representative of three independent experiments.

(C) Relative activities of caspases 2, 3, 6, 8, 9 in A-5RT3$_{ANGPTL4}$ compared with A-5RT3$_{CTRL}$ (assigned value 1) after 2 h of anoikis Values (means±SD) were obtained from three independent experiments with triplicates. *p<0.05, **p<0.01.

(D) Percentage of anoikis-induced apoptotic A-5RT3$_{ANGPT4}$ in the presence of increasing exogenous recombinant cANGPTL4 as analyzed by FACS (5000 events). Vehicle (PBS) treated A-5RT3$_{CTRL}$ and A-5RT3$_{ANGPTL4}$ served as controls for comparison. Apoptotic index as described in (B). See FIG. 20A-C.

(E-F) Representative sensorgrams of three independent experiments showing binding profiles between immobilized-ANGPTL4 and integrin 01 (E) and integrin β5 (F). Integrin β3 at 75 nM did not show any detectable interaction (F, dotted red line). Sensorgram was corrected against a reference flow cell with no immobilized protein. $K_D$ ~10$^{-7}$ M was determined after global fitting (Langmuir 1:1 model) using Scrubber2.

(G-H) Representative sensorgrams showed dose-dependent blocking of integrin β1 (G) and integrin β5 (H) to immobilized-ANGPTL4 by pre-injection with different indicated concentrations of mAb11F6C4. See FIG. 20D-G.

(I-J) In situ proximity ligation (PLA) assay detection of ANGPTL4:integrin β1 (I, left two panels), ANGPTL4: integrin 5 (I, right two panels), and phosphorylated FAK (J) in A-5RT3$_{ANGPTL4}$- and A-5RT3$_{CTRL}$-induced tumor biopsies. Higher magnification images are shown in (H, 2$^{nd}$ and 4$^{th}$ panels; J, right panel). PLA signals are shown in red and nuclei are stained blue by Hoechst dye. Images were acquired in one z-plane using a Zeiss LSM710 META confocal laser scanning microscope. Negative controls were performed with only anti-nANGPTL4 (I) or anti-FAK (J) antibodies. Scale bars represent 40 μm.

(K) Immunoprecipitation and immunodetection of ANGPTL4, integrin β1, integrin β5, total FAK, phosphorylated FAK (pY397FAK), total Rac1 and GTP-bound Rac1 (GTP-Rac1), from indicated tumor sections. Configuration-specific monoclonal anti-Rac-GTP antibody (NewEast Biosciences) was using for immunoprecipitation GTP-Rac1. Total FAK served as loading and transfer control. Experiments in (I-K) were performed using tumor biopsies harvested from A-5RT3$_{CTRL}$- or A-5RT3$_{ANGPTL4}$-inoculated (5×10$^5$ cells each) nude mice at wk 8 (FIG. 11B-C). See FIG. 20H-J. All experiments in (B-K) were repeated for at least three times with consistent results.

Figure 13:
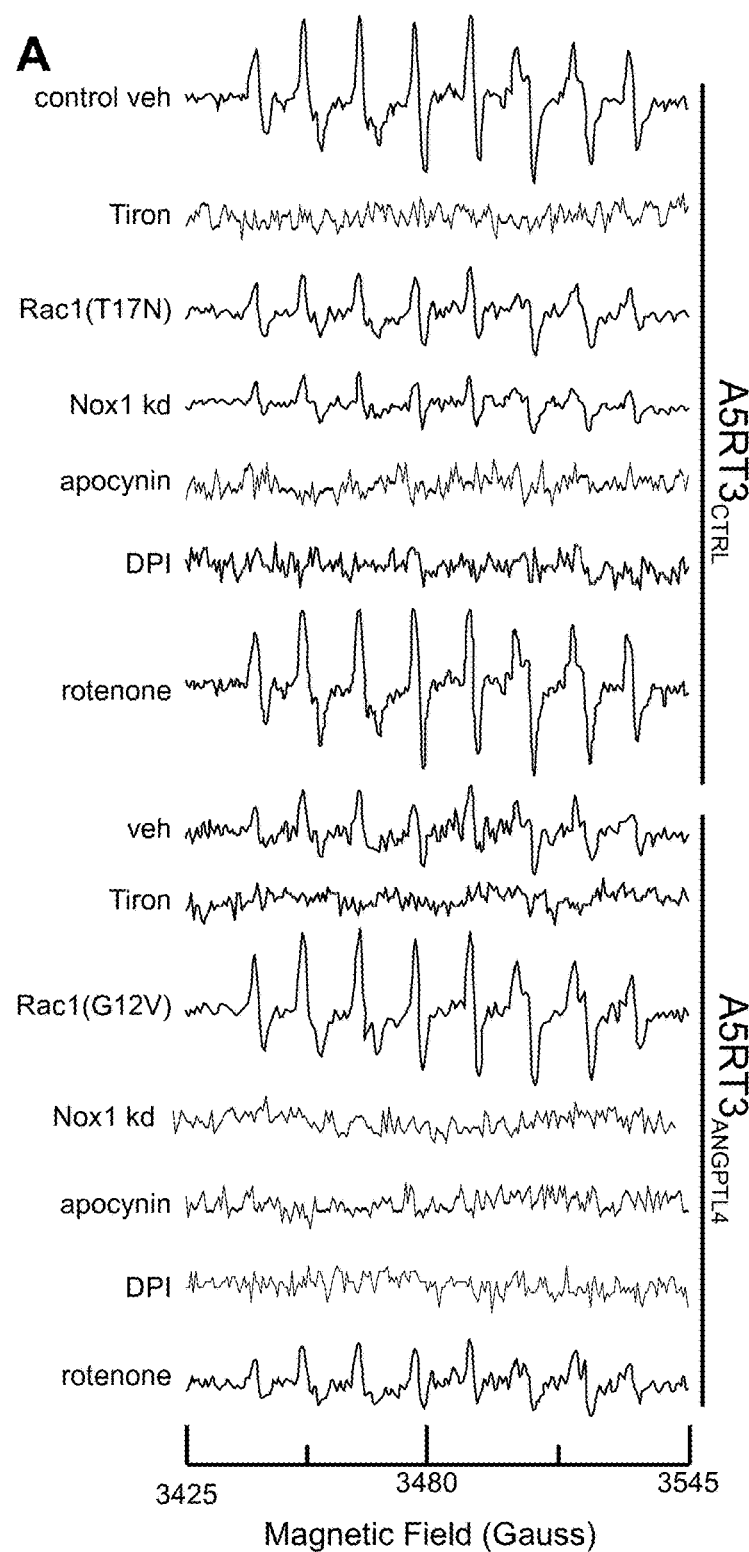
Figure 13:
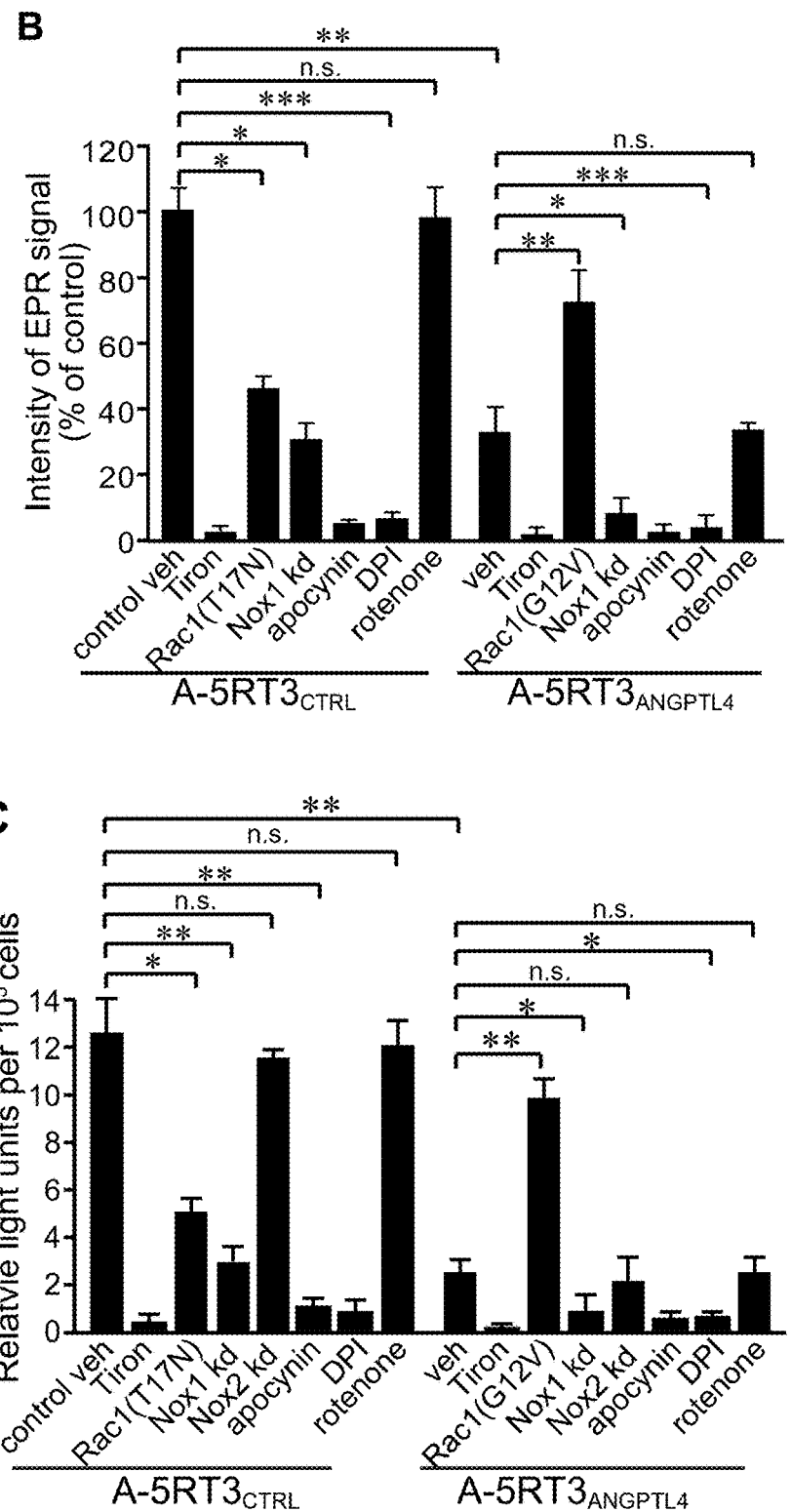
Figure 13:
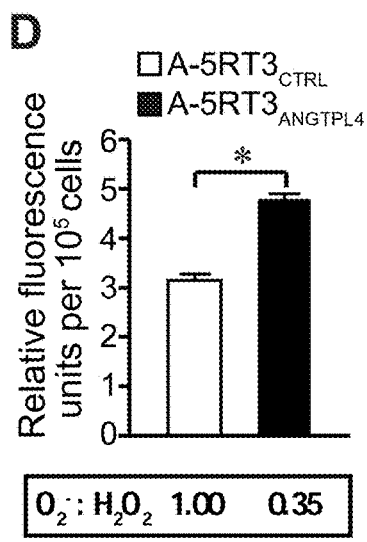
Figure 13:
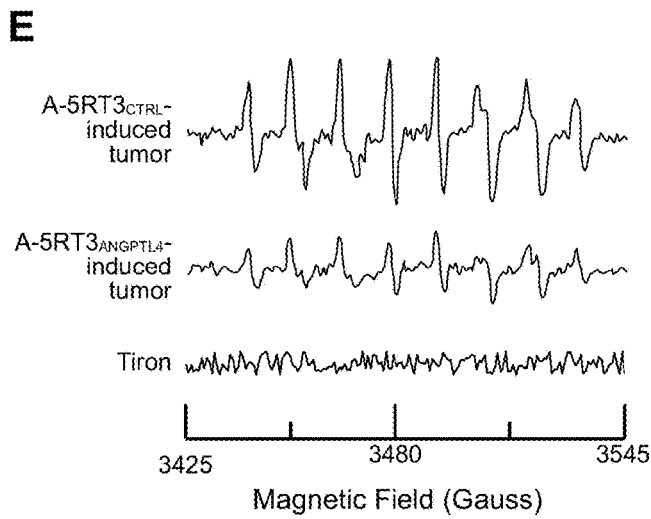
Figure 13:
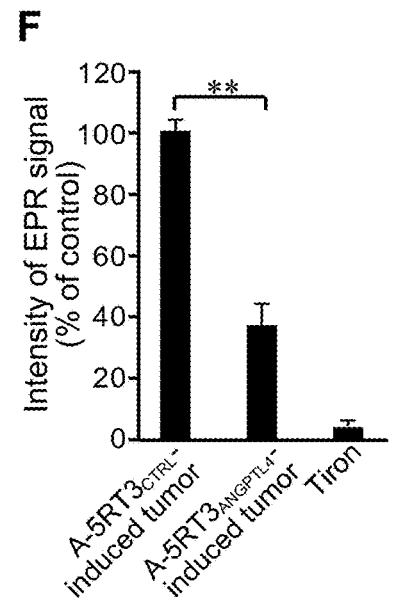
Figure 13:
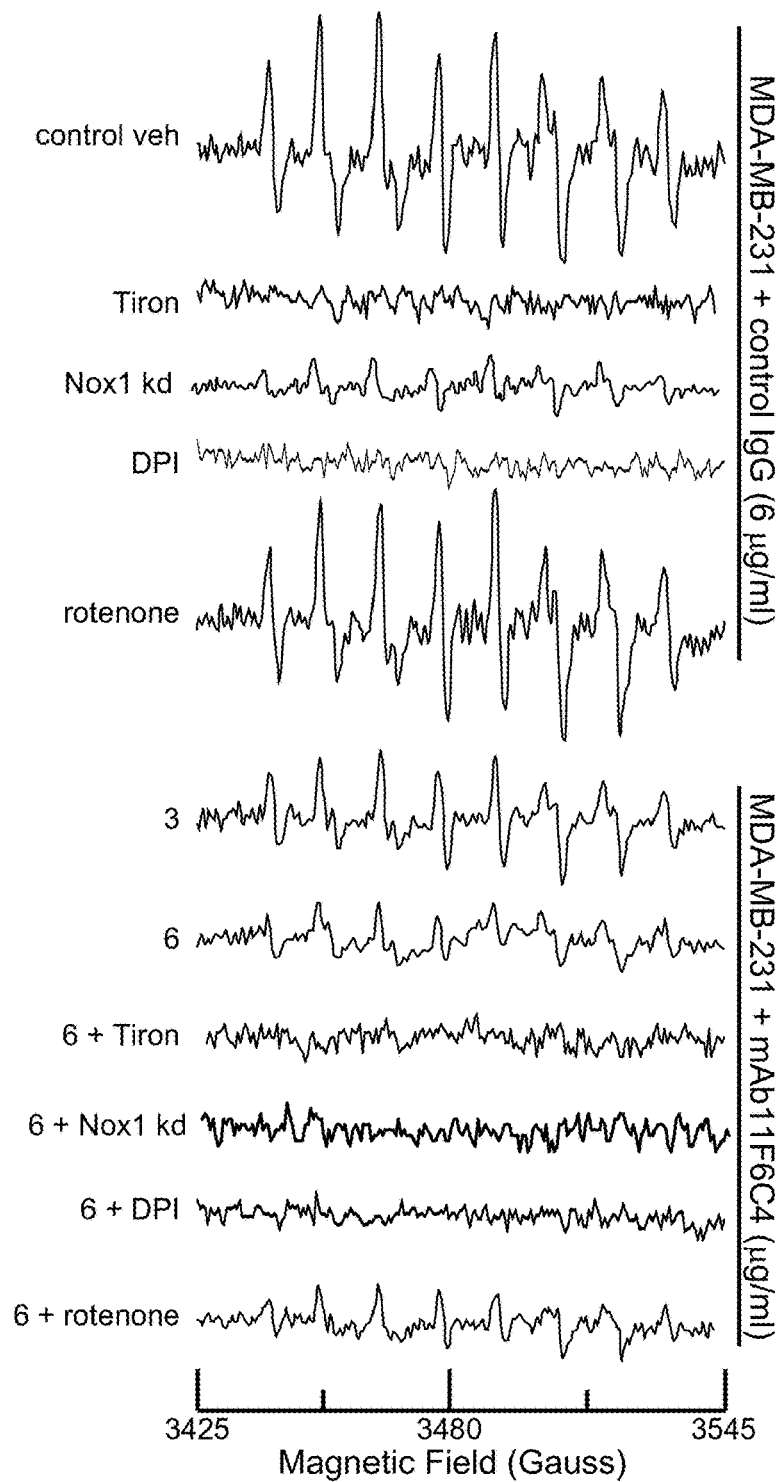
Figure 13:
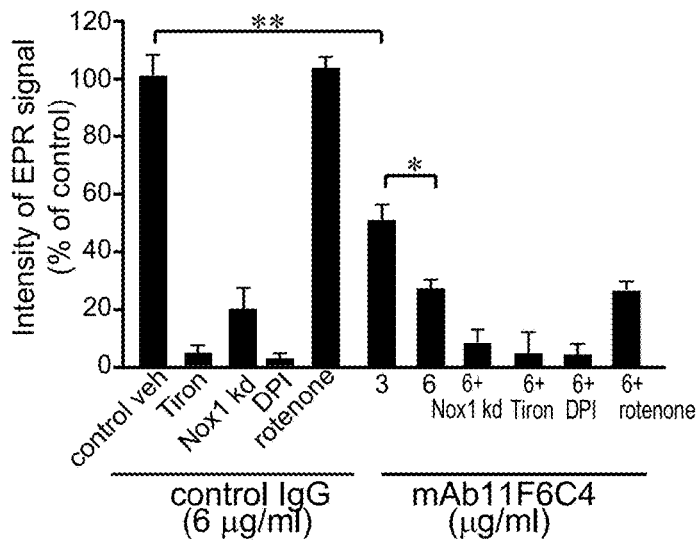
Figure 13:
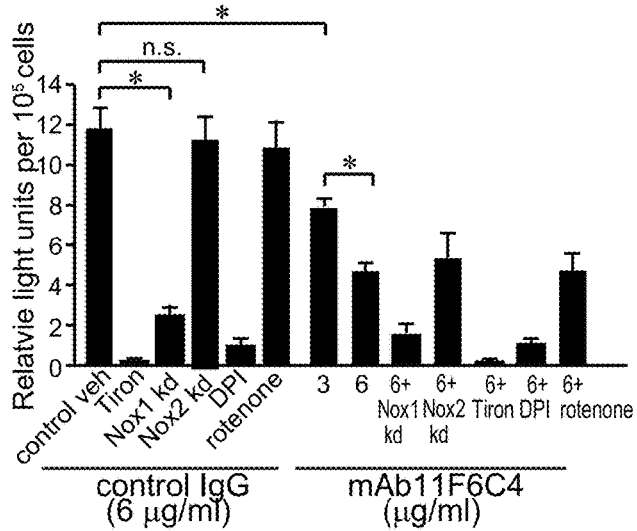
Figure 13:
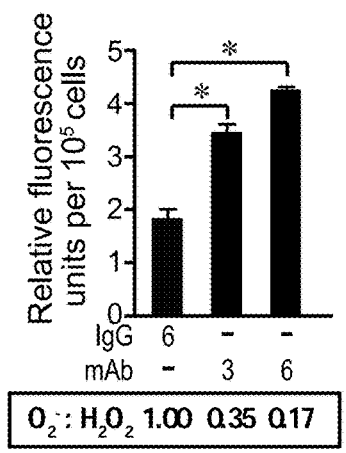

FIG. 13. ANGPTL4 Elevates $O_2^-$ Level and Maintains Relatively High $O_2^-$:$H_2O_2$ Ratio in Tumor Cells.

(A, E and G) Representative electron paramagnetic resonance (EPR) spectra of DEPMPO-superoxide spin adduct from A-5RT3$_{CTRL}$ and A-5RT3$_{ANGPTL4}$ (A), A-5RT3$_{CTRL}$- and A-5RT3$_{ANGPTL4}$-induced tumor (E) or MDA-MB-231 (G) in the absence or presence of indicated chemicals or inhibitors. MDA-MB-231 cells were treated with mAb11F6C4 (3 or 6 µg/ml) or control IgG (6 µg/ml). A-5RT3$_{CTRL}$ and A-5RT3$_{ANGPTL4}$ were transiently transfected with vector expressing Rac1(T17N) or Rac1(G12V), respectively. A-5RT3$_{CTRL}$, A-5RT3$_{ANGPTL4}$ and MDA-MB-231 were transiently transfected with ON-TARGETplus siRNA (Dharmacon) against either Nox1 (Nox1 kd) or Nox2 (Nox2 kd). Superoxide adduct of DEPMPO has a hyperfine splitting constants of $a_N$=13.13 G; ap=55.61 G; $a^β_H$=13.11 G; $a^γ_H$=0.71, 0.42, 0.7, 0.25, and 0.6 G. See FIG. 21.

(B, F and H) EPR signal intensity at 3480 G from A-5RT3$_{CTRL}$ and A-5RT3$_{ANGPTL4}$ in (A), A-5RT3$_{CTRL}$- and A-5RT3$_{ANGPTL4}$-induced tumor in (E) or MDA-MB-231 in (G). Tiron treated measurement served as negative signal control.

(C and I) Measurement of $O_2^-$ levels using MCLA assay in A-5RT3$_{CTRL}$ and A-5RT3$_{ANGPTL4}$ (C), or MDA-MB-231 treated with mAb11F6C4 (3 or 6 µg/ml) or control IgG (6 µg/ml) (I) in the absence or presence of indicated chemicals or inhibitors.

(D and J) Measurement of $H_2O_2$ levels using Amplex red assay in A-5RT3$_{CTRL}$ and A-5RT3$_{ANGPTL4}$ (D), or in MDA-MB-231 treated with mAb11F6C4 (3 or 6 µg/ml) or control IgG (6 µg/ml) (J). Arbitrary relative $O_2^-$:$H_2O_2$ ratios were shown in boxes. See FIG. 21D and S4F.

(B-D and F-J) Values were normalized to total proteins and were presented as mean±SEM as were obtained from three independent experiments with triplicates. *p<0.05; p<0.01; *p<0.001; n.s. represents not significant. Vehicle-treated A-5RT3$_{CTRL}$ (B and C), A-5RT3$_{CTRL}$-induced tumor (F) and MDA-MB-231 in the presence of control IgG (6 µg/ml) (H and I) served as cognate controls.

Figure 12B:
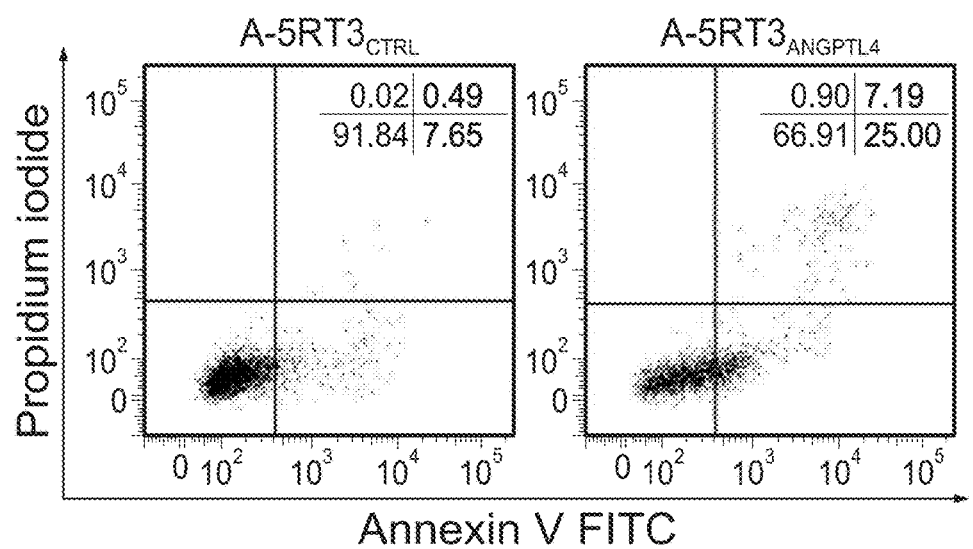
Figure 12:
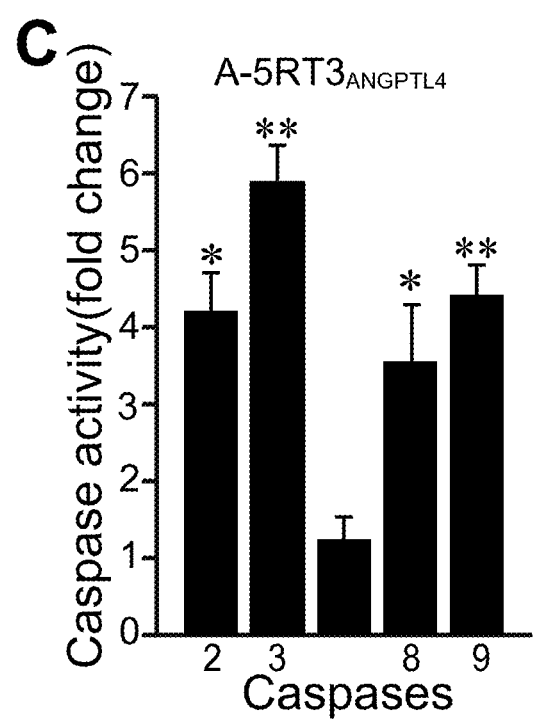

(K) Percentage of apoptotic MDA-MB-231 after 2 h of anoikis as analyzed by FACS (5000 events). Apoptotic index as described in (FIG. 12B). Values (bold) denote apoptotic cells (%) from three independent experiments.

(L) Relative activities of caspases 2, 3, 6, 8, 9 in mAb11F6C4-treated MDA-MB-231 after 2 h of anoikis Values (means±SD) were from three independent experiments with triplicates. *p<0.05; **p<0.01. Fold-increase in caspase activities was calculated by comparing with pre-immune IgG-treated MDA-MB-231.

Figure 14:
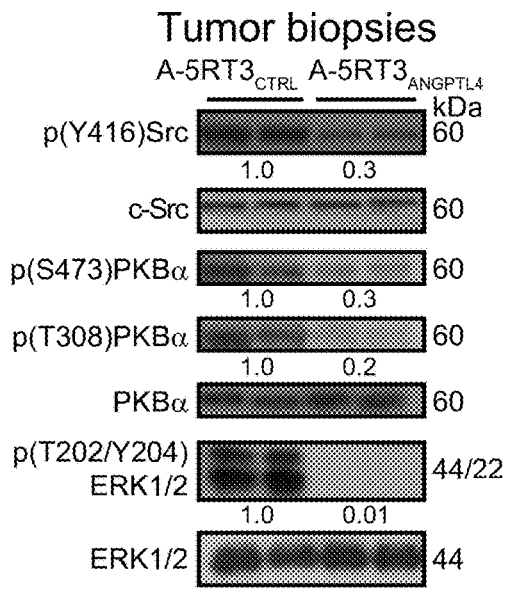
Figure 14:
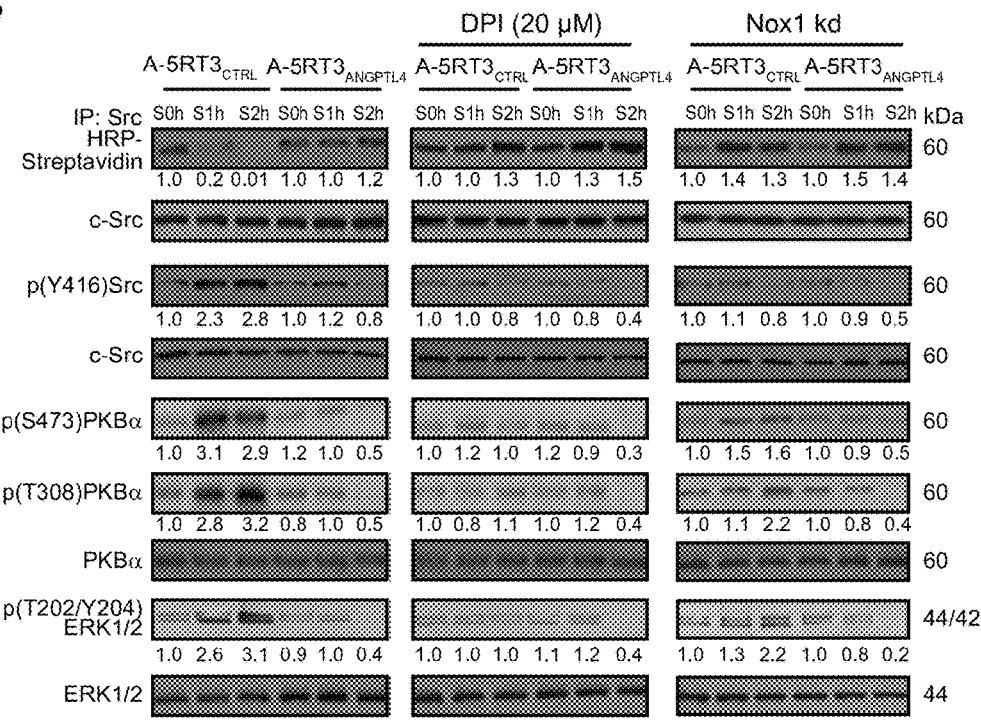

FIG. 14. ANGPTL4-mediated $O_2^-$ Regulates Src and Promotes PI3K/PKB and ERK Survival Pathways.

(A and D) Immunoblot of indicated proteins in A-5RT3$_{ANGPTL4}$- and A-5RT3$_{CTRL}$-induced tumor biopsies. Values represent mean fold change from four independent experiments. c-Src (A) and β-tubulin (D) served as respective loading and transfer control.

(B) Immunoblot of indicated proteins in A-5RT3$_{ANGPTL4}$ and A-5RT3$_{CTRL}$ in the absence or presence of 20 µM diphenylene iodonium (DPI), and in Nox1-knockdown (Nox1 kd) A-5RT3$_{ANGPTL4}$ and A-5RT3$_{CTRL}$. Cells were suspended for 0, 1 and 2 h (S0 h, S1 h and S2 h). Cell lysates were labelled with 100 µM N-(biotinoyl)-N'-(iodoacetyl) ethylenediamine to evaluate Src redox state. HRP-Streptavidin immunoblot performed on anti-Src immunoprecipitate showed reduced Src. Immunoprecipitate was probed with anti-c-Src for normalization. Values (mean±SD) represent mean fold change against value at S0 h. Data shown are representatives of three independent experiments.

(C) Percentage of apoptotic A-5RT3$_{ANGPTL4}$ and A-5RT3$_{CTRL}$ cells, treated with either MEK inhibitor PD98059 or PI3K inhibitors LY294002 and Wortmannin, after 2 h of anoikis challenge and analyzed by FACS (5000 events). The sum of Annexin V$^+$/PI$^-$ and Annexin V$^+$/PI$^+$ cells were considered apoptotic. Values were obtained from three independent experiments.

(E) In situ PLA detection of 14-3-3:Bad complexes in indicated tumor sections and cells. PLA signals were red dots and Hoechst stained nuclei blue. The cells were counterstained with Alexa488-phallodin for actin stress fibers (green). Negative controls were performed with only anti-14-3-3 antibodies. Images were acquired in one z-plane using a Zeiss LSM710 META confocal laser scanning microscope. Data shown are representative of three independent experiments. Scale bars represent 40 µm.

(F) Mean number of 14-3-3:Bad complexes (as shown in E, right panel) was calculated from 200 cells (n=3; total 600 cells) using BlobFinder software. Error bars represent SD. ***p<0.001.

Figure 15:
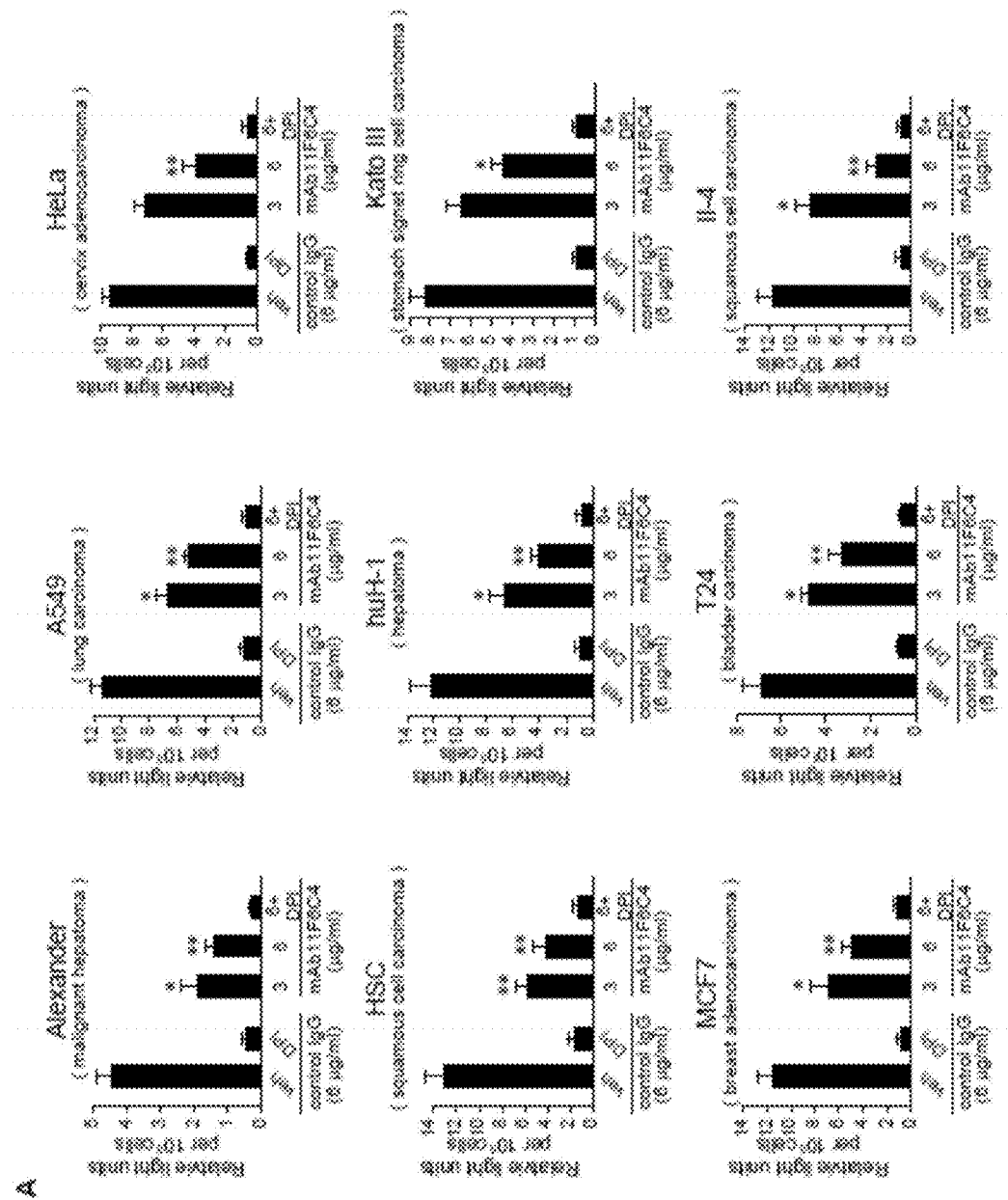
Figure 15:
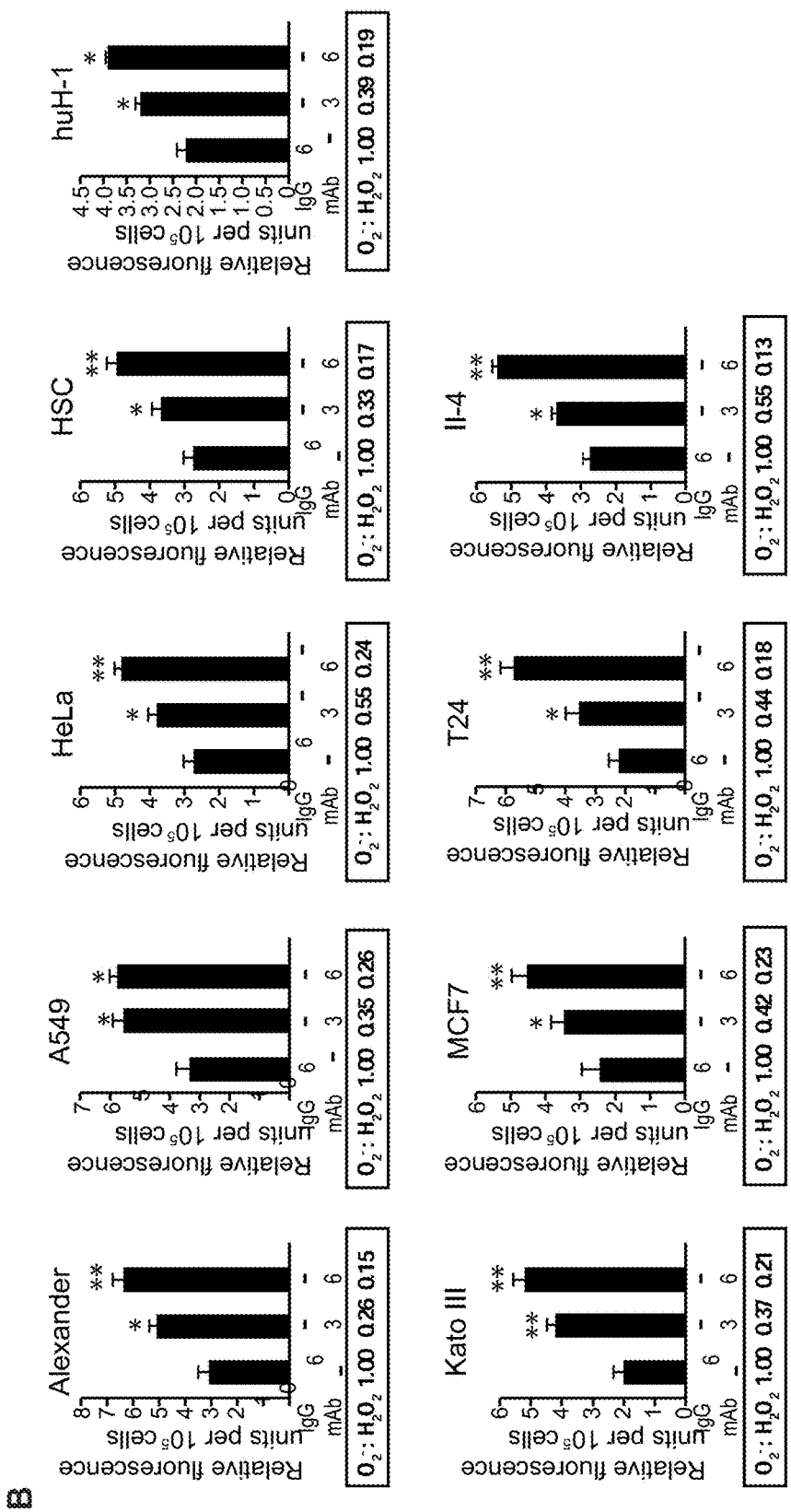

FIG. 15. ANGPTL4 Maintains Relatively High $O_2^-$:$H_2O_2$ Ratio In Tumor Cells Measurement of $O_2^-$ (A) and $H_2O_2$ (B) levels in nine different tumor lines. $O_2^-$ was determined using a chemiluminescence MCLA assay. The level of $H_2O_2$ was determined using Amplex red assay, in the presence of specific catalase inhibitor, 3-amino-1,2,4-triazole. Arbitrary relative $O_2^-$:$H_2O_2$ ratios (B) were shown in boxes. Values (mean±SD) were normalized to total protein content. Three independent experiments were performed with consistent results. *p<0.05; **p<0.01.

Figure 16:
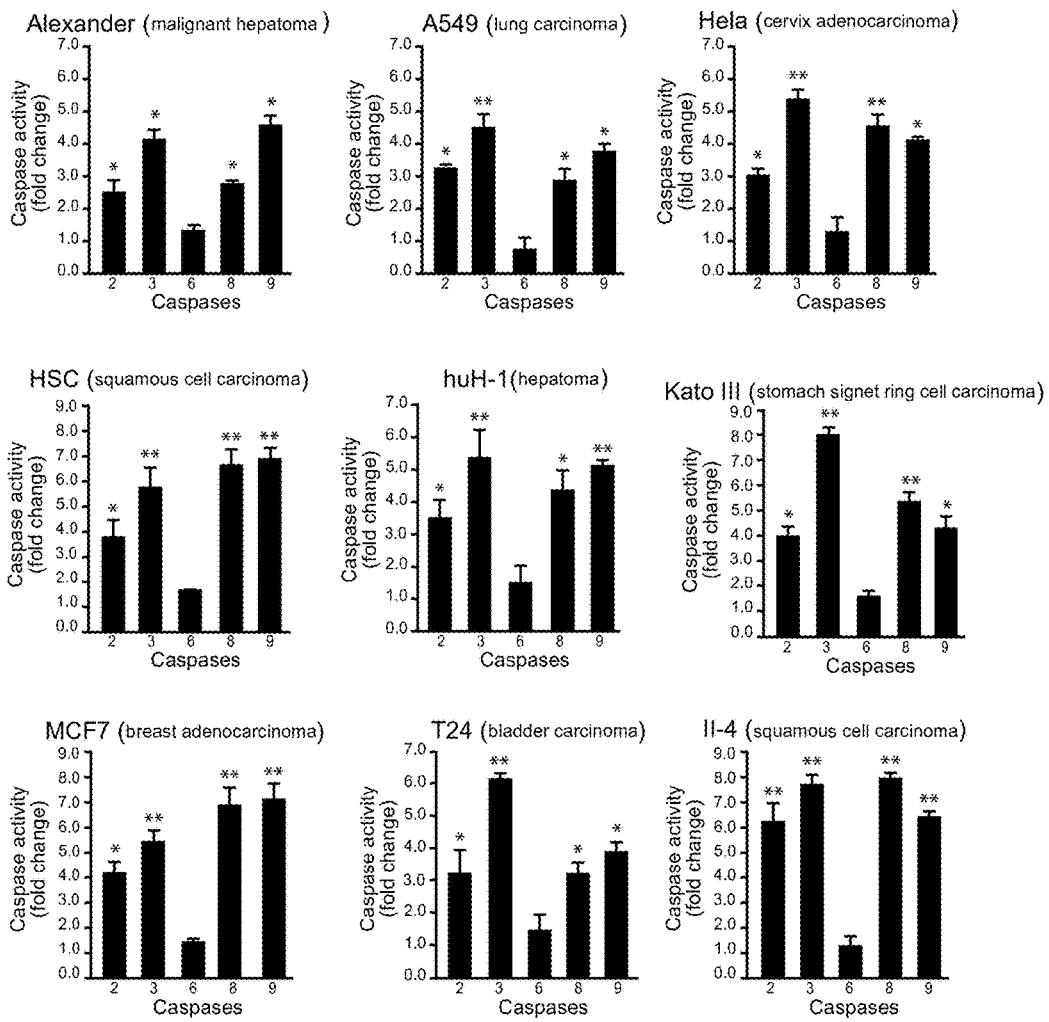

FIG. 16. Deficiency of ANGPTL4 Activates Caspase Activities and Induces Apoptosis Upon Anoikis in Tumor Cells.

(A) Relative activities of caspases 2, 3, 6, 8, 9 were measured after 2 h of anoikis Fold-increase of caspase activities in mAb11F6C4 (6 µg/ml)-treated cells was calculated by comparing with the caspase activities treated with pre-immune IgG (6 µg/ml). Values (mean±SD) were obtained from at least three independent experiments with consistent results.*p<0.05; **p<0.01.

Figure 16B:
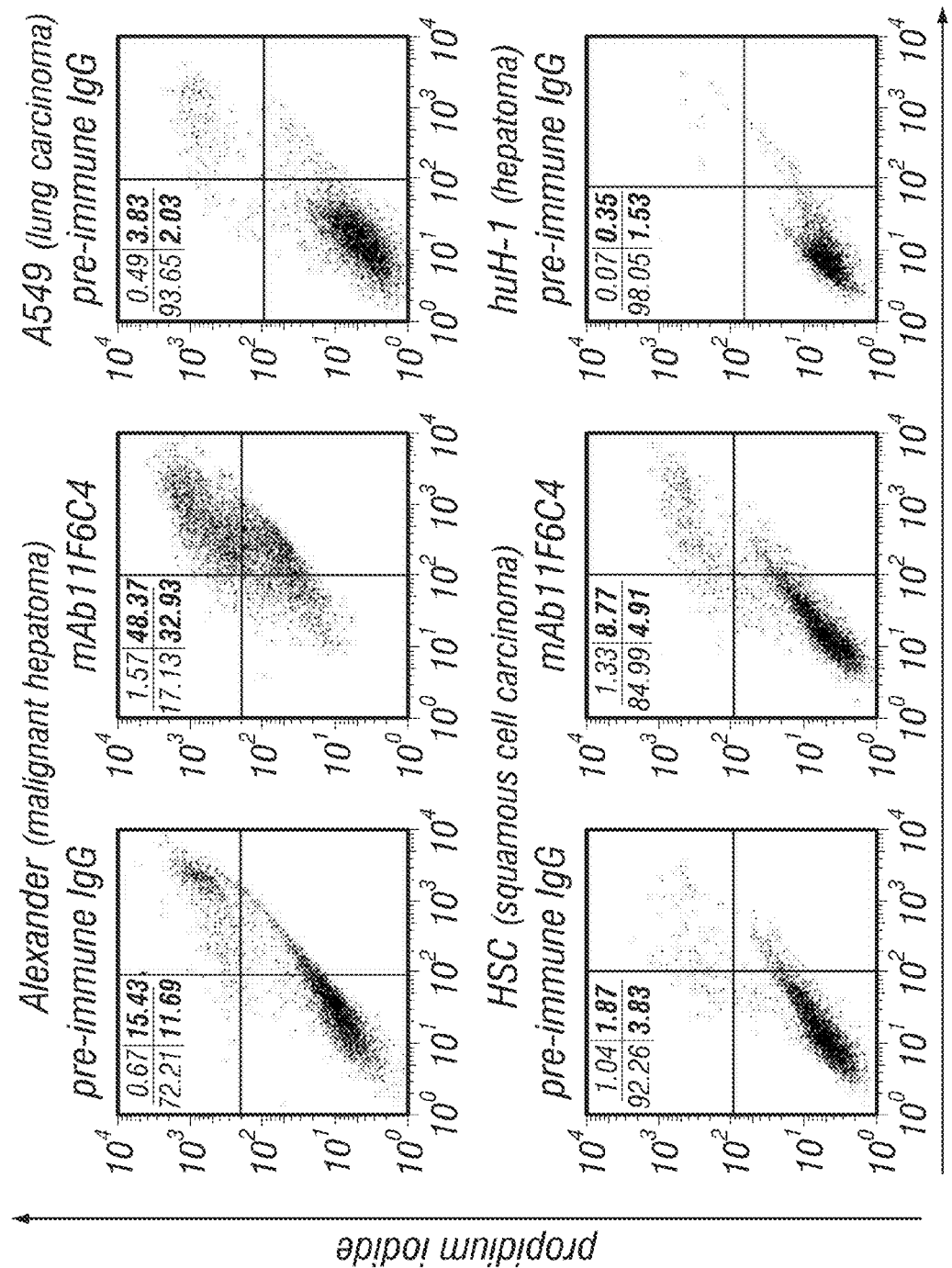
Figure 16:
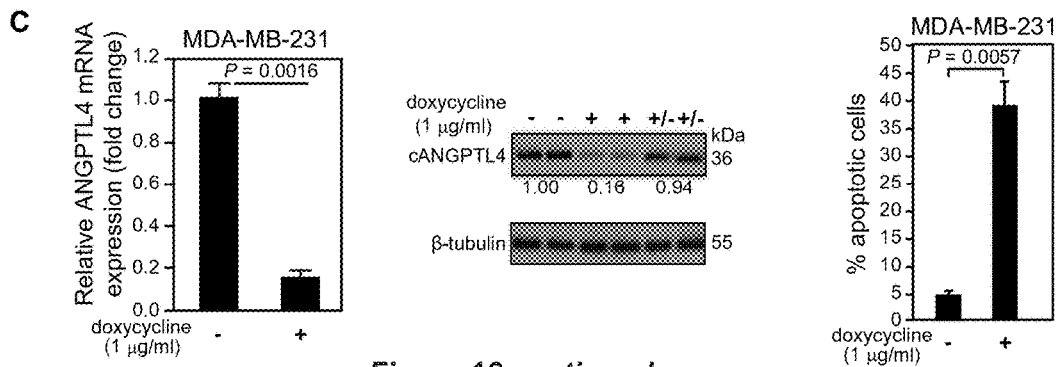

FIG. 16B-16B3 Percentage of apoptotic cells of 9 different tumor cell lines after 2 h of anoikis was evaluated by Annexin V-FITC/propidium iodide labelling followed by FACS analysis (5000 events). Tumor cells were treated with 10 µg/ml of control IgG or mAb11F6C4. Apoptotic index was as described in legend of FIG. 12B. Results are representative of at least three independent experiments. p<0.05.

(C) Relative ANGPTL4 mRNA (left panel) and protein (middle panel) levels in MDA-MB-231, whose ANGPTL4 suppression were doxycycline-inducible. A stable MDA-MB-231 cell line that expresses an anti-ANGPTL4 shRNA (see supplemental experimental procedures) was produced using the Knockout Singe Vector System (Clontech). Cells were grown in the absence (−) or presence (+) of doxycycline (1 µg/ml) for 24 h. +/− denotes the removal of doxycycline after 24 h doxycycline treatment. The right panel shows percentage of apoptotic cells of MDA-MB-231 as evaluated by anoikis assay. Data shown were obtained from three independent experiments with consistent results.

Figure 17:
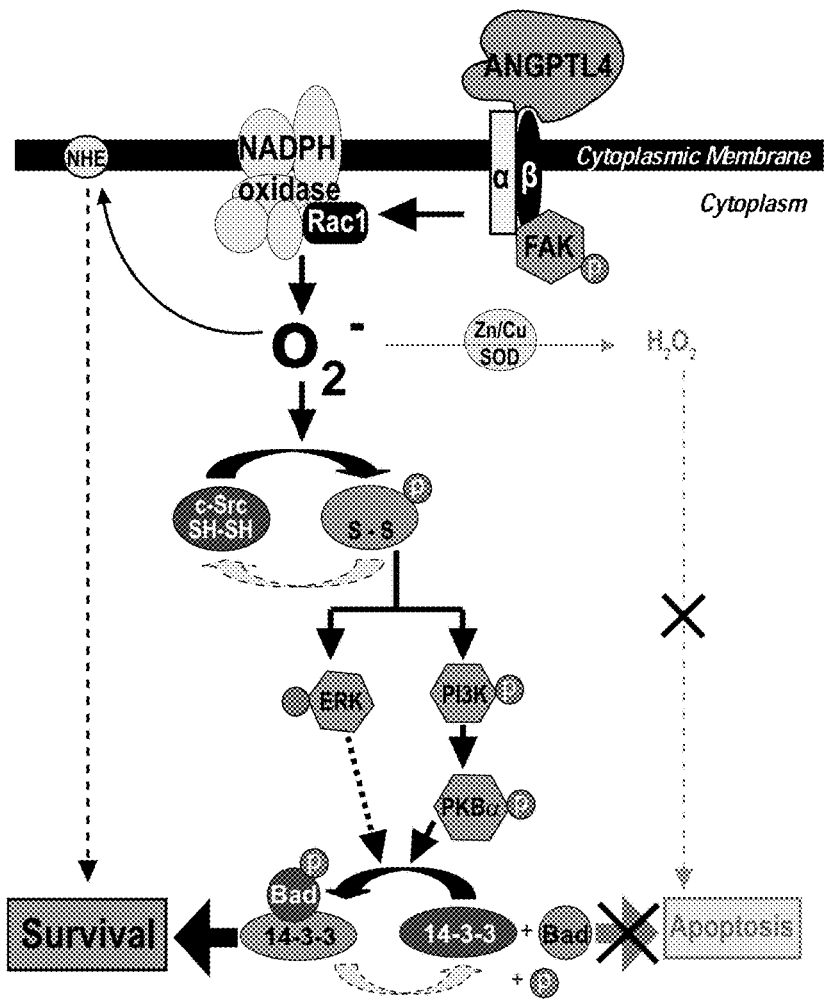

FIG. 17. ANGPTL4-mediated Regulation of $O_2^-$ Production in Tumor.

In an autocrine manner, tumor-derived ANGPTL4 specifically bind to integrins β1 or β5 and subsequently activates the FAK and Rac1 activities, which further activates the NADPH oxidase-dependent generation of "onco-ROS" $O_2^-$, promoting a relatively high $O_2^-$:$H_2O_2$ ratio in tumor cells. This pro-oxidant intracellular milieu, which may subsidiarily maintained through NHE, favours cell survival and proliferation by oxidizing/activating the Src machinery and therefore stimulates its downstream PI3K/PKBα- and ERK-mediated survival pathways. This further triggers the 14-3-3 adaptor protein to sequester the pro-apoptotic Bad from mitochondria to prevent apoptosis and favour cell survival.

Figure 18:
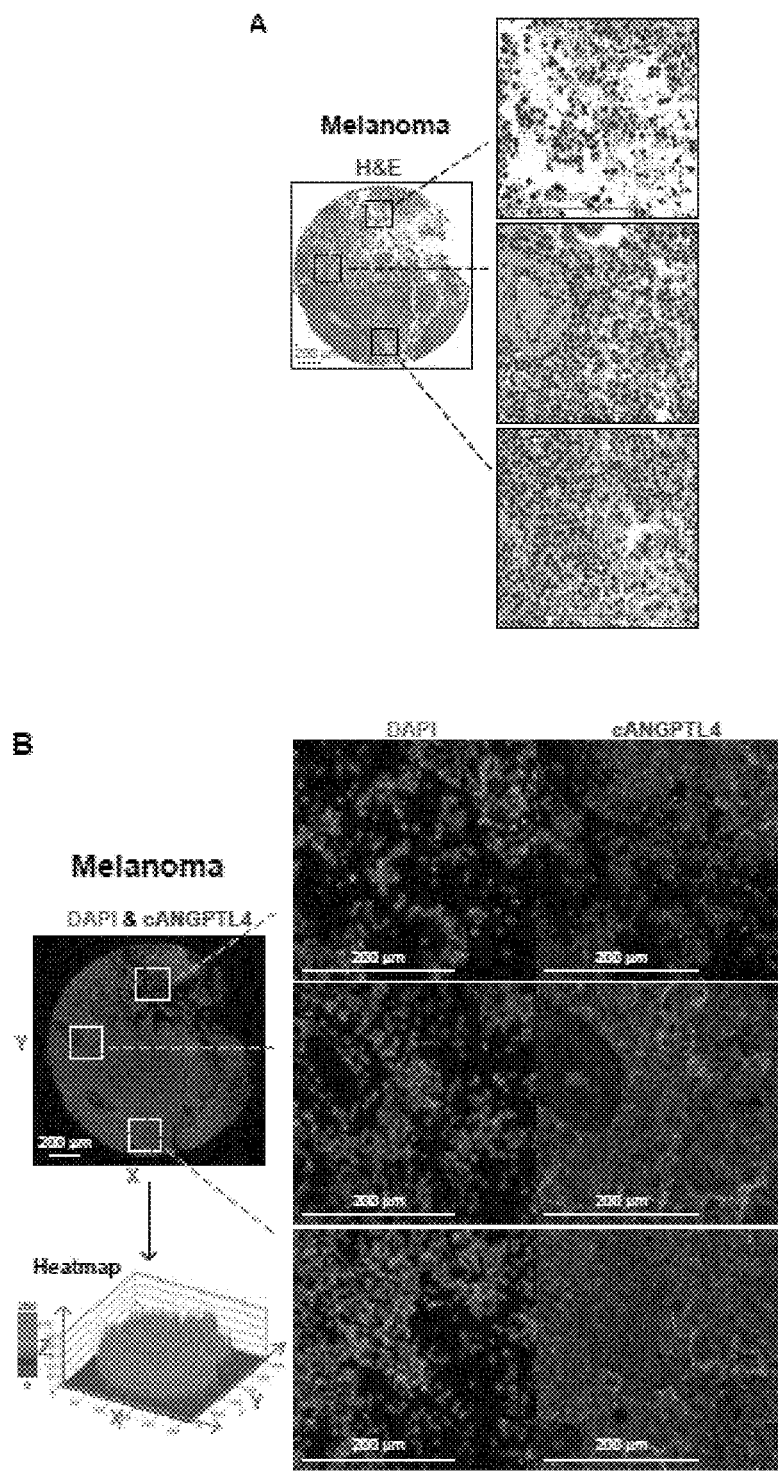
Figure 18:
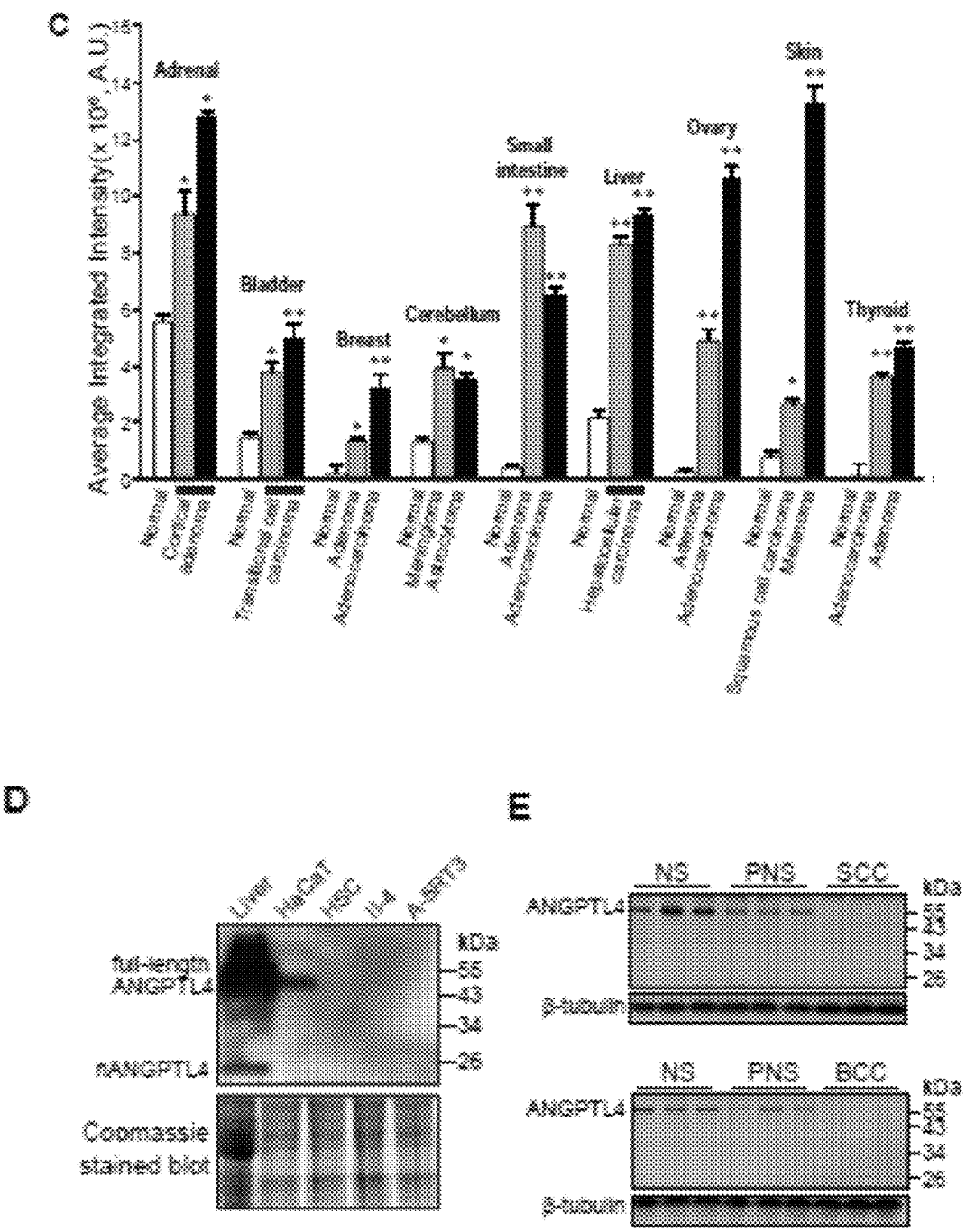
Figure 18:
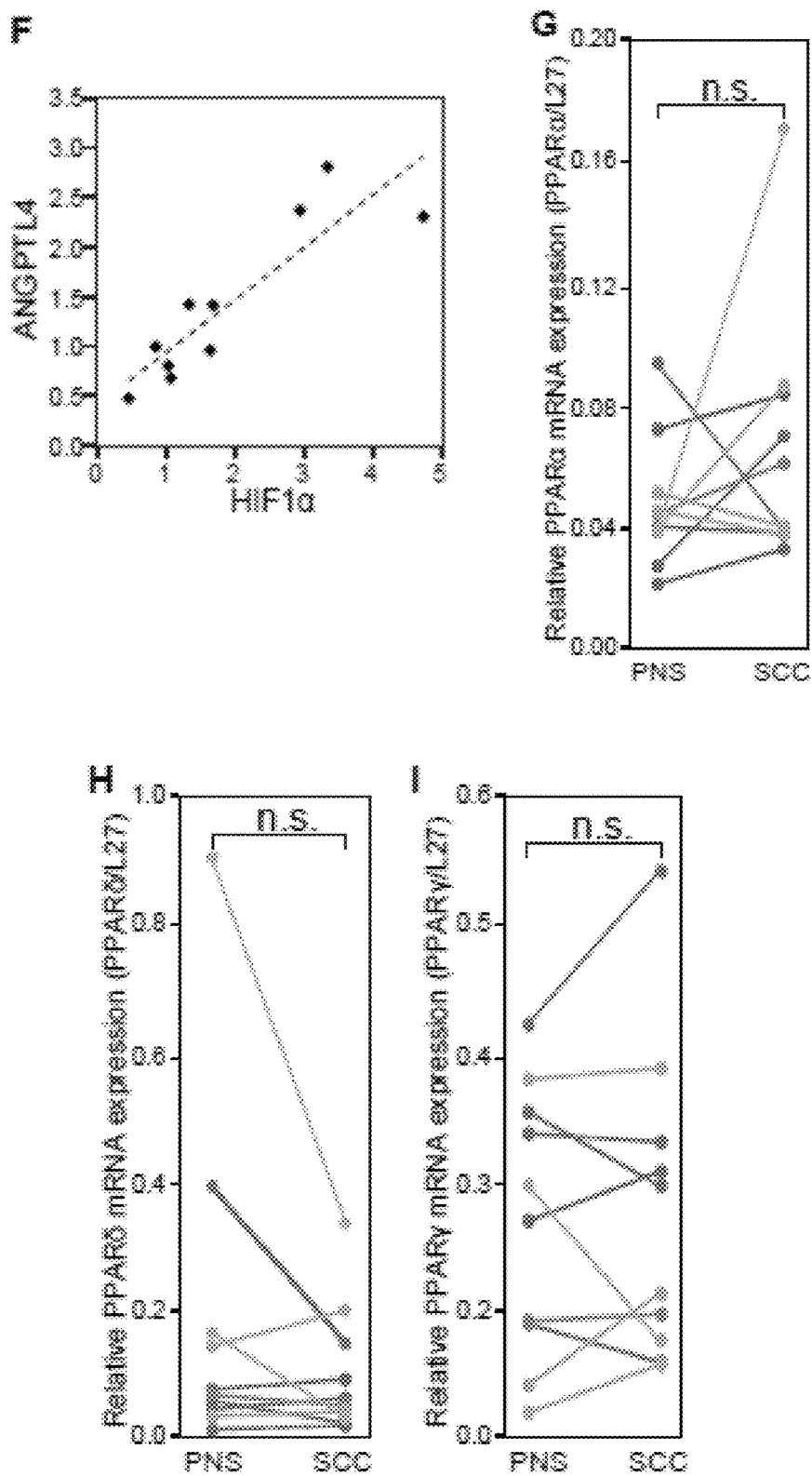

FIG. 18. Elevated Expression of C-terminal ANGPTL4 (cANGPTL4) in Tumors, related to FIG. 10.

(A and B) Hematoxylin and eosin (H&E) image (A) and immunofluorescence image probed with anti-cANGPTL4 antibody (B) on melanoma tumor tissue (representative of the tumor biopsies from array shown in FIG. 10A). Higher magnification pictures randomly selected from the melanoma tissue were shown on (A, right panel) and (B, DAPI on the middle and cANGPTL4 on the right panel), respectively. The heatmap (B, left bottom panel) was transformed from the immunofluorescence image (B, right upper panel) based on the gray value (immunofluorescence intensity) of cANGPTL4 as described in FIG. 10A. Scale bars represent 200 μm (C) Average integrated gray value (immunofluorescence intensity) of cANGPTL4 from various normal and tumor tissues (also see FIG. 10A). Tissues from same anatomic site were grouped and compared. Values (mean±SEM) were calculated from at least three biopsies and microscopic fields of each tissue. *$p<0.05$; **$p<0.01$ (D-E) Immunoblot analysis using anti-nANGPTL4 antibody of tumorigenic skin lines HSC, II-4, and A-5RT3 (D), and human skin squamous cell carcinomas (SCCs), basal cell carcinomas (BCCs) and cognate peri-tumor normal sample (PNS) (E). Liver, non-tumorigenic skin line HaCaT and normal skin biopsies (NS) served as cognate positive controls. Coomassie stained blot or β-tubulin served as loading and transfer control. No full-length or nANGPTL4 was detected in indicated tumor cell line, BCCs or SCCs. Anti-nANGPTL4 antibody was previously described (Kersten et al., 2000).

(F) HIF1α along with ANGPTL4 mRNA levels were concomitantly upregulated in SSCs when compared with PNSs with a Pearson correlation coefficient of 0.88. See the individual mRNA expression of ANGPTL4 and HIF1α in SCCs in FIGS. 10C and 10E.

(G-I) Relative mRNA expressions of peroxisome proliferator-activated receptor α (PPARα) (G), PPARδ (H) and PPARγ (I) in paired human squamous cell carcinomas (SCCs) and peri-tumor normal samples (PNSs) as determined by qPCR. Data spots from same individual were linked by coloured lines. Data shown are mean±SD from two independent qPCR experiments with triplicates. Ribosomal protein L27 (L27) was used as reference housekeeping gene. n.s. represents not significant in the comparison between paired SCCs and PNSs.

Figure 19:
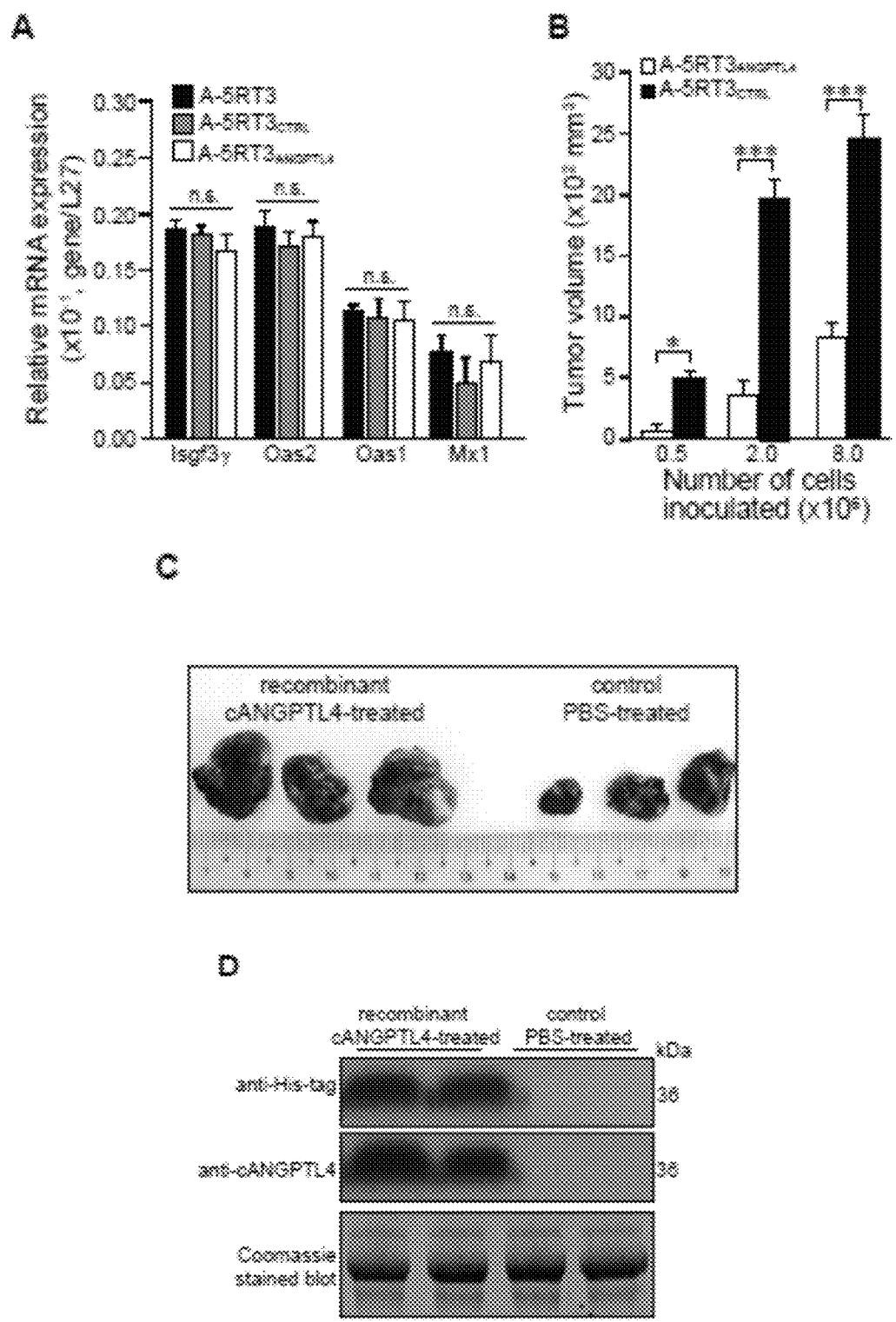

FIG. 19. Suppression of ANGPTL4 Reduces Tumorigenicity and Exogenously Infused cANGPTL4 Accelerates Tumor Growth, related to FIG. 11.

(A) Relative mRNA levels of key interferon response genes: 2′,5′-oligoadenylate synthetase isoforms 1 and 2 (Oas1, Oas2), interferon-induced myxovirus resistance 1 (Mx1) and interferon-stimulated transcription factor 3γ (Isgf3γ) in A-5RT3 (parental cell), A-5RT3$_{CTRL}$ (scrambled control cell) and A-5RT3$_{ANGPTL4}$ (ANGPTL4 knockdown cell). Results shown are mean±SD from three independent qPCR experiments with triplicates. Ribosomal protein L27 (L27) was used as reference housekeeping gene. n.s. represents not significant in the comparisons between A-5RT3 and A-5RT3$_{ANGPTL4}$ or between A-5RT3$_{CTRL}$ and A-5RT3$_{ANGPTL4}$.

(B) Mean size of xenograft tumors induced in nude mice by 0.5×, 2× and 8×10$^6$ A-5RT3$_{ANGPTL4}$ or A-5RT3$_{CTRL}$ after 4 weeks post-inoculation (each group). Values (mean±SEM) were calculated from n=5 (each group) mice. *$p<0.05$; ***$p<0.001$ (C) Representative pictures of B16F10-induced tumors in C57BL/6J mice with i.v. treatments of either 3 mg/kg of cANGPTL4 or control PBS thrice a week and dissected 15 days after injection (scale bar 10 mm). See also FIG. 11E.

(D) Immunoblot detection of recombinant cANGPTL4 using anti-His-tag and anti-cANGTPL4 antibodies. Plasma samples from C57BL/6J mice 1 day post-treatment with cANGPTL4 or control PBS (as described in FIG. 11E) were used. Coomassie stained blot served as loading and transfer control. Experiments were repeated three times with consistent results.

Figure 20:
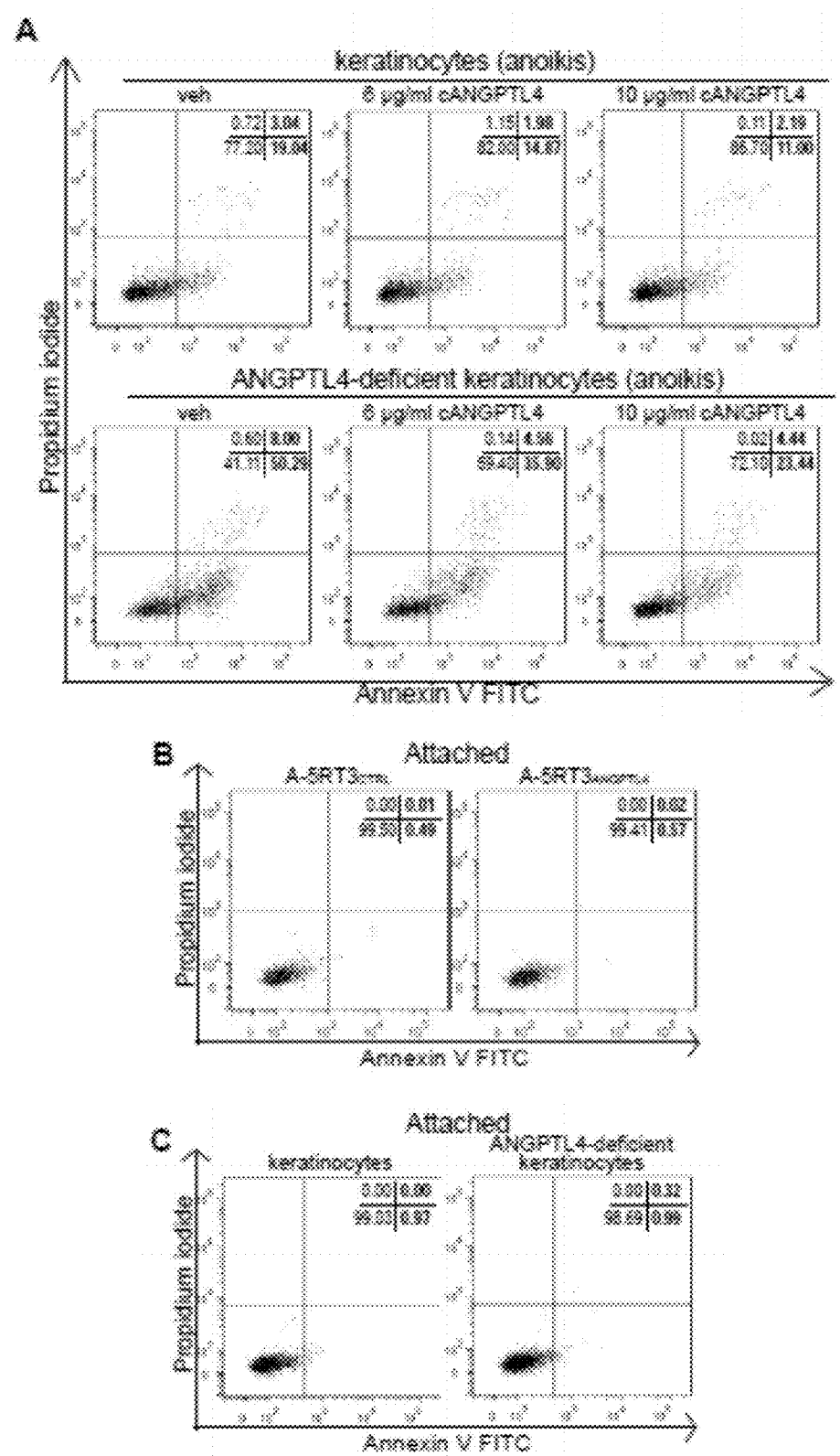
Figure 20:
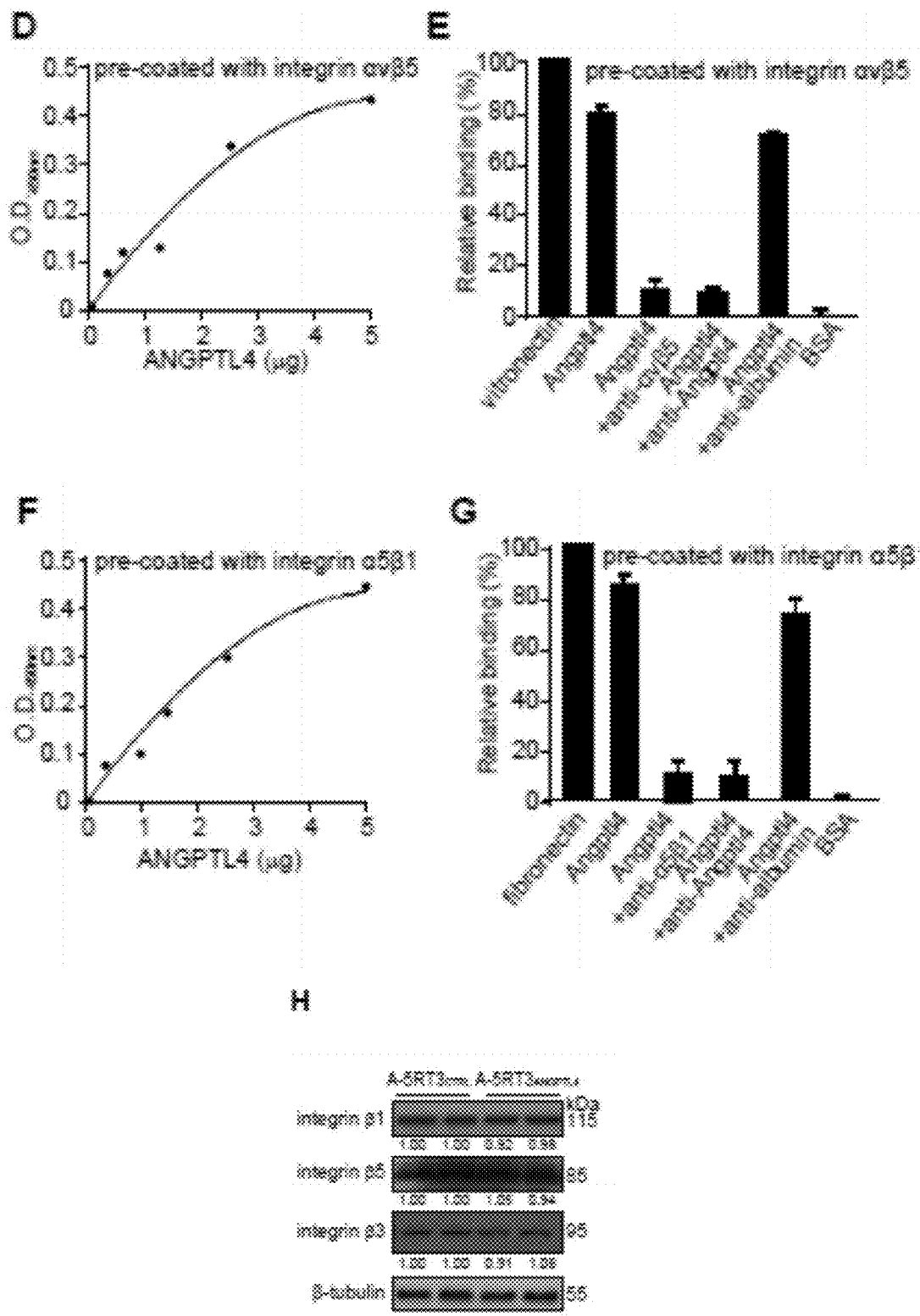
Figure 20:
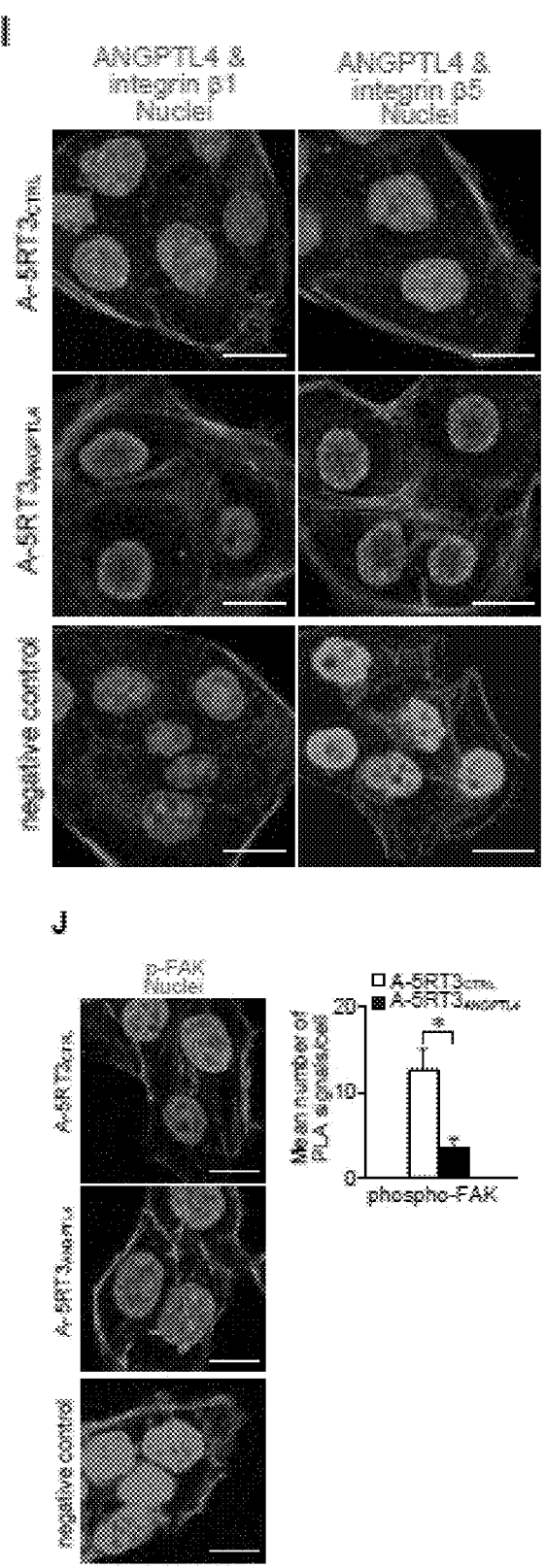

FIG. 20. ANGPTL4 Effects on Keratinocytes and Its Interaction With Integrins to Activate FAK, related to FIG. 12.

(A) Percentage of anoikis-induced apoptotic skin keratinocytes and ANGPTL4-deficient keratinocytes in the presence of increasing exogenous recombinant cANGPTL4 as analysed by FACS (5000 events). Vehicle (PBS)-treated keratinocytes and ANGPTL4-deficient keratinocytes served as cognate controls for comparison. Apoptotic index as described in (FIG. 12B).

(B-C) Apoptotic index of attached epithelial cells. A-5RT3$_{CTRL}$ and A-5RT3$_{ANGPT4}$ (B), and skin keratinocytes and ANGPTL4-deficient keratinocytes (C) were detached by trypsin, subjected for Annexin V and PI staining, and immediately analysed by FACS (5000 events). The sum of Annexin V$^+$/PI$^-$ and Annexin V$^+$/PI$^+$ cells were considered dead. Values (bold) denote death rate (%).

(D-G) Dose-dependent ANGPTL4 bindings to immobilized integrin αvβ5 (D and E) and integrin α5β1 (F and G), which were specifically blocked by anti-cANGPTL4 as determined by ELISA.

(H) Immunoblot detects no significant difference in the protein expressions of integrins β1, β5 and β3 between A-5RT3$_{CTRL}$ and A-5RT3$_{ANGPTL4}$ cells.

(I-J) In situ PLA detection of ANGPTL4:integrin β1 and ANGPTL4:integrin β5 complexes (I), and of phosphorylated FAK (J) in A-5RT3$_{CTRL}$ and A-5RT3$_{ANGPTL4}$ cells. PLA signals are shown in red and nuclei were stained blue by Hoechst dye. The cells were also counterstained with Alexa488-phallodin for actin stress fibers (green). Negative controls were performed with only anti-nANGPTL4 (I) or anti-FAK (J) antibodies. Images were acquired in one z-plane using a Zeiss LSM710 META confocal laser scanning microscope. Scale bars represent 40 μm. PLA images are representative of three independent experiments. Graph (J, right panel) showed mean number of phosphorylated FAK calculated from 200 A-5RT3$_{ANGPTL4}$ and A-5RT3$_{CTRL}$ cells (n=3; total 600 cells) using BlobFinder software (Uppsula University). Error bars represent SD. *$p<0.05$. All experiments were performed three or four times with consistent results.

Figure 21:
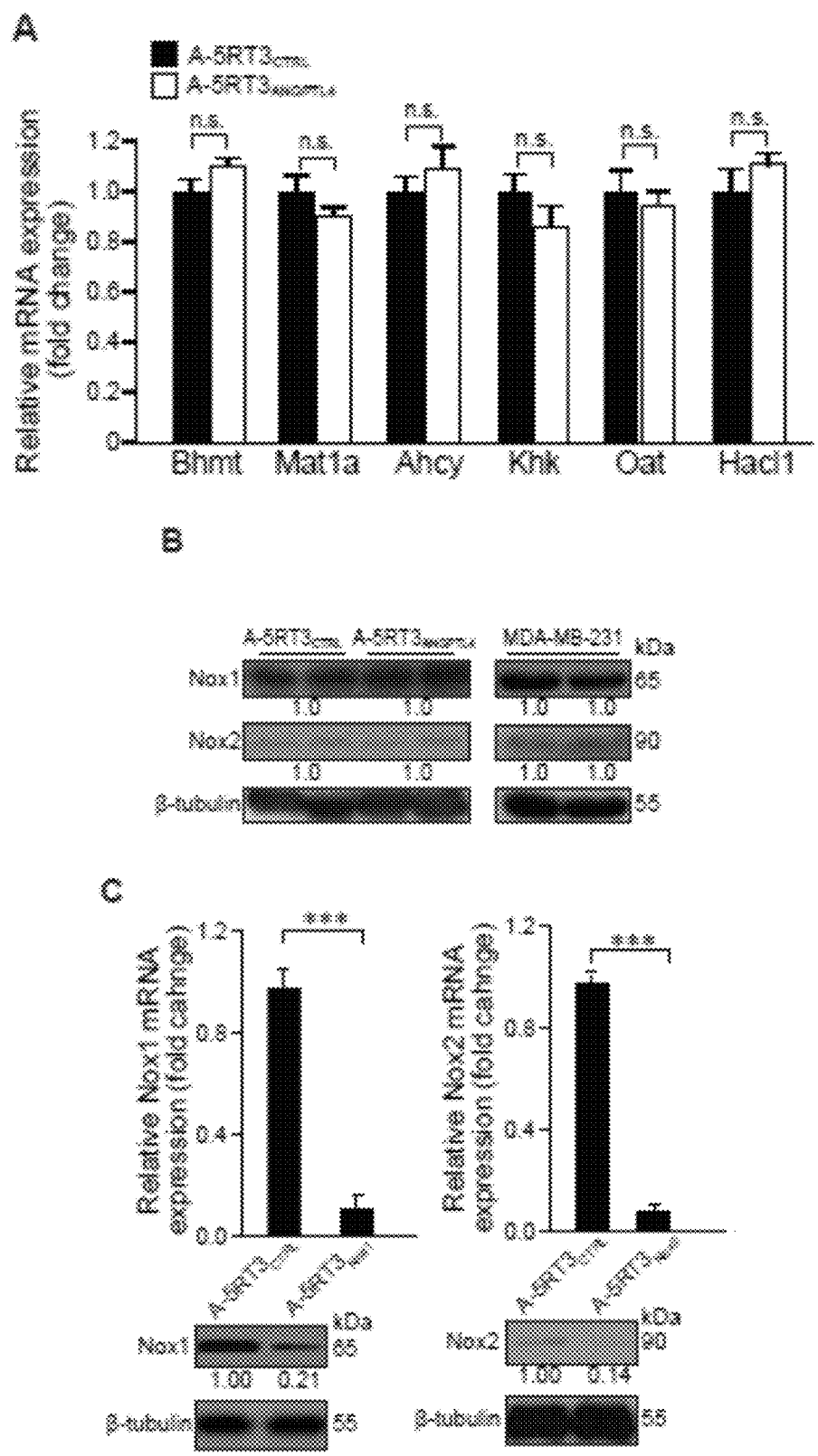
Figure 21:
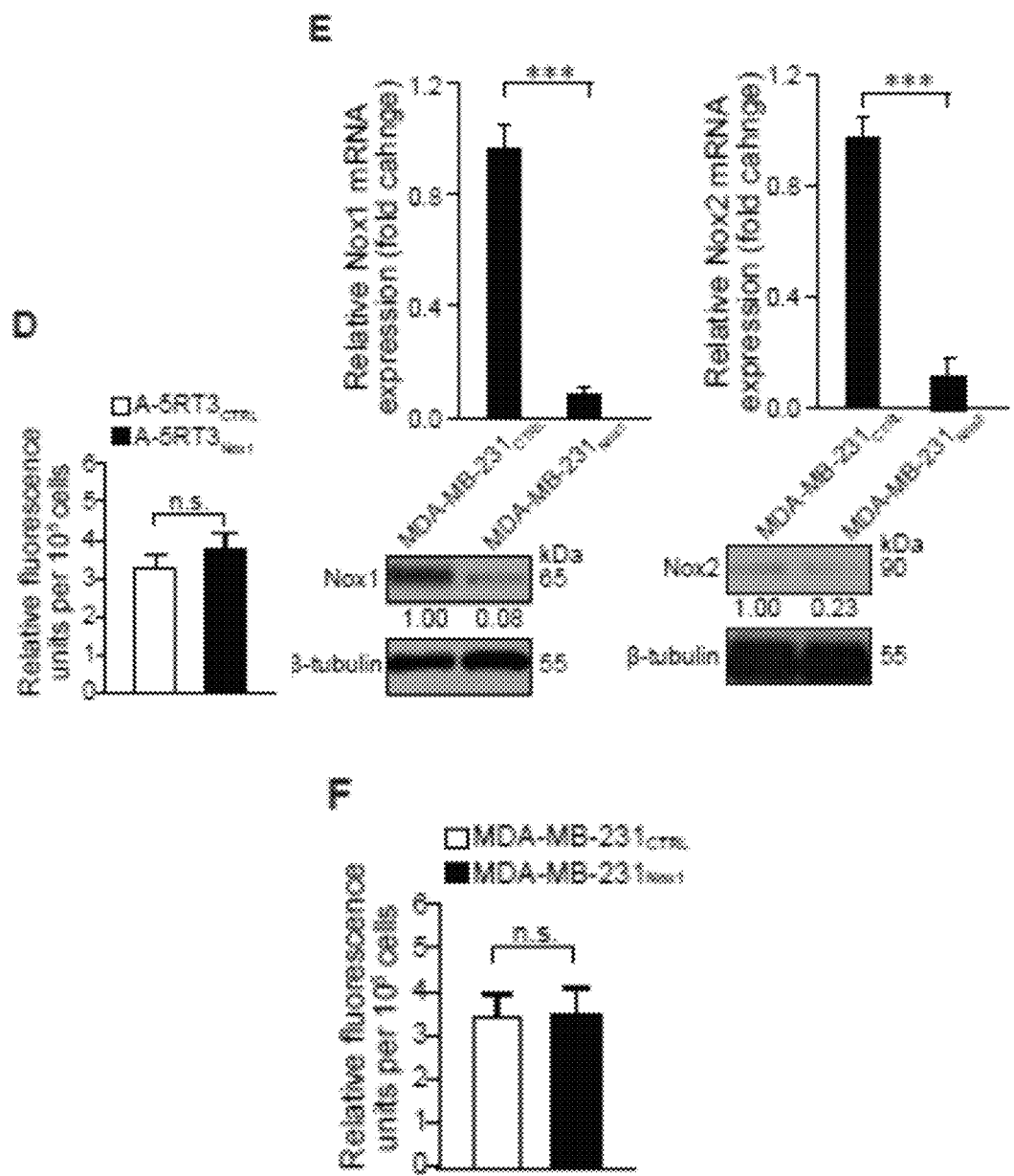

FIG. 21. Suppression of ANGPTL4, Nox1 and Nox2 in Tumor Cells, related to FIG. 13.

(A) Suppression of ANGPTL4 has no effect in the methionine/homocysteine metabolic cycle of tumor cells Relative mRNA level of Bhmt, Mat1a, Ahcy, Khk, Oat and Hacl1

(representative genes in the methionine/homocysteine metabolic cycle) in A-5RT3$_{ANGPTL4}$ and A-5RT3$_{CTRL}$ as determined by qPCR.

(B) Immunoblot of Nox1 and Nox2 in A-5RT3$_{CTRL}$, A-5RT3$_{ANGPTL4}$ and MA-MB-231 cells. β-tubulin served as loading and transfer control. Representative blots of three independent experiments were shown.

(C and E) Relative Nox1 and Nox2 mRNA and protein levels in A-5RT3$_{CTRL}$ (scrambled control), A-5RT3$_{Nox1}$ (Nox1 knockdown) and A-5RT3$_{Nox2}$ (Nox2 knockdown) cells (C), and in MDA-MB-231$_{CTRL}$ (scrambled control), MDA-MB-231$_{Nox1}$ (Nox1 knockdown) and MDA-MB-231$_{Nox2}$ (Nox2 knockdown) cells (E).

(D and F) Measurement of $H_2O_2$ levels using Amplex red assay in A-5RT3$_{CTRL}$ and A-5RT3$_{Nox1}$ (D), and in MDA-MB-231$_{CTRL}$ and MDA-MB-231$_{Nox1}$ cells (F).

(A and C-E) Error bars represent SD from three independent qPCR experiments with triplicates. Ribosomal protein L27 (L27) was used as reference housekeeping gene. ***$p<0.001$; n.s. represents not significant.

DETAILED DISCLOSURE

We examined the expression pattern of ANGPTL4 in various types of human tumor cells and found that an elevated level of ANGPTL4 is a common feature of many tumor types. Next, we found that suppression of ANGPTL4, either by RNA interference or monoclonal antibody, significantly impaired the growth of tumor cells in vivo and their resistance to anoikis in vitro. Further study of the underlying mechanism of ANGPTL4 activity led us to propose that tumor cells express ANGPTL4 to modulate intracellular $O_2^-$ levels, conferring anoikis resistance to tumor cells and promoting tumorigenesis and that, therefore, ANGPTL4 is a potentia We showed that only cANGPTL4 was detected and elevated in many human tumor cells, predominantly secreted by the proliferative tumor epithelial cells. cANGPTL4 specifically binds to integrins β1 and β5 on tumor cells and activates the FAK and Rac1, which further stimulates NADPH oxidase-mediated $O_2^-$ production by an autocrine pathway. However, it is conceivable that in tissues/organs expressing high level of cANGPTL4 in proximity to the tumor site may transmit a paracrine signal.l therapeutic target in cancer treatment.

Consistent with the invention there is provided an antaginost to the angiopoietin like 4 protein (ANGPTL4) such as (a) an antibody specific to the angiopoietin like 4 protein (ANGPTL4) and, or (b) an antibody specific to the C terminal of the protein or (c) SiRNA. Exemplary antibodies include polyclonal, monoclonal, humanized, bispecific, and heteroconjugate antibodies.

Antibodies directed to the C terminus of ANGPTL4 demonstrated superior association, dissociation, and affinity constant. C-terminal expresses fibrinogen-like fragment of ANGPTL4.

Here, we found that elevated ANGPTL4 expression is widespread in tumors, and its suppression impairs tumor growth associated with enhanced apoptosis. Tumor-derived ANGPTL4 interacts with integrins to stimulate the NADPH oxidase-dependent production of $O_2^-$ A high ratio of $O_2^-$:$H_2O_2$ oxidizes/activates Src, triggering the PI3K/PKBα and ERK pro-survival pathways to confer anoikis resistance, thus promoting tumor growth. ANGPTL4 deficiency results in diminished $O_2^-$ production and a reduced $O_2^-$:$H_2O_2$ ratio, creating a cellular environment conducive to apoptosis. Thus, ANGPTL4 is a novel redox factor in cancer biology and a potential therapeutic target.

The following embodiments are encompassed by the present invention:

An immunoglobulin that specifically binds to the C terminal of the ANGPTL4 protein.

The immunoglobulin wherein said immunoglobulin comprises an immunoglobulin heavy chain.

The immunoglobulin comprising an immunoglobulin light chain.

The immunoglobulin wherein said immunoglobulin is an IgG1 kappa immunoglobulin.

The immunoglobulin wherein said immunoglobulin comprises a human IgG1 constant region within a heavy chain of said immunoglobulin and a human constant region within a light chain of said immunoglobulin.

The immunoglobulin wherein said immunoglobulin comprises fully or partially human framework regions within the variable domain of said heavy chain and within the variable domain of said light chain.

The immunoglobulin wherein said immunoglobulin comprises murine framework regions within the variable domain of said heavy chain and within said light chain.

The immunoglobulin wherein said immunoglobulin is conjugated to an agent selected from the group consisting of a therapeutic agent, a prodrug, a peptide, a protein, an enzyme, a virus, a lipid, a biological response modifier, a pharmaceutical agent, and PEG.

A composition comprising the immunoglobulin of the invention and a carrier.

A method for preventing or treating proliferative disorders in a subject comprising administering to said subject an effective amount of a composition comprising the immunoglobulin of the invention.

A pharmaceutical composition comprising the immunoglobulin of the invention.

A method of diagnosing a proliferative disorders, comprising the steps of (a) determining an amount of the angiopoietin like 4 protein (ANGPTL4) protein in body fluids or tissue sampled from a person suspected of having a proliferative disorder (b) comparing the amount of the angiopoietin like 4 protein (ANGPTL4) from a person suspected of having a proliferative disorder with a second amount sampled from a healthy individual wherein elevated ANGPLT4 in the first sample compared with the second sample is indicative that a proliferative disorder is present in the person suspected of having a proliferative disorder.

A method of diagnosing proliferative disorders in a subject comprising, removing a sample from the subject, contacting the sample with a composition of the invention and detecting the presence of ANGPTL4 wherein elevated ANGPLT4 is a sample compared with a standard of normal ANGPTL4 expression is indicative that a proliferative disorder is present in the subject.

Polyclonal Antibodies

The antibodies of the invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant.

Typically, the immunizing agent and/or adjuvant will be injected in the mammal by multiple subcutaneous or intraperitoneal injections. The intensity of the response is determined by several factors including the size of the immunogen molecule, its chemical characteristics, and how different it is from the animal's own proteins. Most natural immunogens are proteins with a molecular weight above 5 kDa that come from sources phylogenically far removed from the host animal (i.e., human proteins injected into rabbits or goats). It is desirable to use highly purified proteins as immunogens, since the animal will produce antibodies to even small amounts of impurities present as well as to the major component. The antibody response increases with repeated exposure to the immunogen, so a series of injections at regular intervals is needed to achieve both high levels of antibody production and antibodies of high affinity.

To the extent that the antagonist is an antibody that engages the c terminal of the fibrinogen-like fragment of ANGPTL4 preventing cell proliferation, the immunogen will be an selected from amino acids comprising the c terminal of the fibrinogen-like fragment of ANGPTL4. Preferably, the amino acid sequence will be selected from the region of about 186-406 in the human ANGPTL4 protein or about 190-410 in the mouse ANGPTL4 protein. Sequences of at least 5, 6, 7, 8, 9, 10, 15, 20, 25, 30 amino acids from this region will generally be used to generate those antibodies. Desirably, the sequence selected will generate an antibody that specifically interferes with binding of ANGPTL4 to apoptosis inducing compounds.

Not all immunogenic molecules will however generate the level of antibody desired. To increase the intensity of the immune response immunogens are combined with complex mixtures called adjuvants. Adjuvants are a mixture of natural or synthetic compounds that, when administered with antigens, enhance the immune response. Adjuvants are used to (1) stimulate an immune response to an antigen that is not inherently immunogenic, (2) increase the intensity of the immune response, (3) preferentially stimulate either a cellular or a humoral response (i.e., protection from disease versus antibody production). Examples of adjuvants which may be employed include Freund's complete adjuvant and MPL-TDM adjuvant (monophosphoryl Lipid A, synthetic trehalose dicorynomycolate). A more extensive discussion of adjuvants and their use in immunization protocols is given in Immunology Methods Manual, vol. 2, I. Lefkovits, ed., Academic Press, San Diego, Calif., 1997, ch. 13. Immunology Methods Manual is available as a four volume set, (Product Code Z37,435-0); on CD-ROM, (Product Code Z37,436-9); or both, (Product Code Z37,437-7)

If the immunogen is still unable to generate an acceptable response, it may be conjugated to a carrier protein that is more immunogenic. Small molecules such as drugs, organic compounds, and peptides and oligosaccharides with a molecular weight of less than 2-5 kDa like, for example, small segments if ANGPTL4 such as those with a fibrinogen-like fragment in their structure, may not be immunogenic, even when administered in the presence of adjuvant. In order to generate an immune response to these compounds, it is necessary to attach them to a protein or other compound, termed a carrier that is immunogenic. When attached to a carrier protein the small molecule immunogen is called a hapten. Haptens are also conjugated to carrier proteins for use in immunoassays. The carrier protein provides a means of attaching the hapten to a solid support such as a microtiter plate or nitrocellulose membrane. When attached to agarose they may be used for purification of the anti-hapten antibodies. They may also be used to create a multivalent antigen that will be able to form large antigen-antibody complexes. When choosing carrier proteins, remember that the animal will form antibodies to the carrier protein as well as to the attached hapten. It is therefore relevant to select a carrier protein for immunization that is unrelated to proteins that may be found in the assay sample. If haptens are being conjugated for both immunization and assay, the two carrier proteins should be as different as possible. This allows the antiserum to be used without having to isolate the anti-hapten antibodies from the anti-carrier antibodies.

Where the immunizing agent is a fibrinogen-like fragment segment such as from the c terminal preferably the fibrinogen-like fragment segment is conjugated to a protein known to be immunogenic in the mammal being immunized.

Examples of such immunogenic proteins include but are not limited to keyhole limpet hemocyanin (KLH), serum albumin, bovine thyroglobulin, soybean trypsin inhibitor, and a toxoid, for example tetanus toxoid.

KLH is a respiratory protein found in molluscs. Its large size makes it very immunogenic, and the large number of lysine residues available for conjugation make it very useful as a carrier for haptens. The phylogenic separation between mammals and molluscs increases the immunogenicity and reduces the risk of cross-reactivity between antibodies against the KLH carrier and naturally occurring proteins in mammalian samples.

KLH is offered both in its native form, for conjugation via amines, and succinylated, for conjugation via carboxyl groups. Succinylated KLH may be conjugated to a hapten containing amine groups (such as a peptide) via cross-linking with carbodiimide between the newly introduced carboxyl groups of KLH and the amine groups of the hapten.

Protocols for conjugation of haptens to carrier proteins may be found in *Antibodies: A Laboratory Manual*, E. Harlow and D. Lane, ed., Cold Spring Harbor Laboratory (Cold Spring Harbor, N.Y., 1988) pp. 78-87 (Product Code A 2926)

The immunization protocol may be selected by one skilled in the art without undue experimentation. Protocols for preparing immunogens, immunization of animals, and collection of antiserum may be found in *Antibodies: A Laboratory Manual*, E. Harlow and D. Lane, ed., Cold Spring Harbor Laboratory (Cold Spring Harbor, N.Y., 1988) pp. 55-120 (Product Code A 2926).

Monoclonal Antibodies

The antibodies may, alternatively, be monoclonal antibodies. Monoclonal antibodies may be prepared using hybridoma methods, such as those described by Kohler and Milstein (1975), *Nature,* 256:495. In a hybridoma method, a mouse, hamster, or other appropriate host animal, is typically immunized with an immunizing agent as described above to elicit lymphocytes that produce or are capable of producing antibodies that will specifically bind to the immunizing agent. Alternatively, the lymphocytes may be immunized in vitro.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. (1984) *Immunol.*, 133:3001).

The culture medium in which the hybridoma cells are cultured can then be assayed for the presence of monoclonal antibodies directed against ANGPTL4 and/or the the c terminal of ANGPTL4 or any of the sequences SEQ ID No. 1 to 3.

After the desired hybridoma cells are identified, the clones may be subcloned by limiting dilution procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

In vitro methods are also suitable for preparing monovalent antibodies. Digestion of antibodies to produce fragments thereof, particularly, Fab fragments, can be accomplished using routine techniques known in the art.

Human and Humanized Antibodies

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding sub-sequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., (1986) *Nature*, 321: 522-525; Riechmann et al., (1988) *Nature*, 332:323-327; Verhoeyen et al., (1988) *Science* 239:1534-1536], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. (1991) *Mol. Biol.*, 227:381; Marks et al., (1991) *J. Mol. Biol.*, 222:581]. The techniques of Cole et al. and Boerner et al. are also available for the preparation of human monoclonal antibodies (Cole et al., (1985) Monoclonal Antibodies and Cancer Therapy, Alan R. Liss, p. 77 and Boemer et al., (1991) *J. Immunol.*, 147(1): 86-95]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., (1992) Bio/Technology 10, 779-783; Lonberg et al., (1994) *Nature* 368 856-859; Morrison, (1994) *Nature* 368, 812-13; Fishwild et al., (1996) *Nature Biotechnology* 14, 845-51; Neuberger, (1996) *Nature Biotechnology* 14, 826; Lonberg and Huszar, (1995) *Intern. Rev. Immunol.* 13 65-93.

Bispecific Antibodies

Bispecific antibodies are monoclonal, preferably human or humanized, antibodies that have binding specificities for at least two different antigens. In the present case, one of the binding specificities is for ANGPTL4 and/or a segment of ANGPTL4 comprising portions of the c terminal of the fibrinogen-like fragment of ANGPTL4, the other one is for another compound having ANGPTL4.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, (1983) *Nature*, 305:537-539].

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Immunoconjugates

The invention also pertains to immunoconjugates comprising an antibody conjugated to a cytotoxic agent such as a chemotherapeutic agent, toxin (e.g., an enzymatically active toxin against hemagglutinin), or a radioactive isotope (i.e., a radioconjugate).

Conjugates of the antibody and cytotoxic agent are made using a variety of bifunctional protein-coupling agents such as N-succinnimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Method of Treatment and or Use of the Antibodies of the Invention

The present invention also provides a method of treating a patient to at least affect a proliferative disorder, which comprises the step of: contacting a cell with an antagonist such as (a) an antibody specific to angiopoietin like 4 protein (ANGPTL4) or (b) an antibody specific to the C terminal region of angiopoietin like 4 protein (ANGPTL4). Preferably, the antagonist interferes with cell proliferation by means that neutralize angiopoietin like 4 protein (ANGPTL4) expression.

An alternative form of the present invention resides in the use of an antibody specific angiopoietin like 4 protein (ANGPTL4) or an antibody specific to the C terminal region of angiopoietin like 4 protein (ANGPTL4) for the treatment of cancer, preferably the use at least affects cell proliferation.

Cancer may include, all types of known tumors that exhibit over expression of angiopoietin like 4 protein (ANGPTL4). Cell proliferating or tumor refers to cells that are growing uncontrollably.

"Treatment" and "treat" and synonyms thereof refer to therapeutic treatment wherein the object is to prevent or slow down (lessen) a tumor. Treatment may include prophylactic passive immunization or immunotherapy treatment of a patent. Those in need of such treatment include those with a proliferative disorder.

As used herein a "therapeutically effective amount" of a compound will be an amount of active agent that is capable of preventing or at least slowing down (lessening) cell proliferation or tumerogenesis. Dosages and administration of an antagonist of the invention in a pharmaceutical composition may be determined by one of ordinary skill in the art of clinical pharmacology or pharmacokinetics. See, for example, Mordenti and Rescigno, (1992) Pharmaceutical Research, 9:17-25; Morenti et al., (1991) Pharmaceutical Research, 8:1351-1359; and Mordenti and Chappell, "The use of interspecies scaling in toxicokinetics" in Toxicokinetics and New Drug Development, Yacobi et al. (eds) (Pergamon Press: NY, 1989), pp. 42-96. An effective amount of the antagonist to be employed therapeutically, for example an antibody, will depend, for example, upon the therapeutic objectives, the route of administration, and the condition of the mammal. Accordingly, it will be necessary for the therapist to titer the dosage and modify the route of administration as required to obtain the optimal therapeutic effect. A typical daily dosage might range from about 10 ng/kg to up to 100 mg/kg of the mammal's body weight or more per day, preferably about 1 µg/kg/day to 10 mg/kg/day. Doses may include an antibody amount any where in the range of 0.1 to 20 mg/kg of bodyweight or more preferably 1, 5, 10 mg/kg of bodyweight.

Compositions of the Invention

Antibodies produced according to the invention, can be administered for the treatment of cell proliferation, tumoregenisis, metastasis, or cancer in the form of pharmaceutical compositions.

Thus, the present invention also relates to compositions including pharmaceutical compositions comprising a therapeutically effective amount of (a) an antibody specific to angiopoietin like 4 protein (ANGPTL4) and, or (b) an antibody specific to the C terminal region of angiopoietin like 4 protein (ANGPTL4). As used herein a compound will be therapeutically effective if it is able to affect cell proliferation.

Pharmaceutical forms of the invention suitable for injectable use include sterile aqueous solutions such as sterile phosphate-buffered saline (where water soluble) or dispersions and sterile powders for the extemporaneous preparation of sterile injectable solutions and or one or more carrier. Alternatively, injectable solutions may be delivered encapsulated in liposomes to assist their transport across cell membrane. Alternatively or in addition such preparations may contain constituents of self-assembling pore structures to facilitate transport across the cellular membrane. It must be stable under the conditions of manufacture and storage and must be preserved against the contaminating/destructive action of microorganisms such as, for example, bacteria and fungi.

The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as, for example, lecithin, by the maintenance of the required particle size in the case of dispersion and by the use of surfactants. Preventing the action of microorganisms in the compositions of the invention is achieved by adding antibacterial and/or antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and freeze-drying, to yield a powder of the active ingredient plus any additional desired ingredient from previously sterile-filtered solution thereof.

The active ingredient may be held within a matrix which controls the release of the active agent. Preferably, the matrix comprises a substance selected from the group consisting of lipid, polyvinyl alcohol, polyvinyl acetate, polycaprolactone, poly(glycolic)acid, poly(lactic)acid, polycaprolactone, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and combinations thereof and other polymers such as those disclosed in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety. Preferably, the matrix sustainedly releases the antibody.

Pharmaceutically acceptable carriers and/or diluents may also include any and all solvents, dispersion media, coatings, antibacterials and/or antifungals, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated.

Preferred Embodiments

The angiopoietin-like 4 sustains an elevated pro-survival intracellular $O_2^-:H_2O_2$ ratio and confers anoikis resistance to tumor.

Tumor regression in malignant cancers remain a most significant anticancer strategy. Here we showed that elevated ANGPTL4 expression is widespread in tumors, and its suppression impairs tumor growth associated with enhanced apoptotis. ANGPTL4 interacts with integrins to modulate intracellular ROS generation that confers anoikis resistance and sustains tumor growth, underscoring ANGPTL4 as a novel player in redox cancer biology, a tumor biomarker, and thus a potential therapeutic target.

Our results demonstrate that tumor-derived ANGPTL4 confers anoikis resistance to tumors via autocrine adhesion mimicry. We show that elevated expression of ANGPTL4 is widespread in tumors. Our findings, that ANGPTL4 hijacks integrin-mediated signaling to maintain an elevated, oncogenic $O_2^-:H_2O_2$ ratio to confer anoikis resistance to tumor cells, identify ANGPTL4 as a novel factor in redox cancer biology and suggest anticancer strategies focused on redox-based apoptosis induction in tumors. Treatment of cancer cells with ANGPTL4-targeted RNAi or monoclonal antibodies imparts a significant decrease in in vivo tumor growth and induces apoptosis in 10 different cancer cell lines upon anoikis challenge. These findings should appeal to a broad audience of clinicians, cancer biologists, molecular biologists and drug designers.

Highlights

Elevated expression of ANGPTL4 is a common feature of many human tumor types.

ANGPTL4 binds integrin to stimulate the NADPH oxidase-dependent production of $O_2^-$.

ANGPTL4 sustains a high $O_2^-:H_2O_2$ ratio to activate pro-survival pathways.

Suppression of ANGPTL4 impairs tumor growth and enhances anoikis/apoptosis.

Analysis of human tumor cell lines (FIG. 1a), squamous cell carcinoma biopsies (SCC) and tumor tissue arrays (FIG. 3) revealed a widespread elevated ANGPTL4 mRNA and protein in epithelial tumors, regardless of anatomical site. ANGPTL4 expression increases as tumors progress from benign to invessive/metastatic state. To assess the role of ANGPTL4 in tumorigenesis, we suppressed it by RNAi in a highly metastatic skin tumor cell, A-5RT3 (FIG. 3b, FIG. 4a), generating the A-5RT3$_{ANGPTL4}$ line. Injection of A-5RT3$_{ANGPTL4}$ line into immunodeficient mice yielded ~90% tumor regression, associated with increased apoptosis and reduced cell proliferation, compared to control A-5RT3$_{CTRL}$. (FIG. 1c, 1d, 4b, 4c). qPCR-focused array of A-5RT3$_{ANGPTL4}$ tumor displayed increased expression of many pro-apoptotic genes, whilst cell proliferation genes were reduced (FIG. 4d). Notably, immunosuppression of ANGPTL4 with a monoclonal antibody, mAb11F6C4, significantly attenuated in vivo tumor growth (FIG. 1e, 4e, 4f). A-5RT3$_{ANGPTL4}$ formed 4-fold lower tumor colonies on soft agar (FIG. 1f) and were more suceptable to anoikis resistance, with 40% more apoptosis within 2 h (FIG. 1g).

We hypothesized that ANGPTL4 modulates oxidative stress of tumor via integrin-mediated signaling. ANGPTL4 interacted with integrins β1 and β5 but not with β3 (FIG. 2a, 5a, 5b), which were blocked by either mAb11F6C4 or integrin-specific antibodies (FIG. 5 c) In situ proximity ligation assay detected ANGPTL4-integrin complexes in vivo (FIG. 2b,5d, 5e). Integrin activation triggered focal adhesion kinase (FAK) in A-5RT3$_{CTRL}$ cells and tumors, which were reduced by ~70% in A-5RT3$_{ANGPTL4}$ (FIG. 2c, 2d). The expression of phosphorylated ERK1 (FIG. 2e) and the number of 14-3-3/Bad complexes (FIG. 2c, 2d, 5f) were reduced by ~85%, with 80% reduction of the 14-3-3β/σ proteins in the A-5RT3$_{ANGPTL4}$ induced tumors (FIG. 2e). The 14-3-3 adaptor protein sequesters pro-apoptotic Bad from mitochondria to prevent apaptosis (11). Further analysis showed diminished oxidized/activated Src (8), Na+/H_exchanger 1 (12), and increased catalase in A-5RT3$_{ANGPTL4}$ (FIG. 2f, 2g), suggesting that ANGPTL4 modulates ROS generation for tumor survival.

To underscore the prevalence of ANGPTL4 in ROS generation in tumors, we examined the impact of reduced ANGPTL4 against anoikis in 12 tumor cell lines. The suppression of ANGPTL4, either by constitutive (FIG. 1g), inducible (FIG. 6a 6b) RNAi or immunosuppression with mAb11F6C4 (FIG. 6c) resulted in 30%-60% more apoptosis within 2 hours. High intracellular ROS were reduced dose-dependantly by ANGPTL4 suppression (FIG. 2h, FIG. 7). Importantly, caspases 2, 3, 8, and 9 activities were increased by 3-8-fold (FIG. 2i; FIG. 8), indicating reduced anoikis resistance.

Altogether, ANGPTL4 is a candidate biomarker for human tumors, predominantly produced by epithelial tumor cells and a novel player in redox cancer biology. ANGPTL4 interacts with integrins to modulate ROS production, confers anoikis resistance to promote tumerogenesis, and is thus a potential therapeutic target.

It is known that in response to microenvironmental stress, such as hypoxia and inflammation, tumor cells exploit various signaling molecules to promote their growth, invasiveness and metastasis. The loss of dependence on integrin-mediated ECM contact for growth (or anoikis resistance) is an essential feature of tumor cells, yet how it is acquired is a central problem in cancer biology. Our study demonstrates a novel role for tumor-secreted ANGPTL4, which confers anoikis resistance to tumors via an autocrine adhesion mimicry that stimulates a redox-based pro-survival pathway (FIG. 17). Tumor-secreted ANGPTL4 interacts with integrins in an autocrine fashion to stimulate the NADPH oxidase-dependent generation of $O_2^-$, promoting a high $O_2^-$:$H_2O_2$ ratio, and consequently activating downstream PI3K/PKBα and ERK activities. Our findings identify ANGPTL4 as an important novel redox player in cancer biology and suggest that anticancer therapeutics focused on redox-based apoptosis induction in tumors represent an exciting and viable strategy.

The full-length ANGPTL4 is proteolytically cleaved, giving rise to the N-terminal coiled-coil domain (nANGPTL4) and the C-terminal fibrinogen-like domain (cANGPTL4). Depending on the tissue examined, differential expression of the various domains of ANGPTL4 was observed (Kersten et al., 2000). These observations raise the intriguing possibility that the different domains of ANGPTL4 have distinct biological functions. Furthermore, how cANGPTL4 triggers intracellular signaling to propagate its effect remains an unsolved question, hampering our understanding of the role of ANGPTL4.

We showed that only cANGPTL4 was detected and elevated in many human tumor cells, predominantly secreted by the proliferative tumor epithelial cells. cANGPTL4 specifically binds to integrins β1 and β5 on tumor cells and activates the FAK and Rac1, which further stimulates NADPH oxidase-mediated $O_2^-$ production by an autocrine pathway. However, it is conceivable that in tissues/organs expressing high level of cANGPTL4 in proximity to the tumor site may transmit a paracrine signal. Although integrins alone are not oncogenic, integrin-mediated signalings are often required to enable tumor survival and influence tumor growth (Desgrosellier and Cheresh, 2010). Our findings show that ANGPTL4-mediated integrin engagement activates ROS production, which leads to a pro-survival signal and sustained anchorage-related signals even in the absence of ECM and cell contact. The pro-oxidant intracellular environment leads to redox-mediated activation of the Src machinery, and therefore stimulates downstream PI3K/PKBα and ERK pro-survival pathways, which further triggers the 14-3-3 adaptor protein to sequester the pro-apoptotic Bad from mitochondria, which confers resistance to anoikis and favors tumor survival and growth. More importantly, our findings indicating that cANGPTL4 can modulate integrin-mediated signaling, are a pivotal step toward a better mechanistic understanding of the role of ANGPTL4.

A cell's fate is determined by the cellular redox state, through a complicated regulation mechanism, delicately maintained by intracellular ROS generators and antioxidant enzyme systems. Low or transient levels of intracellular ROS stimulate cellular signals essential for normal cellular functions. The dysregulation of intracellular ROS levels, resulting in excessive level or persistent elevation of ROS have been linked to tumor growth, invasiveness and metastasis. Indeed, elevated levels of ROS have been detected in almost all cancers (Liou and Storz, 2010). An elevated $O_2^-$ or $O_2^-$:$H_2O_2$ ratio is particularly important for cancer cells to sustain their tumorigenicity and metastatic potential (Clement and Pervaiz, 2001; Pervaiz and Clement, 2007). Indeed, the disruption of ANGPTL4-mediated redox signaling via genetic and antibody-mediated suppression of ANGPTL4 essentially reduced the activities of FAK, Rac1 and $O_2^-$ production. These changes resulted in an increase in tumor cells' sensitivity to anoikis and impaired tumorigenesis. ANGPTL4-stimulated NADPH oxidase activity, leading to $O_2^-$ production, can be inhibited by DPI and apocynin, two structurally and functionally distinct NADPH oxidase inhibitors, but not by the mitochondrial complex I inhibitor rotenone, suggesting that $O_2^-$ was "purposely" produced by enzymatic NADPH oxidase, rather than as a by-product of mitochondrial activity. Two survival pathways—the PKBα and ERK, which have been shown to exert anoikis-suppressing effects, were complementarily employed by ANGPTL4 to confer resistance to anoikis in tumor cells.

The tumor microenvironment plays a pivotal role in modulating gene expression and epithelial tumor cells' behavior. The tumor-promoting role of inflammation in the tumor microenvironment are well-recognized. The nuclear hormone receptors PPAR, in particular PPARγ and δ/βisotypes, play major roles in the regulation of inflammation, and have been implicated in tumorigenesis (Peters and Gonzalez, 2009; Wagner and Wagner, 2010; Panigrahy et al., 2005; Murphy and Holder, 2000). Although, in our analysis of paired PNSs and SSCs, we did not observe any correlation between the expression of either PPARγ or δ/β and their target gene ANGPTL4, we cannot exclude their involvement and/or other oncogenic pathways or cell types in the tumor microenvironment that enhanced the expression of cANGPTL4 in tumors. It is also conceivable that PPARs in cancer-associated fibroblasts play a more dominant role in the regulation of epithelial tumor growth. Indeed, we showed that PPAR β/δ-deficient fibroblasts can increase the proliferation of normal epithelial cells and SCCs via regulating interleukin-1 signaling pathway. The activation of interleukin-1 signaling was reported to enhance the growth of tumors, whereas its repression by the interleukin-1 receptor antagonist has an anti-tumor effect. A dysregulated inflammatory response can promote tumoriogenesis and maglinancy by stimulating ROS production. Although not examined in this study, we cannot rule out the possibility that other producers of $O_2^-$, such as cytosolic 5-lipooxygenase, which also requires Rac1 activation to function, may act in conjunction with ANGPTL4-stimulated NADPH oxidase activity to maintain an elevated intracellular $O_2^-$ level for tumor growth.

In summary, we provided evidence that tumor cells employ ANGPTL4 to hijack integrin-mediated signaling that modulates intracellular $O_2^-$ levels to confer anoikis resistance to tumor cells and to enhance tumorigenesis. Our findings identify ANGPTL4 as a novel tumor biomarker and redox factor in cancer biology, making ANGPTL4 a potential therapeutic target in cancer treatment.

Elevated Expression of ANGPTL4 in Various Tumor Types.

To examine the expression profile of ANGPTL4 in known human tumors, we first screened its expression pattern on two commercially available human tumor tissue arrays, which cover most of the common benign, malignant and metastatic tumors originating from various anatomic sites. By immunofluorescence with an anti-cANGPTL4 antibody, we observed a widespread elevated expression of ANGPTL4 in all epithelial tumor samples compared with the corresponding normal tissues, regardless of anatomical site of origin (FIGS. 10A and 18A-B). The level of immunofluorescence signal, however, varied among different types of tumor. Notably, the expression of ANGPTL4 increases as tumors progress from a benign state to an invasive/metastatic state (FIG. 18C). Next, we determined the expression of ANGPTL4 on three human skin tumorigenic lines (HSC, II-4 and A-5RT3), 10 human squamous cell carcinoma biopsies (SCCs) and 13 basal cell carcinoma biopsies (BCCs) by quantitative real-time PCR (qPCR) and immunoblot analyses. Consistent with our prior results, we observed significant upregulation of ANGPTL4 mRNA and protein levels in these epithelial tumor cells when compared with the non-tumorigenic human skin line HaCaT or cognate peri-tumor normal samples (PNSs), respectively (FIGS. 10B-D). No difference was observed between normal skin biopsies (NS) and PNS (FIGS. 10C-D). Interestingly, the three SCCs expressing the highest mRNA level of ANGPTL4 corresponded with an invasive prognosis (FIG. 10C), underscoring our finding in tumor tissue arrays. In addition, polyclonal antibodies against either the N- or C-termini of ANGPTL4 detected only the cANGPTL4 in these tumor lines and SSCs (FIGS. 10B-D and 18D-E). The expression of ANGPTL4 is upregulated by hypoxia and by peroxisome-proliferator activated receptors (PPARs). To understand the reason for the increased expression of ANGPTL4 in tumor cells, we examined the expression of hypoxia-inducible factor 1 alpha (HIF1α) and PPARs in the SCC samples. We found a concomitant upregulation of HIF1α along with ANGPTL4 in SSCs when compared with PNSs and with a Pearson correlation coefficient of 0.88 (FIGS. 10E and 18F). Although no clear correlation was observed between the expression of ANGPTL4 and the three PPAR isotypes (FIGS. 18G-I), we cannot exclude an involvement of PPARs and/or other oncogenic pathways that enhanced the expression of cANGPTL4 in tumors. These results suggested that, at least for SCC, the elevated expression of ANGPTL4 reflected the tumor's hypoxic microenvironment. Being a secreted protein highly detected in tumor cells, ANGPTL4 may perform an important paracrine or autocrine function in tumors. Therefore, we sought to determine the source of ANGPTL4 in tumors. We isolated epithelial tumor and stromal tissues, which consist mainly of fibroblasts, from SCCs and PNSs, using laser capture microdissection (LCM). qPCR and immunoblot analyses were performed on these samples. Our results revealed that epithelial tumor cells, rather than tumor stroma, were the major contributor of ANGPTL4 in SCCs (FIG. 10F), and only a low, baseline level of ANGPTL4 expression was found in normal PNS stroma and epithelia, suggesting that ANGPTL4 may have an autocrine role in tumors.

Suppression of ANGPTL4 Impairs In Vivo Tumor Growth.

Our findings revealed an elevated expression level of ANGPTL4 in tumors. Next, we investigated its biological relevance to tumor growth by RNA interference. Four sets of siRNAs targeting different segments of the ANGPTL4 sequence were permanently introduced into the metastatic skin tumor line A-5RT3, and the sub-line with highest knockdown efficiency (designated A-5RT3$_{ANGPTL4}$) was selected for subsequent studies. A non-targeting scrambled siRNA was also integrated into A-5RT3 (designated A-5RT3$_{CTRL}$), serving as a negative control. ANGPTL4 mRNA and protein levels were successfully suppressed by >85% in A-5RT3$_{ANGPTL4}$ when compared with the parental control A-5RT3 or the scrambled control A-5RT3$_{CTRL}$ (FIG. 11A). The induction of interferon responses has been reported as a challenge to the specificity of some RNA interference approaches. To test whether the RNAi-mediated silencing of ANGPTL4 was associated with interferon responses, we measured the expression of some key interferon response genes by qPCR. No induction of Oas1, Oas2, Mx1 or Isgf3 was detected in the A-5RT3$_{ANGPTL4}$ when compared with either wild-type, untreated A-5RT3 or A-5RT3$_{CTRL}$ (FIG. 19A), verifying that our RNAi experiment did not produce an off-target effect. As expected, the injection of A-5RT3$_{CTRL}$ cells into immunodeficient mice induced large primary tumors (~1000 mm³) in all five mice at week eight, however A-5RT3$_{ANGPTL4}$-induced tumors showed a 90% reduction in tumor growth (FIGS. 11B-C). A-5RT3$_{ANGPTL4}$-induced tumor growth was similarly reduced, albeit a 40% reduction, when mice were implanted with increasing number of tumor cells (FIG. 19B). To strengthen the above observation, we implanted B16F10 cells subcutaneously into ANGPTL4-knockout (KO) and control (WT) mice. WT and KO mice were maintained in a C57BL/6J background and B16F10 melanoma was derived from the same background. Notably, B16F10 tumor cells implanted in KO mice grew significantly slower than those implanted in WT mice; at 15 days post implantation, the average tumor volume in KO mice was ~6-fold smaller than that in WT mice (FIG. 11D). The injection of ANGPTL4-knockdown (B16F10$_{ANGPTL4}$) cells into KO mice induced little tumor growth, and showed similar growth profile in WT mice to control B16F10 (B16F10$_{CTRL}$)-induced tumors in KO mice (FIG. 11D). Conversely, WT mice implanted with B16F10$_{CTRL}$ and intravenously injected thrice weekly with recombinant N-terminal histidine-tagged recombinant cANGPTL4 showed greater tumor growth, the average tumor volume in cANGPTL4-treated mice was ~3-fold larger than PBS-treated mice (FIGS. 11E and 19C-D). B16F10$_{ANGPTL4}$-induced tumor growth was diminished in PBS-treated mice when compared to cANGPTL4-treated mice (FIG. 11E). Next, we reasoned that treating mice injected with A-5RT3$_{CTRL}$ cells with an antibody that interferes with the action of ANGPTL4 will recapitulate the observation made with A-5RT3$_{ANGPTL4}$. To this end, the monoclonal human cANGPTL4-directed antibody mAb11F6C4 was identified and produced for our immunotherapy experiment based on its superior $k_{on}$, $k_{off}$ and $K_D$ values, as determined by surface plasmon resonance (SPR) (FIG. 11F). Notably, immunosuppression of ANGPTL4 with mAb11F6C4 significantly attenuated in vivo tumor growth in immunodeficient mice, compared with control IgG-treated mice (n=6 each group) (FIGS. 11G-H). Immunoblot and immunofluorescence analysis of A-5RT3$_{ANGPTL4}$-induced tumor biopsies indicated significantly reduced cell proliferation and enhanced cell apoptosis when compared with A-5RT3$_{CTRL}$-induced tumors (FIGS. 11I-J). A qPCR-focused array of A-5RT3$_{ANGPTL4}$-induced tumor biopsies further suggested increased expression of many pro-apoptotic genes, whereas expression of cell proliferation genes were diminished (FIG. 11K; Table 1). Altogether, these observations clearly supported a tumor-promoting role of cANGPTL4.

ANGPTL4-Deficient Tumor Cells Showed Increase Susceptibility to Anoikis.

Figure 12D:
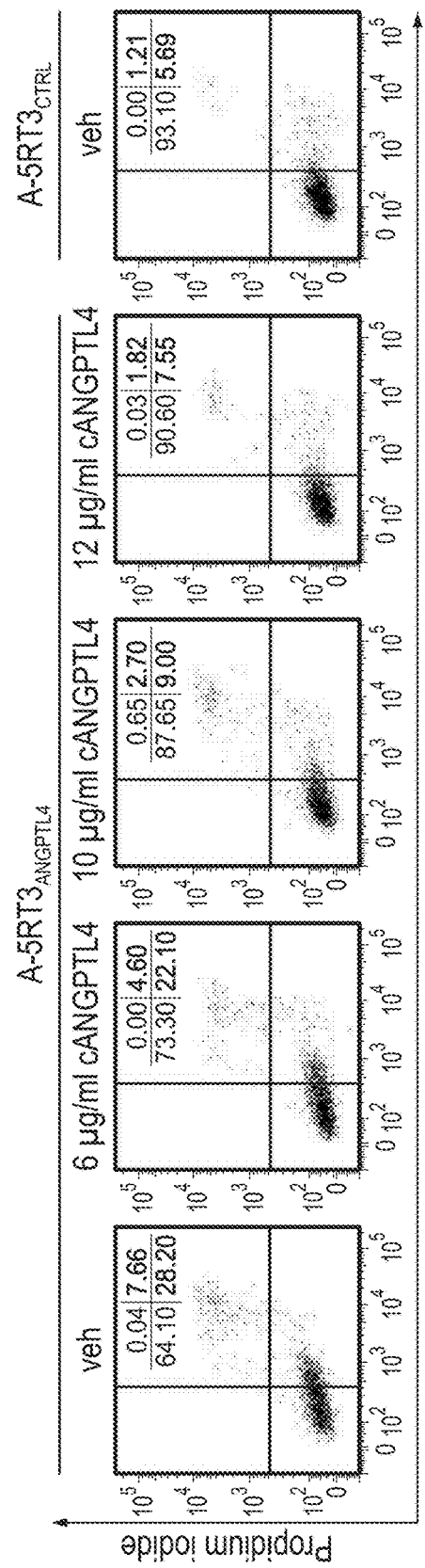
Figure 12:
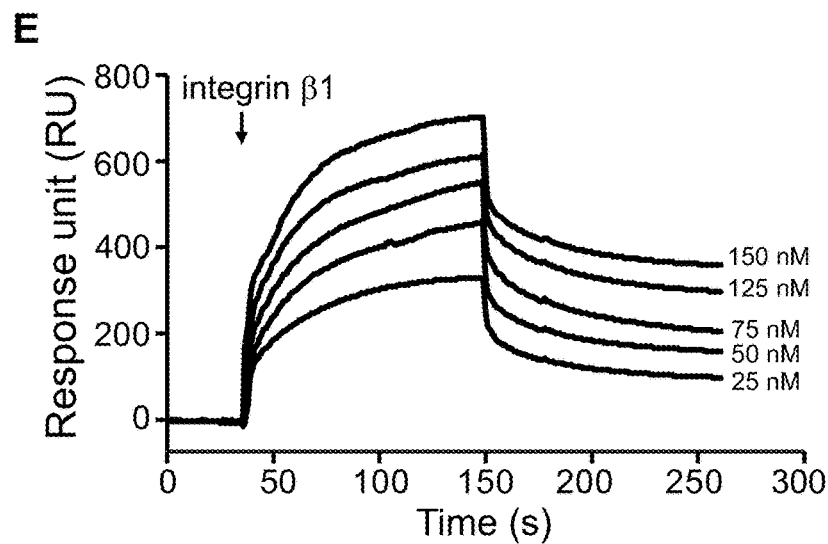
Figure 12:
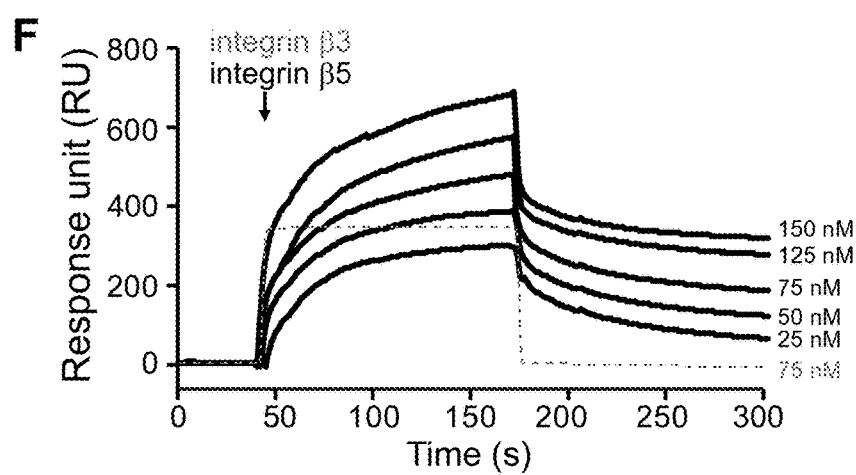
Figure 12:
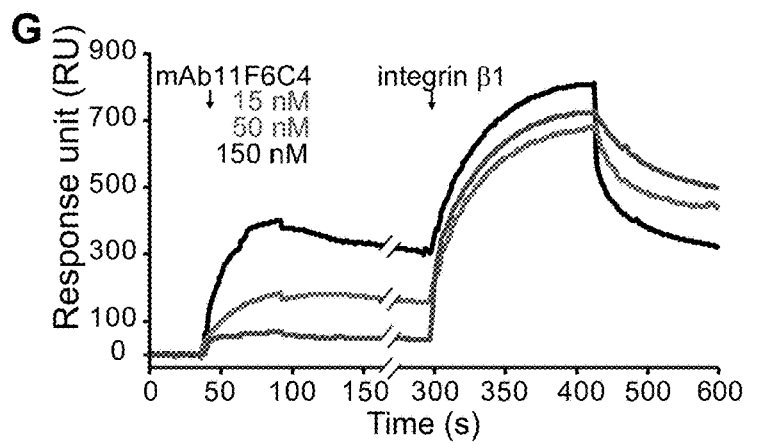
Figure 12:
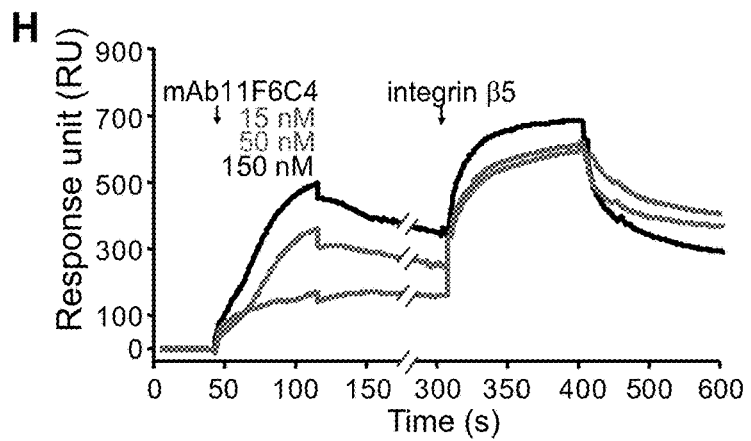
Figure 12:
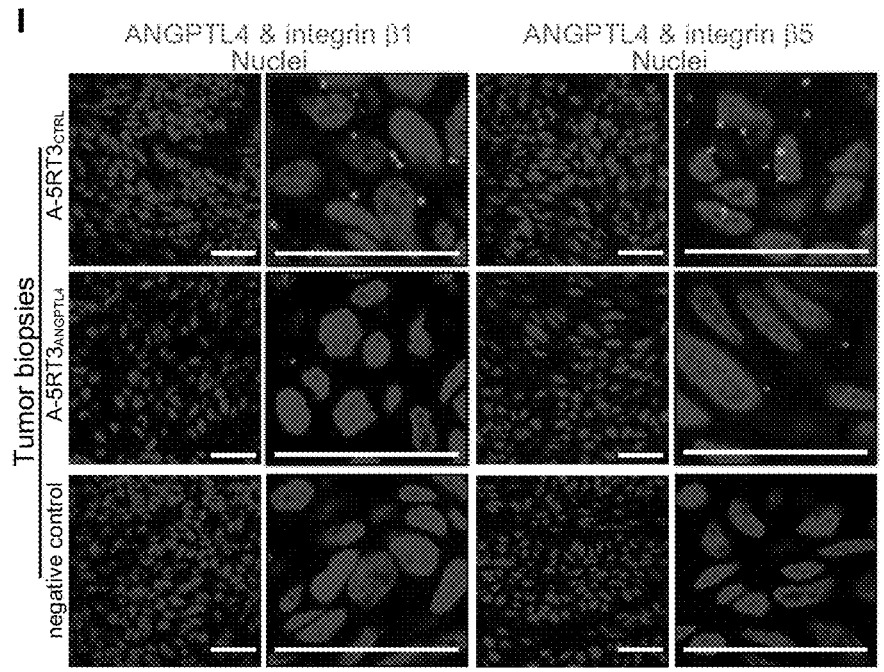
Figure 12:
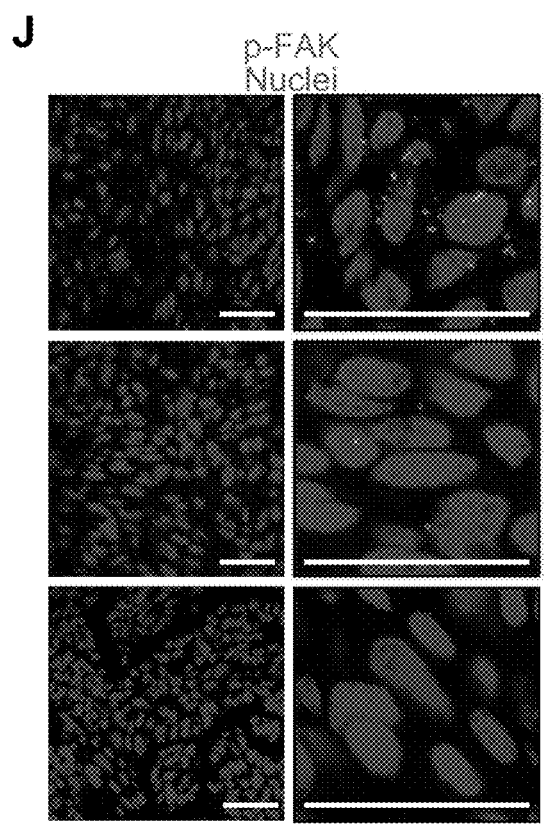
Figure 12:
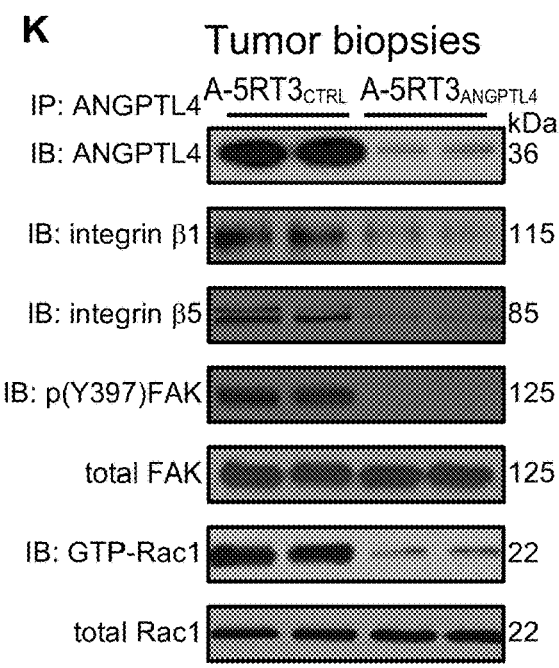

Anchorage-independent growth or anoikis resistance of tumor cells, a hallmark of tumor malignancy, can be investigated by tumor colony formation in soft agar and anoikis assays, which are well-established in vitro approaches to study and predict self-renewal and metastatic potentials of in vivo tumor cells. Underscoring our in vivo findings, the colony-forming potential of A-5RT3$_{ANGPTL4}$ was dramatically undermined and formed significantly (~85%) fewer tumor colonies on soft agar when compared with A-5RT3$_{CTRL}$ (FIG. 12A). Furthermore, A-5RT3$_{ANGPTL4}$ was also more susceptible to anoikis, having 30% more apoptotic A-5RT3$_{ANGPTL4}$ cells, as well as significantly enhanced activities from caspases 2, 3, 8 and 9 when compared with A-5RT3$_{CTRL}$ after 2 h of anoikis (FIG. 12B-C). The addition of exogenous recombinant cANGPTL4 reduced the apoptotic index of A-5RT3$_{ANGPTL4}$ in a dose-dependent manner (FIG. 12D). Similarly, ANGPTL4 deficiency in human keratinocytes rendered these cells ~50% more susceptible to anoikis when compared to control keratinocytes, suggesting that low amount of ANGPTL4 was also necessary to confer anoikis resistance in normal epithelial cells (FIG. 20A). No difference in apoptotic index was observed with adhered A-5RT3 and keratinocytes (FIG. 20A-B).

ANGPTL4 Interacts with Integrins β1 and β5.

Our above findings indicated that ANGPTL4 endows tumor cells with resistance to anoikis and therefore sustain their growth, but how ANGPTL4 mediates this process remains a central question in our understanding of ANGPTL4 in cancer biology. Previous studies have revealed that anoikis is an integrin-dependent process, thus we hypothesize that ANGPTL4 also exerts its role in tumor cells through integrins-mediated signaling. First, we examined if cANGPTL4 can interact with integrin. Indeed, results obtained from SPR and ELISA assays showed that ANGPTL4 specifically interacts with integrins β1 and β5, but not with β3 (FIG. 12E-F), which were blocked by either mAb11F6C4 or integrin-specific antibodies (FIGS. 12G-H and 20D-G). ANGPTL4 deficiency did not affect the expression of integrins β1, β3 and β5 (FIG. 20H). An in situ proximity ligation assay (PLA) detected ANGPTL4-integrin complexes both in A-5RT3$_{CTRL}$ cells and A-5RT3$_{CTRL}$-induced tumor biopsies (FIGS. 20I and 12I), confirming that this interaction also exists in vivo. Further investigation revealed that integrin activation by ANGPTL4 binding triggered focal adhesion kinase (FAK) in A-5RT3$_{CTRL}$ cells and tumors, which were reduced by >70% in A-5RT3$_{ANGPTL4}$ (FIGS. 12J and 20J). All of these findings were further corroborated by results from immunodetection on tumor biopsies (FIG. 12K). Our findings suggest that ANGPTL4 secreted by epithelial tumor cells acts in an autocrine manner to hijack the integrin/FAK-regulated pathway to confer anoikis resistance to tumors, and thus sustain tumor growth.

ANGPTL4 Elevates $O_2^-$ Level and Maintains a High $O_2^-$:$H_2O_2$ Ratio in Tumor Cells.

Reactive oxygen species (ROS; e.g. $O_2^-$ and $H_2O_2$) have long been recognized as important second messengers, functioning in the relay of intracellular signals in normal and cancer cells. ROS can be regulated through integrin engagement and an elevated $O_2^-$ level or relatively high $O_2^-$:$H_2O_2$ ratio allows tumor cells to survive and to avoid anoikis In this regard, we asked whether ANGPTL4-integrin interaction can regulate ROS production in tumor cells. Using electron paramagnetic resonance spectroscopy (EPR) in combination with 5-(diethoxyphosphoryl)-5-methyl-1-pyrroline-N-oxide (DEPMPO) spin trapping, we measured a significant decrease in $O_2^-$ level in A-5RT3$_{ANGPTL4}$ when compared with A-5RT3$_{CTRL}$ (FIG. 13A-B), suggesting ANGPTL4 is vital in sustaining $O_2^-$ production in tumor cells. To determine the source of $O_2^-$, similar experiments were performed using specific inhibitors that block the mitochondrial respiratory chain complex I and membrane-bound NADPH oxidase, which are two major producers of $O_2^-$ in mammalian cells. Treatment of tumor cells with rotenone, a mitochondrial respiratory chain complex I inhibitor, did not alter their cellular $O_2^-$ level (FIG. 13A-B) suggesting that such a complex has little role in generating $O_2^-$ in tumors. Further excluding mitochondria as the source of ANGPTL4-mediated $O_2^-$ generation, our qPCR analysis showed no change in the expression of selected genes in the methionine/homocysteine metabolic cycle (FIG. 21A), as previously studied in db/db diabetic rodent hepatocytes. In contrast, $O_2^-$ level was significantly abrogated by using two different NADPH oxidase inhibitors, namely, diphenylene iodonium (DPI) and apocynin (FIG. 13A-B). Reactive oxygen species generated through the involvement of the small GTPase Rac1 and NADPH oxidase upon integrin engagement exert a mandatory role in transmitting a pro-survival signal that ensures the tumor cells escape from anoikis. In accordance with these results, comparative immunoblot analysis of anti-cANGPTL4 immunoprecipitates from A-5RT3$_{CTRL}$- and A-5RT3$_{ANGPTL4}$-induced tumor lysates detected integrins β1 and β5, along with phosphorylated FAK and active GTP-bound Rac1, in A-5RT3$_{CTRL}$-induced tumor, but were significantly reduced in A-5RT3$_{ANGPTL4}$-induced tumor (FIG. 12K). To further validate the relevance of Rac1 in ANGPTL4-mediated $O_2^-$ production, we next transiently transfected A-5RT3$_{CTRL}$ and A-5RT3$_{ANGPTL4}$ with dominant-negative Rac1 (T17N) and constitutively active Rac1 (G12V), respectively. We measured a significantly diminished $O_2^-$ level in the former system and, conversely, an obvious rescued level of $O_2^-$ production in the latter one. The percentage of inhibition and recovery was consistent with the ~65% transfection efficiencies, as estimated using a GFP-expressing vector. The requirement of Rac1 suggested a Nox-dependent mechanism. Thus, we examined the expression of Nox1 and Nox 2 in A-5RT3 (FIG. 21B). Nox 3 is expressed predominantly in the inner ear and is involved in the biogenesis of otoconia/otolith. Next, we performed Nox1 and Nox2 knockdown (Nox1 kd and Nox2 kd, respectively) in A-5RT3$_{CTRL}$ and A-5RT3$_{ANGPTL4}$ (FIG. 21C), and measured $O_2^-$ level using EPR (FIG. 13A-B). The results indicated that Nox 1 NADPH oxidase is the predominant producer of ANGPTL4-mediated $O_2^-$ generation in tumor cells. As expected, $O_2^-$ was completely abolished when treated with the superoxide scavenger Tiron, which serves as a negative control for superoxide measurement (FIG. 13A-B). These data were reproduced by a reliable chemiluminescence method using 2-methyl-6-(4-methoxyphenyl)-3,7-dihydroimidazo[1,2-a]pyrazin-3-one hydrochloride (MCLA; FIG. 13C). Next, we measured the level of $H_2O_2$ in tumor cells in the presence of a specific catalase inhibitor, 3-amino-1,2,4-triazole. $H_2O_2$ levels in A-5RT3$_{ANGPTL4}$ were significantly higher when compared with A-5RT3$_{CTRL}$ (FIG. 13D). Nox1 knockdown did not affect the $H_2O_2$ level, suggesting that ANGPTL4 modulated $H_2O_2$ production via a linked as-yet-unknown mechanism (FIG. 21D). Notably, the lower $O_2^-$ level and $O_2^-$:$H_2O_2$ ratio was concurrent with threefold more apoptosis and significantly enhanced caspase activities within 2 h of anoikis in A-5RT3$_{ANGPTL4}$ when compared with A-5RT3$_{CTRL}$ (FIGS. 13A-D and 12B-C). In concordance, we observed a reduced $O_2^-$ level in A-5RT3$_{ANGPTL4}$-induced tumors when compared with A-5RT3$_{CTRL}$-induced tumors as determined by EPR (FIG. 13E-F) which was associated with increased apoptosis (FIG. 11I-K).

Figure 13K:
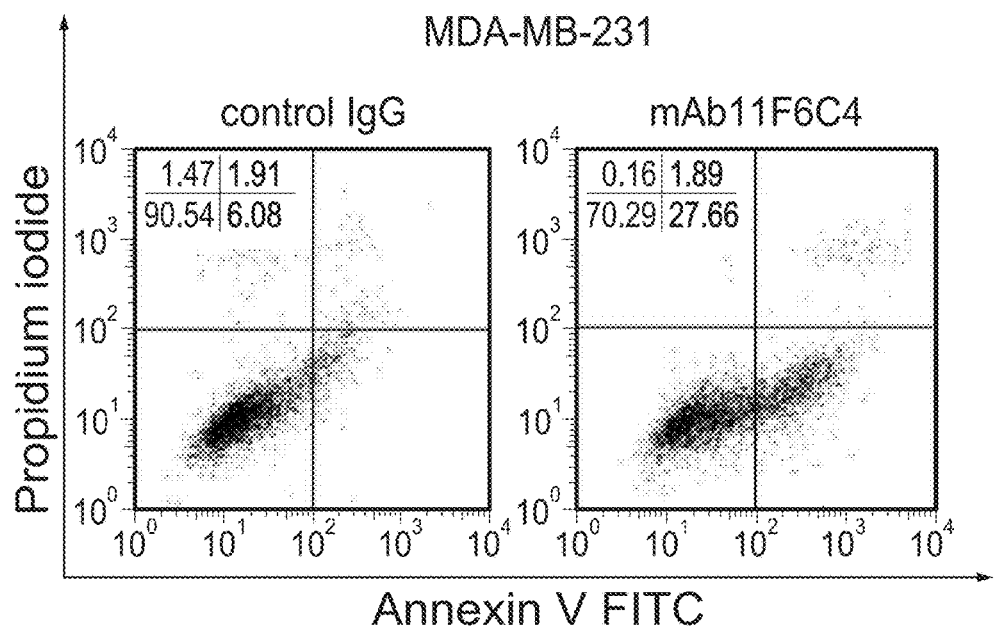
Figure 13L:
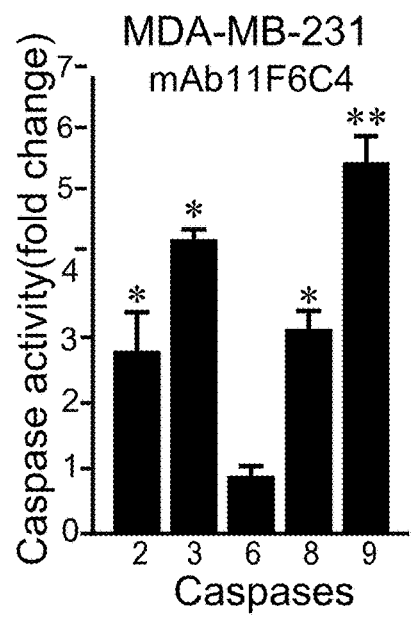

To underscore the relevance of these findings to other cancers, similar experiments were performed using the breast cancer line MDA-MB-231, after using the monoclonal antibody mAb11F6C4 to dose-dependently neutralize endogenous cANGPTL4. We showed earlier that mAb11F6C4 was able to block cANGPTL4-integrin interaction (FIGS. 12G-H and 20D-G). Consistent with the above results, the immunosuppression of cANGPTL4 in MDA-MB-231 reduced the $O_2^-$ level (FIG. 13G-I), lowered the $O_2^-$:$H_2O_2$ ratio (FIG. 13J), and enhanced apoptosis and caspase activities (FIG. 13K-L). The knockdown of Nox1 (FIG. 21E), but not Nox2, reduced ANGPTL4-mediated $O_2^-$ production (FIG. 13G-I) with little effect on $H_2O_2$ production (FIG. 21F). Taken together, these findings indicated that ANGPTL4 could protect tumor cells from anoikis via an NADPH oxidase-dependent $O_2^-$ generation mechanism.

ANGPTL4-Mediated $O_2^-$ Activates Src, PI3K/PKB and ERK Survival Pathways

Figure 14C:
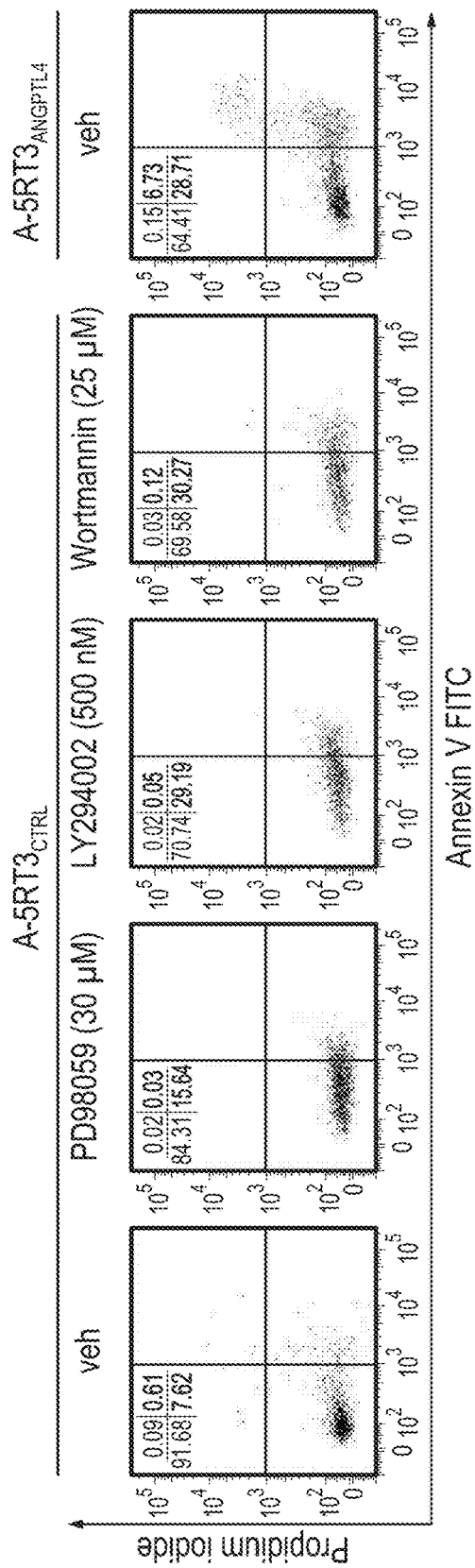
Figure 14:
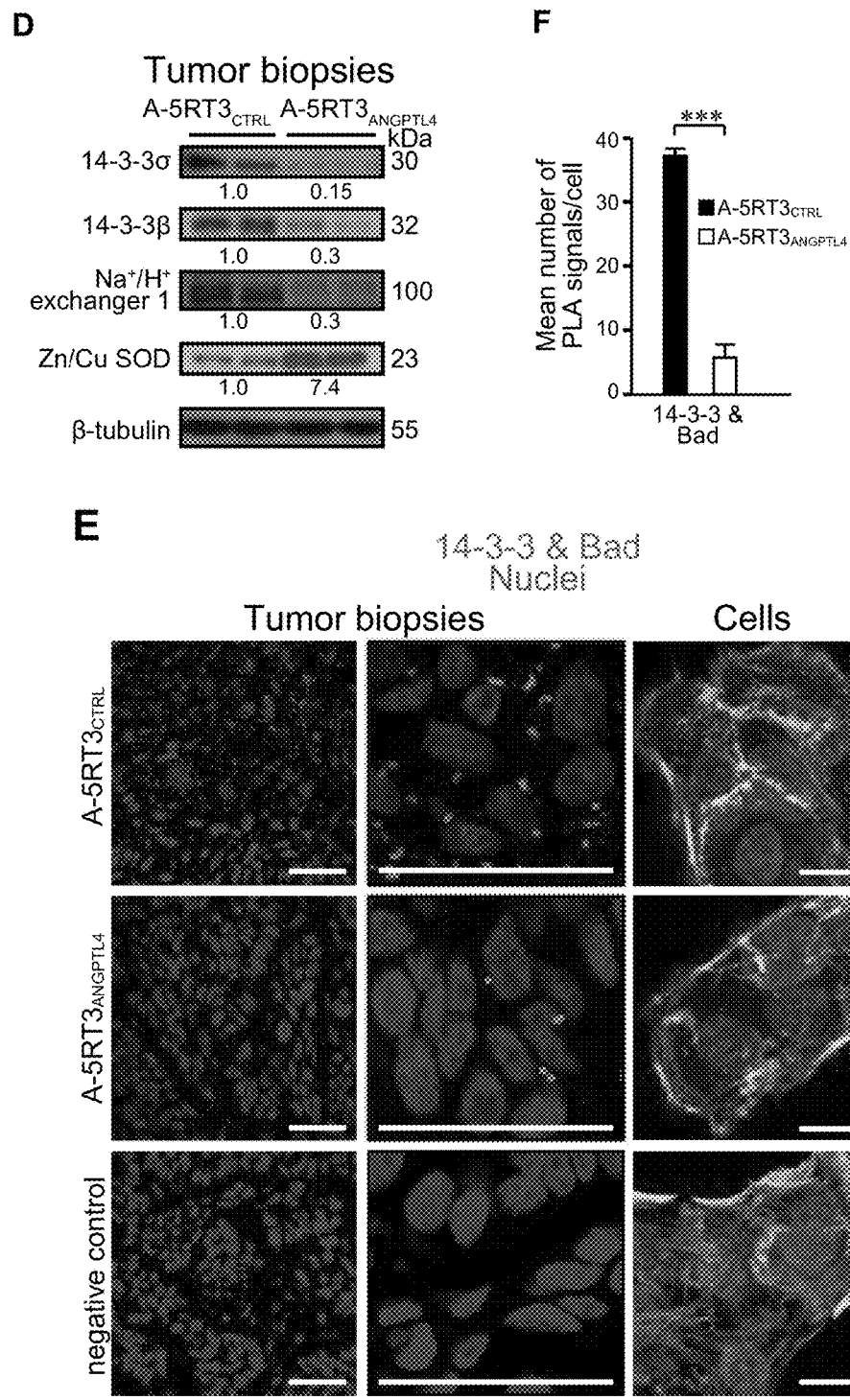

Reports have shown that ROS produced via integrin engagement oxidizes and activates Src, which stimulates the ERK and PKBα pro-survival pathways. Both pathways regulate the subcellular localization or stability of BH3-only apoptotic proteins (e.g. Bad and Bim), essential for executing anoikis Thus, we asked whether ANGPTL4-integrin engaged $O_2^-$ generation employs these downstream signaling pathways to modulate tumor cell behavior. Indeed, immunoblot analysis revealed significantly diminished expression of oxidized/activated Src, phosphorylated PKBα and ERK1 in A-5RT3$_{ANGPTL4}$-induced tumors and A-5RT3$_{ANGPTL4}$ cells (FIG. 14A and left panel of 14B). Similar immunoblot analysis performed in the presence of DPI and with Nox1 knockdown cells, which attenuate ANGPTL4-mediated $O_2^-$ production, found severely diminished Src, PKBα and ERK1 activations, emphasizing the role of $O_2^-$ in their activities (FIG. 14B). The inhibition of PI3K by LY29402 and Wortmannin, a pivotal upstream mediator of PKBα, caused significantly (four-fold) more apoptosis of tumor cells within 2 h of anoikis challenge, reaching levels comparable to those of A-5RT3$_{ANGPTL4}$ (FIG. 14C). In addition, inhibition of MEK1/2, the upstream signal of ERK1, by PD98059 also resulted in a significant enhancement of apoptotic cell numbers upon anoikis challenge, albeit to a lesser extent (~50%) when compared with PI3K inhibitors (FIG. 14C). These results suggested that PI3K/PKBα and ERK1/2 downstream survival pathways were modulated and exploited by ANGPTL4 engagement in tumor cells, the former being the predominant path.

The 14-3-3 adaptor protein is known to act downstream of the survival pathways by sequestering pro-apoptotic Bad from the mitochondria to prevent apoptosis. In agreement with these previous findings, the number of 14-3-3/Bad complexes and 14-3-3β/δ proteins were significantly reduced by ~70% in A-5RT3$_{ANGPTL4}$-induced tumors (FIG. 14D-F). The Na$^+$/H$^+$ exchanger 1 (NHE), which positively influences cell proliferation by maintaining an alkaline intracellular environment, was diminished in A-5RT3$_{ANGPTL4}$-induced tumors (FIG. 14D), indicating that NHE plays a subsidiary role to ANGPTL4-mediated tumor cell growth. Upon oxidant challenge in tumor cells, the induction of superoxide dismutase (SOD) expression was muted, allowing tumor cell proliferation. In agreement with these studies, we found that expression of the cytosolic Zn/CuSOD was significantly enhanced in A-5RT3$_{ANGPTL4}$-induced tumors (FIG. 14D), which indirectly contribute to the reduced $O_2^-$:$H_2O_2$ ratio in ANGPTL4-deficient tumor cells (see FIGS. 13D, J and 21D, F).

ANGPTL4 Deficiency Abrogates $O_2^-$ Production and Sensitizes Cancer Cells to Anoikis Our results revealed that the suppression of ANGPTL4, either by constitutive RNAi (FIG. 13A-C) or immunosuppression with mAb11F6C4 (FIG. 13G-I) resulted in a dose-dependent reduction of $O_2^-$ levels. To underscore the importance of ANGPTL4 in the regulation of $O_2^-$ production, maintenance of high $O_2^-$:$H_2O_2$ ratio, and hence tumor survival, we examined the impact of reduced ANGPTL4 against anoikis in nine different cancer cell lines, in addition to A-5RT3 and MDA-MB-231. Treatment with mAb11F6C4, which blocked cANGPTL4-integrin interaction, resulted in a dose-dependent reduction of $O_2^-$ levels (40-80% for 6 μg/mL mAb11F6C4; FIG. 15A), a reduction in $O_2^-$:$H_2O_2$ ratio (70-90% for 6 μg/mL mAb11F6C4; FIG. 15B), a 3-8 fold increase in the activities of caspases 2, 3, 8 and 9 (FIG. 16A) and 30-60% more apoptotic tumor cells (FIG. 16B), all indicating weakened anoikis resistance and further corroborating our previous observations on A-5RT3 and MDA-MB-231. Higher percentage of apoptotic tumor cells was also observed using inducible RNAi against ANGPTL4 in MDA-MB-231 (FIG. 16C). These findings indicated that ANGPTL4-mediated $O_2^-$ production for anoikis resistance may be a common feature in tumor cells.

TABLE 1

Figure 2:
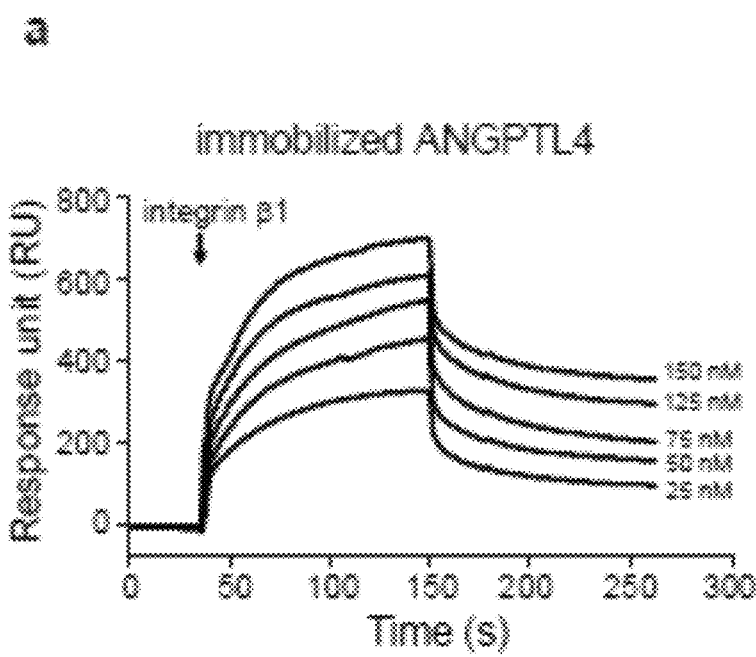
FIG. 2. ANGPTL4 modulates ROS generation via interactions with integrins.
Figure 2:
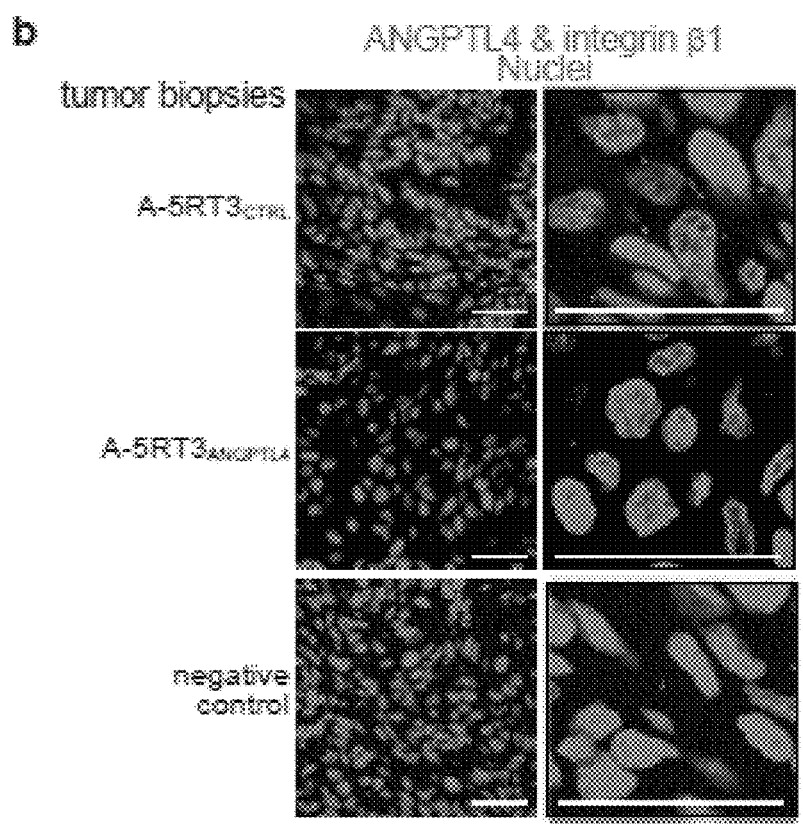
Figure 2:
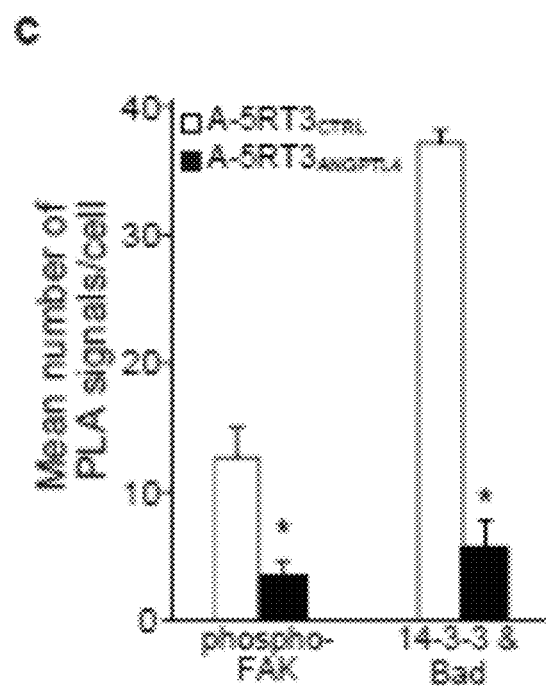
Figure 2:
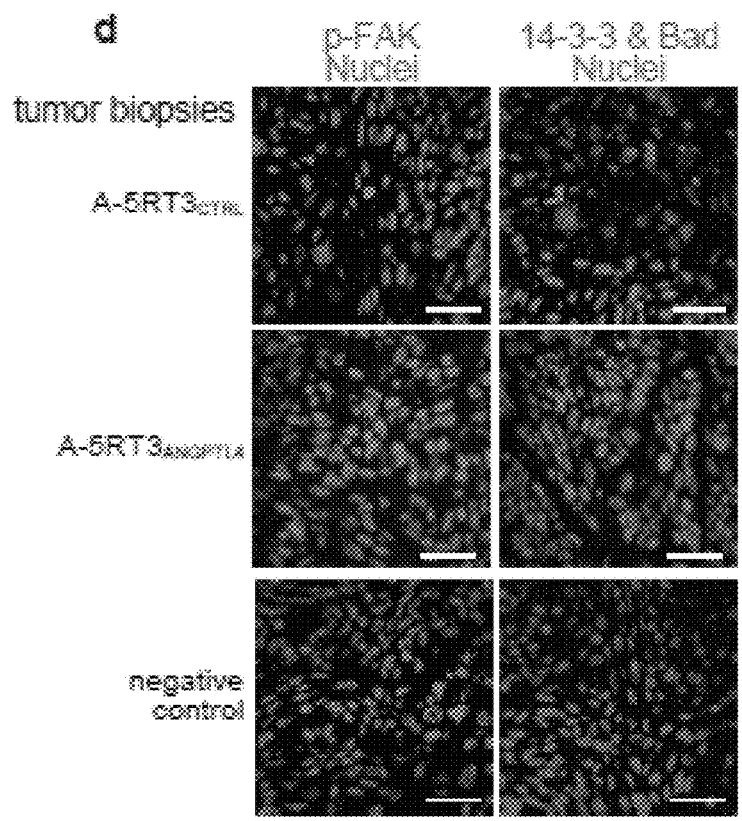
Figure 2:
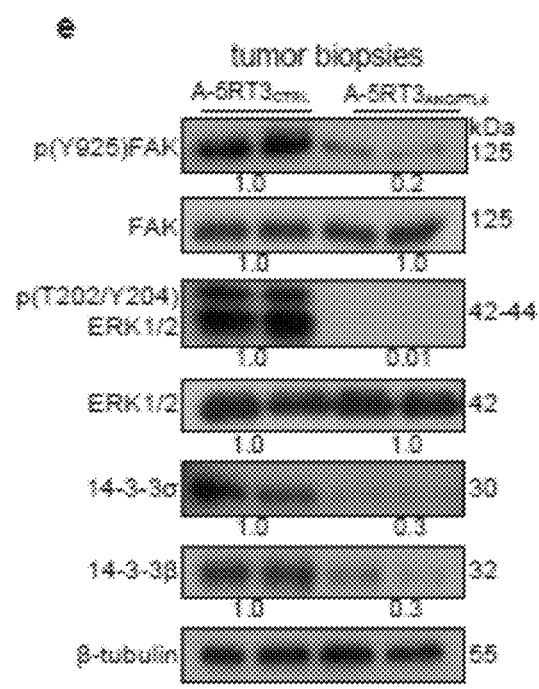
Figure 2:
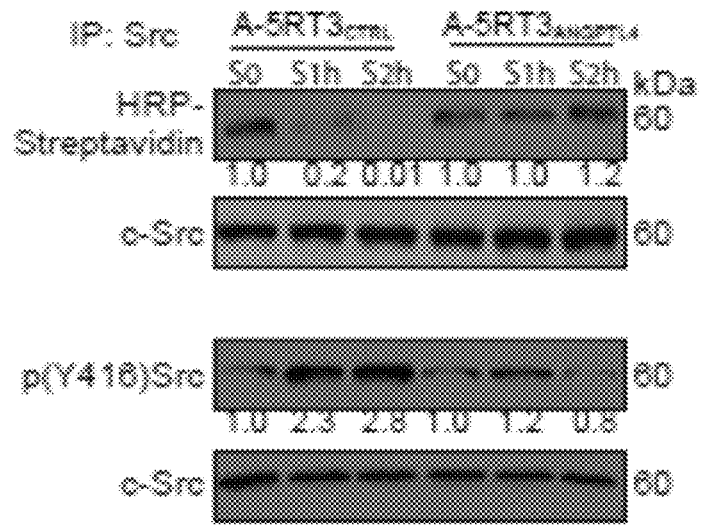
Figure 2:
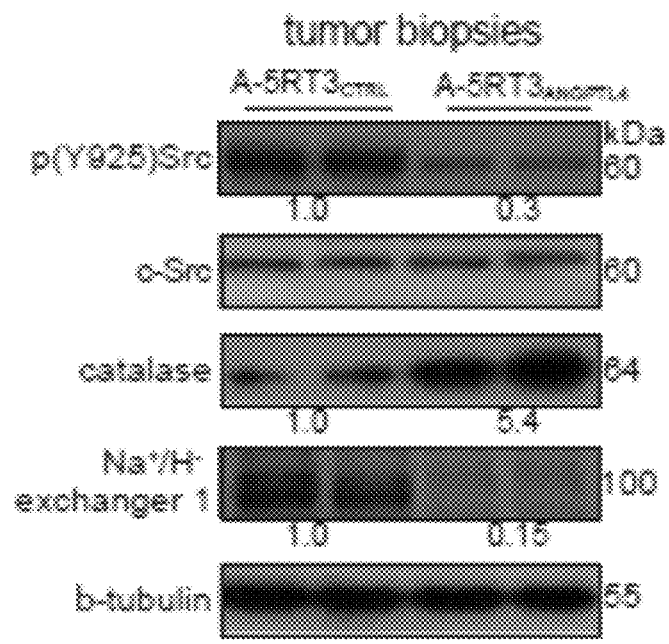
Figure 2:
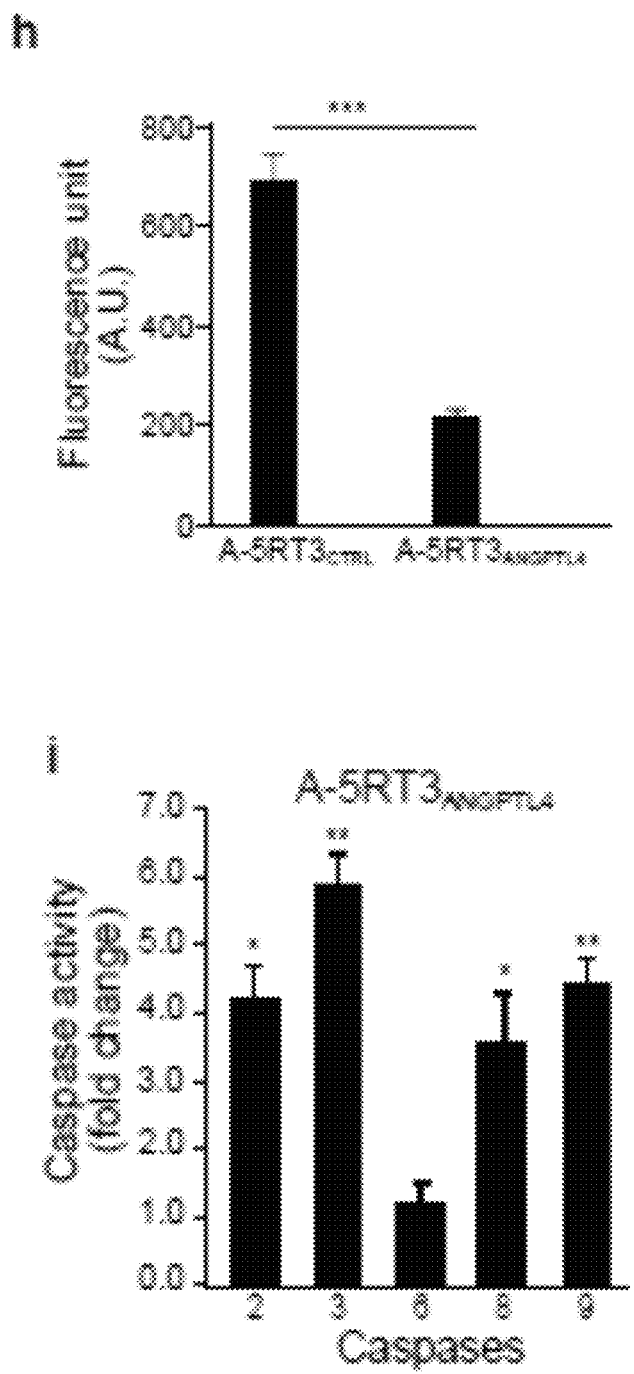

Relative fold change of gene expressions in A-5RT3$_{ANGPTL4}$-induced tumors as compared with that of A-5RT3$_{CTRL}$-induced tumors, related to FIG. 2 and 11

| Down-regulated (>2-fold) | | |
|---|---|---|
| Gene | A-5RT3$_{CTRL}$ | A-5RT3$_{ANGPTL4}$ |
| Diablo | 1.000 | 0.070 |
| Ccnd1 | 1.000 | 0.102 |
| Ccna2 | 1.000 | 0.119 |
| Xiap | 1.000 | 0.120 |
| Pcna | 1.000 | 0.177 |
| Cox10 | 1.000 | 0.223 |
| Birc2 | 1.000 | 0.247 |
| Ki67 | 1.000 | 0.269 |
| Birc3 | 1.000 | 0.345 |
| Cdk5 | 1.000 | 0.498 |
| Mcl1 | 1.000 | 0.500 |
| Cdk4 | 1.000 | 0.549 |

| Up-regulated (>2-fold) | | |
|---|---|---|
| Gene | A-5RT3$_{CTRL}$ | A-5RT3$_{ANGPTL4}$ |
| Casp7 | 1.000 | 1.927 |
| Bid | 1.000 | 2.051 |
| Bbc3 | 1.000 | 2.075 |
| Perp | 1.000 | 2.246 |
| Parp1 | 1.000 | 2.308 |
| Pxn | 1.000 | 2.947 |
| Bcl2l1 | 1.000 | 3.112 |
| Cdkn1c | 1.000 | 3.609 |
| Fas | 1.000 | 6.171 |
| Chuk | 1.000 | 6.353 |
| Bax | 1.000 | 8.363 |
| Casp1 | 1.000 | 10.499 |
| Casp2 | 1.000 | 10.560 |
| Cdkn1a | 1.000 | 13.037 |
| Bcl2l2 | 1.000 | 14.671 |
| Casp10 | 1.000 | 24.740 |

Note: The Gene expression levels in A-5RT3$_{CTRL}$-induced tumors were assigned value one.

TABLE 2

Sequences of ANGPTL4, Nox 1, Nox2 and Control siRNAs

| siRNA | Sense Primer (5'→3') | Antisense Primer (5'→3') |
|---|---|---|
| ANGPTL4 set 1* | AAAGCTGCAAGATGACCTC AGATGGAGGCTG (SEQ ID NO. 4) | AAAACAGCCTCCATCTGAGG TCATCTTGCAG (SEQ ID NO. 5) |
| ANGPTL4 set 2# | TCGAGGCAGCACCTGCGAA TTCAGCATCTGCATTCAAG AGATGCAGATGCTGAATTC GCAGGTGCTGCTTTTTTAC GCGTA (SEQ ID NO. 6) | AGCTTACGCGTAAAAAGCAGC ACCTGCGAATTCAGCATCTGC ATCTCTTGAATGCAGATGCTG AATTCGCAGGTGCTGCC (SEQ ID NO. 7) |
| Nox1 | AAAGGGCCACAGATGGCTC CCTTGCCTCCAT (SEQ ID NO. 8) | AAAAATGGAGGCAAGGGAGCC ATCTGTGGCC (SEQ ID NO. 9) |

TABLE 2-continued

Sequences of ANGPTL4, Nox 1, Nox2 and Control siRNAs

| siRNA | Sense Primer (5'→3') | Antisense Primer (5'→3') |
|---|---|---|
| Nox2 | AAAGGGCCAGATGTTCTTT CTACAGAAGAAT (SEQ ID NO. 10) | AAAAATTCTTCTGTAGAAAGA ACATCTGGCC (SEQ ID NO. 11) |
| Mouse ANGPTL4 | AAAGCTGTGAGATGACTTC AGATGGAGGCTG (SEQ ID NO. 12) | AAAACAGCCTCCATCTGAAGT CATCTCACAG (SEQ ID NO. 13) |
| Control siRNA | AAAGCTGTCTTCAAGCTTG ATATCGAAGACTA (SEQ ID NO. 14) | AAAAATAGTCTTCGATATCAA GCTTGAAGACAG (SEQ ID NO. 15) |

*ANGPTL4 Set 1 siRNA used for lentivirus-mediated RNA interference (SEQ ID NO. 4 & 5).
ANGPTL4 set 2 shRNA was cloned into pSingle-tTS-shRNA vector (Clontech) and used for doxycycline-inducible knockdown in MDA-MB-231 cells (SEQ ID NO. 6 & 7).

TABLE 3

Sequences of Quantitative Real-time PCR (qPCR) Primers

| GenBank Accession | Official | Sense Primer (5'→3') | Antisense (5'→3') |
|---|---|---|---|
| NM_004324 | Bax | GGGTGGTTGGGTGAGACTC (SEQ ID NO. 16) | AGACACGTAAGGAAAACGC ATTA (SEQ ID NO. 17) |
| NM_014417 | Bbc3 | GACCTCAACGCACAGTACGAG (SEQ ID NO. 18) | AGGAGTCCCATGATGAGAT TGT (SEQ ID NO. 19) |
| NM_138578 | Bcl2l1 | TGCGTGGAAAGCGTAGACAAG (SEQ ID NO. 20) | GCTGCTGCATTGTTCCCATA (SEQ ID NO. 21) |
| NM_004050 | Bcl2l2 | GCGGAGTTCACAGCTCTATAC (SEQ ID NO. 21) | AAAAGGCCCCTACAGTTAC CA (SEQ ID NO. 23) |
| NM_001196 | Bid | GACAGCATGGACCGTAGCATA (SEQ ID NO. 24) | AGGTGCGTAGGTTCTGGTTA ATA (SEQ ID NO. 25) |
| NM_001166 | Birc2 | GTTTCAGGTCTGTCACTGGAAG (SEQ ID NO. 26) | TGGCATACTACCAGATGAC CA (SEQ ID NO. 27) |
| NM_182962 | Birc3 | TCCTGGATAGTCTACTAACT GCC (SEQ ID NO. 28) | GCTTCTTGCAGAGAGTTTCT GAA (SEQ ID NO. 29) |
| NM_033292 | Casp1 | TCCAATAATGGACAAGTCA AGCC (SEQ ID NO. 30) | GCTGTACCCCAGATTTTGTA GCA (SEQ ID NO. 31) |
| NM_001230 | Casp10 | ATTGGTCCCAAGACATGAA GAC (SEQ ID NO. 32) | TGTTCCCTGTTTGTCCACTC T (SEQ ID NO. 33) |
| NM_032982 | Casp2 | AAACGAGGTTCCTGGTACA TCG (SEQ ID NO. 34) | TCCTTGATAAGTGCGTTCAC C (SEQ ID NO. 35) |
| NM_033340 | Casp7 | AGTGACAGGTATGGGCGTTC (SEQ ID NO. 36) | GAGGTTGCAGTCTTCCGAG AT (SEQ ID NO. 37) |
| NM_001237 | Ccna2 | GATGGTAGTTTTGAGTCAC CACA (SEQ ID NO. 38) | CACGAGGATAGCTCTCATA CTGT (SEQ ID NO. 39) |
| NM_053056 | Ccnd1 | GCTGGAGCCCGTGAAAAGA (SEQ ID NO. 40) | CTCCGCCTCTGGCATTTTG (SEQ ID NO. 41) |
| NM_000075 | Cdk4 | CAGATGGCACTTACACCCGTG (SEQ ID NO. 42) | GCAGCCCAATCAGGTCAAA GA (SEQ ID NO. 43) |

TABLE 3-continued

Sequences of Quantitative Real-time PCR (qPCR) Primers

| GenBank Accession | Official | Sense Primer (5'→3') | Antisense (5'→3') |
|---|---|---|---|
| NM_004935 | Cdk5 | GCCGCAATGTGCTACACAG (SEQ ID NO. 44) | GAGTAACAGCGGACGGGAATC (SEQ ID NO. 45) |
| NM_000389 | Cdkn1 | GTCACTGTCTTGTACCCTTGTG (SEQ ID NO. 46) | CGGCGTTTGGAGTGGTAGAAA (SEQ ID NO. 47) |
| NM_000076 | Cdkn1 | ACATCCACGATGGAGCGTC (SEQ ID NO. 48) | GGAAGTCGTAATCCCAGCGG (SEQ ID NO. 49) |
| NM_001278 | Chuk | CAGCCATTTACCTGGCATGAG (SEQ ID NO. 50) | GAGGGTCCCAATTCAACATCAA (SEQ ID NO. 51) |
| NM_001303 | Cox10 | CCAGCAAGTAAGACCCAAGCC (SEQ ID NO. 52) | TCATCTCTTTCCACCGCTTTTC (SEQ ID NO. 53) |
| NM_019887 | Diablo | GGTACAGACAGTGTTTGTGTGT (SEQ ID NO. 54) | CTACTAAGGGAATGAGGCTGA (SEQ ID NO. 55) |
| NM_000043 | Fas | TATCACCACTATTGCTGGAGTCA (SEQ ID NO. 56) | ACGAAGCAGTTGAACTTTCTGTT (SEQ ID NO. 57) |
| NM_002417 | Ki67 | TGTTCCCACTACACAATGTCTTG (SEQ ID NO. 58) | ACTTACGCGAGACCAACAGTT (SEQ ID NO. 59) |
| NM_021960 | Mcl1 | GTGCCTTTGTGGCTAAACACT (SEQ ID NO. 60) | AGTCCCGTTTTGTCCTTACGA (SEQ ID NO. 61) |
| NM_001618 | Parp1 | GATGCCTATTACTGCACTGGG (SEQ ID NO. 62) | CGGTCCTGCTTTTTAACCTTCAA (SEQ ID NO. 63) |
| NM_022121 | Perp | CAACCCTGCTGTCACTTACAT (SEQ ID NO. 64) | AGGTCATCTTCGTAGTTGGGG (SEQ ID NO. 65) |
| NM_182649 | Pcna | ACACTAAGGGCCGAAGATAACG (SEQ ID NO. 66) | CGGCATATACGTGCAAATTCAC (SEQ ID NO. 67) |
| NM_002859 | Pxn | GCGGACTTGGAGTCTACCAC (SEQ ID NO. 68) | TCCAGTTGGGTATGAGTAGGG (SEQ ID NO. 69) |
| NM_001167 | Xiap | GACAGGCCATCTGAGACACAT (SEQ ID NO. 70) | GGGGTTAGGTGAGCATAGTCTG (SEQ ID NO. 71) |
| NM_000687 | Ahcy | GCATCCGAGGCATCTCTGAG (SEQ ID NO. 72) | GCCATAGAGGTTGTCAAACTTGC (SEQ ID NO. 73) |
| NM_001713 | Bhmt | GACACCTTCATACCTTAGCTGC (SEQ ID NO. 74) | ACAGGTTTACCGGATGCTATCAA (SEQ ID NO. 75) |
| NM_012260 | Hacl1 | CCTTCTTATCATCGGGAAAGGTG (SEQ ID NO. 76) | CCCATAGGGGTGGGCAAAAAT (SEQ ID NO. 77) |
| NM_000221 | Khk | GCTATTCTGTGGACCTACGCT (SEQ ID NO. 78) | AGTATAGGATGGTGCGGCTAC (SEQ ID NO. 79) |

TABLE 3 -continued

Sequences of Quantitative Real-time PCR (qPCR) Primers

| GenBank Accession | Official | Sense Primer (5'→3') | Antisense (5'→3') |
|---|---|---|---|
| NM_000429 | Mat1a | CATCAAGCACATCGGCTACGA (SEQ ID NO. 80) | CCGAACATCAAACCCTGAT CTC (SEQ ID NO. 81) |
| NM_000274 | Oat | TGCTGTCAACCAAGGGCATT (SEQ ID NO. 82) | GCCTCCACTCCTGTATTCAT AGG (SEQ ID NO. 83) |
| NM_000988 | L27 | TGATGGCACCTCAGATCGC (SEQ ID NO. 84) | AGAGTACCTTGTGGGCATTA GG (SEQ ID NO. 85) |

Note:
Melt curve analysis was included to assure that only one PCR product was formed.

Experimental Reagents

Antibodies were used: cyclinD1, keratin 10, integrins β1 and B5, involucrin (Chemicon); caspase-3 (R&D Systems); PCNA, transglutaminase 1 (TGase 1), β-tubulin, 14-3-3β, 14-3-3α, catalase, ERK1/2, p(T202/Y204)ERK1/2 (Santa Cruz Biotechnology); c-Src, p(Y416)Src, FAK, p(Y925) FAK (Cell Signaling Technology); pan-14-3-3 and BAD (Abcam); Bax and Cleaved PARP (Millipore); Ki67 (Nova-Castra); secondary Alexa488-conjugated antibodies (Invitrogen); secondary HRP-conjugated antibodies (Santa Cruz Biotechnology). Rat tail collagen type I (BD Biosciences, USA), pFIV lentivirus-based siRNA vector and packaging kit (System acetyl ester was from Molecular Probes. Transfection reagent ExGen 500 and restriction enzymes were from Fermentas. Monoclonal and polyclonal antibodies against the C-terminal region human (186-406 amino acids) and mouse (190-410 amino acids) ANGPTL4 were produced according to standard procedures. Unless specified, all reagents were obtained from Sigma.

Cell Culture.

HaCat is a non-tumor human keratinocyte cell line, II-4 and A-5RT3 are tumoriogenic HaCat derivatives were provided by the German Cancer Research Center. HSC is a human squamous cell carcinoma cell line was provided by Prof. Aso (Yamagata University School of Medicine, Japan). All cell lines were cultured in Dulbecco's Modified Eagle's Medium (DMEM; Hyclone, USA) supplemented with 10% heat-inactivated fetal bovine serum (FBS, Hyclone). All cells were cultured at 37° C., 5% $CO_2$ and 75% humidified incubator.

Human Tumor Samples.

Human squamous cell carcinoma biopsies along with their paired peri-tumor normal samples were provided by the National Skin Centre of Singapore. Whole SCCs and PNSs samples, inclusive of epithelia and stroma, were subjected to total protein or RNA extraction for immunoblotting or qPCR analyses. For LCM samples, epithelial and stromal fractions were microdissected from 8-μm-thick sectioned tissues using PALM Microbeam Axio Observer Z1 (Carl Zeiss) and qPCR was performed as described.

Commercial tumor tissue arrays #MTU951 and #MET961 (Pantomics, Inc., USA) were utilized to study the expression profile of ANGPTL4 in a large known human tumor set by immunofluorescence imaging. The #MTU951 human tumor tissue array contains 40 tumor types, covering most of the common benign, malignant and metastatic tumors originated from 27 anatomic sites, and the #MET961 human cancer metastasis tissue array consists of 48 cases of metastatic cancers from >8 anatomic sites. The two tissue arrays were probed with anti-cANGPTL4 polyclonal antibody followed by Alexa488 goat-anti-rabbit IgG. Images were taken by an inverted microscope (ECLISPSE TE2000-U; Nikon) with equal exposure and gain. The 3D heatmaps were generated using IMARIS software (Bitplane Scientific Software). In the heatmaps, the X-Y axis represents the length and width, while the Z axis represents the IF intensity.

Human basal cell carcinoma biopsies (BCCs) and squamous cell carcinoma biopsies (SCCs) along with their paired peri-tumor normal samples (PNSs) were provided by Dr. Pan, Dr. Tan (National Skin Centre, Singapore) and purchased from Asterand plc, USA. BCC, SCC and PNS samples, inclusive of epithelia and stroma, were subjected to protein and RNA extraction for immunoblotting and qPCR analyses, respectively.

Commercial tumor tissue arrays #MTU951 and #MET961 (Pantomics, Inc., USA) were utilized to study the expression profile of ANGPTL4 in a large human tumor set by immunofluorescence (IF) imaging. The #MTU951 human tumor tissue array contains 40 tumor types, covering most of the common benign, malignant and metastatic tumors originating from 27 anatomic sites, and the #MET961 human cancer metastasis tissue array consists of 48 cases of metastatic cancers from >8 anatomic sites. The two tissue arrays were probed with anti-cANGPTL4 polyclonal antibody followed by Alexa488 goat-anti-rabbit IgG. Images were taken using MIRAX MIDI with Plan-Apochromatic 20x/0.8 objective, with equal exposure and gain and each images automatically stitched by MIRAX Scan software (Carl Zeiss). The 3D heatmaps were generated using IMARIS software (Bitplane Scientific Software). In the heatmaps, the X-Y axes represent the length and width, whereas the Z axis represents the IF intensity. The gray value (IF intensity) was obtained from three biopsies using TissueQuest software (TissueGnostic GmbH).

Suppression of ANGPTL4 by RNA Interference (RNAi).

Four sets of siRNAs against human ANGPTL4 and a scrambled sequence as control (Table 2) were subcloned into the pFIV-H1/U6-puro pFIV/siRNA lentivirus system. The correct pFIV siRNA constructs were verified by sequencing using H1 primer. Pseudovirus purification and transduction were performed[1]. ANGPTL4-knockdown tumor cells were enriched by puromycin selection for 1 week. The A-5RT3 sub-cell line designated A-5RT3$_{ANGPTL4}$, with the highest knockdown efficiency was chosen in this study, and the non-targeted siRNA transduced line was denoted as A-5RT3$_{CTRL}$. The expression of endogenous ANGPTL4 in MDA-MB-231 cells was also suppressed using tetracycline-inducible pSingle-tTS-shRNA vector (Clontech). Knockdown efficiency of ANGPTL4 and relative expression level of indicated genes were determined by qPCR and immunoblotting.

Total RNA Isolation and Quantitative Real-Time PCR (qPCR).

Total RNA was extracted and qPCR was performed. Expression was related to the housekeeping gene 60S ribosomal protein L27 (RPL27) which did not change under any of the experimental conditions studied. The sequence of primers is available in Table 3. For focused mRNA array, genes whose expression was changed significantly (>2-fold) were listed and heatmaps were generated using Orange Canvas 1.0 software.

Immunoblotting.

Total protein was extracted from cells, or tumor tissues with ice-cold lysis buffer (20 mM Na$_2$H$_2$PO$_4$, 250 mM NaCl, 1% Triton-100, 0.1% SDS). Equal amount of protein extracts were resolved by SDS-PAGE and electrotransferred onto PVDF membranes. Membranes were processed according to standard procedure and proteins were detected by chemiluminesence (Millipore, USA). β-tubulin was used as loading and transfer control.

In Vivo Tumorigenecity Assay.

Five BALB/c athymic nude female mice (20-22 g), aged 5-6 weeks, were purchased from A*STARBiological Resources Centre (Singapore), and maintained in panthogen-free conditions. The animal studies were approved by the Institutional Animal Care and Use Committee (IACUC0092), Nanyang Technological University, and all experiments were carried out in strict compliance with their regulations. A total of 5×10$^5$ cells (A-5RT3$_{CTRL}$ or A-5RT3$_{ANGPTL4}$) was injected subcutaneously into the interscapular region of each nude mouse. Injection site was rotated to avoid site bias. The injected tumor cells were allowed to grow for 8 weeks, The subcutaneous xenograft tumors were measured externally with a vernier caliper every other day, and tumor volume was estimated by using the equation, V=(L×W$^2$)/2, where L is the length of the major axis of the tumor, and W is the length of the minor axis. Mice were sacrificed at the end of the experiment, and their tumors were harvested for further analysis.

For the antibody treatment, 6 nude mice were implanted with A-5RT3$_{CTRL}$ as above. One week post implantation, 30 mg/kg/week of either mAb11F6C4 or isotype control IgG were intravenously administrated once weekly for 4 weeks. The dose of antibody and delivery mode was consistent with studies using mAb14D12, another anti-ANGPTL4 mAb[2]. Mice were sacrificed after treatments and tumors were harvested for further analyses. Laser scanning microscope with a Plan-Apochromat 63×/1.40 Oil objective and ZEN 2008 software (Carl Zeiss).

Soft Agar and Anoikis Assay.

A-5RT3$_{CTRL}$ and A-5RT3$_{ANGPTL4}$ cells were used in soft agar assay. 0.6% Noble agar (Sigma Aldrich) in DMEM with 10% FBS was allowed to solidify in 6-well plate, and 1×10$^4$ cells were plated in 0.3% Noble agar in DMEM with 10% FBS on top. Tumor cell colonies were stained with 1 mg/ml thiazolyl blue tetrazolium in PBS after 4 weeks.

Cells were subjected to anoikis assay. Briefly, anoikis was induced by forced suspension where 5.0×10$^5$ cells were seeded onto 1.0% serum-free DMEM equilibrated agarose in the presence either 10 μg/ml of pre-immune IgG or mAb11F6C4. For MBA-MD-231, the cells were exposed to 1 μg/ml doxycyline for 24 h to knockdown ANGPTL4 prior anoikis Cells were harvested at indicated time points, and analyzed for apoptosis by FACS analysis.

A-5RT3$_{CTRL}$ and A-5RT3$_{ANGPTL4}$ cells were used in soft agar assay. 0.6% Noble agar (Sigma Aldrich) in DMEM with 10% FBS was allowed to solidify in 6-well plate, and 1×10$^4$ cells were plated in 0.3% Noble agar in DMEM with 10% FBS on top. Tumor-cell colonies were stained with 1 mg/ml thiazolyl blue tetrazolium in PBS after four weeks.

Cells were subjected to an anoikis assay. Briefly, anoikis was induced by forced suspension, wherein 5.0×10$^5$ cells were seeded onto 1.0% serum-free DMEM equilibrated agarose in the presence of either 10 g/ml of pre-immune IgG or mAb11F6C4. For MBA-MD-231, the cells were exposed to 1 g/ml doxycyline for 24 h to knockdown ANGPTL4 prior anoikis. For rescue experiments, cells were subjected to anoikis in the presence of either indicated concentrations of exogenous recombinant cANGPTL4 or vehicle (PBS). Cells were harvested at indicated time points, and analyzed for apoptosis by FACS analysis. Apoptotic index of attached cells were determined immediately after harvesting with trypsin.

Membrane Protein Extraction.

HEK293T cells were transferred with either empty mammalian expression vector pEF1-mycA (Invitrogen) or vector carrying cDNAs encoding human integrins β1, β3 and β5 by means of ExGen 500. Forty-eight hours post-transfection, cell membranes were first isolated using ProteoExtractNative Protein Extraction Kit (Calbiochem) and subjected to enrichment by sucrose step gradient. The proteins were displayed against PBS prior to SPR analysis.

Fluorescence-Activated Cell Sorting (FACS).

Cells were analyzed for apoptosis using the Annexin V-FITC apoptosis kit (BD Pharmingen) according to manufacturer's instructions. After 2 h of anoikis challenge, cells were harvested, washed in cold PBS and strained with annexin V-FITC and propidium iodide for 15 min at room temperature in the dark. Cells were resuspended in binding buffer (10 mM HEPES, pH 7.4, 140 mM NaCl, 2.5 mM CaCL$_2$), and subjected to flow cytometry on a FACS Calibur (Becton Dickinson). Data were analyzed using the CellQuest software (Becton Dickinson). The analyser threshold was adjusted on the flow cytometer channel to exclude most of the subcellular debris to reduce the background noise. The totality of Annexin V$^+$/PI$^-$ (early apoptosis) and Annexin V$^+$/PI$^+$ cells (late apoptosis) were considered apoptotic.

Surface Plasmon Resonance (SPR Analysis)

Purified fibrinogen-like fragment of ANGPTL4 (cANGPTL4) was immobilized onto ProteOn GLC chip by amine coupling as recommended by the manufacturer (Bio-Rad). Different concentrations of integrins were introduced into the GLC chip at a flow rate of 25 μl/min for 5 min with running buffer (50 mM Tris, pH8.0, 100 mMNaCl). Polyclonal anti-cANGPTL4 antibodies against the immobilized cANGPTL4 determined the Rmax value to be 423.1 resonance unit (RU). Global fitting of the data to a Languir 1:1 model was used to determine the association (K$_{on}$) dissociation (K$_{off}$) and affinity constant (K$_D$) using scrubber2 (Biologic Software Pty Ltd). The experimental Rmax values of integrins β1 and β5 for cANGPTL4 were determined to be 365.6 and 341.9 RU, respectively. The affinity constants of the 6 mAbs for ANGPTL4 were determined using the one shot Kinetics protocol as described by manufacturer (Bio-Rad).

Purified fibrinogen-like fragment of ANGPTL4 (cANGPTL4) was immobilized onto ProteOn GLC chip by amine coupling, as recommended by the manufacturer (Bio-Rad). Different concentrations of integrins were introduced into the GLC chip at a flow rate of 25 µl/min for 5 min with running buffer (50 mM Tris, pH 8.0, 100 mM NaCl). Polyclonal anti-cANGPTL4 antibodies against the immobilized cANGPTL4 determined the Rmax value to be 423.1 resonance unit (RU). Global fitting of the data to a Langmuir 1:1 model was used to determine the association ($k_{on}$), dissociation ($k_{off}$) and affinity constant ($K_D$) using Scrubber2 (BioLogic Software Pte Ltd). The experimental Rmax values of integrins β1 and β5 for cANGPTL4 were determined to be 365.6 and 341.9 RU, respectively. The affinity constants of the 6 mAbs for ANGPTL4 were determined using the One-Shot Kinetics protocol as described by manufacturer (Bio-Rad).

Detection of Src Oxidation by Carboxymethylation.

The detection of reduced Src was performed with minor modifications to the method described in (5). Cells were subjected to anoikis as described above. At indicated times, cells were lysed with 500 µl of lysis buffer (50 mM Tris-HCl, pH 7.5, 150 mM NaCl, 0.5% Triton X100, 10 µg/ml leupeptin) containing 100 µM of N-(biotinoyl)-N'-(iodoacetyl)ethylenediamine. Lysate was clarified by centrifugation and c-Src was immunoprecipitated using specific anti-c-Src antibodies. Immunocomplexese were resolved by SDS-PAGE and the biotinylated/reduced fraction of Src Kinase was detected with horseradish peroxidase (HRP)-conjugated streptavidin and by chemiluminescence.

The detection of reduced Src was performed with minor modifications. Cells were subjected to anoikis as described above. At indicated time, cells were lysed and with 500 µl of lysis buffer (50 mM Tris-HCl, pH 7.5, 150 µM NaCl, 0.5% Triton X-100, 10 µg/ml aprotinin and 10 µg/ml leupeptin) containing 100 µM of N-(biotinoyl)-N-(iodoacetyl)ethylenediamine. Lysates were clarified by centrifugation and c-Src was immunoprecipitated using specific anti-c-Src antibodies. Immunocomplexes were resolved by SBS-PAGE and the biotinylated/reduced fraction of Src kinase was detected with horseradish peroxidase (HRP)-conjugated streptavidin and by chemiluminesence.

Intracellular ROS Assay.

Cells were subjected to anoikis as described above. Five minutes before the end of each incubation time, 5-(and 6)-chloromethyl-2',7'-dichlorodihydro-fluorescein diacetate acetyl ester was added to a final concentration of 10 µM. Cells were lysed in 500 µl of RIPA buffer and analysed by fluorescence analysis using a Perkin Elmer Fluorescence Spectrophotometer at excitation of 485 nm and emission of 525 nm.

Laser Capture Microdissection (LCM)

For LCM samples, epithelial and stromal fractions were microdissected from 8-µm-thick sectioned tissues using PALM Microbeam Axio Observer Z1 (Carl Zeiss) separately. LCM tissues were collected into microfuge tubes with opaque AdhesiveCaps (Carl Zeiss). RNA was extracted using Optimum™ FFPE RNA Isolation kit (Ambion) pooled from 8 LCM tissues. 5 ng RNA was subjected to Full Spectrum Complete Transcriptome RNA Amplification kit (System Biosciences) prior to qPCR as previously described.

Generation cANGPTL4 and Antibodies

Recombinant ANGPTL4 proteins were purified from the conditioned medium of stable cANGPTL4-expressing S2 cells by preparative isoelectric membrane electrophoresis as previously described. Rabbit polyclonal antibodies against the C-terminal region and N-terminal region of human ANGPTL4 were produced in-house and previously described. Monoclonal antibodies (mAbs) against human cANGPTL4 (a.a. 186-406) were made according to standard protocols Briefly, mice were immunized with adjuvant conjugated-cAngptl4. The spleen of the mouse was removed and a single cell suspension was prepared. These cells were fused with myeloma cells and cultured in hybridoma selection medium (HAT; Gibco). The fused cells were cultured in microtiter plates with peritoneal macrophages for 48 hours post-fusion (2-4×10$^6$ cells/ml). The cultures were maintained in a 5% $CO_2$ humidified incubator for 7-21 days, and routinely fed with HAT medium. mAbs in medium were first screened using ELISA to identify positive clones. Positive clones were expanded and recloned by a limiting dilution technique to ensure monoclonality. Next, surface plasmon resonance was performed to determine the binding kinetics of mAbs. Global fitting of the data to a Langmuir 1:1 model was used to determine the association ($k_{on}$), dissociation ($k_{off}$) and affinity constant ($K_D$) using Scrubber2 (BioLogic Software Pte Ltd). mAb 11F6C4 was chosen for immunotherapy and other experiments based on its superior $k_{on}$, $k_{off}$ and $K_D$ values as well as its ability to block interaction between cANGPTL4 and integrins.

In Vivo Tumorigenicity Assay

BALB/c athymic nude female mice (20-22 g), aged 5-6 weeks, and C57BL/6J female mice (20-25 g) wide-type (WT), aged 6-8 weeks, were purchased from A*STAR Biological Resources Centre (Singapore). C57BL/6J female ANGPTL4 wild type (WT) and ANGPTL4-knockout (KO) mice were used. All animals were maintained in pathogen-free conditions. The animal studies were approved by the Institutional Animal Care and Use Committee (IACUC0092), Nanyang Technological University, and all experiments were carried out in strict compliance with their regulations.

For nude mice experiments, a total of 5×10$^5$ cells (A-5RT3$_{CTRL}$ or A-5RT3$_{ANGPTL4}$) were injected subcutaneously (s.c.) into the interscapular region of each nude mouse (n=5 for each group). Injection site was rotated to avoid site bias. The injected tumor cells were allowed to grow for eight weeks. The subcutaneous xenograft tumors were measured externally with a vernier caliper every other day, and tumor volume was estimated by using the equation, $V=(L \times W^2)/2$, where L is the length of the major axis of the tumor, and W is the length of the minor axis. Mice were sacrificed at the end of the experiment (week 8), and their tumors were harvested for further analyses. To test the effect of the number of injected cells on tumorigencity, 0.5×, 2× and 8×10$^{-6}$ A-5RT3$_{CTRL}$ or A-5RT3$_{ANGPTL4}$ were inoculated into nude mice (n=5) as above. Experiments were terminated at week 4, as tumor volume on 8×10$^{-6}$ inoculated group approached 3000 mm$^3$, accordingly to IACUC protocol. For the antibody treatment, nude mice (n=6 for each group) were implanted with A-5RT3 as described above. One week post implantation, 30 mg/kg/week of either mAb11F6C4 or isotype control IgG were intravenously (i.v.) administrated once weekly for four weeks. The dose of antibody and delivery mode was consistent with studies using mAb14D12, another anti-ANGPTL4 mAb27 (Desai et al., 2007). Mice were sacrificed after treatments, and tumors were harvested for further analyses.

KO mice and cANGPTL-treated C57BL/6J mice studies were performed as previously described (Sun and Lodish, 2010). Briefly, 1×10$^6$ B16F10$_{CTRL}$ (scrambled control cells) or B16F10$_{ANGPTL4}$ (ANGPTL4 knockdown cells) were s.c. injected into the interscapular region of indicated mice (n=4-6 each group). Mice were i.v. treated with either 3 mg/kg of cANGPTL4 or control PBS thrice a week. All the animals were monitored and tumor volume measured as above. Mice were sacrificed at the end of the experiment (day 15), and tumors were harvested for photographed.

In Situ Proximity Ligation Assay (PLA)

DUOLink™ in situ PLA (OLink Biosciences) was performed on tumor biopsies or cells as described. Paired-primary antibodies used in the present study were rabbit anti-p(Y397)FAK and mouse anti-FAK antibodies, rabbit anti-pan-14-3-3 and mouse anti-BAD antibodies, mouse anti-cANGPTL4 with either rabbit anti-β1, β3 or β5 integrin antibodies. As a negative control, PLA was performed by using only anti-FAK, anti-pan-14-3-3 or anti-nANGPTL4 antibodies, respectively. Briefly, sections/cells were fixed with 4% paraformaldehyde for 15 min. The slides were washed twice with PBS, blocked for 1 h at room temperature with 2% BSA in PBS containing 0.1% Triton-X, followed by incubation with indicated antibody pairs overnight at 4° C. PLA was performed as recommended by the manufacturer (OLink Biosciences). Images were taken using LSM710 META confocal laser scanning microscope with a Plan-Apochromat 63×/1.40 Oil objective and ZEN 2008 software (Carl Zeiss).

Electron Paramagnetic Resonance (EPR) Measurement of $O_2^-$

Entire excised tumor biopsies were dispersed enzymatically into single cell suspensions. The tissue was minced and incubated in digestion buffer containing hyaluronidase (1 mg/ml), collegenase D (1 mg/ml) and DNase (100 unit/ml) (Sigma-Aldrich) in a 37° C. shaking incubator for 2 h. The dispase and hyaluronidase digests were pooled and filtered through a 70 μm Nylon cell strainer. Cells were washed, pelleted and resuspended in PBS containing 3% FBS. Equal cell number was used for EPR measurement of $O_2^-$. Direct trapping of superoxide in aqueous media was performed using the spin trap DEPMPO, which forms a relatively stable superoxide adduct. EPR spectra were recorded at room temperature with a Bruker D-200 ER spectrometer, operating at X-band with a TM 110 cavity with a quartz flat cell. The EPR parameters were set at 100 KHz, X-band microwave frequency, 9.5 GHz; microwave power, 20 mW; modulation amplitude, 1 G; time constant, 160 s; scan time, 50 s; and receiver gain, $5 \times 10^5$. The EPR spectra represent the averaged signals of 10 scans. EPR signal amplitude at 3480 G represents the pure line, corresponding only to the superoxide adduct. All experiments were performed three times.

Measurement of $O_2^-$ and $H_2O_2$

Production of $O_2^-$ from tumor cells were measured using an $O_2^-$-sensitive luciferin derivative, 2-methyl-6-(p-methoxyphenyl)-3,7-dihydroimidazo[1,2-a]pyrazin-3-one (MCLA; Invitrogen). $5 \times 10^4$ of cells were trypsinized, washed, lysed in Krebs buffer and treated either individually or combinatorially for 0.5 h with the following chemicals: superoxide scavenger Tiron (10 mM), NADPH oxidase inhibitor diphenyleneiodonium chloride (DPI, 20 μM) or apocynin (500 μM), mitochondrial complex I inhibitor rotenone (50 μM) and monoclonal human anti-cANGPTL4 antibody mAb11F6C4 (3 or 6 μg/ml). MCLA (2 μM) was added, and the luminescent signal was recorded immediately thereafter for 1 min with a GloMax® 20/20 Luminometer (Promega). Intracellular $H_2O_2$ was measured as previously described. We performed two control experiments to verify that we were measuring $H_2O_2$. The specificity of the assay for $H_2O_2$ was checked with catalase, and the degradation of $H_2O_2$ or inhibition of the assay system by the sample was checked by determining the recovery of exogenously added $H_2O_2$. The fold change in $O_2^-:H_2O_2$ ratio of A-5RT3$_{ANGPTL4}$ and mAb11F6C4-treated tumor cells were determined by direct comparison with the value of either A-5RT3$_{CTRL}$ or control IgG-treated tumor cells, which was arbitrarily assigned the value one.

Caspases Activities Assay

Cells were subjected to anoikis as described above. The activities of caspases 2, 3, 6, 8 and 9 were measured with Apotarget caspase colorimetric protease assay kit (Biosource International, Camarillo, Calif.) according to the manufacturer's instructions. O.D.$_{405nm}$ was read and the fold-increase in caspase activities were determined by direct comparison with the level of the A-5RT3$_{CTRL}$ or cognate pre-immune IgG treated cells.

Statistical Analysis.

Statistical significance between two groups was analysed by an unpaired nonparametric test (Mann-Whitney test) or with a student's t-test (SPSS Inc.) All statistical tests were two-sided. P values of <0.05 were considered significant. Values (±S.D.) from 3-5 independent experiments with triplicates.

Statistical significance between two groups was analyzed by an unpaired nonparametric test (Mann-Whitney test) or with a Student's t-test (SPSS, Inc.). All statistical tests were two-sided. p value of <0.05 was considered significant.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

What is claimed is:

1. An antagonist to angiopoietin like 4 (ANGPTL4) protein that suppresses endogenous ANGPTL4 by 85%, reduces cell proliferation and reduces a level of Reactive Oxygen Species in a tumor cell, wherein the antagonist is an anti-ANGPTL4 shRNA expressed by a vector comprising a sequence as set out in SEQ ID NO. 86 and a sequence as set out in SEQ ID NO. 87.

2. An antagonist to angiopoietin like 4 (ANGPTL4) protein for the treatment of a cancer that suppresses endogenous ANGPTL4 by 85%, reduces cell proliferation and reduces the level of Reactive Oxygen Species in a tumor cell, wherein the antagonist is an anti-ANGPTL4 shRNA expressed by a vector comprising a sequence as set out in SEQ ID NO. 86 and a sequence as set out in SEQ ID NO. 87.

3. A composition comprising a therapeutically effective amount of an antagonist to angiopoietin like 4 (ANGPTL4) protein that suppresses endogenous ANGPTL4 by 85%, wherein the antagonist is an anti-ANGPTL4 shRNA expressed by a vector comprising a sequence as set out in SEQ ID NO. 86 and a sequence as set out in SEQ ID NO. 87, wherein the antagonist suppresses tumor growth.

4. The composition of claim 3 wherein the antagonist is suitable for use in treating metastasis.

5. The antagonist according to claim 1, wherein the vector is a tetracycline-inducible pSingle-tTS shRNA vector.

6. The antagonist according to claim 2, wherein the vector is a tetracycline-inducible pSingle-tTS shRNA vector.

7. The composition according to claim 3, wherein the vector is a tetracycline-inducible pSingle-tTS shRNA vector.

8. The antagonist according to claim 5, wherein the anti-ANGPTL4 shRNA is inducible in the presence of doxycycline.

9. The antagonist according to claim 6, wherein the anti-ANGPTL4 shRNA is inducible in the presence of doxycycline.

10. The composition according to claim 7, wherein the anti-ANGPTL4 shRNA is inducible in the presence of doxycycline.

11. The antagonist according to claim 8, wherein the anti-ANGPTL4 shRNA is inducible in the presence of 1 µg/ml of doxycycline.

12. The antagonist according to claim 9, wherein the anti-ANGPTL4 shRNA is inducible in the presence of 1 µg/ml of doxycycline.

13. The composition according to claim 10, wherein the anti-ANGPTL4 shRNA is inducible in the presence of 1 µg/ml of doxycycline.

* * * * *

UNITED STATES PATENT AND TRADEMARK OFFICE
CERTIFICATE OF CORRECTION

PATENT NO. : 10,087,447 B2  
APPLICATION NO. : 14/590397  
DATED : October 2, 2018  
INVENTOR(S) : Nguan Soon Tan et al.

Page 1 of 1

It is certified that error appears in the above-identified patent and that said Letters Patent is hereby corrected as shown below:

On the Title Page

At item (73), please correct the assignee "Nanyang Technologies University" to read
-- NANYANG TECHNOLOGICAL UNIVERSITY --.

Signed and Sealed this  
Seventh Day of May, 2019

Andrei Iancu  
*Director of the United States Patent and Trademark Office*